(12) United States Patent
Chiaur et al.

(10) Patent No.: US 6,720,181 B1
(45) Date of Patent: Apr. 13, 2004

(54) UBIQUITIN LIGASES AS THERAPEUTIC TARGETS

(75) Inventors: Dah Shiarn Chiaur, New York, NY (US); Michele Pagano, New York, NY (US); Esther Latres, New York, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 09/385,219

(22) Filed: Aug. 27, 1999

Related U.S. Application Data

(60) Provisional application No. 60/124,449, filed on Mar. 15, 1999, provisional application No. 60/118,568, filed on Feb. 3, 1999, and provisional application No. 60/098,355, filed on Aug. 28, 1998.

(51) Int. Cl.[7] ................ C12N 5/00; C12N 15/63; C07H 21/02; C07H 21/04; C12Q 1/68
(52) U.S. Cl. ................ 435/325; 435/320.1; 435/6; 514/23.1; 514/23.5
(58) Field of Search ................ 536/23.1, 23.5; 435/320.1, 325, 6; 800/8

(56) References Cited

PUBLICATIONS

DS Chiaur et al., Cytogenetics and Cell Genetics, "Five human genes encoding F–box proteins:chromosome mapping and analysis in human tumors," (2000), 88:255–258.*

JJ Mullins et al., Hypertension, "Trasgenesis in Nonmurine Species," Oct. 1993, vol. 22, No. 4, pp. 630–633.*

J. Rudinger, Peptide Hormones, "Characteristics of the amino acids as components of a peptide hormone sequence," edited by JA Parsons, pp. 1–7, University Park Press, Baltimore, 1976.*

ER Cmeron, Molecular Biotechnology, "Recent Advances in Transgenic Technology," Review, 1997, vol. 7, pp. 253–265.*

RE Hammer et al., Cell, "Spontaneous Inflammatory Disease in Transgenic Rats Expressing HLA–B 27 and Human Beta2m:An Animal Model of HLA–B27–Associated Human Disorders," Nov. 1990, vol. 63, pp. 1099–1112.*

RF Seamark, Reprod.Fertil.Dev., "Progress and Emerging Problems in Livestock Transgenesis: a Summary Perspective," 1994, 6, 653–7.*

TL Hawkins et al., Genebank Accession No. AC001226, May 1997.*

C Auffray et al., EST Database Accession Nol Z43904, Nov. 1994.*

T Klockars et al., Genebank Accession No. AF126028, Mar.00.*

* cited by examiner

*Primary Examiner*—Ram Shukla
(74) *Attorney, Agent, or Firm*—Jones Day

(57) ABSTRACT

The present invention relates to the discovery, identification and characterization of nucleotides that encode novel substrate-targeting subunits of ubiquitin ligases. The invention encompasses nucleotides encoding novel substrate-targeting subunits of ubiquitin ligases: FBP1, FBP2, FBP3, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, transgenic mice, knock-out mice, host cell expression systems and proteins encoded by the nucleotides of the present invention. The present invention relates to screening assays that use the novel substrate-targeting subunits to identify potential therapeutic agents such as small molecules, compounds or derivatives and analogues of the novel ubiquitin ligases which modulate activity of the novel ubiquitin ligases for the treatment of proliferative and differentiative disorders, such as cancer, major opportunistic infections, immune disorders, certain cardiovascular diseases, and inflammatory disorders. The invention further encompasses therapeutic protocols and pharmaceutical compositions designed to target ubiquitin ligases and their substrates for the treatment of proliferative disorders.

12 Claims, 87 Drawing Sheets

FIG. 1

Figure 2:
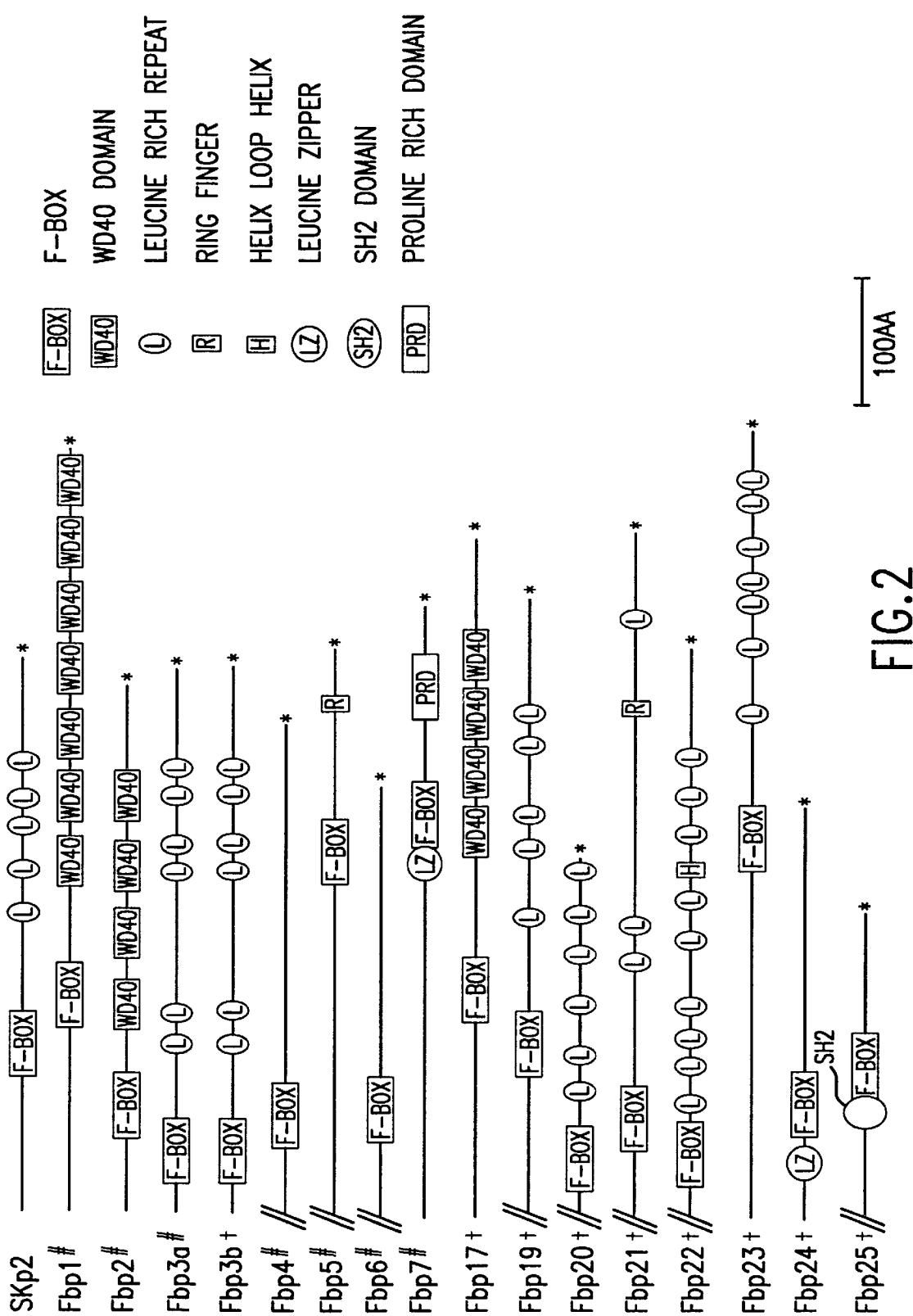

```
             10         20         30         40         50         60
MDPAEAVLQEKALKFMNSSEREDCNNGEPPRKIIPEKNSLRQTYNSCARLCLNQETVCLA 70         80         90        100        110        120
STAMKTENCVAKTKLANGTSSMIVPKQRKLSASYEKEKELCVKYFEQWSESDQVEFVEHL 130        140        150        160        170        180
ISQMCHYQHGHINSYLKPMLQRDFITALPARGLDHIAENILSYLDAKSLCAAELVCKEWY 190        200        210        220        230        240
RVTSDGMLWKKLIERMVRTDSLWRGLAERRGWGQYLFKNKPPDGNAPPNSFYRALYPKII 250        260        270        280        290        300
QDIETIESNWRCGRHSLQRIHCRSETSKGVYCLQYDDQKIVSGLRDNTIKIWDKNTLECK 310        320        330        340        350        360
RILTGHTGSVLCLQYDERVIITGSSDSTVRVWDVNTGEMLNTLIHHCEAVLHLRFNNGMM 370        380        390        400        410        420
VTCSKDRSIAVWDMASPTDITLRRVLVGHRAAVNVVDFDDKYIVSASGDRTIKVWNTSTC 430        440        450        460        470        480
EFVRTLNGHKRGIACLQYRDRLVVSGSSDNTIRLWDIECGACLRVLEGHEELVRCIRFDN 490        500        510        520        530        540
KRIVSGAYDGKIKVWDLVAALDPRAPAGTLCLRTLVEHSGRVFRLQFDEFQIVSSSHDDT 550        560
ILIWDFLNDPAAQAEPPRSPSRTYTYISR
```

FIG. 3A

```
        10        20        30        40        50        60        70        80        90
TGCGTTGGCTGCGGGCCTGCCACCAAAGGGGCGGGCCCCCGGGAGAGCGGACCCAGTGCCTCGGCGATTATGGACCCGGCGAGGCGGTGCTGC 100       110       120       130       140       150       160       170       180
AAGAGAAGGCACTCAAGTTTATGAATTCCTCAGAGAGAAGACTGTAATAATGGCAACCCCCTAGGAAGATAATACCAGAGAAGAATTCACT 190       200       210       220       230       240       250       260       270       280
TAGACAGAGACATACAACAGCTGTGCCAGACTCTGCTTAAACAAGAAACAGTATGTTTAGCAAGCACTGCTATGAAGACTGAGAATTGTGGCC 290       300       310       320       330       340       350       360       370
AAAACAAAACTTGCCAATGGCACTTCCAGTATGATTGTGCCCAAGCAACCGAAACTCTCAGCAAGCTATGAAAAGGAAACTGTGTCA 380       390       400       410       420       430       440       450       460       470
AATACTTTGAGCAGTGTCAGAGTCAGATCAAGTGGAATTTGTGAACATCTTATATCCCAAATGTCATTACCAACATGGCACATAAACTC 480       490       500       510       520       530       540       550       560
GTATCTTAAACCTATGTTGCAGAGATTTCATAACTGCTCTGCCAGCTCGGGATTGGATCATATCGCTGAGAACATTCTGTCATACCTGGAT 570       580       590       600       610       620       630       640       650
GCCAAATCACTAGTGCTGAACTTGTGTGCAAGGAATGGTACCGAGTGACCTCTGATGCCATGCGTGTGGAAGAAGCTTATCGGAGAGAATGG 660       670       680       690       700       710       720       730       740       750
TCAGGACAGATTCTCTGTGGAGAGGCCTGGACAGAACAAGGACAGTATTTATTCAAAAACAAACCTCCTGACGGGAATGCCTCCTCC 760       770       780       790       800       810       820       830       840
CAACTCTTTTTATAGAGCACTTTATCCTAAAATTATACAAGACAATAGAATCTAATTGGAGATGTGGAAGACATAGTTTACAGAGA 850       860       870       880       890       900       910       920       930       940
ATTCACTGCCGAAGTGAAACAAGCAAAGGAGTTTACGTGTTTACAGTATGATGATCAGAAAAATAGTAAGCGGCCCTTCGAGACAACAATCAAGA
```

FIG.3B

```
       950       960       970       980       990       1000      1010      1020      1030
TCTGGGATAAAAACACATTGGAATGCAAGCGAATTCTCACAGGCCATACAGGTTCAGTCCTCTGTCTCCAGTATGATGAGAGTGATCATAAC 1040      1050      1060      1070      1080      1090      1100      1110      1120
AGGATCATCGGATTCCACGGTCAGAGTGTGGGATGTAAATACAGGTGAAATGCTAAACACGTTGATTCACCATTGAAGCAGTTCTGCACTTG 1130       1140      1150      1160      1170      1180      1190      1200      1210      1220
CGTTTCAATAATGGCATGATGGTGACCTGCTCCAAAGATCGTTCCATTGCTGTATGGGATATGGCCTCCCAACTGACATTACCCTCCGGAGGC 1230      1240      1250      1260      1270      1280      1290      1300      1310
TGCTGGTCGGACACCGAGCTGCTGTCCAAATGTTGTAGACTTTGATGACAAGTACATTGTTTCTGCATCTGGGATAGAACTATAAAGGTATGAA 1320       1330      1340      1350      1360      1370      1380      1390      1400      1410
CACAAGTACTTGTGAATTTGTAAGGACCTTAAATGGACACAACGAGGCATTGCCTGTTTGCAGTACAGGCTGGTAGTGAGTGGCTCA 1420      1430      1440      1450      1460      1470      1480      1490      1500
TCTGACAACACTATCAGATTATGGGACATAGAATGTGGTGCATGTTACGAGTGTTAGAAGGCCATGAGGAATTGGTGCCTTGTATTCGATTTG 1510      1520      1530      1540      1550      1560      1570      1580      1590
ATAACAAGAGGATAGTCAGTGGGCCTATGATGATGAAAAATTAAAGTGTGGGATCTTGTGCCTCGTCCTTTGACCCCCGTGCTCCTCGCAGGGACACT 1600       1610      1620      1630      1640      1650      1660      1670      1680      1690
CTGTCTACGGACCCTTGTGGAGCATTCCGGAAGAGTTTTTCGACTACAGTTTTGATGAATTCCAGATTGTCAGTAGTTCACATGATGACACAATC
```

FIG.3C

```
1700      1710      1720      1730      1740      1750      1760      1770      1780
CTCATCTGGGACTTCCTAAATGATCAGCTGCCCAAGCTGAACCCCCGTTCCCTTCTGAACATACACCTACATCTCCAGATAAATAACCA 1790      1800      1810      1820      1830      1840      1850      1860      1870      1880
TACACTGACCTCATACTTGCCCAGGACCCATTAAAGTTGCGGTATTTAACGTATCTGCCAATACCAGGATGAGCAACAGTAACAATCAAAC 1890      1900      1910      1920      1930      1940      1950      1960      1970
TACTGCCCAGTTTCCCTGGACTAGCCGAGGAGCAGGGCTTTGAGACTCCTGTTGGGACACAGTGGTCTGCAGTCGGCCCAGGACGGTCTACTC 1980      1990      2000      2010      2020      2030      2040      2050      2060
AGCACAACTGACTGCTTCAGTCGTCGCTATCAGAAGATGTCTTCTATCAATTGTGAATGATTGGAACTTTAAACCTCCCCTCTCCTCCTCTTT 2070      2080      2090      2100      2110      2120      2130      2140      2150
CACCTCTGCCACCTAGTTTTTTCCCATTGGTTCCAGACAAAGGTGACTTATAAATATATTTAGTGTTTTGCCCAGAAAAAAAAA
```

FIG.3D

```
         10        20        30        40        50        60
MERKDFETWLDNISVTFLSLTDLQKNETLDHLISLSGAVQLRHLSNNLETLLKRDFLKLL 70        80        90       100       110       120
PLELSFYLLKWLDPQTLLTCCLVSKQWNKVISACTEVWQTACKNLGWQIDDSVQDALHWK 130       140       150       160       170       180
KVYLKAILRMKQLEDHEAFETSSLIGHSARVYALYYKDGLLCTGSDDLSAKLWDVSTGQC 190       200       210       220       230       240
VYGIQTHTCAAVKFDEQKLVTGSFDNTVACWEWSSGARTQHFRGHTGAVFSVDYNDELDI 250       260       270       280       290       300
LVSGSADFTVKVWALSAGTCLNTLTGHTEWVTKVVLQKCKVKSLLHSPGDYILLSADKYE 310       320       330       340       350       360
IKIWPIGREINCKCLKTLSVSEDRSICLQPRLHFDGKYIVCSSALGLYQWDFASYDILRV 370       380       390       400       410       420
IKTPEIANLALLGFGDIFALLFDNRYLYIMDLRTESLISRWPLPEYRESKRGSSFLAGEH

PG
```

FIG. 4A

```
        10         20         30         40         50         60         70         80         90
ATGGAGAAAGGACTTTGAGACATGGCTTGATAACATTTCTTCTCTGACCGACTTGCAGAAAATGAAACTCTGGATCACC 100        110        120        130        140        150        160        170        180
TGATTAGTCTCGAGTGGGGCAGTCCAGTCCAGCTCCAGGCCATCTCTCCAATAACCTAGAGACTCTCCTCAAGCGGACTTCCTCAAACTCCTTCCCCTGGA 190        200        210        220        230        240        250        260        270        280
GCTCAGTTTTTATTTGTTAAAATGCCTCGATCCTCAGACTTTACTCACATGCTGCCTCGTCTCTAAACAGTGGAATAAGTGATAAGTGCCTGT 290        300        310        320        330        340        350        360        370
ACAGAGGTGCAGACTGCATGTAAAAATTTGGGCTGGCAGATAGATTCTGTTCAGGACGCTTTGCACTGGAAGAAGGTTTATTTGAAGC 380        390        400        410        420        430        440        450        460        470
CTATTTGAGAATGAAGCAACTGGAGGACCATGAAGCCTTTGAAACCTCGTCATTAATTGGACACAGTGCCAGAGTGTATGCACTTTACTACAA 480        490        500        510        520        530        540        550        560
AGATGGACTTCTCTGTACAGGGTCAGATGACTTGTCTGCAAAGCTGTGAGCACAGGGCAGTGCCTTTATGGCATCCAGACCCACACT 570        580        590        600        610        620        630        640        650
TGTGCAGCGGTGAAGTTTGATGAACAGAAGCTTGTGACAGGCTCCTTTGACACAGGCTCGTGGGAATGAGTTCCGAGCCAGGACCC 660        670        680        690        700        710        720        730        740        750
AGCCACTTTCCGGGGGCACACGGGGGGCGGTATTTAGCGTGGACTACAATGATGAAACTGGATATCTTGGTGAGCGGCTCCGCAGACTTCACTGTGAA 760        770        780        790        800        810        820        830        840
AGTATGGGCTTTATCTGCTCGGGACATGCCTGAACACACTCACCGGGCACACGGAATGGGTCACCAAGGTAGTTTTGCAGAAGTGCAAAGTCAAG 850        860        870        880        890        900        910        920        930        940
TCTCTCTTGCCACAGTCCTGGAGACTACATCCTCTCTTAAGTCAGACAAATATGAGATTAAGATTGGCCAATTGGGAGAGAAATCAACTGTAAGT
```

FIG.4B

```
      950       960       970       980       990      1000      1010      1020      1030
GCTTAAAGACATTGTCTGTCTCTGAGGATAGAAGTATCTGCCTGCAGCCAAGACTTCATTTTGATGGCAAATACATTGTCTGTAGTTCAGCACT 1040      1050      1060      1070      1080      1090      1100      1110      1120
TGGTCTCTACCAGTGGGACTTTGCCAGTTATGATATTCTCAGGTCATCAAGAGACTCCTGAGATAGCAAACTTGGCCTTGCTTGGCTTTGGAGAT 1130      1140      1150      1160      1170      1180      1190      1200      1210      1220
ATCTTGCCCTGCTGTTTGACAACCGCTACCTGTACATCATGGACTTGCGGACAGAGAGCCTGATTAGTCGCTGGCCTCTGCCAGAGTACAGGG 1230      1240      1250      1260      1270      1280      1290      1300      1310
AATCAAAGAGAGGCTCAAGCTTCCTGCAGGCGAACATCCTGGCATGGGATGGGCACAATGACACGGGCTTGGTCTTTGCCACCAGC 1320      1330      1340      1350      1360      1370      1380      1390      1400      1410
ATGCCCTGACCACAGTATTCACCTGCTGTGTTGTGGAAGGAGCACGGCTGACACCACCGCTGACTTTGGGTGCCCGGGGCTGCG 1420      1430      1440      1450      1460      1470
GGTTTGGGTGCACCTCTGCGGCACGCGACTGCATGAACCAAAGTTCTCACCTAATGGTATCATCA
```

FIG.4C

```
          10        20        30        40        50        60
MKRGGRDSDRNSSEEGTAEKSKKLRTTNEHSQTCDWGNLLQDIILQVFKYLPLLDRAHAS 70        80        90       100       110       120
QVCRNWNQVFHMPDLWRCFEFELNQPATSYLKATHPELIKQIIKRHSNHLQYVSFKVDSS 130       140       150       160       170       180
KESAEAACDILSQLVNCSLKTLGLISTARPSFMDLPKSHFISALTVVFVNSKSLSSLKID 190       200       210       220       230       240
DTPVDDPSLKVLVANNSDTLKLLKMSSCPHVSPAGILCVADQCHGLRELALNYHLLSDEL 250       260       270       280       290       300
LLALSSEKHVRLEHLRIDVVSENPGQTHFHTIQKSSWDAFIRHSPKVNLVMYFFLYEEEF 310       320       330       340       350       360
DPFFRYEIPATHLYFGRSVSKDVLGRVGMTCPRLVELVVCANGLRPLDEELIRIAERCKN 370       380       390       400       410       420
LSAIGLGECEVSCSAFVEFVKMCGGRLSQLSIMEEVLIPDQKYSLEQIHWEVSKHLGRVW

FPDMMPTW
```

FIG.5A

CGGGGTGGTGTGTGGGGGAAGCCGGCCCCCGGCAGCCAGGATGAAACGAGGAGGAAGAGATAGTGACCGTAATTCATCAGAGAAGAACTGCAGA

GAAATCCAAGAAACTGAGGACTACAAATGAGCATTCTCAGACTGTGTGATTGCGGTAATCTCCTTCAGGACATTATTCTCCAAGTATTAAATAT

TTGCCTCTTCTTGACCGGCTCATGCTTCACAAGTTTGCCGCAACTGGAACCAGGTATTTCACATGCCTGACTTGTGGAGATGTTTTGAATTTG

AACTGAATCAGCCAGCTACATCTTATTTGAAAGCTACCCATCCAGAGCTGATCAAACAGATTATTAAAAGACATTCAAACCATCTACAATATGT

CAGCTTCAAGGTGGACAGCAGCAAGGAATCAGCTGAAGCAGTCTGTGATATACTATCGCCAACTTGTGCTTCTTTAAAAACACTTGGACTT

ATTTCAACTGCTCGACCAAGCTTTATGGATTTACCAGATGATGATCCATCTCCTCACTTTATCTCTGCACTGACAGTTGTGTTCGTAAACTCCAAATCCTGTCTT

CGCTTAAGATAGATACTCCAGTAGATGATGCATCCATCTCAAAGTACTAGTGCCAACAATAGTGATACACTCAAGCTGTTGAAAATGAGCAG

CTGTCCCTCATGTCTCTCCAGCAGGTATCCTTGTGTGGCTGATCAGTGTCACGGCTTAAGAGAACTAGCCCTGAACTACCACTTATTGAGTGAT

GAGTGTGTTACTTGCCATTGTCTTCTGAAAAACATGTTCGATTAGAACATTGGCCATTGATGATCAGTAGTGAGAATCCTGGACAGACACTTCC

ATACTATTCAGAAGAGTAGCTGGGATGCTTTCATCAGACACTTCACCCAAAGTGAACTTAGTGATGTGATTTTTTTTATATGAAGAAGAATTTGA

FIG.5B

```
     950     960     970     980     990     1000    1010    1020    1030
CCCCTTCTTTCGCTATGAAATACCTGCCACCCATCTGTACTTTGGGAGATCAGTAAGCAAAGATGTCTTGGCCCTGTGGAATGACATGCCCT 1040    1050    1060    1070    1080    1090    1100    1110    1120
AGACTGGTTGAACTAGTGTGTGCAAATGGATTACGGCCACTTGATGAAGAGTTAATTCGCATTGCAGAACGTTGCAAAAATTTGTCAGCTA 1130     1140    1150    1160    1170    1180    1190    1200    1210    1220
TTGGACTAGGGGAATGTGAAGTCTCATGTAGTGCCTTTGTTGTTGAGTTTGTGAAGATGTGTGGCCCCTATCTCAATTATCCATTATGGAAGA 1230    1240    1250    1260    1270    1280    1290    1300    1310
AGTACTAATTCCTGACCAAAGTATAGTTTGGAGCAGATTCACTGGGAAGTCCAAGCATCTTGGTAGGGTGTGGTTTCCCGACATGATGCCC 1320    1330    1340    1350    1360    1370    1380    1390    1400
ACTTGGTAAAAACTGCATGATGAATAGCACCTTAATTCAAGCAAATGTATTATAATTAAAGTTTTATTTGCTGTAAAAAAAAAAAAAAA
```

FIG.5C

```
         10         20         30         40         50         60
MKRNSLSVENKIVQLSGAAKQPKVGFYSSLNQTHTHTVLLDWGSLPHHVVLQIFQYLPLL 70         80         90        100        110        120
DRACASSVCRRWNEVFHISDLWRKFEFELNQSATSSFKSTHPDLIQQIIKKHFAHLQYVS 130        140        150        160        170        180
FKVDSSAESAEAACDILSQLVNCSIQTLGLISTAKPSFMNVSESHFVSALTVVFINSKSL 190        200        210        220        230        240
SSIKIEDTPVDDPSLKILVANNSDTLRLPKMSSCPHVSSDGILCVADRCQGLRELALNYY 250        260        270        280        290        300
ILTDELFLALSSETHVNLEHLRIDVVSENPGQIKFHAVKKHSWDALIKHSPRVNVVMHFF 310        320        330        340        350        360
LYEEEFETFFKEETPVTHLYFGRSVSKVVLGRVGLNCPRLIELVVCANDLQPLDNELICI 370        380        390        400        410        420
AEHCTNLTALGLSKCEVSCSAFIRFVRLCERRLTQLSVMEEVLIPDEDYSLDEIHTEVSK

430
YLGRVWFPDVMPLW
```

FIG. 6A

```
        10        20        30        40        50        60
ACATTTTCTAATGTTTACAGAATGAAGAGGAACAGTTTATCTGTTGAGAATAAAATTGTCCAGTTGTCA 70        80        90       100       110       120       130
GGAGCAGCGAAACAGCCAAAAGTTGGGTTCTACTCTTCTCTCAACCAGACTCATACACACACGGTTCTT 140       150       160       170       180       190       200
CTAGACTGGGGGAGTTTGCCTCACCATGTAGTATTACAAATTTTTCAGTATCTTCCTTTACTAGATCGG 210       220       230       240       250       260       270
GCCTGTGCATCTTCTGTATGTAGGAGGTGGAATGAAGTTTTTCATATTTCTGACCTTTGGAGAAAGTTT 280       290       300       310       320       330       340
GAATTTGAACTGAACCAGTCAGCTACTTCATCTTTTAAGTCCACTCATCCTGATCTCATTCAGCAGATC 350       360       370       380       390       400       410
ATTAAAAAGCATTTTGCTCATCTTCAGTATGTCAGCTTTAAGGTTGACAGTAGCGCTGAGTCAGCAGAA 420       430       440       450       460       470       480
GCTGCCTGTGATATACTCTCTCAGCTGGTAAATTGTTCCATCCAGACCTTGGGCTTGATTTCAACAGCC 490       500       510       520       530       540       550
AAGCCAAGTTTCATGAATGTGTCGGAGTCTCATTTTGTGTCAGCACTTACAGTTGTTTTTATCAACTCA 560       570       580       590       600       610       620
AAATCATTATCATCAATCAAAATTGAAGATACACCAGTGGATGATCCTTCATTGAAGATTCTTGTGGCC 630       640       650       660       670       680       690
AATAATAGTGACACTCTAAGACTCCCAAAGATGAGTAGCTGTCCTCATGTTTCATCTGATGGAATTCTT 700       710       720       730       740       750
TGTGTAGCTGACCGTTGTCAAGGCCTTAGAGAACTGGCGTTGAATTATTACATCCTAACTGATGAACTT 760       770       780       790       800       810       820
  TTCCTTGCACTCTCAAGCGAGACTCATGTTAACCTTGAACATCTTCGAATTGATGTTGTGAGTGAAAAT 830       840       850       860       870       880       890
CCTGGACAGATTAAATTTCATGCTGTTAAAAAACACAGTTGGGATGCACTTATTAAACATTCCCCTAGA 900       910       920       930       940       950       960
GTTAATGTTGTTATGCACTTCTTTCTATATGAAGAGGAATTCGAGACGTTCTTCAAAGAAGAAACCCCT
```

FIG.6B

```
       970       980       990       1000      1010      1020      1030
GTTACTCACCTTTATTTTGGTCGTTCAGTCAGCAAAGTGGTTTTAGGACGGGTAGGTCTCAACTGTCCT 1040      1050      1060      1070      1080      1090      1100
CGACTGATTGAGTTAGTGGTGTGTGCTAATGATCTTCAGCCTCTTGATAATGAACTTATTTGTATTGCT 1110      1120      1130      1140      1150      1160      1170
GAACACTGTACAAACCTAACAGCCTTGGGCCTCAGCAAATGTGAAGTTAGCTGCAGTGCCTTCATCAGG 1180      1190      1200      1210      1220      1230      1240
TTTGTAAGACTGTGTGAGAGAAGGTTAACACAGCTCTCTGTAATGGAGGAAGTTTTGATCCCTGATGAG 1250      1260      1270      1280      1290      1300      1310
GATTATAGCCTAGATGAAATTCACACTGAAGTCTCCAAATACCTGGGAAGAGTATGGTTCCCTGATGTG

1230
ATGCCTCTCTGG
```

FIG.6C

```
              10        20        30        40        50        60
MAGSEPRSGTNSPPPPFSDWGRLEAAILSGWKTFWQSVSKDRVARTTSREEVDEAASTLT 70        80        90        100       110       120
RLPIDVQLYILSFLSPHDLCQLGSTNHYWNETVRNPILWRYFLLRDLPSWSSVDWKSLPY 130       140       150       160       170       180
LQILKKPISEVSDGAFFDYMAVYLMCCPYTRRASKSSRPMYGAVTSFLHSLIIPNEPRFA 190       200       210       220       230       240
LFGPRLEQLNTSLVLSLLSSEELCPTAGLPQRQIDGIGSGVNFQLNNQHKFNILILYSTT 250       260       270       280       290       300
RKERDRAREEHTSAVNKMFSRHNEGDDRPGSRYSVIPQIQKLCEVVDGFIYVANAEAHKR 310       320       330       340       350       360
HEWQDEFSHIMAMTDPAFGSSGRPLLVLSCISQGDVKRMPCFYLAHELHLNLLNHPWLVQ 370       380       390       400       410       420
DTEAETLTGFLNGIEWILEEVESKRAR*FSFQILGTETI*NLLLRS*CEYLLSQPTLSCL 430       440       450       460       470       480
FADRLSFGQL*LLCFLYYFYFLP*INYKKRVSVLVFSPKMNL*TFFW*FLYFLSF*KY*I

L
```

FIG.7A

```
        10        20        30        40        50        60
ATGGCGGGAAGCGAGCCGCGCAGCGGAACAAATTCGCCGCCGCCGCCCTTCAGCGACTGGGGCCGCCTG 70        80        90       100       110       120       130
GAGGCGGCCATCCTCAGCGGCTGGAAGACCTTCTGGCAGTCAGTGAGCAAGGATAGGGTGGCGCGTACG 140       150       160       170       180       190       200
ACCTCCCGGGAGGAGGTGGATGAGGCGGCCAGCACCCTGACGCGGCTGCCCGATTGATGTACAGCTATAT 210       220       230       240       250       260       270
ATTTTGTCCTTTCTTTCACCTCATGATCTGTGTCAGTTGGGAAGTACAAATCATTATTGGAATGAAACT 280       290       300       310       320       330       340
GTAAGAAATCCAATTCTGTGGAGATACTTTTTGTTGAGGGATCTTCCTTCTTGGTCTTCTGTTGACTGG 350       360       370       380       390       400       410
AAGTCTCTTCCATATCTACAAATCTTAAAAAAGCCTATATCTGAGGTCTCTGATGGTGCATTTTTTGAC 420       430       440       450       460       470       480
TACATGGCAGTCTATCTAATGTGCTGTCCATACACAAGAAGAGCTTCAAAATCCAGCCGTCCTATGTAT 490       500       510       520       530       540       550
GGAGCTGTCACTTCTTTTTTACACTCCCTGATCATTCCCAATGAACCTCGATTTGCTCTGTTTGGACCA 560       570       580       590       600       610       620
CGTTTGGAACAATTGAATACCTCTTTGGTGTTGAGCTTGCTGTCTTCAGAGGAACTTTGCCCAACAGCT 630       640       650       660       670       680       690
GGTTTGCCTCAGAGGCAGATTGATGGTATTGGATCAGGAGTCAATTTTCAGTTGAACAACCAACATAAA 700       710       720       730       740       750
TTCAACATTCTAATCTTATATTCAACTACCAGAAAGGAAAGAGATAGAGCAAGGGAAGAGCATACAAGT 760       770       780       790       800       810       820
GCAGTTAACAAGATGTTCAGTCGACACAATGAAGGTGATGATCGACCAGGAAGCCGGTACAGTGTGATT 830       840       850       860       870       880       890
CCACAGATTCAAAAACTGTGTGAAGTTGTAGATGGGTTCATCTATGTTGCAAATGCTGAAGCTCATAAA 900       910       920       930       940       950       960
AGACATGAATGGCAAGATGAATTTTCTCATATTATGGCAATGACAGATCCAGCCTTTGGGTCTTCGGGA
```

FIG.7B

```
        970       980       990       1000      1010      1020      1030
AGACCATTGTTGGTTTTATCTTGTATTTCTCAAGGGGATGTAAAAAGAATGCCCTGTTTTTATTTGGCT 1040      1050      1060      1070      1080      1090      1100
CATGAGCTGCATCTGAATCTTCTAAATCACCCATGGCTGGTCCAGGATACAGAGGCTGAAACTCTGACT 1110      1120      1130      1140      1150      1160      1170
GGTTTTTTGAATGGCATTGAGTGGATTCTTGAAGAAGTGGAATCTAAGCGTGCAAGATGATTCTCTTTT 1180      1190      1200      1210      1220      1230      1240
CAGATCTTGGGAACTGAAACCATTTGAAATTTATTACTAAGGTCGTGATGTGAATATTTGCTCAGTCAG 1250      1260      1270      1280      1290      1300      1310
CCCACCTTGTCCTGCCTTTTTGCAGATAGGCTTTCATTTGGACAGCTATAACTGCTGTGTTTTTTATAT 1320      1330      1340      1350      1360      1370      1380
TATTTTTACTTTTTACCATAAATCAATTACAAGAAAAGAGTTTCAGTCCTAGTATTTAGCCCCAAAATG 1390      1400      1410      1420      1430      1440
AACCTTTAAACATTTTTTTGGTAATTTTTATATTTTCTGTCTTTTTAAAAATATTAAATTTTGG
```

FIG.7C

```
         10        20        30        40        50        60
MSRRPCSCALRPPRCSCSASPSAVTAAGRPRPSDSCKEESSTLSVKMKCDFNCNHVHSGL 70        80        90       100       110       120
KLVKPDDIGRLVSYTPAYLEGSCKDCIKDYERLSCIGSPIVSPRIVQLETESKRLHNKEN 130       140       150       160       170       180
QHVQQTLNSTNEIEALETSRLYEDSGYSSFSLQSGLSEHEEGSLLEENFGDSLQSCLLQI 190       200       210       220       230       240
QSPDQYPNKNLLPVLHFEKVVCSTLKKNAKRNPKVDREMLKEIIARGNFRLQNIIGRKMG 250       260       270       280       290       300
LECVDILSELFRRGLRHVLATILAQLSDMDLINVSKVSTTWKKILEDDKGAFQLYSKAIQ 310       320       330       340       350       360
RVTENNNKFSPHASTREYVMFRTPLASVQKSAAQTSLKKDAQTKLSNQGDQKGSTYSRHN 370       380       390       400       410       420
EFSEVAKTLKKNESLKACIRCNSPAKYDCYLQRATCKREGCGFDYCTKCLCNYHTTKDCS 430       440
DGKLLKASCKIGPLPGTKKSKKNLRRL
```

FIG.8A

```
         10         20         30         40         50         60         70         80         90
AGGTTGCTCAGCTGCCCCGGAGCGGTTCCTCCACCTGAGGCAGCAGACCACCTCGGTTGGCATGAGCCGGCCCCCTGCAGCTGCCCCTACGG 100        110        120        130        140        150        160        170        180
CCACCCCGCTGCTCCTGCAGCGCCAGCGCCCAGCGACAGCGGGCCTCGACCTCGGATAGTTGTAAAGAAGAAAGTTCTACCC 190        200        210        220        230        240        250        260        270        280
TTTCTGTCAAAATGAAGTGTGATTTTAATTGTAACCATGTCATTCCGGACTTAAACCTGATGACATTGGAAGACTAGTTTCCTA 290        300        310        320        330        340        350        360        370
CACCCCTGCATATCTGGAAGGTTCCTGTAAAGACTGCATTAAAGACTATGAAAGCGTCATGTATTGGTCACCGATTGTGAGCCCTAGGATT 380        390        400        410        420        430        440        450        460        470
GTACAACTTGAAACTGAAACTGGCTTGCCATAACAAGCAAGGAAATCAACATGTGCAACAGACACTTAATAGTACAAATGAAATAGAAGCACTAG 480        490        500        510        520        530        540        550        560
AGACCAGTAGAGACTTTATGAAGACAGTGCCTATTCCCTCATTTTCTCTACAAAGTGCCTCAGTGAACATGAAGAAGGTAGCCTCCTGGAGGAGAA 570        580        590        600        610        620        630        640        650
TTTCGGTGACAGTCTACAATCCTGCCTGCTACAAATACAAAGCCCAGACCAATATCCAACAAAAACTGCTGCCAGTTCTTCATTTTGAAAAA 660        670        680        690        700        710        720        730        740        750
GTGGTTTGTTCAACATTAAAAAAGAATGCAAAAGCAAATCCTAAAGTAGATCGGGAGATGCTGAAGGAAATTATAGCCAGAGGAAATTTTAGAC 760        770        780        790        800        810        820        830        840
TGCAGAATATAATTGGCAGAAAAATGGGCCTAGAATGTGTAGATATTCTCAGGGAACTCTTTCGGAACTCAGACATGTCTTAGCAACTAT 850        860        870        880        890        900        910        920        930        940
TTTAGCCACAACTCAGTGACATGGACTTAATCAATGTGTCTAAAGTGAGCACACAACTTGGAAGAAGAATCTAGAAGATGATAAGGGGCCATTCCAG
```

FIG.8B

```
       950       960       970       980       990      1000      1010      1020      1030
TTGTACAGTAAAGCAATACAAAGAGTTACCGAAAACAACAATAAATTTTCACCTCATGCTTCAACCAGAGAATATGTTATGTTCAGAACCCCAC 1040      1050      1060      1070      1080      1090      1100      1110      1120
TGGCTTCTGTTCAGAAATCAGCAGCCCAGACTTCTCTCAAAAAAGATGCTCAAACCAAGTTATCCAATCAAGGTGATCAGAAAGGTTCTACTTA 1130      1140      1150      1160      1170      1180      1190      1200      1210      1220
TAGTCGACACAATGAATTCTCTGAGGTTGCCAAGACATTGAAAAAGAACGAAAGCCTCAAAGCCTGTATTCGCTGTAATTCACCTGCAAAATAT 1230      1240      1250      1260      1270      1280      1290      1300      1310
GATTGCTATTTACAACGGGCAACCTGCAAACGAGAAGGCTGTGGATTTGATTATTGTACGAAGTGTCTCTGTAATTATCATACTACTAAAGACT 1320      1330      1340      1350      1360      1370      1380      1390      1400      1410
GTTCAGATGGCAAGCTCCTCAAAGCCAGTTGTAAAATAGGTCCCCTGCCTGGTACAAAGAAAAGCAAAAAGAATTTACGAAGATTGTGATCTCT 1420      1430      1440      1450      1460      1470      1480      1490      1500
TATTAAATCAATTGTTACTGATCATGAATGTTAGTTAGAAAATGTTAGGTTTTAACTTAAAAAAAATTGTATTGTGATTTTCAATTTTATGTTG 1510      1520      1530      1540      1550      1560      1570      1580      1590
AAATCGGTGTAGTATCCTGAGGTTTTTTTCCCCCCAGAAGATAAAGAGGATAGACAACCTCTTAAAATATTTTTACAATTTAATGAGAAAAAGT 1600      1610      1620      1630      1640      1650      1660      1670      1680      1690
TTAAAATTCTCAATACAAATCAAACAATTTAAATATTTTAAGAAAAAAGGAAAAGTAGATAGTGATACTGACGGTAAAAAAAAAAATTGATTCAA 1700      1710      1720      1730      1740      1750      1760      1770      1780
TTTTATGGTAAAGGAAACCCATGCAATTTTACCTAGACAGTCTTAAATATGTCTGGTTTTCCATCTGTTAGCATTTCAGACATTTTATGTTCCT 1790      1800      1810      1820      1830      1840      1850      1860      1870      1880
CTTACTCAATTGATACCAACAGAAATATCAACTTCTGGAGTCTATTAAATGTGTTGTCACCTTTCTAAAGCTTTTTTTCATTGTGTGTATTTCC 1890      1900      1910      1920      1930      1940      1950      1960      1970
CAAGAAAGTATCCTTTGTAAAAACTTGCTTGTTTTCCTTATTTCTGAAATCTGTTTTAATATTTTTGTATACATGTAAATATTTCTGTATTTTT 1980      1990      2000      2010      2020      2030      2040      2050      2060
TATATGTCAAAGAATATGTCTCTTGTATGTACATATAAAAATAAATTTTGCTCAATAAAATTGTAAGCTTAAAAAAAAAAAAAAAAAAACTCGAG

2070
ACTAGTGC
```

FIG.8C

```
         10         20         30         40         50         60
ARSGASALRRRRVQVWVLSRPPPGGGDSFRTRRPQRGPGPGGSQAMDAPHSKAALDSINE 70         80         90        100        110        120
LPDNILLELFTHVPARQLLLNCRLVCSLWRDLIDLLTLWKRKCLRKGFITKDWDQPVADW 130        140        150        160        170        180
KIFYFLRSLHRNLLRNPCAENDMFAWQIDFNGGDRWKVDSLPGAHGTEFPDPKVKKSFVT 190        200        210        220        230        240
SYELCLKWELVDLLADRYWEELLDTFRPDIVVKDWFAARADCGCTYQLKVQLASADYFVL 250        260        270        280        290        300
ASFEPPPVTIQQWNNATWTEVSYTFSDYPRGVRYILFQHGGRDTQYWAGWYGPRVTNSSI 310        320        330
VVSPKMTRNQASSEAQPGQKHGQEEAAQSPYGAVVQIF
```

FIG.9A

```
         10         20         30         40         50         60         70         80         90
GCGCGTTCGGGAGCTTCGGCCCTGCTGGTAGGAGGCGGGTGCAGGTGTGGGTGCTGAGCGCCGCCCTGGAGGGGAGACAGCTTCAGGACAC 100        110        120        130        140        150        160        170        180
GCAGGCCCGCAGCGAGGGCCCGGGCCCGGGGATCCCAGGCCATGGACGCTCCCCACTCCAAAGCAGCCCTGGACAGCATTAACGAGCTGCCCGA 190        200        210        220        230        240        250        260        270        280
TAACATCCTGCTGGAGCTGTTCACGCCACGTGCCCCCCCCAGCTGCTGCTGAACTGCCGCCTGGTCTCGAGCCTCTGCGGGGACCTCATCGAC 290        300        310        320        330        340        350        360        370
CTCCTGACCCTCTGGAAACGCAAGTGCCTCGCGAAAGGGCTTCATCACCAAGGACTGGGACCAGCCCGTGCCGACTGGAAAATCTTCTACTTCC 380        390        400        410        420        430        440        450        460        470
TACGGAGCCTGCATAGGAACCTCCTGCGCAACCGTGTGCTGAAAACGATATGTTTGCATGGCAAATTGATTTCAATGTGGGGACCGCTGGAA 480        490        500        510        520        530        540        550        560
GGTGGATAGCCTCCCTGGAGCCCACGGGACAGAATTCCCTGACCCCCAAAGTCAAGAGTCTTTGTCACATCCTACGAACTGTGCCTCAAGTGG 570        580        590        600        610        620        630        640        650
GAGCTGGTGACCTTCTAGCCGACCACCGCTACTGGAGGAGCTACTAGACACATTCCGCCCGGACATCGTGTTAAGGACTGTTGCTGCCAGAG 660        670        680        690        700        710        720        730        740        750
CCGACTGTGGCTGCACCTACCAACTCAAAGTGCAGCTGGCCTCGGCTGACTACTTCGTGTTGGCCTCCTTCGAGCCCCACCTGTGACCATCCA 760        770        780        790        800        810        820        830        840
ACAGTGGAACAATGCCACATGGACAGAGGTCTCCTACACCTTCTCAGACTACCCCCGGGTGTCCGCTACATCCTCTTCCAGCATGGGGCAGG 850        860        870        880        890        900        910        920        930        940
GACACCCAGTACTGGGCAGGCTGGTATGGGCCCCGAGTCACCAACAGCAGCATTGTCGTCAGCCCAAGATGACCAGGAACCAGGCCTCGTCCG
```

FIG.9B

```
      950        960        970        980        990       1000       1010       1020       1030
AGGCTCAGCCTGGGCAGAAGCATGGACAGGAGGAGCCTGCCCAATCGCCCTACGGAGCTGTGTCCAGATTTCTGACAGCTGTCCATCCTGTG 1040       1050       1060       1070       1080       1090       1100       1110       1120
TCTGGGTCAGCCAGAGGTTCCTCCAGCAGGAGCATGGGGTGGCAGTGAGGTCCCTGTACCAGCGACTCCTGCCCCGGTTCAACCCTA 1130       1140       1150       1160       1170       1180       1190       1200       1210       1220
CCAGCTTGTGTGGTAACTTACTGTCACATAGCTCTGACGTTTTGTTGTAATAAATGTTTTCAGGCCCGGGCACTGTGGCTCACGCCTGTAATCCCAG 1230       1240       1250       1260       1270       1280       1290       1300       1310
CACTTTGGGAGACCGAGGCAGGTGGATCACGAGGTCAGGAGACAGACCATCCTGGCCAACACGGTGAAACCCTGTCTCTACTAAAAATACAA 1320       1330       1340       1350       1360       1370       1380       1390       1400       1410
AAAATTAGCCGGGCGTGGTGGCGGGCCCTGTAGTCCCAGCTACTCGGGAGGCTGATGCAGAAGAATGGCGTGAACCCGGGAGGCAGAGCTTGC 1420       1430       1440       1450       1460       1470       1480       1490       1500
AGTGAGCCGAGATCACGCCACTGCCACTCCAGCCTGGGTGACAGAGCGAGACTCTGGCTCATAAAATAATAATAATAAATAAAAAATA 1510       1520       1530
AATGGTTTTCAGTAAAAAAAAAAAAAAAA
```

FIG.9C

```
          10         20         30         40         50         60
MSNTRFTITLNYKDPLTGDEETLASYGIVSGDLICLILHDDIPPPNIPSSTDSEHSSLQN 70         80         90        100        110        120
NEQPSLATSSNQTSIQDEQPSDSFQGQAAQSGVWNDDSMLGPSQNFEAESIQDNAHMAEG 130        140        150        160        170        180
TGFYPSEPLLCSESVEGQVPHSLETLYQSADCSDANDALIVLIHLLMLESGYIPQGTEAK 190        200        210        220        230        240
ALSLPEKWKLSGVYKLQYMHHLCEGSSATLTCVPLGNLIVVNATLKINNEIRSVKRLQLL 250        260        270        280        290        300
PESFICKEKLGENVANIYKDLQKLSRLFKDQLVYPLLAFTRQALNLPNVFGLVVLPLELK 310        320        330        340        350        360
LRIFRLLDVRSVLSLSAVCRDLFTASNDPLLWRFLYLRDFRDNTVRVQDTDWKELYRKRH 370        380        390        400        410        420
IQRKESPKGRFVLLLPSSTHTIPFYPNPLHPRPFPSSRLPPGIIGGEYDQRPTLPYVGDP 430        440        450        460        470        480
ISSLIPGPGETPSQLPPLRPRFDPVGPLPGPNPILPGRGGPNDRFPFRPSRGRPTDGRLS
FM
```

FIG.10A

```
                                                                                    10         20         30         40         50         60         70         80         90
                                                                          TGGAATTCCCATGACCATGTCTAATACCGATTACAATTACATTGAACTACAAGGATCCCTCACTGGAGATGAAGAGACCTTGGCTTCATA
         100        110        120        130        140        150        160        170        180
TGGGATTGTTTCTGGGGACTTGATATGTTGATTCTTCACGATGACATTCCACCGCCTAATATACCTTCATCCACAGATTCAGAGCATTCTTCA
         190        200        210        220        230        240        250        260        270        280
CTCCAGAACAATGAGCAACCCTCTTGGCCACCAGCTCCAATCAGACTAGCATACAGGATGAACAACAAGTGATTCATTCCAAGGACAGGCAG
         290        300        310        320        330        340        350        360        370
CCCAGTCTGGTGTTTGGAATGACGACAGTATGTTAGGGCCTAGTCAAAATTTGAAGCTGAGTCAATTCAAGATAATGCGCATATGGCAGAGGC
         380        390        400        410        420        430        440        450        460        470
CACAGGTTTCTATCCCTCAGAACCCCTGCTCTGTGAATCGGTGGAAGGCAAGTGCCACATTCATTAGAGACCTTGTATCAATCAGCTGAC
         480        490        500        510        520        530        540        550        560
TGTTCTGATGCCAATGATGCCTTGATAGTGTTGATACATCTTCTCATGTTGGAGTCAGGTTACATACCTCAGGGCACCGAAGCCAAAGCACTGT
         570        580        590        600        610        620        630        640        650
CCCTGCCCGAGAAGTGGAAGTTGAGCGGGGTGTATAAGCTGCAGTACATGCATCATCTCTGCGAGGGCAGCTCCGCTACTCTCCACCTGTGCC
         660        670        680        690        700        710        720        730        740        750
TTTGGGAAACCTGATTGTTGTAAATGCTACACTAAAAATCAACACTAGAAGTGTGAAAAGATTGCAGCTGCTACCAGAATCTTTTATT
         760        770        780        790        800        810        820        830        840
TGCAAAGAGAAACTAGCGGAAAATGTAGCCAACATATACAAAGATCTTCTCGCCCTCTTTAAAGACCAGCTGGTGTATCCTCTTC
         850        860        870        880        890        900        910        920        930        940
TGGCTTTTACCCGACAAGCACTGAACCTGAAACTACCAAATGTATTTGGGTTGGTCGTCCTCCCATTGGAACTGAAACTGAAACTACGGATCTTCCGACTTCTGGA
```

FIG.10B

```
      950       960       970       980       990       1000      1010      1020      1030
TGTTCGTTCCGCTCTTGTCTTGTCTCGGGTTTGTCGTGACCTCTTACTGCTTCAAATGACCCACTCCTGTGGAGGTTTTTATATCTGCTGAT 1040      1050      1060      1070      1080      1090      1100      1110      1120
TTTCGAGACAATACTGTCAGAGTTCAAGACACAGATTGGAAAGAACTGTACAGGAAGAGGCACACAAAGAAAGAATCCCCGAAAGGGCGGT 1130       1140      1150      1160      1170      1180      1190      1200      1210      1220
TTGTGCTGCTCCTGCCATCGTCAACCCACACCATTCCATTCTATCCCAACCCCTTGCCACCTAGGCCATTTCCTAGCTCCCGCTTCCTCCAGG 1230      1240      1250      1260      1270      1280      1290      1300      1310
AATTATCGGGGTGAATATGACCAAAGACCAACACTTCCTATGTTGGAGACCCAATCAGTTCACTCATTCCTGGTCCTGGGGAGACGCCCAGC 1320       1330      1340      1350      1360      1370      1380      1390      1400      1410
CAGTTACCTCCACTGAGACCTTGATCCCAGTGGCCCACTTCCAGGACCTAACCCCATCTGCCAGGGCGAGGCGGCCCAATGACACAGAT 1420      1430      1440      1450      1460      1470      1480      1490      1500
TTCCCTTTAGACCAGCAGGGGTCGCCCAACTGATGGCCGCCTGTCATTCATGTCGAGTGTTATTTTCTGATTGTAATTTCATTCTGGAGCTCCATTTGTTTT 1510       1520      1530      1540      1550      1560      1570      1580      1590
TGTTTCTAAACTACAGATGTCACTCCTGGGGTGCTGATCGAGTGTTATTTTCTGATTGGTGGTTGAGAGTTGCACTCCCAGAAACCTTTT 1600       1610      1620      1630      1640      1650      1660      1670      1680      1690
AAGAGATACATTTATAGCCCTAGGGGTGGTATGACCCAAAGGTTCCTCTGTGACAAGGTTGGCCTTGGGAATAGTTGGCTGCCAATCTCCCTGC 1700      1710      1720      1730      1740      1750      1760
TCTTGGTTCTCCCTCTAGATTGAAGTTTGTTTCTGATGCTGTTCTTACCAGATTAAAAAAAGTGTAAATT

FIG.10C
```

```
         10         20         30         40         50         60
ETSKLG*SAVLAPAAGGTLSSEGRSAVSGILIAVTSTGVDK*SLNQLLHGLGTSSRLSHF 70         80         90        100        110        120
PFG*KSPPRGQFVAAAVEIAGRSGLQMGQGLWRVVRNQQLQQEGYSEQGYLTREQSRRMA 130        140        150        160        170        180
ASNISNTNHRKQVQGGIDIYHLLKARKSKEQEGFINLEMLPPELSFTILSYLNATDLCLA 190        200        210        220        230        240
SCVWQDLANDELLWQGLCKSTWGHCSIYNKNPPLGFSFRKXYMQLDEGSLTFNANPDEGV 250        260        270        280        290        300
NYFMSKGILDDSPKEIAKFIFCTRTLNWKKLRIYLDERRDVLDDLVTLHNFRNQFLPNAL 310        320        330        340        350        360
REFFRHIHAPEERGEYLETLITKFSHRFCACNPDLMRELGLSPDAVYVLCYSLILLSIDL 370        380        390        400        410        420
TSPHVKNKMSKREFIRNTRRAAQNISEDFVGHLYDNIYLIGHVAA*KAQLLGLQFLLQTK 430        440        450        460        470        480
ATQGLSRYGGYISAGHCSLSIQSSFSVQPFFLLPFSILVISLGN*IILQNFS*FCLSRFA 490        500        510        520        530        540
QSRATV*HSC*RMIN*HYTLKDGVFVH*ICLKNFIHFHSLYKYHVMCTYLTKEIYSHNYF 550        560        570        580        590        600
IVKILTKVFPFLSN*VLKFI*F*SETIVXVKVRSDFRQKPIPASFSFKL*RVLICYYITM 610        620        630        640        650
QNWQLFL*YKFII*FFILKTGLIKSR*VL*TI*DF*NIKIYDLHS*E*NKIXLELW
```

FIG.11A

```
        10         20         30         40         50         60         70         80         90
GGAAACGTCAAAAATTGGGATAGTCGGCAGTTCTGCCCCTGCAGCTGAGCCCTGAGTTCTGAGGGTCGTAGTGCTGTTTCTGGTATTCTC 100        110        120        130        140        150        160        170        180
ATCGCGGTCACCTCTACCGGTGTGGACAAGTAAAGTTTGAATCAGCTTCTCCATGGCCTGGGCACCAGTTCCCGGCTGAGCCATTTCCTTTTG 190        200        210        220        230        240        250        260        270        280
GCTAAAAGTCCCCGAGGCCAATTCGTCGCGGCGGCGGTGGAGATCGCAGGTCCTCAGGCTTGCAGATGGGTCAAGGGTTGTGGAGAGT 290        300        310        320        330        340        350        360        370
GGTCAGAAACCAGCAGCTGCAACAGAGAAGGCTACAGTGAGCAAGGCTACCTCACCAGAGAGCAGAGGAGAATGCTGCGAGCAACATTCT 380        390        400        410        420        430        440        450        460        470
AACACCAATCATCGTAAACAGTCCAAGGAGGCATTGACATATATCATCTTTTGAAGGCAAGAAATCGAAAGAACAGGAAGGATTCATTAATT 480        490        500        510        520        530        540        550        560
TGGAAAATGTTGCCTCCTGAGCTAAGCTTCTGCCAAGGGTTGTGCAAATCCACTTGGGGTCACGTGTTCCATATACAATAAGAACCACCTTTAGGATTTCTTTTAGA 570        580        590        600        610        620        630        640        650
GAATGATGAACTTCTCTGCCAAGGGTTGTGATGAAGGCAGCCTCACCTTTAATGCCAACCCAGATGAGGGAGTGAACTACTTTATGTCCAAGGGTATCCTGGATG 660        670        680        690        700        710        720        730        740        750
AAAKTGTATATGCGCTGGATGAAGGCAGCCTCACCTTTAATGCCAACCCAGATGAGGGAGTGAACTACTTTATGTCCAAGGGTATCCTGGATG 760        770        780        790        800        810        820        830        840
ATTCGGCCAAAGGAAATAGCAAAGTTTATCTTCTGTACAAGAACACTAAATTGGAAAAAACTGAGAATCTATCTTGATGAAGGAGATGTCTT 850        860        870        880        890        900        910        920        930        940
GGATGACCTTGTAACATTGCATAATTTTAGAAATCAGTTCTTGCCAAATGCACTGAGAGAATTTTTCGTCATATCCATGCCCCTGAAGAGCGT
```

FIG. 11B

```
      950       960       970       980       990      1000      1010      1020      1030
GGAGAGTATCTTGAAACTCTTATAACAAGTCTCACATAGATTCTGTGCTTGCAACCCTGATTAATGCCAGAACTTGGCCTTAGTCCTGATG 1040      1050      1060      1070      1080      1090      1100      1110      1120
CTGTCTATGTACTGTGCTACTCTTTGATTCTACTTTCCATTGACCTCACTAGCCCTCATGTGAAGAATAAAATGTCAAAAGGGAATTTATTCG 1130      1140      1150      1160      1170      1180      1190      1200      1210      1220
AAATACCCGTCGCGTCGCTGCTCAAAATATTGTAAGATTTTGTAGGGCATCTTTATGACAATATCTACCTTATGGCCATGTGGCTGCATAAAAA 1230      1240      1250      1260      1270      1280      1290      1300      1310
GCACAATTGCTAGGACTTCAGTTTTACTTCAGACTAAAGCTACCCAAGGACTTAGCAGATATGGGGGTTACATCAGTGCTGGTCATTGTAGCC 1320      1330      1340      1350      1360      1370      1380      1390      1400      1410
TGAGTATACAATCAAGCTTCAGTGTGCAACCTTTTTCTTTTCTATTTCTATTTTAGTAATTCCTGGGAACTAAATAATTTGCAGAA 1420      1430      1440      1450      1460      1470      1480      1490      1500
TTTTTCCTAATTTGTTTATCACGTTTGCACAAAGCAGAGCCACTGTCTAACCAGCTGTTAACGAATGATAAACTGACATTATACTCTAAAA 1510      1520      1530      1540      1550      1560      1570      1580      1590
GATGGTGTATTTGTGCATTAGATTGCCTGAAAAACTTATCCATTCTTATACAAATACCATGTAATGTGTACATATTTAACTAAAG 1600      1610      1620      1630      1640      1650      1660      1670      1680      1690
AGATTTATAGTCATAATTATTTATTGTAAAGATTTAACTAAAGTTTTCCTTTCTCTCCAAACTGAGTTCTGAAATTTATTTGATTCTGATC
```

FIG. 11C

```
1700      1710      1720      1730      1740      1750      1760      1770      1780
TGAAACTATTGTCTYCGTAAAAGTTAGATCTGACTTCAGRCAGAAACCAATACCAGCTTCCTTTCCTTAAACTTTGAAGAGTGTTGATTTGT 1790      1800      1810      1820      1830      1840      1850      1860      1870      1880
TACTATATTACTATGCAAAACTGGCAGTTATTTTTATAATATAAATTTGATTTTTATTTTAAAACTGGTTAATCAAGTCTCGGT 1890      1900      1910      1920      1930      1940      1950      1960      1970
AAGTCCTTTAAACCATTTAGGATTTTTAAAACATCAAAATTTATGATTTACATTCATAGGAATAAAATAAAATATYATTAGAACTCTGGT
```

FIG.11D

```
          10         20         30         40         50         60
MAAAAVDSAMEVVPALAEEAAPEVAGLSCLVNLPGEVLEYILCCGSLTAADIGRVSSTCR 70         80         90        100        110        120
RLRELCQSSGKVWKEQFRVRWPSLMKHYSPTDYVNWLEEYKVRQKAGLEARKIVASFSKR 130        140        150        160        170        180
FFSEHVPCNGFSDIENLEGPEIFFEDELVCILNMEGRKALTWKYYAKKILYYLRQQKILN 190        200        210        220        230        240
NLKAFLQQPDDYESYLEGAVYIDQYCNPLSDISLKDIQAQIDSIVELVCKTLRGINSRHP 250        260        270        280        290        300
SLAFKAGESSMIMEIELQSQVLDAMNYVLYDQLKFKGNRMDYYNALNLYMHQVLIRRTGI 310        320        330        340        350        360
PISMSLLYLTIARQLGVPLEPVNFPSHFLLRWCQGAEGATLDIFDYIYIDAFGKGKQLTV 370        380        390        400        410        420
KECEYLIGQHVTAALYGVVNVKKVLQRMVGNLLSLGKREGIDQSYQLLRDSLDLYLAMYP 430        440        450        460        470        480
DQVQLLLLQARLYFHLGIWPEKVLDILQHIQTLDPGQHGAVGYLVQHTLEHIERKKEEVG 490        500        510        520        530        540
VEVKLRSDEKHRDVCYSIGLIMKHKRYGYNCVIYGWDPTCMMGHEWIRNMNVHSLPHGHH 550        560        570        580        590        600
QPFYNVLVEDGSCRYAAQENLEYNVEPQEISHPDVGRYFSEFTGTHYIPNAELEIRYPED 610        620
LEFVYETVQNIYSAKKENIDE
```

```
        2790      2800      2810      2820      2830      2840      2850      2860      2870      2880      2890      2900      2910
TTGCTCTTAGAAGTCATACTCCATGCTCTTCAAAGACCAAAGACCAAAGTGAGGTTTTGCCTTTGTAATCAGGAAAAAAAAATTAATGAACCTTAAAAAAAAAAAAGGTTTTGAAGGGAAAAAAGTGGTTTCACACCT 2920      2930      2940      2950      2960      2970      2980      2990      3000      3010      3020      3030      3040      3050
CTGTTATTCCTTAGAGTCACTTCAAGCCCTGTTGAATGTGGCAGGTTAGAAAGAGAGAATGTCTTTCATTTGAAGACTGTGTGACTGTGTGAAGGAGATGCCGTTGGAATCGCTTTTCCAAGCCCGCCAG 3060      3070      3080      3090      3100      3110      3120      3130      3140      3150      3160      3170      3180      3190
GGTCCTGACGGCAGGAGGACGAAGCCTGTGTGTGGCGTCTCTGGGAAAGCCTGACCGTGTGTTCGGACGGCACTGCCTCCTTCCGAAGTTCTCAGTTACTTCCGAAGTTCTCAGTAACTGCACGCCTTTGTGCAGCTCTGGA 3200      3210      3220      3230      3240      3250      3260      3270      3280      3290      3300      3310      3320      3330
GCTCCACCAACTCTCGGGCTGCCAGTTCTCAACGGAGCTAATCTGTCATTAATCGATAGAAGCTAACTTCCGAAGTTAGGACCTAGTTACTTGCTCTCAACATTTAAAATAATGCAGTTGCTCTAGTGAATGGGCG 3340      3350      3360      3370      3380      3390      3400      3410      3420      3430      3440      3450      3460      3470
TTAGGGCCTGTCTCTGCGACCGTGTCTGTCCATCGCAGTATTCTCACCATGTGAATGCCTGCTGTTACCCTTTGGAAACCCTGGGCTGACCAAGGTTGGAAAGCCACCTGAGACCACTTCATAGCAA 3480      3490      3500      3510      3520      3530      3540      3550      3560      3570      3580      3590      3600      3610
CGGAAGGCTTTAAGCAGTTACTAGAAGAGATGGGGATTGGCCCCTGGCTCCTCCAGCCTGAATGAGCTATTTAATCCACTGTCCTCATCAGTCAAATCCAAAGTCAAAGGATTCAACCTGCATCTGAA 3620      3630      3640      3650      3660      3670      3680      3690      3700      3710      3720      3730      3740      3750
ACGTAACCACTCACAGCCACCTGGCCCCGCCCAAGGTGTACACTACTTTCATTTAAAGGGAAAGTTTGATAATACGGAATTAATTAATAGAATGCATTAATAGAATGAGCATGCTGAGAGTT 3760      3770      3780      3790      3800      3810      3820      3830      3840      3850      3860      3870      3880      3890
GCAATTGTTTTTCTGGTTTTGATTGAATTCCTTTTTTCTTAGACACATCAAAGTCAAGAAAGATGGTTTACCTTTACTGACCCAGCTGTACATATGTACTGTAGACTGTTTTAAAATGTCTTTCTTCATGAATGCTT 3900      3910      3920      3930      3940      3950      3960      3970      3980      3990      4000      4010      4020      4030
CATGGGCTCCAGGAAGCCTCCATCACCGGTGTATTGGGCACTTTATATTTTCTAAAAACGTGTTTTGGATCCGTACTCTAATAACATAAGTTTCTTTTTAAAATGCTTCTCTTTTTCTTCATGAATGCTT 4040      4050      4060      4070      4080      4090      4100      4110      4120      4130      4140      4150      4160
TTAAAAAGCCCTGTTGAACTTTCACAATGTTAAATGTTAAAATGTTAAATATTTGGATATAGCAACTTCTTTTCTTCTTCAAATGAATGCAAGATTTTTTGTACAATGATTAATAAAATGGAACTTATCCAGAG
```

FIG.12D

```
          10        20        30        40        50        60
RSTGFRRAGEEWSR*XLAASPGXLRRPAXTFVLSNLAEVVERVLTFLPAKALLRVACVCR 70        80        90
LWRECVRRVLRTHRSVTWISAGLAEAGHLXGH
```

FIG.13A

```
          10        20        30        40        50        60
CCGTAGTACTGGNTTCCGGCGGGCTGGTGAGGAATGGAGCCGGTAGNTGCTTGCGGCGAG 70        80        90       100       110       120
TCCCGGGNTCCTCCGTAGACCCGCGGANACCTTCGTGTTGAGTAACCTGGCGGAGGTGGT 130       140       150       160       170       180
GGAGCGTGTGCTCACCTTCCTGCCCGCCAAGGCGTTGCTGCGGGTGGCCTGCGTGTGCCG 190       200       210       220       230       240
CTTATGGAGGGAGTGTGTGCGCAGAGTATTGCGGACCCATCGGAGCGTAACCTGGATCTC 250       260       270
CGCAGGCCTGGCGGAGGCCGGCCACCTGGNGGGGCATT
```

FIG.13B

```
         10        20        30        40        50        60
RPRPVQQQQQQPPQQPPPQPPQQQPPQQQPPPPPQQQQQQQPPPPPPPPPPLPQERNNVG 70        80        90       100       110       120
ERDDDVPADMVAEESGPGAQNSPYQLRRKTLLPKRTACPTKNSMEGASTSTTENFGHRAK 130       140       150       160       170       180
RARVSGKSQDLSAAPAEQYLQEKLPDEVVLKIFSYLLEQDLCRAACVCKRFSELANDPNL

190
WKRLYMEVFEYTRPMMH
```

FIG.14A

```
         10        20        30        40        50        60
GCGGCCGCGCCCGGTGCAGCAACAGCAGCAGCAGCCCCCGCAGCAGCCGCCGCCGCAGCC 70        80        90       100       110       120
GCCCCAGCAGCAGCCGCCCCAGCAGCAGCCTCCGCCGCCGCCGCAGCAGCAGCAGCAGCA 130       140       150       160       170       180
GCAGCCTCCGCCGCCGCCACCGCCGCCTCCGCCGCTGCCTCAGGAGCGGAACAACGTCGG 190       200       210       220       230       240
CGAGCGGGATGATGATGTGCCTGCAGATATGGTTGCAGAAGAATCAGGTCCTGGTGCACA 250       260       270       280       290       300
AAATAGTCCATACCAACTTCGTAGAAAAACTCTTTTGCCGAAAAGAACAGCGTGTCCCAC 310       320       330       340       350       360
AAAGAACAGTATGGAGGGCGCCTCAACTTCAACTACAGAAAACTTTGGTCATCGTGCAAA 370       380       390       400       410       420
ACGTGCAAGAGTGTCTGGAAAATCACAAGATCTATCAGCAGCACCTGCTGAACAGTATCT 430       440       450       460       470       480
TCAGGAGAAACTGCCAGATGAAGTGGTTCTAAAAATCTTCTCTTACTTGCTGGAACAGGA 490       500       510       520       530       540
TCTTTGTAGAGCAGCTTGTGTATGTAAACGCTTCAGTGAACTTGCTAATGATCCCAATTT 550       560       570       580       590
GTGGAAACGATTATATATGGAAGTATTTGAATATACTCGCCCTATGATGCAT
```

FIG.14B

```
        10         20         30         40         50         60
RPRPGLRGGRAPCEVTMEAGGLPLELWRMILAYLHLPDLGRCSLVCRAWYELILSLDSTR 70         80         90        100        110        120
WRQLCLGCTECRHPNWPNQPDVEPESWREAFKQHYLASKTWTKNALDLESSICFSLFRRR 130        140        150        160        170
RERRTLSVGPGREFDSLGSALAMASLYDRIVLFPGVYEEQGEIILKVPVEIVGQGKLG
```

FIG.15A

```
        10         20         30         40         50         60
GCGGCCGCGGCCCGGACTCCGCGGTGGGCGAGCGCCCTGTGAGGTGACCATGGAGGCTGG 70         80         90        100        110        120
TGGCCTCCCCTTGGAGCTGTGGCGCATGATCTTAGCCTACTTGCACCTTCCCGACCTGGG 130        140        150        160        170        180
CCGCTGCAGCCTGGTATGCAGGGCCTGGTATGAACTGATCCTCAGTCTCGACAGCACCCG 190        200        210        220        230        240
CTGGCGGCAGCTGTGTCTGGGTTGCACCGAGTGCCGCCATCCCAATTGGCCCAACCAGCC 250        260        270        280        290        300
AGATGTGGAGCCTGAGTCTTGGAGAGAAGCCTTCAAGCAGCATTACCTTGCATCCAAGAC 310        320        330        340        350        360
ATGGACCAAGAATGCCTTGGACTTGGAGTCTTCCATCTGCTTTTCTCTATTCCGCCGGAG 370        380        390        400        410        420
GAGGGAACGACGTACCCTGAGTGTTGGGCCAGGCCGTGAGTTTGACAGCCTGGGCAGTGC 430        440        450        460        470        480
CTTGGCCATGGCCAGCCTGTATGACCGAATTGTGCTCTTCCCAGGTGTGTACGAAGAGCA 490        500        510        520        530
AGGTGAAATCATCTTGAAGGTGCCTGTGGAGATTGTAGGGCAGGGGAAGTTGGGTGA
```

FIG.15B

```
         10        20        30        40        50        60
ETETAPLTLESLPTDPLLLILSFLDYRDLINCCYVSRRLSQLSSHDPLWRRHCKKYWLIS 70        80        90       100       110       120
EEEKTQKNQCWKSLFIDTYSDVGRYIDHYAAIKKASGMISRNIWSPGVLGWVLSLKEGCS 130       140       150       160       170       180
RGRPRCCGSADWAASFLDDYRCSYRIHNGQKLVGSWGYWEAWHCLITIVLKIC*TSIQLP 190       200       210       220       230       240
EIPAETGTEILSPFNFCIHTGLSQYIAVEAAEG*NKNEVFYQCQTVERVFKYGIKMCSDG

250
CINGMH*VFS
```

FIG.16A

```
         10         20         30         40         50         60
GAGACCGAGACGGCGCCGCTGACCCTAGAGTCGCTGCCCACCGATCCCCTGCTCCTCATC 70         80         90        100        110        120
TTATCCTTTTTGGACTATCGGGATCTAATCAACTGTTGTTATGTCAGTCGAAGATTAAGC 130        140        150        160        170        180
CAGCTATCAAGTCATGATCCGCTGTGGAGAAGACATTGCAAAAAATACTGGCTGATATCT 190        200        210        220        230        240
GAGGAAGAGAAAACACAGAAGAATCAGTGTTGGAAATCTCTCTTCATAGATACTTACTCT 250        260        270        280        290        300
GATGTAGGAAGATACATTGACCATTATGCTGCTATTAAAAAGGCCTCGGGAATGATCTCA 310        320        330        340        350        360
AGAAATATTTGGAGCCCAGGTGTCCTCGGATGGGTTTTATCTCTGAAAGAGGGGTGCTCG 370        380        390        400        410        420
AGAGGAAGACCTCGATGCTGTGGAAGCGCAGATTGGGCTGCAAGTTTCCTGGACGATTAT 430        440        450        460        470        480
CGATGTTCATACCGAATTCACAATGGACAGAAGTTAGTTGGTTCCTGGGGTTATTGGGAA 490        500        510        520        530        540
GCATGGCACTGTCTAATCACTATCGTTCTGAAGATTTGTTAGACGTCGATACAGCTGCCG 550        560        570        580        590        600
GAGATTCCAGCAGAGACAGGGACTGAAATACTGTCTCCCTTTAACTTTTGCATACATACT 610        620        630        640        650        660
GGTTTGAGTCAGTACATAGCAGTGGAAGCTGCAGAGGGTTGAAACAAAAATGAAGTTTTC 670        680        690        700        710        720
TACCAATGTCAGACAGTAGAACGTGTGTTTAAATATGGCATTAAGATGTGTTCTGATGGT 730        740        750
TGTATAAATGGCATGCATTAGGTATTTTCAG
```

FIG.16B

```
          10        20        30        40        50        60
GSGFRAGGWPLTMPGKHQHFQEPEVGCCGKYFLFGFNIVFWVLGALFLAIGLWAWGEKGV 70        80        90       100       110       120
LSNISALTDLGGLDPVWLVCGSWRRHVGAGLCWAAIGALRENTFLLKFFXXFLGLIFFLE

LA
```

FIG.17A

```
          10        20        30        40        50        60
GGCTCCGGTTTCCGGGCCGGCGGGTGGCCGCTCACCATGCCCGGNAAGCACCAGCATTTC 70        80        90       100       110       120
CAGGAACCTGAGGTCGGCTGCTGCGGGAAATACTTCCTGTTTGGCTTCAACATTGTCTTC 130       140       150       160       170       180
TGGGTGCTGGGAGCCCTGTTCCTGGCTATCGGCCTCTGGGCCTGGGGTGAGAAGGGCGTT 190       200       210       220       230       240
CTCTCGAACATCTCAGCGCTGACAGATCTGGGAGGCCTTGACCCCGTGTGGCTTGTTTGT 250       260       270       280       290       300
GGTAGTTGGAGGCGTCATGTCGGTGCTGGGCTTTGCTGGGCTGCAATTGGGGCCCTCCGG 310       320       330       340       350       360
GAGAACACCTTCCTGCTCAAGTTTTTCTNCGNGTTCCTCGGTCTCATCTTCTTCCTGGAG

CTGGCAAC
```

FIG.17B

```
          10        20        30        40        50        60
AAAAAAYLDELPEPLLLRVLAALPAAELVQACRLVCLRWKELVDGAPLWLLKCQQEGLVP 70        80        90       100       110       120
EGGVEEERDHWQQFYFLSKRRRNLLRNPCGEEDLEGWCDVEHGGDGWRVEELPGDSGVEF 130       140       150       160       170       180
THDESVKKYFASSFEWCRKAQVIDLQAEGYWEELLDTTQPAIVVKDWYSGRSDAGCLYEL 190       200       210       220       230       240
TVKLLSEHENVLAEFSSGQVAVPQDSDGGGWMEISHTFTDYGPGVRFVRFEHGGQGSVYW

250
KGWFGARVTNSSVWVEP*
```

FIG.18A

```
        10        20        30        40        50        60
GCGGCGGCCGCCGCCGCGTACCTGGACGAGCTGCCCGAGCCGCTGCTGCTGCGCGTGCTGGCCGCACTG
70        80        90       100       110       120       130
CCGGCCGCCGAGCTGGTGCAGGCCTGCCGCCTGGTGTGCCTGCGCTGGAAGGAGCTGGTGGACGGCGCC
140       150       160       170       180       190       200
CCGCTGTGGCTGCTCAAGTGCCAGCAGGAGGGGCTGGTGCCCGAGGGCGGCGTGGAGGAGGAGCGCGAC
210       220       230       240       250       260       270
CACTGGCAGCAGTTCTACTTCCTGAGCAAGCGGCGCCGCAACCTTCTGCGTAACCCGTGTGGGGAAGAG
280       290       300       310       320       330       340
GACTTGGAAGGCTGGTGTGACGTGGAGCATGGTGGGGACGGCTGGAGGGTGGAGGAGCTGCCTGGAGAC
350       360       370       380       390       400       410
AGTGGGGTGGAGTTCACCCACGATGAGAGCGTCAAGAAGTACTTCGCCTCCTCCTTTGAGTGGTGTCGC
420       430       440       450       460       470       480
AAAGCACAGGTCATTGACCTGCAGGCTGAGGGCTACTGGGAGGAGCTGCTGGACACGACTCAGCCGGCC
490       500       510       520       530       540       550
ATCGTGGTGAAGGACTGGTACTCGGGCCGCAGCGACGCTGGTTGCCTCTACGAGCTCACCGTTAAGCTA
560       570       580       590       600       610       620
CTGTCCGAGCACGAGAACGTGCTGGCTGAGTTCAGCAGCGGGCAGGTGGCAGTGCCCCAAGACAGTGAC
630       640       650       660       670       680       690
GGCGGGGGCTGGATGGAGATCTCCCACACCTTCACCGACTACGGGCCGGGCGTCCGCTTCGTCCGCTTC
700       710       720       730       740       750
GAGCACGGGGGGCAGGGCTCCGTCTACTGGAAGGGCTGGTTCGGGGCCCGGGTGACCAACAGCAGCGTG
760       770
TGGGTAGAACCCTGA
```

FIG.18B

```
          10         20         30         40         50         60
MGEKAVPLLRRRRVKRSCPSCGSELGVEEKRGKGNPISIQLFPPELVEHIISFLPVRDLV 70         80         90        100        110        120
ALGQTCRYFHEVCDGEGVWRRICRRLSPRLQDQDTKGLYFQAFGGRRRCLSKSVAPLLAH 130        140        150        160        170        180
GYRRFLPTKDHVFILDYVGTLFFLKNALVSTLGQMQWKRACRYVVLCRGAKDFASDPRCD 190        200        210        220        230        240
TVYRKYLYVLATREPQEVVGTTSSRACDCVEVYLQSSGQRVFKMTFHHSMTFKQIVLVGQ 250        260        270        280        290        300
ETQRALLLLTEEGKIYSLVVNETQLDQPRSYTVQLALRKVSHYLPHLRVACMTSNQSSTL

310
YVTDPILCSWLQPPWPGG
```

FIG.19A

```
        10        20        30        40        50        60
ATGGGCGAGAAGGCGGTCCCTTTGCTAAGGAGGAGGCGGGTGAAGAGAAGCTGCCCTTCTTGTGGCTCG 70        80        90       100       110       120       130
GAGCTTGGGGTTGAAGAGAAGAGGGGGAAAGGAAATCCGATTTCCATCCAGTTGTTCCCCCCAGAGCTG 140       150       160       170       180       190       200
GTGGAGCATATCATCTCATTCCTCCCAGTCAGAGACCTTGTTGCCCTCGGCCAGACCTGCCGCTACTTC 210       220       230       240       250       260       270
CACGAAGTGTGCGATGGGGAAGGCGTGTGGAGACGCATCTGTCGCAGACTCAGTCCGCGCCTCCAAGAT 280       290       300       310       320       330       340
CAGGACACGAAGGGCCTGTATTTCCAGGCATTTGGAGGCCGCCGCCGATGTCTCAGCAAGAGCGTGGCC 350       360       370       380       390       400       410
CCCTTGCTAGCCCACGGCTACCGCCGCTTCTTGCCCACCAAGGATCACGTCTTCATTCTTGACTACGTG 420       430       440       450       460       470       480
GGGACCCTCTTCTTCCTCAAAAATGCCCTGGTCTCCACCCTCGGCCAGATGCAGTGGAAGCGGGCCTGT 490       500       510       520       530       540       550
CGCTATGTTGTGTTGTGTCGTGGAGCCAAGGATTTTGCCTCGGACCCAAGGTGTGACACAGTTTACCGT 560       570       580       590       600       610       620
AAATACCTCTACGTCTTGGCCACTCGGGAGCCGCAGGAAGTGGTGGGTACCACCAGCAGCCGGGCCTGT 630       640       650       660       670       680       690
GACTGTGTTGAGGTCTATCTGCAGTCTAGTGGGCAGCGGGTCTTCAAGATGACATTCCACCACTCAATG 700       710       720       730       740       750
ACCTTCAAGCAGATCGTGCTGGTTGGTCAGGAGACCCAGCGGGCTCTACTGCTCCTCACAGAGGAAGGA 760       770       780       790       800       810       820
AAGATCTACTCTTTGGTAGTGAATGAGACCCAGCTTGACCAGCCACGCTCCTACACGGTTCAGCTGGCC 830       840       850       860       870       880       890
CTGAGGAAGGTGTCCCACTACCTGCCTCACCTGCGCGTGGCCTGCATGACTTCCAACCAGAGCAGCACC 900       910       920       930       940       950
CTCTACGTCACAGATCCTATTCTGTGCTCTTGGCTACAACCACCTTGGCCTGGTGGATGA
```

FIG.19B

```
         10         20         30         40         50         60
RGGSEGRGRGREKRARGARRKRKQGGREARAADGEGGSGPGAEAGARTRPREEAEGGGSV 70         80         90        100        110        120
EEGARGIIKGDEGSVGAGKEAQGRKYGKEEWRVRARRREGARPGRVQGQGGQVWAYIPGT 130        140        150        160        170        180
GAAMAAAAREEEEEAARESAACPAAGPALWRLPEVLLLHMCSYLDMRALGRLAQVYRWLW 190        200        210        220        230        240
HFTNCDLLRRQIAWASLNSGFTRLGTNLMTSVPVKVSQNWIVGCCREGILLKWRCSQMPW 250        260        270        280        290        300
MQLEDDALYISQANFILAYQFRPDGASLNRQPLGVSAGHDEDVCHFVLATSHIVSAGGDG 310        320        330        340        350        360
KIGLGKIHSTFAAKYWAHEQEVNCVDCKGGIISFGSRDRTAKVWPLASGQLGQCLYTIQT 370        380        390        400        410        420
EDQIWSVAIRPLLSSFVTGTACCGHFSPLKIWDLNSGQLMTHLDRDFPPRAGVLDVIYES 430        440        450        460        470        480
PFALLSCGYDTYVRYWDCRTSVRKCVMEWEEPHNSTLYCLQTDGNHLLATGSSFYSVVRL 490        500        510        520        530
WDRHQRACPHTFPLTSTRLGSPVYCLHLTTKHLYAALSYNLHVLDIQNP*
```

FIG.20A

```
        10         20         30         40         50         60         70         80         90
CGAGGGGAAGCCGAAGGGAAGAGGAAGGGAAAAGCCAGCCGAGAGGGCAAGCCGAAGAGGAAGCCAGGGCAAGGGAAGCCAGCCCGGCCG 100        110        120        130        140        150        160        170        180
CAGACGGCGAAGGAGGCAGCGGCGGGCCCGGGGCTGAGGCGGAGGAGACACGCCCAAGAGAGGAGGCAGAGGGAGGCGGAGGCGTGGAGGAAGG 190        200        210        220        230        240        250        260        270        280
GGCCAGAGGCATCATCAAAGGAGATGAGGGGAGCGTAGGGGAGCCCGGGAAAGAGGCACAAGGAAGAAAGTATGGAAGGAGGAATGGAGGGTCAGG 290        300        310        320        330        340        350        360        370
GCTAGGCGGGCCGGGGAGGGCCCAGGCCGGAACAGTACAAGGAGAGTTCAGGTTTGGGCCTACATCCCGGGACAGGGGCCCATGGCCG 380        390        400        410        420        430        440        450        460        470
CGGCAGCCAGGAGGAGGAGGCCGCTCGGGAGCCTCAGCGCCCTGCCGGCTGCCGGGCCAGCGCTCTGCCGCCTGCCGAAGTGCTGCT 480        490        500        510        520        530        540        550        560
GCTGCCACATGTGCTCCTACCTCGACATGCGGGGCCCTCGGCCCAGGTGTACCGCTGTGGCCACTTCACCAACTGCCGACCTGCTC 570        580        590        600        610        620        630        640        650
CGGCGCCCAGATAGCCTGGGCTCGCTCAACTCCCGGGCTTCACGCGGCTCGGCACCACCAGTGCCCCAGTGAAGGTGTCTCAGAACT 660        670        680        690        700        710        720        730        740        750
GGATAGTGGGGTGCTGCCGAGAGGGGATTCTGCTGAAGTGGAGATGCAGTCAGATGCCCTGATGCAGCTAGAGCATGATGCTTTGTACATATC 760        770        780        790        800        810        820        830        840
CCAGGCTAATTCATCCTGGCCACCTCGGCCTACCAGTTCCGTCCAGATGTCCAGCTTGAACCGTTCAGCCTCTGGGAGTCTCGTGCTGGGCATGAGGAC 850        860        870        880        890        900        910        920        930        940
GTTTGCCACTTTGTCCTGGCCACTCGCCATATTGTCAGTGCAGGAGGAGATTGGGCCTTGGTAAGATTCACAGCCACCTTCGCTGCCA
```

FIG.20B

```
         950       960       970       980       990      1000      1010      1020      1030
AGTACTGGGCTCATGAACAGGAGGTGAACTGTGTGGATTGCAAAGGGGCATCATATCATTTGGCTCCAGGACAGGACGGCCAAGGTGTGGCC 1040      1050      1060      1070      1080      1090      1100      1110      1120
TTTGGGCCTCAGGCCAGCTGGGGCAGTGTTTATACACCATCCAGACTGAAGACCAAATCTGGTCTCTGTTCTATCAGGCCATTACTCAGCTCTTT 1130      1140      1150      1160      1170      1180      1190      1200      1210      1220
GTGACAGGGACCGGCTTGTTGTGGCCACTTCTCACCCTGAAAATCTGGGACCTCAACAGTGGGCAGCTGATGACACACTTGGACACAGACTTC 1230      1240      1250      1260      1270      1280      1290      1300      1310
CCCCAAGGGCTGGGTGCTGGATGTCATATGAGTCCCCTTTCGCACTGCTCTCCTGTGGCTATGACACCTATGTTCGCTACTGGGACTGCCG 1320      1330      1340      1350      1360      1370      1380      1390      1400      1410
CACCAGTGTCCGGAAATGTCATGGAGTGGGAGGAGCCCCACAACAGCCTGTACTGCCTGCAGACAGATGGCAACCACTTGCTTGCCACA 1420      1430      1440      1450      1460      1470      1480      1490      1500
GGTTCCTCCTTCTATAGCGTTGTACGGCGTGTGGGACCGTGGGACCGTGGGGACCACCTTCCCGCTGACGTCGACCCCCTCGGCAGCC 1510      1520      1530      1540      1550      1560      1570      1580      1590
CTGTGTACTGCCTGCATCTCACCACCAAGCATCTCTATGCTGGCGTCTTACAACCTCCAGTCCTCCTGGATATTCAAAACCCGTGA
```

FIG.20C

```
         10        20        30        40        50        60
LILTSVLLFQRHGYCTLGEAFNRLDFSSAIQDIRTFNYVVKLLQLIAKSQLTSLSGVAQK 70        80        90       100       110       120
NYFNILDKIVQKVLDDHHNPRLIKDLLQDLSSTLCILIRGVGKSVLVGNINIWICRLETI 130       140       150       160       170       180
LAWQQQLQDLQMTKQVNNGLTLSDLPLHMLNNILYRFSDGWDIITLGQVTPTLYMLSEDR 190       200       210       220       230       240
QLWKKLCQYHFAEKQFCRHLILSEKGHIEWKLMYFALQKHYPAKEQYGDTLHFCRHCSIL 250       260       270
FWKDSGHPCTAADPDSCFTPVSPQHFIDLFKF
```

FIG.21A

```
         10        20        30        40        50        60
GCATTGCTATAATTTTACTATACTCTCATCTAAATCTAAAATCAGTCTTCAAAATAAAAACAAATTGTC 70        80        90       100       110       120       130
CTTTGCCAAAAATTTTTTTAATCGCACAATTAATTGACATTAACTGCCAATTCTTTTTGGCTAATTGAC 140       150       160       170       180       190       200
TAATTTTAACTTCTGTGTTGCTTTTCCAGAGGCATGGCTATTGCACCTTGGGAGAAGCCTTTAATCGGT 210       220       230       240       250       260       270
TAGACTTCTCAAGTGCAATTCAAGATATCCGAACGTTCAATTATGTGGTCAAACTGTTGCAGCTAATTG 280       290       300       310       320       330       340
CAAAATCCCAGTTAACTTCATTGAGTGGCGTGGCACAGAAGAATTACTTCAACATTTTGGATAAAATCG 350       360       370       380       390       400       410
TTCAAAAGGTTCTTGATGACCACCACAATCCTCGCTTAATCAAAGATCTTCTGCAAGACCTAAGCTCTA 420       430       440       450       460       470       480
CCCTCTGCATTCTTATTAGAGGAGTAGGGAAGTCTGTATTAGTGGGAAACATCAATATTTGGATTTGCC 490       500       510       520       530       540       550
GATTAGAAACTATTCTCGCCTGGCAACAACAGCTACAGGATCTTCAGATGACTAAGCAAGTGAACAATG 560       570       580       590       600       610       620
GCCTCACCCTCAGTGACCTTCCTCTGCACATGCTGAACAACATCCTATACCGGTTCTCAGACGGATGGG 630       640       650       660       670       680       690
ACATCATCACCTTAGGCCAGGTGACCCCCACGTTGTATATGCTTAGTGAAGACAGACAGCTGTGGAAGA 700       710       720       730       740       750
AGCTTTGTCAGTACCATTTTGCTGAAAAGCAGTTTTGTAGACATTTGATCCTTTCAGAAAAAGGTCATA 760       770       780       790       800       810       820
TTGAATGGAAGTTGATGTACTTTGCACTTCAGAAACATTACCCAGCGAAGGAGCAGTACGGAGACACAC 830       840       850       860       870       880       890
TGCATTTCTGTCGGCACTGCAGCATTCTCTTTTGGAAGGACTCAGGACACCCCTGCACGGCGGCCCGACC 900       910       920       930       940       950       960
CTGACAGCTGCTTCACGCCTGTGTCTCCGCAGCACTTCATCGACCTCTTCAAGTTTTAAGGGCTGCCCC
```

FIG.21B

```
     970       980       990       1000      1010      1020      1030
TGCCATCCCTATTGGAGATTGTGAATCCTGCTGTCTGTGCAGGGCTCATAGTGAGTGTTCTGTGAGGTG 1040      1050      1060      1070      1080      1090      1100
GGTGGAGACTCCTCGGAAGCCCCTGCTTCCAGAAAGCCTGGGAAGAACTGCCCTTCTGCAAAGGGGGA 1110      1120      1130      1140      1150      1160      1170
CTGCATGGTTGCATTTTCATCACTGAAAGTCAGAGGCCAAGGAAATCATTTCTACTTCTTTAAAAACTC 1180      1190      1200      1210
CTTCTAAGCATATTAAAATGTGAAATTTTGCGTACTCTCTC
```

FIG.21C

```
         10        20        30        40        50        60
YGSEGKGSSSISSDVSSSTDHTPTKAQKNVATSEDSDLSMRTLSTPSPALICPPNLPGFQ 70        80        90       100       110       120
NGRGSSTSSSSITGETVAMVHSPPPTRLTHPLIRLASRPQKEQASIDRLPDHSMVQIFSF 130       140       150       160       170       180
LPTNQLCRCARVCRRWYNLAWDPRLWRTIRLTGETINVDRALKVLTRRLCQDTPNVCLML 190       200       210       220       230       240
ETVTVSGCRRLTDRGLYTIAQCCPELRRLEVSGCYNISNEAVFDVVSLCPNLEHLDVSGC 250       260       270       280       290       300
SKVTCISLTREASIKLSPLHGKQISIRYLDMTDCFVLEDEGLHTIAAHCTQLTHLYLRRC 310       320       330       340       350       360
VRLTDEGLRYLVIYCASIKELSVSDCRFVSDFGLREIAKLESRLRYLSIAHCGRVTDVGI 370       380       390       400       410       420
RYVAKYCSKLRYLNARGCEGITDHGVEYLAKNCTKLKSLDIGKCPLVSDTGLECLALNCF 430       440       450       460       470       480
NLKRLSLKSCESITGQGLQIVAANCFDLQTLNVQDCEVSVEALRFVKRHCKRCVIEHTNP

AFF
```

```
2790   2800   2810   2820   2830   2840   2850   2860   2870   2880   2890   2900   2910
TGTAAGTGTTTAATTGTGCAAATTGCCACCCTGTGTACCTCCTGTCTCTCGGTGTTTCCACCAAAGAATGCAAAGCACACTTCCAGGTGTTTAAATTCTGTTCACTCAACAATGCCAGAATGAAGAGG 2920   2930   2940   2950   2960   2970   2980   2990   3000   3010   3020   3030   3040   3050
GAACACACTGAGATGACTTAGACTCTGGTCCACCAGACCCTTGGAAAGGAATACTAAAATCATTACAGGTATGGATTTTAAATGAAACTTCAAATTATCTTATTTGGATAGAAGTCTATATTCTAGCCTC 3060   3070   3080   3090   3100   3110   3120   3130   3140   3150   3160   3170   3180   3190
ATTTGCATGAAGTCAGATAGCCAGAAGAAATTCCATTGCTGGTTTTCACGGAAAATTCACTTGTCTTTTGCTAATAAACACATGCCCTTTCCAGATTATTCTCTAGCCAAGCCCCACCTTTGTTACGTTGAAATCCCTC 3200   3210   3220   3230   3240   3250   3260   3270   3280   3290   3300   3310   3320   3330
ATTTATTTCTTCTCAAAATGCCATTATCAAATGCAGTCCTCCAAGCCCAGTTATGTATGCTGAATTGTCAAACTTAGACACCCTTGACAACTGCACTCCTACTGTAGGCTCCTGTCATACTGTCGTCTTC 3340   3350   3360   3370   3380   3390   3400   3410   3420   3430   3440   3450   3460   3470
TGTGGGGATGGAGAGGTTAGTGTGATGAGGTGGTCTCGCCCAGGAGGTTTCTTCTTCAAACATCAACATCATCAAATTACATGTGTAATCAAGGCTCTGTGCCATGGGGAAATGAATCAT 3480   3490   3500   3510   3520   3530   3540   3550   3560   3570   3580   3590   3600   3610
TTAGCTAGGCCAGGATCTAGTGAAAGCCACAGTTTAAAACCATGAAAGAAGTTGAAGGCAGCAGCCATTCCTCAGCTCTGTGACTTGTGACCCTATTTGAAGTTTCAGGATTTGGGTGTCACAAGCGATTGTCCCTAATCC 3620   3630   3640   3650   3660   3670   3680   3690   3700   3710   3720   3730   3740   3750
TTGCCCCTGGGGTCTTCCGAGTGAGCTGGTTTAATACTCTGAGAATGAGCAGGAGATCCAGAGAATGAAATCCTGACCCTGACCCATCACCTAAACTGTCTTCCAAACATGACGACAAGCTGACTGTTCACACTGATTGCCCA 3760   3770   3780   3790   3800   3810   3820   3830   3840   3850   3860   3870   3880   3890
GCACATACCGTCTCTGCCAGTTCTTCTTTCTCCCCAGTCTCCATTCTGTTCATCCCTGTCTTCCTGCTGGGTGGGAATCTATGATGGAGGTTACTGGGGAAACAGCTCAGGCAGATTTTTGGAGACCAAACCAAAGGTCTC 3900   3910   3920   3930   3940   3950   3960   3970   3980   3990   4000   4010   4020   4030
ACTAGGAAATTTATCTGTTTAAAAACATTGCTTCCTTCCTGCGCTCTGCTAAATTGAAATGCTAAATCTAATGTTTGTGTGTGTTTTTAATTCTAATGTTCAAATCACTGCGTGCGTATGAATCTAGAAACCTTAATTTA 4040   4050
CTACCAAGAAATAAAGCAATATGTTCGT
```

FIG.22D

```
          10        20        30        40        50        60
AAAPAPAPAPTPTPEEGPDAGWGDRIPLEILVQIFGLLVAADGPMPFLGRAARVCRRWQE 70        80        90       100       110       120
AASQPALWHTVTLSSPLVGRPAKGGVKAEKKLLASLEWLMPNRFSQLQRLTLIHWKSQVH 130       140       150       160       170       180
PVLKLVGECCPRLTFLKLSGCHGVTADALVMLAKACCQLHSLDLQHSMVESTAVVSFLEE 190       200       210       220       230       240
AGSRMRKLWLTYSSQTTAILGALLGSCCPQLQVLEVSTGINRNSIPLQLPVEALQKGCPQ 250       260       270       280
LQVLRLLNLMWLPKPPGRGVAPGPGFPSLEELCLASSTCNFVS
```

FIG.23A

```
          10        20        30        40        50        60
TGCGGCCGCGCCCGCACCCGCACCGGCACCCACGCCCACGCCCGAGGAAGGGCCCGACGCGGGCTGGGG 70        80        90       100       110       120       130
AGACCGCATTCCCTTGGAAATCCTGGTGCAGATTTTCGGGTTGTTGGTGGCGGCGGACGGCCCCATGCC 140       150       160       170       180       190       200
CTTCCTGGGCAGGGCTGCGCGCGTGTGCCGCCGCTGGCAGGAGGCCGCTTCCCAACCCGCGCTCTGGCA 210       220       230       240       250       260       270
CACCGTGACCCTGTCGTCCCCGCTGGTCGGCCGGCCTGCCAAGGGCGGGGTCAAGGCGGAGAAGAAGCT 280       290       300       310       320       330       340
CCTTGCTTCCCTGGAGTGGCTTATGCCCAATCGGTTTTCACAGCTCCAGAGGCTGACCCTCATCCACTG 350       360       370       380       390       400       410
GAAGTCTCAGGTACACCCCGTGTTGAAGCTGGTAGGTGAGTGCTGTCCTCGGCTCACTTTCCTCAAGCT 420       430       440       450       460       470       480
CTCCGGCTGCCACGGTGTGACTGCTGACGCTCTGGTCATGCTAGCCAAAGCCTGCTGCCAGCTCCATAG 490       500       510       520       530       540       550
CCTGGACCTACAGCACTCCATGGTGGAGTCCACAGCTGTGGTGAGCTTCTTGGAGGAGGCAGGGTCCCG 560       570       580       590       600       610       620
AATGCGCAAGTTGTGGCTGACCTACAGCTCCCAGACGACAGCCATCCTGGGCGCATTGCTGGGCAGCTG 630       640       650       660       670       680       690
CTGCCCCCAGCTCCAGGTCCTGGAGGTGAGCACCGGCATCAACCGTAATAGCATTCCCCTTCAGCTGCC 700       710       720       730       740       750
TGTCGAGGCTCTGCAGAAAGGCTGCCCTCAGCTCCAGGTGCTGCGGCTGTTGAACCTGATGTGGCTGCC 760       770       780       790       800       810       820
CAAGCCTCCGGGACGAGGGGTGGCTCCCGGACCAGGCTTCCCTAGCCTAGAGGAGCTCTGCCTGGCGAG 830       840       850
CTCAACCTGCAACTTTGTGAGC
```

FIG.23B

```
         10         20         30         40         50         60
QHCSQKDTAELLRGLSLWNHAEERQKFFKYSVDEKSDKEAEVSEHSTGITHLPPEVMLSI 70         80         90        100        110        120
FSYLNPQELCRCSQVSMKWSQLTKTGSLWKHLYPVHWARGDWYSGPATELDTEPDDEWVK 130        140        150        160        170        180
NRKDESRAFHEWDEDADIDESEESAEESIAISIAQMEKRLLHGLIHNVLPYVGTSVKTLV 190        200        210        220        230        240
LAYSSAVSSKMVRQILELCPNLEHLDLTQTDISDSAFDSWSWLGCCQSLRHLDLSGCEKI 250        260        270        280        290        300
TDVALEKISRALGILTSHQSGFLKTSTSKITSTAWKNKDITMQSTKQYACLHDLTNKGIG 310        320        330        340        350        360
EEIDNEHPWTKPVSSENFTSPYVWMLDAEDLADIEDTVEWRHRNVESLCVMETASNFSCS 370        380        390        400        410        420
TSGCFSKDIVGLRTSVCWQQHCASPAFAYCGHSFCCTGTALRTMSSLPESSAMCRKAART 430        440        450        460        470        480
RLPRGKDLIYFGSEKSDQETGRVLLFLSLSGCYQITDHGLRVLTLGGGLPYLEHLNLSGC 490        500        510        520        530        540
LTITGAGLQDLVSACPSLNDEYFYYCDNINGPHADTASGCQNLQCGFRACCRSGE*PLTS 550        560        570        580        590
DLCLLHLAEQAFFHALYS*HISCVNHPFLSVTCFGPIXYNFRNLNYQXIVML
```

FIG.24A

```
         10         20         30         40         50         60         70         80         90
ACAACACTGCTCTCAGAAGGATACTGCAGAACTCCTTAGAGGTCTTAGCCTATGGAATCATGCTGAAGAGCGACAGAARTTTTTAAATATTCC 100        110        120        130        140        150        160        170        180
GTGGATGAAAAGTCAGATAAAGAAGCAGAAGTGTCAGAACACTCCACAGGTATAACCCATCTTCCTCCTGAGGTAATGCTGTCAATTTCAGCT 190        200        210        220        230        240        250        260        270        280
ATCTTAATCCTCAAGAGTTATGTCGATGCAGTCAAGTAAGCATGAAATGGTCTCAGCTGACAAAAACGGGATCGCTTTGAAACATCTTTACCC 290        300        310        320        330        340        350        360        370
TGTTCATTGGGCCAGAGGTGACTGGTATAGTGGTCCCGCCAACTGATACTGAACCTGATGATGAACCTGATGAATGGTGAAAAATAGGAAAGATGAA 380        390        400        410        420        430        440        450        460        470
AGTCGTGCTTTCATGAGTGGGATGAAGATGCTGACATTGATGAATCTGAAGAGTCTCGGAGGAATCAATTGCTATCAGCATTGCACAAATGG 480        490        500        510        520        530        540        550        560
AAAAACGTTACTCCATGGCTTAATTCATAAGCGTTCTACCATATGTTGGTACTTCTGTAAAAACCTTAGTATTAGCATACAGCTCTGCAGTTTC 570        580        590        600        610        620        630        640        650
CAGGAAATGGTTAGGCAGATTTTAGAGCTTTGTCTCCTAACCTGGAGCATCGATCTTACCCAGACTGACATTCAGATTCTGATCATTGACAGT 660        670        680        690        700        710        720        730        740        750
TGGTCTTGGCTTGGTTGCTGCCAGAGTCTCGGCATCTTGATCGTCTGGTTGTGAGAAATCACAGATGGCCCTAGAGAAGATTTCCAGAG 760        770        780        790        800        810        820        830        840
CTCTTGGAATTCTGACATCTCATCAAAGTGGCTTTCATGAGCTTGCACGATTTAACTAACAAGGGCATTGACAGAATTACTTCAACTGCCTGGAAAAATAAAGACATTACCAT 850        860        870        880        890        900        910        920        930        940
GCAGTCCACCAAGCAGTATGCCCTGTTTGCACGATTTAACTAACAAGGGCATTGGAGAAGAAATAGATAATGAACACCCCTGACTAAGCCTGTT
```

FIG.24B

```
       950       960       970       980       990       1000      1010      1020      1030
TCTTCTGAGAATTTCACTTCTCCTTATGTGTGGATGTTAGATGCTGAAGTGTCTGATATTGGCTGATATTGAAGATACTGTGGAATGGAGACATAGAAATG 1040      1050      1060      1070      1080      1090      1100      1110      1120
TTGAAAGTCTTTGTGTAATGAAACAGCATCCAACTTAGTGTTGTTCCACCTCTGGTTGTTTTAGTAAGGACATGTTGGACTAAGGACTAGTGT 1130      1140      1150      1160      1170      1180      1190      1200      1210      1220
CTGTTGGCCAGCAGCATTGTGCTTCTCCCAGCCCTTTGCGTATTGTGGTCACTCATTTGTTGTGTACAGGAACAGCTTAAGAACTATGTCATCACTC 1230      1240      1250      1260      1270      1280      1290      1300      1310
CCAGAATCTCTGCAATGTGTAGAAAAGCAGCAAGGACTAGATTGCCTAGGGGAAAAGACTTAATTACTTTGGGAGTGAAAAATCTGATCAAG 1320      1330      1340      1350      1360      1370      1380      1390      1400      1410
AGACTGGACGTGTACTTCTGTTCTCAGTTATCTGGATGTTATCAGATCACAGACCATGGTCTCAGGGTTTGACTCTGGGAGGAGGGCTGCC 1420      1430      1440      1450      1460      1470      1480      1490      1500
TTATTGGAGCACCTTAATCTCTCGGTTGTCTTACTACTAAACTGGTCCTACTATAAACTGTGCAGGATTGGTTCAGCATGTCCTTCTCTGAATGATGAA 1510      1520      1530      1540      1550      1560      1570      1580      1590
TACTTTTACTACTGTGACAACATTAACGGTCCTCATGCTGATACCGCCAGTGGATGCCAGAATTTGCAGTGTGGTTTTCCAGCCTGCTGCCCGCT 1600      1610      1620      1630      1640      1650      1660      1670      1680      1690
CTGGCGAATGACCCTTGACTTCTGATCTTTGTCTACTTCATTTAGCTGAGCAGGCTTTCTTCATGCACTTACTCATAGCCACATTTCTTGTGT 1700      1710      1720      1730      1740      1750      1760      1770
CTGGCGAATGACCCTTTTTGAGCGTGACTTGTTTTGGGCCCATTNYTTACAACTTCAGAAATCTTAATTACCAGTGRATTGTAATGTTG

TAACCATCCCTTTTTGAGCGTGACTTGTTTTGGGCCCATTNYTTACAACTTCAGAAATCTTAATTACCAGTGRATTGTAATGTTG
```

FIG. 24C

```
         10        20        30        40        50        60
RVTSGCGLARGSSAMVFSNNDEGLINKKLPKELLLRIFSFLDIVTLCRCAQISKAWNILA 70        80        90       100       110       120
LDGSNWQRIDLFNFQIDVEGRVVENISKRCVGFLRKLSLRGCIGVGDSSLKTFAQNCRNI 130       140       150       160       170       180
EHLNLNGCTKITDSTCYSLSRFCSKLKHLXLTSCVSITNSSLKGISEGCRNLEYLNLSWC 190       200       210       220       230       240
DQITKDGIEALVRGCRGLKALLLRGCTQLEDEALKHIQNYCHELVSLNLQSCSRITDEGV 250       260       270       280       290       300
VQICRGCHRLQALCLSGCSNLTDASLTALGLNCPRLQILEAARCSHLTDAGFTLLARNCH 310       320       330       340       350       360
ELEKMDLEXCILITDSTLIQLSIHCPKLQALSLSHCELIXDDGILHLSNSTCGHERLRVL 370       380       390       400       410       420
ELDNCLLITDVALXHLENCRGLERLELYDCQQVTRAGIKRMRAQLPHVKVHAYFAPVTPP 430       440       450       460       470       480
TAVAGSGQRLCRCCVIL*QQLPGPKG**GILSSRRPESS*PTPPSPNLLILHWERHLQFP 490       500       510       520       530       540
NRHLSRFKNGEDKKGFISNI*HHIVT*NMALT*LVLLLPSSLMSSLTSTHLLL*YL*RLI

550
ILKTDQTGPASKYINCVQ*
```

FIG.25A

```
      10         20         30         40         50         60         70         80         90
TTTACTGTACACAGTTGATGTATTTGATGCTGGGCCTGTCTGGTCTGTCTTGAGGATTATTAACCTTTAGAGGTATCAGAGAAGCAAATGGG 100        110        120        130        140        150        160        170        180
TACTGGTGAGGCTGCTCATTAGGGAAGAGGGCAAAGGAGCACTAGTAGGTCAGAGCCATGTTTCAGTCACAATGTGATGTCAGATGTTGCT 190        200        210        220        230        240        250        260        270        280
TATAAATCCTTTCTTGTCTTCGCCATTCTTAAATCTTGATAGGTGCCTGTTGGGAAACTGTAAATCCTTTCCCAATGGAGAATCAACAGATTG 290        300        310        320        330        340        350        360        370
GGTGATGGTGGAGTCGGTCAGGAAGACTCAGGTCTTCTAGAGGAAAGGATGCCTCATCACCCCTTNGGCCCAGGGAGCAAAGTAGGCGTGTCAGAGAATGA 380        390        400        410        420        430        440        450        460        470
CACAGCACCTGCACAGTCGCTGTCCACTTCCTGCCACTGCTGTCGGTGGGGTGACGGAGCAAAGTAGGCGTGACTTTGACATGAGGGAGCTG 480        490        500        510        520        530        540        550        560
AGCCCGATCCGCTTGATGCCTGCACGGGTAACCTGCTGGCAGTCGTACAGCTCGAGGCGCTCCAGGCCTCGAGTTCTCTAGGTGTYCCAGG 570        580        590        600        610        620        630        640        650
GCCACATCAGTGAGGAGCAGTTGTCCAACTCCCAGTACCCGCAGCCCTCATGGCCACAGGTACTGTTGCTCAGGTGCAGGATCCATCAT 660        670        680        690        700        710        720        730        740        750
CTGKGATGAGTTCACAGTGGGACAGGCTCAGGGCTTGCAGTTTAGGACAGTGAATGAGAGCTGGATGTGTCGGTTATCAGGATGCA 760        770        780        790        800        810        820        830        840
WTCTTCAAGATCCATCTTCTCCAATTCGTGGCCAATTCCGAGCTAAAAGTGTAAAACCTGCCTCAGTCAGTTGCAAATGGGAGCATCGGGCCAGCCTCCAAA
```

FIG.25B

```
        850         860         870         880         890         900         910         920         930         940
ATTGCAGTCGCGGGACAGTTCAAACCCAGGGCTGTAAGAGAGGCATCTGTGAGGTTGCTGCAACCCGAAAGGCAGAGAGCCTGTAGCCGTGAC 950         960         970         980         990        1000        1010        1020        1030
AGCCCCTGCATATCTGCACCACACCCTTCATCCGTGATACGTGAGCAGGACTGCAAGTTGAGGCTCACAAGCTCATGGCAGTAATTCTGAATGTG 1040        1050        1060        1070        1080        1090        1100        1110        1120
TTCAGAGAGCTTCATCTTCTAACTGTGTGCAGCAGGGCTTTCAGGCCTCAGGGGCTTTCAGGCCTCAGGAGACCAGGGCTTTCAGGCCTCAGACAACCTCGCACCAGTGCCTCGATGCCATCCTTC 1130        1140        1150        1160        1170        1180        1190        1200        1210        1220
GTGATCTGATCACACCAAGAGAGGTTCAGTACTCCAGGTTTCGGCAGCCCCTCACTGATCCCCTTCAAGGAGCTGTTTGTAATAGACACAGG 1230        1240        1250        1260        1270        1280        1290        1300        1310
AGGTCAGAWCCAGATGTTTCAGCTTGGAACAGAATCTGCTAAGGCTATAACACGTGCTGTCAGTGATTTTTGTGCATCCATTGAGGTTCAAATG 1320        1330        1340        1350        1360        1370        1380        1390        1400        1410
TTCAATGTTTCGGCAGTTCTGTGTGCAAAGGTCTTCAAGGAGGAAATCCCCAACACCAATGCAGCCTGCAAGCTTCCTCAGGAATCCAACG 1420        1430        1440        1450        1460        1470        1480        1490        1500
CATCGCTTCGAGATATTTTCCACCACTCGACCCTCTACATCTATTTGAAAGTTAAAAGATCTATTCTTTGCCAGTTGCTTCCATCCAGGGCTA 1510        1520        1530        1540        1550        1560        1570        1580        1590
AGATGTTCCAAGCCTTGGAAATCTGTGCACATCGGCACAAAGTTACTACTATCCAAGAAGGAAAATATTCTTAACAGAAGTTCTTTGGGTAACTT 1600        1610        1620        1630        1640        1650        1660        1670        1680
TTTGTTAATAAGGCCTTCATCATTGTTTGAGAAAACCATGCCCGAAGAGCCCGAGCCCCACAGCCCCAAGTCACACGGC
```

FIG.25C

```
           10        20        30        40        50        60
MSPVFPMLTVLTMFYYICLRRRARTATRGEMMNTHRAIESNSQTSPLNAEVVQYAKEVVD 70        80        90       100       110       120
FSSHYGSENSMSYTMWNLAGVPNVFPSSGDFTQTAVFRTYGTWWDQCPSASLPFKRTPPN 130       140       150       160       170       180
FQSQDYVELTFEQQVYPTAVHVLETYHPGAVIRILACSANPYSPNPPAEVRWEILWSERP 190       200       210       220       230       240
TKVNASQARQFKPCIKQINFPTNLIRLEVNSSLLEYYTELDAVVLHGVKDKPVLSLKTSL 250       260       270       280       290       300
IDMNDIEDDAYAEKDGCGMDSLNKKFSSAVLGEGPNNGYFDKLPYELIQLILNHLTLPDL 310       320       330       340       350       360
CRLAQTCKLLSQHCCDPLQYIHLNLQPYWAKLDDTSLEFLQSRCTLVQWLNLSWTGNRGF 370       380       390       400       410       420
ISVAGFSRFLKVCGSELVRLELSCSHFLNETCLEVISEMCPNLQALNLSSCDKLPPQAFN 430       440       450       460       470       480
HIAKLCSLKRLVLYRTKVEQTALLSILNFCSELQHLSLGSCVMIEDYDVIASMIGAKCKK 490       500       510       520       530       540
LRTLDLWRCKNITENGIAELASGCPLLEELDLGWCPTLQSSTGCFTRLAHQLPNLQKLFL 550       560       570       580       590       600
TANRSVCDTDIDELACNCTRLQQLDILGTRMVSPASLRKLLESCKDLSLLDVSFCSQIDN 610       620
RAVLELNASFPKVFIKKSFTQ
```

FIG.26A

```
        10         20         30         40         50         60         70         80         90
ATGTCACCGGTCTTTCCCATGTTAACAGTTCTGACAGTTTATTATATATGCCTTCGGGCCGCCGAGCCAGGACAGCTACAAGAGGAGAAATGA 100        110        120        130        140        150        160        170        180
TGAACACCCATAGAGCTATAGAATCAAACAGCCAGACTTCCCCTCTCAATGCAGAGGTAGTCCAGTATGCCAAAGAGTAGTGGATTCAGTTC 190        200        210        220        230        240        250        260        270        280
CCATTATGGAAGTGAGAATAGTGTCCTATACTATGTGGAATTGGCTGGTGTACCAAATGTATTCCCAAGTTCTGTGACTTTACTCAGACA 290        300        310        320        330        340        350        360        370
GCTGTGTTTCGAACTTATGGGACATGGTGGATCAGTGTCCTAGTGCTTCCTTGCCATTCAAGAGGACGCCACCTAATTTTCAGAGCCAGOACT 380        390        400        410        420        430        440        450        460        470
AATGTGGAACTTACTTTTTGAACAACAGGTGTATCCTACAGCTGTACATGTTCTAGAAACCTATCATCCCGGAGCAGTCATTAGAATTCTCCGCTTG 480        490        500        510        520        530        540        550        560
TTCTGCAAATCCTTATTCCCCAAATCCACCAGCTGAAGTAAGCTGAAGATGGGAGATTCTTTGGTCAGAGAGACCTACGAAGGTGAATGCTTCCCAAGCT 570        580        590        600        610        620        630        640        650
CGGCCAGTTTAAACCTTGTATTAAGCAGATAAATTTCCCCACAAATCTTATACGACTGGAAGTAAATAGTTCTCTTCTGAATATTACACTGAAT 660        670        680        690        700        710        720        730        740        750
TAGATGCAGTGTGCTACATGGTGTGAAGGACAGTCTTAACAAAAAGTTTAGCAGTGCTGTCCTCCTCGGGAAGGGCCAAATAATGGTATTTGATAAA 760        770        780        790        800        810        820        830        840
TGCAGAAAAGGATGTGTGTGGAATGGACAGTCTTAACAAAAAGTTTAGCAGTGCTGTCCTCCTCGGGAAGGGCCAAATAATGGTATTTGATAAA 850        860        870        880        890        900        910        920        930        940
CTACCTTATGAGCTTATTCAGCTTGAATCATCTTACACTACCAGACCTGTAGATTAGCCACAGACTTGCAAACTACTGAGCCAGCATT

FIG.26B
```

```
      950         960         970         980         990        1000        1010        1020        1030
GCTGTGATCCTCTGCAATACATCCACCTCAATCTGCAACCATACTGGGCAAAACTAGATGACACTTCTCTGGAATTTCTACAGTCTCGCTGCAC 1040        1050        1060        1070        1080        1090        1100        1110        1120
TCTTGTCCAGTGGCTTAATTTATCTGGACTGGCAATAGAGGCTTCATCTCTGTGCAGGATTAGCAGGTTTCTGAAGGTTTGTGGATCCGAA 1130        1140        1150        1160        1170        1180        1190        1200        1210        1220
TTAGTACGGCCTTGAATTGTCTTGCAGCCACTTTCTAATGAAACTTGCTTAGAAGTTATTTCTGAGATGTGTCCAAATCTACAGGCCTTAAATC 1230        1240        1250        1260        1270        1280        1290        1300        1310
TCTCCCTCGTGATAAGCTACCACCTCAAGCTTTCAACCACATTGCCAAGTTATGCAGCCTTAAACGACTTGTCTCTATCGAACAAAAGTAGA 1320        1330        1340        1350        1360        1370        1380        1390        1400        1410
GCAAACAGCACTGCTCAGCATTTTGAACTTCTGTCAGAGCTTCAGCACCTCAGTTTAGGCAGTTGTGTCATGATTGAAGACTATGATGTGATA 1420        1430        1440        1450        1460        1470        1480        1490        1500
GCTAGCATGATAGGAGCCAAGTGTAAAAACTCCGGACCTGGATCTGTGGAGATGTAAGAATATTACTGAGAATGGAATAGCAGAACTGGCTT 1510        1520        1530        1540        1550        1560        1570        1580        1590
CTGGGTGTCCACTACTGGAGGAGCTTGACCTTGGCTGTGCCCAACTCTGCAGAGCAGCACCGGGTGCTTCACCAGACTGGCCACCAGCTCCC 1600        1610        1620        1630        1640        1650        1660        1670        1680        1690
AAACTTGCAAAACTCTTTCTTACAGCTAATAGATCTGTGTGACACAGACATTGATGAATTGGCATGTAATTGTACCAGGTTACAGCAGCTG 1700        1710        1720        1730        1740        1750        1760        1770        1780
GACATATTAGGAACAAGAATGTAAGTCCGGCATCCTTAAGAAAACTCTGGAATCTTGTAAAGATCTTTCTTTACTTGATGTGTCCTTCTGTT 1790        1800        1810        1820        1830        1840        1850        1860
CGCAGATTGATAACAGAGCTGTGCTAGAACTGAATGCAAGCTTTCCAAAAGTGTTCATAAAAAGAGCTTTACTCAGTGA
```

FIG.26C

```
              10        20        30        40        50        60
     MQLVPDIEFKITYTRSPDGDGVGNSYIEDNDDDSKMADLLSYFQQQLTFQESVLKLCQPE 70        80        90       100       110       120
     LESSQIHISVLPMEVLMYIFRWVVSSDLDLRSLEQLSLVCRGFYICARDPEIWRLACLKV 130       140       150       160       170       180
     WGRSCIKLVPYTSWREMFLERPRVRFDGVYISKTTYIRQGEQSLDGFYRAWHQVEYYRYI 190       200       210       220       230       240
     RFFPDGHVMMLTTPEEPQSIVPRLRTRNTRTDAILLGHYRLSQDTDNQTKVFAVITKKKE 250       260       270       280       290       300
     EKPLDYKYRYFRRVPVQEADQSFHVGLQLCSSGHQRFNKLIWIHHSCHITYKSTGETAVS 310       320
     AFEIDKMYTPLFFARVRSYTAFSERPL
```

FIG.27A

```
        10        20        30        40        50        60
ATGCAACTTGTACCTGATATAGAGTTCAAGATTACTTATACCCGGTCTCCAGATGGTGATGGCGTTGGA 70        80        90        100       110       120       130
AACAGCTACATTGAAGATAATGATGATGACAGCAAAATGGCAGATCTCTTGTCCTACTTCCAGCAGCAA 140       150       160       170       180       190       200
CTCACATTTCAGGAGTCTGTGCTTAAACTGTGTCAGCCTGAGCTTGAGAGCAGTCAGATTCACATATCA 210       220       230       240       250       260       270
GTGCTGCCAATGGAGGTCCTGATGTACATCTTCCGATGGGTGGTGTCTAGTGACTTGGACCTCAGATCA 280       290       300       310       320       330       340
TTGGAGCAGTTGTCGCTGGTGTGCAGAGGATTCTACATCTGTGCCAGAGACCCTGAAATATGGCGTCTG 350       360       370       380       390       400       410
GCCTGCTTGAAAGTTTGGGGCAGAAGCTGTATTAAACTTGTTCCGTACACGTCCTGGAGAGAGATGTTT 420       430       440       450       460       470       480
TTAGAACGGCCTCGTGTTCGGTTTGATGGCGTGTATATCAGTAAAACCACATATATTCGTCAAGGGGAA 490       500       510       520       530       540       550
CAGTCTCTTGATGGTTTCTATAGAGCCTGGCACCAAGTGGAATATTACAGGTACATAAGATTCTTTCCT 560       570       580       590       600       610       620
GATGGCCATGTGATGATGTTGACAACCCCTGAAGAGCCTCAGTCCATTGTTCCACGTTTAAGAACTAGG 630       640       650       660       670       680       690
AATACCAGGACTGATGCAATTCTACTGGGTCACTATCGCTTGTCACAAGACACAGACAATCAGACCAAA 700       710       720       730       740       750
GTATTTGCTGTAATAACTAAGAAAAAAGAAGAAAAACCACTTGACTATAAATACAGATATTTTCGTCGT 760       770       780       790       800       810       820
GTCCCTGTACAAGAAGCAGATCAGAGTTTTCATGTGGGGCTACAGCTATGTTCCAGTGGTCACCAGAGG 830       840       850       860       870       880       890
TTCAACAAACTCATCTGGATACATCATTCTTGTCACATTACTTACAAATCAACTGGTGAGACTGCAGTC 900       910       920       930       940       950       960
AGTGCTTTTGAGATTGACAAGATGTACACCCCCTTGTTCTTCGCCAGAGTAAGGAGCTACACAGCTTTC 970       980
TCAGAAAGGCCTCTGTAG
```

FIG.27B

```
         10        20        30        40        50        60
AALDPDLENDDFFVRKTGAFHANPYVLRAFEDFRKFSEQDDSVERDIILQCREGELVLPD 70        80        90       100       110       120
LEKDDMIVRRIPAQKKEVPLSGAPDRYHPVPFPEPWTLPPEIQAKFLCVLERTCPSKEKS 130       140       150       160       170       180
NSCRILVPSYRQKKDDMLTRKIQSWKLGTTVPPISFTPGPCSEADLKRWEAIREASRLRH 190       200       210       220       230       240
KKRLMVERLFQKIYGENGSKSMSDVSAEDVQNLRQLRYEEMQKIKSQLKEQDQKWQDDLA

250
KWKDRRKSYTSDLQK
```

FIG. 28A

```
         10        20        30        40        50        60
GCAGCCCTGGATCCTGACTTAGAGAATGATGATTTCTTTGTCAGAAAGACTGGGGCTTTCCATGCAAAT 70        80        90       100       110       120       130
CCATATGTTCTCCGAGCTTTTGAAGACTTTAGAAAGTTCTCTGAGCAAGATGATTCTGTAGAGCGAGAT 140       150       160       170       180       190       200
ATAATTTTACAGTGTAGAGAAGGTGAACTTGTACTTCCGGATTTGGAAAAAGATGATATGATTGTTCGC 210       220       230       240       250       260       270
CGAATCCCAGCACAGAAGAAAGAAGTGCCGCTGTCTGGGGCCCCAGATAGATACCACCCAGTCCCTTTT 280       290       300       310       320       330       340
CCCGAACCCTGGACTCTTCCTCCAGAAATTCAAGCAAAATTTCTCTGTGTACTTGAAAGGACATGCCCA 350       360       370       380       390       400       410
TCCAAAGAAAAAAGTAATAGCTGTAGAATATTAGTTCCTTCATATCGGCAGAAGAAAGATGACATGCTG 420       430       440       450       460       470       480
ACACGTAAGATTCAGTCCTGGAAACTGGGAACTACCGTGCCTCCCATCAGTTTCACNCCTGGCCCCTGC 490       500       510       520       530       540       550
AGTGAGGCTGACTTGAAGAGATGGGAGGCCATCCGGGAGGCCAGCAGACTCAGGCACAAGAAAAGGCTG 560       570       580       590       600       610       620
ATGGTGGAGAGACTCTTTCAAAAGATTTATGGTGAGAATGGGAGTAAGTCCATGAGTGATGTCAGCGCA 630       640       650       660       670       680       690
GAAGATGTTCAAAACTTGCGTCAGCTGCGTTACGAGGAGATGCAGAAAATAAAATCACAATTAAAAGAA 700       710       720       730       740       750
CAAGATCAGAAATGGCAGGATGACCTTGCAAAATGGAAAGATCGTCGAAAAAGTTACACTTCAGATCTG

760
CAGAAG
```

FIG.28B

FIG.32A  FIG.32C  FIG.32E  FIG.32G  FIG.32I  FIG.32K
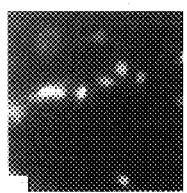 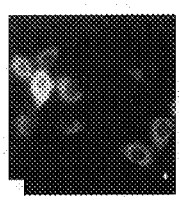 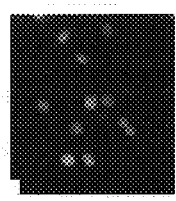 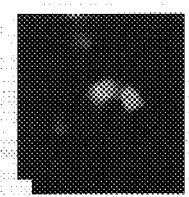 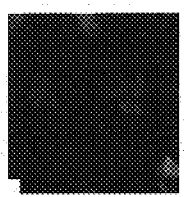 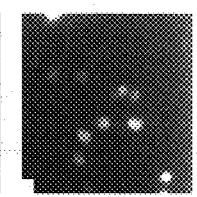
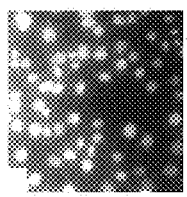 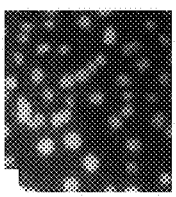 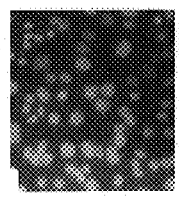 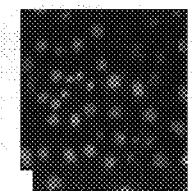  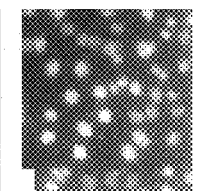
FIG.32B  FIG.32D  FIG.32F  FIG.32H  FIG.32J  FIG.32L

UBIQUITIN LIGASES AS THERAPEUTIC TARGETS

This application claims priority under 35 U.S.C. §119(e) to U.S. application Ser. No. 60/098,355, filed Aug. 28, 1998, application Ser. No. 60/118,568, filed Feb. 3, 1999, and application Ser. No. 60/124,449 filed Mar. 15, 1999, the contents of which are incorporated herein by reference in their entirety.

1. INTRODUCTION

The present invention relates to the discovery, identification and characterization of nucleotide sequences that encode novel substrate-targeting subunits of ubiquitin ligases. The invention encompasses nucleic acid molecules comprising nucleotide sequences encoding novel substrate-targeting subunits of ubiquitin ligases: FBP1, FBP2, FBP3a, FBP3b, FBP4, FBP5, FBP6, FBP7, FBP8, FBP11, FBP12, FBP13, FBP14, FBP15, FBP17, FBP18, FBP20, FBP21, FBP22, FBP23, AND FBP25, transgenic mice, knock-out mice, host cell expression systems and proteins encoded by the nucleotides of the present invention. The present invention relates to screening assays to identify potential therapeutic agents such as small molecules, compounds or derivatives and analogues of the novel ubiquitin ligases which modulate activity of the novel ubiquitin ligases for the treatment of proliferative and differentiative disorders, such as cancer, major opportunistic infections, immune disorders, certain cardiovascular diseases, and inflammatory disorders. The invention further encompasses therapeutic protocols and pharmaceutical compositions designed to target ubiquitin ligases and their substrates for the treatment of proliferative disorders.

2. BACKGROUND OF THE INVENTION

2.1 CELL CYCLE REGULATORY PROTEINS

The eukaryotic cell cycle is regulated by a family of serine/threonine protein kinases called cyclin dependent kinases (Cdks) because their activity requires the association with regulatory subunits named Cyclins (Hunter & Pines, 1994, Cell 79:573). Cdks also associate with Cdk inhibitors (Ckis) which mediate cell cycle arrest in response to various antiproliferative signals. So far, based on their sequence homology, two families of Ckis have been identified in mammalian cells: the Cip/Kip family, which includes p21, p27 and p57; and the Ink family, which includes p15, p16, p18, and p20 (Sherr & Roberts, 1999, Genes & Dev. 13:1501).

2.2 THE UBIQUITIN PATHWAY

Ubiquitin-mediated proteolysis is an important pathway of non-lysosomal protein degradation which controls the timed destruction of many cellular regulatory proteins including, p27, p53, p300, cyclins, E2F, STAT-1, c-Myc, c-Jun, EGF receptor, IkBα, NFkB and β-catenin (reviewed in Pagano, 1997, FASEB J. 11:1067). Ubiquitin is an evolutionary highly conserved 76-amino acid polypeptide which is abundantly present in all eukaryotic cells. The ubiquitin pathway leads to the covalent attachment of a poly-ubiquitin chain to target substrates which are then degraded by the multi-catalytic proteasome complex (see Pagano, supra, for a recent review). Many of the steps regulating protein ubiquitination are known. Initially the ubiquitin activating enzyme (E1), forms a high energy thioester with ubiquitin which is, in turn, transferred to a reactive cysteine residue of one of many ubiquitin conjugating enzymes (Ubcs or E2s). The final transfer of ubiquitin to an e-amino group of a reactive lysine residue in the target protein occurs in a reaction that ay or may not require an ubiquitin ligase (E3) protein. The large number of ubiquitin ligases ensures the high level of substrate specificity.

2.3 THE UBIQUITIN PATHWAY AND THE REGULATION OF THE G1 PHASE BY F BOX PROTEINS

Genetic and biochemical studies in several organisms have shown that the G1 phase of the cell cycle is regulated by the ubiquitin pathway. Proteolysis of cyclins, Ckis and other G1 regulatory proteins is controlled in yeast by the ubiquitin conjugating enzyme Ubc3 (also called Cdc34) and by an E3 ubiquitin ligase formed by three subunits: Cdc53, Skp1 and one of many F box proteins (reviewed in E. Patton et al., 1998, TIG. 14:6). The F box proteins (FBPs) are so called because they contain a motif, the F box, that was first identified in Cyclin F, and that is necessary for FBP interaction with Skp1 (Bai, et al., 1996, Cell 86:263). In addition, F box proteins also contain either WD-40 domains or Leucine-Rich Repeats (LRR) protein-protein interaction domains. Cdc53 (also called Cul A) and Skp1 appear to participate in the formation of at least three distinct E3, each containing a different F box protein. Because these ligases are similar protein modules composed of Skp1, Cul A, and an F box protein, they have been named SCF. The interaction of the ligase with its substrates occurs via the F box subunit. The three SCFs identified so far in *S. cerevisiae* are: $SCF^{Cdc4}$ (which recruits the Ckis Sic1 and Far1, the replication factor Cdc6, and the transcriptional activator Gcn4, as substrates through the F box protein Cdc4), $SCF^{Grr1}$ (which recruits the G1 cyclins Cln1 and Cln2 as substrates through the F box protein GRR1), and $SCF^{Met30}$ (which recruits the G1 cyclin Cln3 as a substrate throughout the F box protein MET30; see Pagano and Patton, supra, for recent reviews).

The intracellular level of the human Cki p27 is mainly regulated by degradation and it is known that the ubiquitin system controls p27 degradation (Pagano et al., 1995, Science 269:682). Similarly, degradation of other G1 human regulatory proteins (Cyclin E, Cyclin D1, p21, E2F, β-catenin) is controlled by the ubiquitin-pathway (reviewed in M. Pagano, supra). Yet, the specific enzymes involved in the degradation of G1 regulatory proteins have not been identified.

A family of 6 genes (CUL1, 2, 3, 4a, 4b, and 5) homologous to *S. cerevisiae* cul A have been identified by searching the EST database (Kipreos, et al., 1996, Cell 85:829). Human Skp1 and the F box protein Skp2 (that contains five LRRs) were identified as two proteins associated in vivo with Cyclin A and thus designated as S-phase kinase-associated protein 1 and 2 (Zhang, et al., 1995, Cell 82:915).

2.4 DEREGULATION OF THE UBIQUITIN PATHWAY IN CANCER AND OTHER PROLIFERATIVE DISORDERS

Cancer develops when cells multiply too quickly. Cell proliferation is determined by the net balance of positive and negative signals. When positive signals overcome or when negative signals are absent, the cells multiply too quickly and cancer develops.

Ordinarily cells precisely control the amount of any given protein and eliminate the excess or any unwanted protein. To do so, the cell specifically tags the undesired protein with a long chain of molecules called ubiquitin. These molecules are then recognized and destroyed by a complex named proteasome. However, all this mechanism goes awry in tumors leading to the excessive accumulation of positive signals (oncogenic proteins), or resulting in the abnormal degradation of negative regulators (tumor suppressor proteins). Thus, without tumor suppressor proteins or in the presence of too much oncogenic proteins, cells multiply ceaselessly, forming tumors (reviewed by Ciechanover, 1998, EMBO J. 17: 7151; Spataro, 1998, Br. J. Cancer 77: 448). For example, abnormal ubiquitin-mediated degradation of the p53 tumor suppressor (reviewed by J. Brown and M. Pagano, 1997, Biochim. Biophys. Acta1332: 1), the putative oncogene β-catenin (reviewed by Peifer, 1997, Science 275:1752) and the Cki p27 (reviewed in Ciechanover, supra; Spataro, supra; Lloyd, 1999, Am. J. Pathol.154: 313) have been correlated with tumorigenesis, opening to the hypothesis that some genes encoding ubiquitinating enzymes may be mutated in tumors.

Initial evidence indicates that human F-box proteins play a role in the ubiquitination of G1 regulatory proteins as their homologs do in yeast (see below). Unchecked degradation of cell cycle regulatory proteins has been observed in certain tumors and it is possible that deregulated ubiquitin ligase play a role in the altered degradation of cell cycle regulators. A well understood example is that of Mdm2, a ubiquitin ligase whose overexpression induces low levels of its substrate, the tumor suppressor p53.

3. SUMMARY OF THE INVENTION

The present invention relates to novel F box proteins and therapeutic protocols and pharmaceutical compositions designed to target the novel F box proteins and their interactions with substrates for the treatment of proliferative and differentiative disorders. The present invention also relates to screening assays to identify substrates of the novel F box proteins and to identify agents which modulate or target the novel ubiquitin ligases and interactions with their substrates. The invention further relates to screening assays based on the identification of novel substrates of known F box proteins, such as the two novel substrates of the known F box protein Skp2, E2F and p27. The screening assays of the present invention may be used to identify potential therapeutic agents for the treatment of proliferative or differentiative disorders and other disorders that related to levels of expression or enzymatic activity of F box proteins.

The invention is based in part, on the Applicants' discovery, identification and characterization of nucleic acids comprising nucleototide sequences that encode novel ubiquitin ligases with F box motifs. These twenty-six novel substrate-targeting subunits of ubiquitin ligase complexes, FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, described herein, were first identified based on their interaction with components of the ubiquitin ligase complex (FBP1, FBP2, FBP3a, FBP4, FBP5, FBP6 and FBP7) or by sequence comparison of these proteins with nucleotide sequences present in DNA databases (FBP3b, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25). These novel substrate-targeting subunits of ubiquitin ligase complexes each contain an F box motif through which they interact with the other components of the ubiquitin ligase complex. In addition, some of these FBPs contain WD-40 domains and LRRs (which appear to be involved in their interaction with substrates), while other FBPs contain potential protein-protein interaction modules not yet identified in FBPs, such as leucine zippers, ring fingers, helix-loop-helix motifs, proline rich motifs and SH2 domains. The invention is also based, in part, on the Applicants' discovery and identification of FBP specific substrates p27 and β-catenin and on methods to identify novel FBP substrates. Some of the genes encoding the novel F box proteins were also mapped to chromosome sites frequently altered in breast, prostate and ovarian cancer, nasopharyngeal and small cell lung carcinomas, gastric hepatocarcinomas, Burkitt's lymphoma and parathyroid adenomas. Finally, the invention is also based, in part, on the Applicants' generation of transgenic mice expressing wild type or dominant negative versions of FBP proteins and on the generation of FBP knock-out mice.

The invention encompasses the following nucleotide sequences, host cells expressing such nucleotide sequences, and the expression products of such nucleotide sequences: (a) nucleotide sequences that encode mammalian FBP1, FBP2, FBP3a, FBP3b, FBP4, FBP5, FBP6, FBP7, FBP8, FBP11, FBP12, FBP13, FBP14, FBP15, FBP17, FBP18, FBP20, FBP21, FBP22, FBP23, and FBP25, including the human nucleotides, and their gene products; (b) nucleotides that encode portions of the novel substrate-targeting subunits of ubiquitin ligase complexes, and the polypeptide products specified by such nucleotide sequences, including but not limited to F box motifs, the substrate binding domains; WD-40 domains; and leucine rich repeats, etc.; (c) nucleotides that encode mutants of the novel ubiquitin ligases in which all or part of the domain is deleted or altered, and the polypeptide products specified by such nucleotide sequences; (d) nucleotides that encode fusion proteins containing the novel ubiquitin ligases or one of its domains fused to another polypeptide.

The invention further encompasses agonists and antagonists of the novel substrate-targeting subunits of ubiquitin ligase complexes, including small molecules, large molecules, mutants that compete with native F box binding proteins, and antibodies as well as nucleotide sequences that can be used to inhibit ubiquitin ligase gene expression (e.g., antisense and ribozyme molecules, and gene regulatory or replacement constructs) or to enhance ubiquitin ligase gene expression (e.g., expression constructs that place the ubiquitin ligase gene under the control of a strong promoter system), and transgenic animals that express a ubiquitin ligase transgene or knock-outs that do not express the novel ubiquitin ligases.

Further, the present invention also relates to methods for the use of the genes and/or gene products of novel substrate-targeting subunits of ubiquitin ligase complexes for the identification of compounds which modulate, i.e., act as agonists or antagonists, of ubiquitin ligase activity. Such compounds can be used as agents to control proliferative or differentiative disorders, e.g. cancer. In particular, the present invention encompasses methods to inhibit the interaction between β-catenin and FBP1 or p27 and Skp2. In fact, agents able to block these interactions can be used to modulate cell proliferation and/or growth.

Still further, the invention encompasses screening methods to identify derivatives and analogues of the novel substrate-targeting subunits of ubiquitin ligase complexes which modulate the activity of the novel ligases as potential therapeutics for proliferative or differentiative disorders. The invention provides methods of screening for proteins that interact with novel components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 or derivatives, fragments or domains thereof, such as the F box motif. In accordance with the invention, the screening methods may utilize known assays to identify protein-protein interactions including phage display assays or the yeast two-hybrid assay system or variations thereof.

In addition, the present invention is directed to methods that utilize FBP gene sequences and/or FBP gene product sequences for the diagnostic evaluation, genetic testing and/or prognosis of an FBP-related disorder, such as a proliferative disorder. For example, the invention relates to methods for diagnosing FBP-related disorders, e.g., proliferative disorders, wherein such methods can comprise measuring FBP gene expression in a patient sample, or detecting an FBP mutation that correlates with the presence or development of such a disorder, in the genome of a mammal suspected of exhibiting such a disorder. In particular, the invention encompasses methods for determining if a subject (e.g., a human patient) is a risk for a disorder characterized by one or more of: (i) a mutation of an FBP gene encoding a protein represented in part A of FIGS. 3–28, or a homolog thereof; (ii) the mis-expression of an FBP gene; (iii) the mis-expression of an FBP protein.

The invention is illustrated by way of working examples which demonstrate the identification and characterization of the novel substrate-targeting subunits of ubiquitin ligase complexes. The working examples of the present invention further demonstrate the identification of the specific interaction of (i) FBP1 with β-catenin and (ii) the known FBP, Skp2, with the cell-cycle regulatory proteins E2F and p27. These interactions suggest that β-catenin is a specific substrate of FBP1, while E2F and p27 are substrates of Skp2. In fact, the working examples of the present invention further demonstrate that β-catenin is a specific substrate of FBP1, while p27 is substrates of Skp2. The identification of proteins interacting with the novel FBPs will be possible using the methods described herein or with a different approach.

3.1 DEFINITIONS

As used herein, the term "F-box motif" refers to a stretch of approximately 40 amino acid that was identified as being necessary for the interaction of F-box containing proteins with Skp1. The consensus sequence of an F-box motif is described in Bai et al., 1996, Cell 86:263–274, incorporated herein by reference in its entirety.

As used herein the term "F-box protein" (FBP) refers to peptide, polypeptide or protein which contains an F-box motif.

Although, FBPs are substrate-targeting subunits of ubiquitin ligase complexes, as used herein the term "ubiquitin ligase" refers to a peptide, polypeptide or protein that contains an F-box motif and interacts with Skp1.

As used herein, the term "functionally equivalent to an FBP gene product" refers to a gene product that exhibits at least one of the biological activities of the endogenous FBP gene product. For example, a functionally equivalent FBP gene product is one that is capable of interacting with Skp1 so as to become associated with a ubiquitin ligase complex. Such a ubiquitin ligase complex may be capable of ubiquitinating a specific cell-cycle regulatory protein, such as a cyclin or cki protein.

As used herein, the term "to target" means to inhibit, block or prevent gene expression, enzymatic activity, or interaction with other cellular factors.

As used herein, the term "therapeutic agent" refers to any molecule, compound or treatment that alleviates of assists in the treatment of a proliferative disorder or related disorder.

As used herein, the terms "WD-40 domain", "Leucine Rich Repeat", "Leucine Zipper", "Ring finger", "Helix-loop-helix motif", "Proline rich motif", and "SH2 domain" refer to domains potentially involved in mediating protein-protein interactions. The "WD-40 domain" refers to a consensus sequence of forty amino acid repeats which is rich in tryptophan and aspartic acid residues and is commonly found in the beta subunits of trimeric G proteins (see Neer et al., 1994 Nature 371:297–300 and references therein, which are incorporated herein by reference in their entirety). An "LRR" or a "Leucine Rich Repeat" is a leucine rich sequence also known to be involved in mediating protein-protein interactions (see Kobe & Deisenhofer, 1994, Trends. Biochem. Sci. 19:415–421 which are incorporated herein by reference in their entirety). A "leucine zipper" domain refers to a domain comprising a stretch of amino acids with a leucine residue in every seventh position which is present in a large family of transcription factors (see Landshultz et al., 1988, Science 240:1759–64; see also Sudol et al., 1996, Trends Biochem. 21:1–3, and Koch et al., 1991, Science 252:668–74).

4. BRIEF DESCRIPTION OF THE FIGURES

Figure 1:
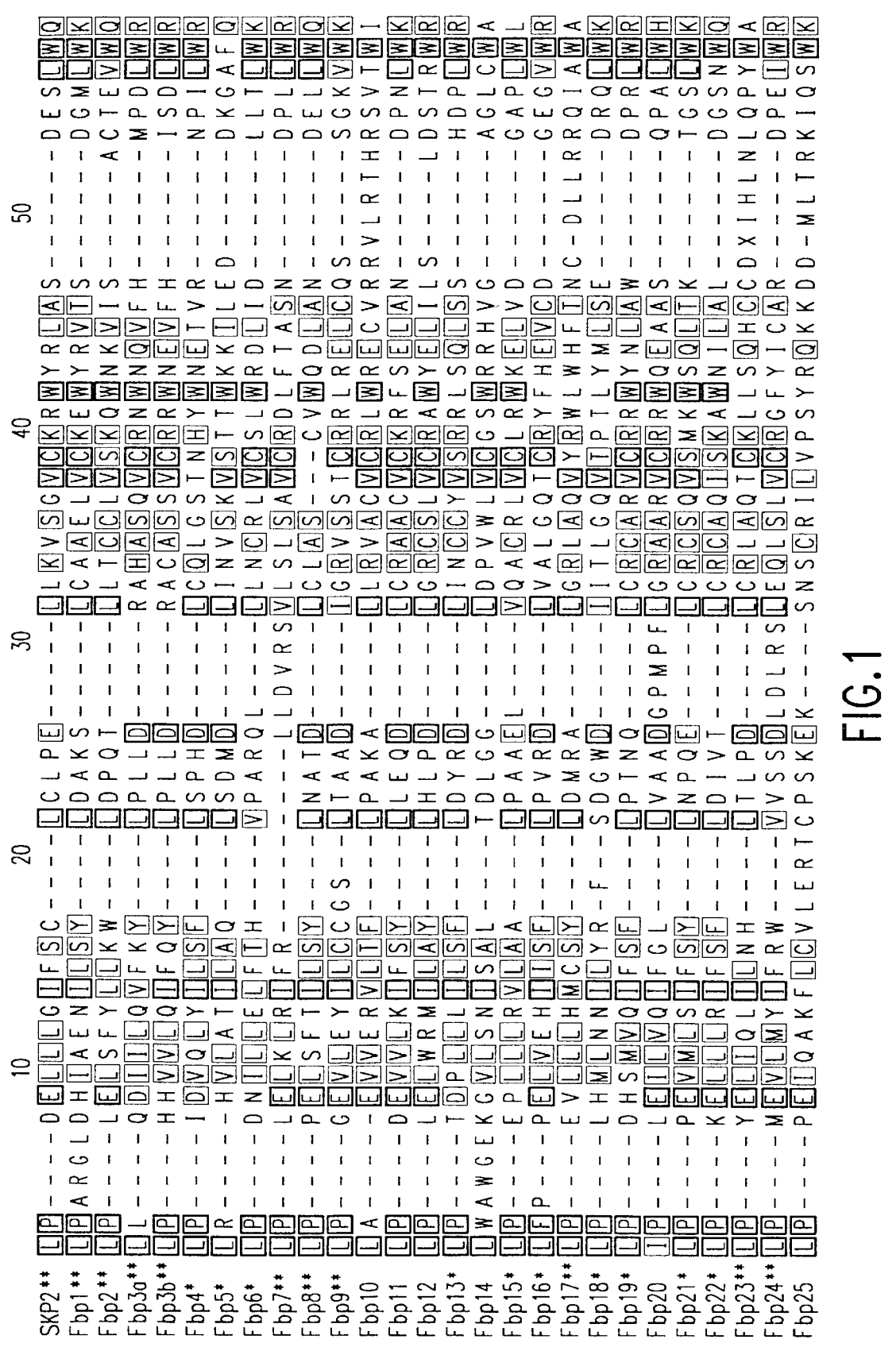

FIG. 1. Alignment of the conserved F-box motif amino acid residues in the human F-box proteins FBP1 (SEQ ID NO:15), FBP2 (SEQ ID NO:16), FBP3a (SEQ ID NO:17), FBP3b (SEQ ID NO:78), FBP4 (SEQ ID NO:18), FBP5 (SEQ ID NO:19), FBP6 (SEQ ID NO:20), FBP7 (SEQ ID NO:21), Skp2 (SEQ ID NO:22), FBP8 (SEQ ID NO:61) FBP9 (SEQ ID NO:62), FBP10 (SEQ ID NO:63), FBP11 (SEQ ID NO:64), FBP12 (SEQ ID NO:65), FBP13 (SEQ ID NO:79); FBP14 (SEQ ID NO:66); FBP15 (SEQ ID NO:67), FBP16 (SEQ ID NO:68), FBP17 (SEQ ID NO:69), FBP18 (SEQ ID NO:70), FBP19 (SEQ ID NO:71), FBP20 (SEQ ID NO:72), FBP21 (SEQ ID NO:73), FBP22 (SEQ ID NO:74), FBP23 (SEQ ID NO:75), FBP24 (SEQ ID NO:76), FBP25 (SEQ ID NO:77). Alignment of the F-boxes of a previously known FBP, Skp2, with the F-boxes of FBPs identified through a two-hybrid screen (designated by the pound symbol) or BLAST searches (designated by a cross) was performed using the Clustal W method (MacVector(™)) followed by manual re-adjustment. Identical residues in at least 15 F-boxes are shaded in dark gray, while similar residues are shaded in light gray. One asterisk indicates the presence in the cDNA of a STOP codon followed by a polyA tail, while potential full length clones are designated with two asterisks. The asterisks on the bottom of the figure indicate the amino acid residues mutated in FBP3a (see FIG. 29).

FIG. 2. Schematic representation of FBPs. Putative protein-protein interaction domains in human FBPs are represented (see key-box for explanation). FBPs identified by a two-hybrid screen are designated by the pound symbol, FBPs identified through BLAST searches by a cross. The double slash indicates that the corresponding cDNAs are incomplete at the 5' end; the asterisks indicate the presence in the cDNA of a STOP codon followed by a polyA tail.

FIGS. 3A–B. A. Amino acid sequence of human F-box protein FBP1 (SEQ ID NO:2). B. Corresponding cDNA (SEQ ID NO:1).

FIGS. 4A–B. A. Amino acid sequence of human F-box protein FBP2 (SEQ ID NO:4). B. Corresponding cDNA (SEQ ID NO:3).

FIGS. 5A–B. A. Amino acid sequence of human F-box protein FBP3a (SEQ ID NO:6). B. Corresponding cDNA (SEQ ID NO:5).

FIGS. 6A–B. A. Amino acid sequence of human F-box protein FBP3b (SEQ ID NO:24). B. Corresponding cDNA (SEQ ID NO:23).

FIGS. 7A–B. A. Amino acid sequence of human F-box protein FBP4 (SEQ ID NO:8). B. Corresponding cDNA (SEQ ID NO:7).

FIGS. 8A–B. A. Amino acid sequence of human F-box protein FBP5 (SEQ ID NO:10). B. Corresponding cDNA (SEQ ID NO:9).

FIGS. 9A–B. A. Amino acid sequence of human F-box protein FBP6 (SEQ ID NO:12). B. Corresponding cDNA (SEQ ID NO:11).

FIGS. 10A–B. A. Amino acid sequence of human F-box protein FBP7 (SEQ ID NO:14). B. Corresponding cDNA (SEQ ID NO:13).

FIGS. 11A–B. A. Amino acid sequence of human F-box protein FBP8 (SEQ ID NO:26). B. Corresponding cDNA (SEQ ID NO:25).

Figure 12B:
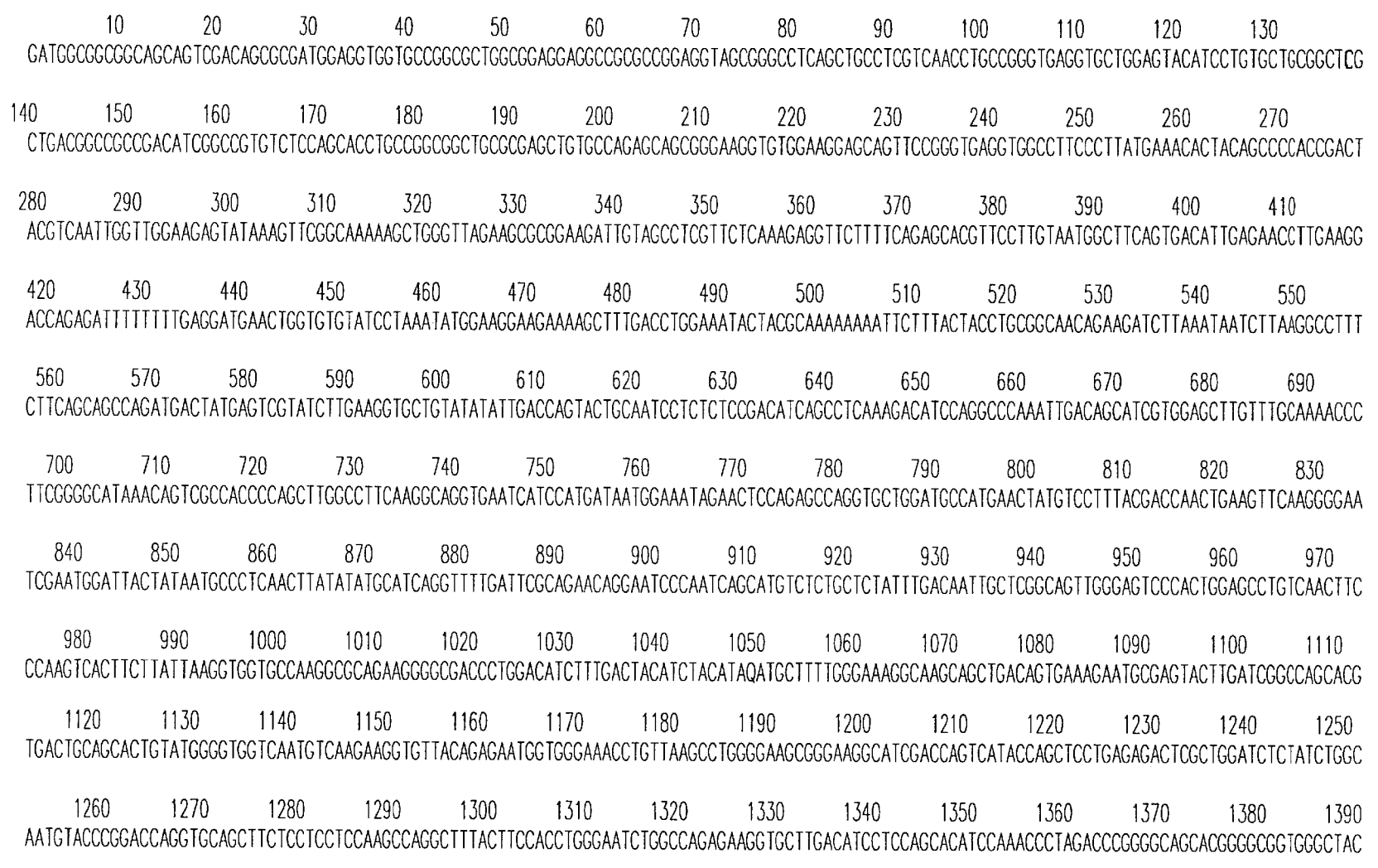
Figure 12C:
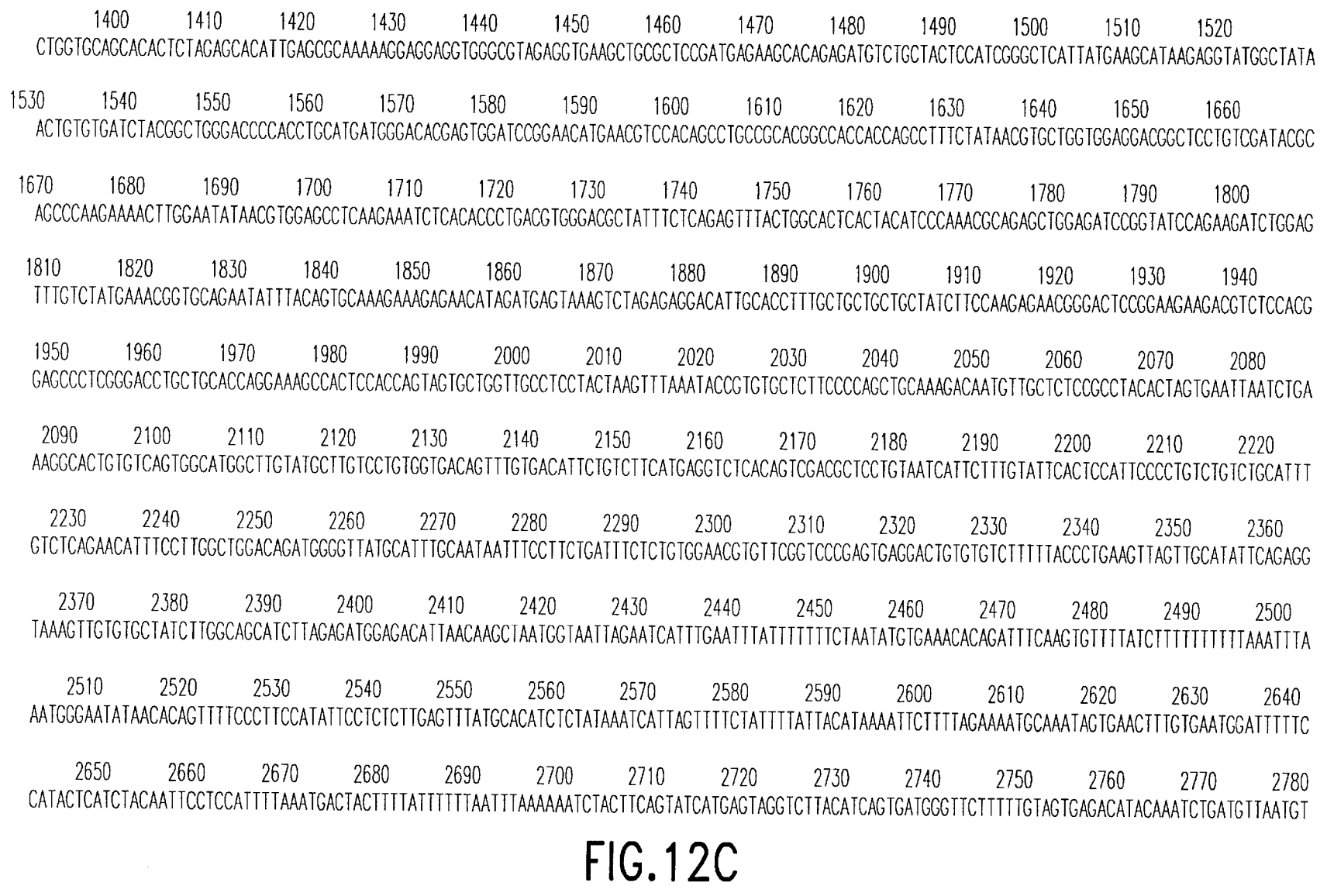

FIGS. 12A–B. A. Amino acid sequence of human F-box protein FBP9 (SEQ ID NO:28). B. Corresponding cDNA (SEQ ID NO:27).

FIGS. 13A–B. A. Amino acid sequence of human F-box protein FBP10 (SEQ ID NO:30). B. Corresponding cDNA (SEQ ID NO:29).

FIGS. 14A–B. A. Amino acid sequence of human F-box protein FBP11 (SEQ ID NO:32). B. Corresponding cDNA (SEQ ID NO:31).

FIGS. 15A–B. A. Amino acid sequence of human F-box protein FBP12 (SEQ ID NO:34). B. Corresponding cDNA (SEQ ID NO:33).

FIGS. 16A–B. A. Amino acid sequence of human F-box protein FBP13 (SEQ ID NO:36). B. Corresponding cDNA (SEQ ID NO:35).

FIGS. 17A–B. A. Amino acid sequence of human F-box protein FBP14 (SEQ ID NO:38). B. Corresponding cDNA (SEQ ID NO:37).

FIGS. 18A–B. A. Amino acid sequence of human F-box protein FBP15 (SEQ ID NO:40). B. Corresponding cDNA (SEQ ID NO:39).

FIGS. 19A–B. A. Amino acid sequence of human F-box protein FBP16 (SEQ ID NO:42). B. Corresponding cDNA (SEQ ID NO:41).

FIGS. 20A–B. A. Amino acid sequence of human F-box protein FBP17 (SEQ ID NO:44). B. Corresponding cDNA (SEQ ID NO:43).

FIGS. 21A–B. A. Amino acid sequence of human F-box protein FBP18 (SEQ ID NO:46). B. Corresponding cDNA (SEQ ID NO:45).

Figure 22B:
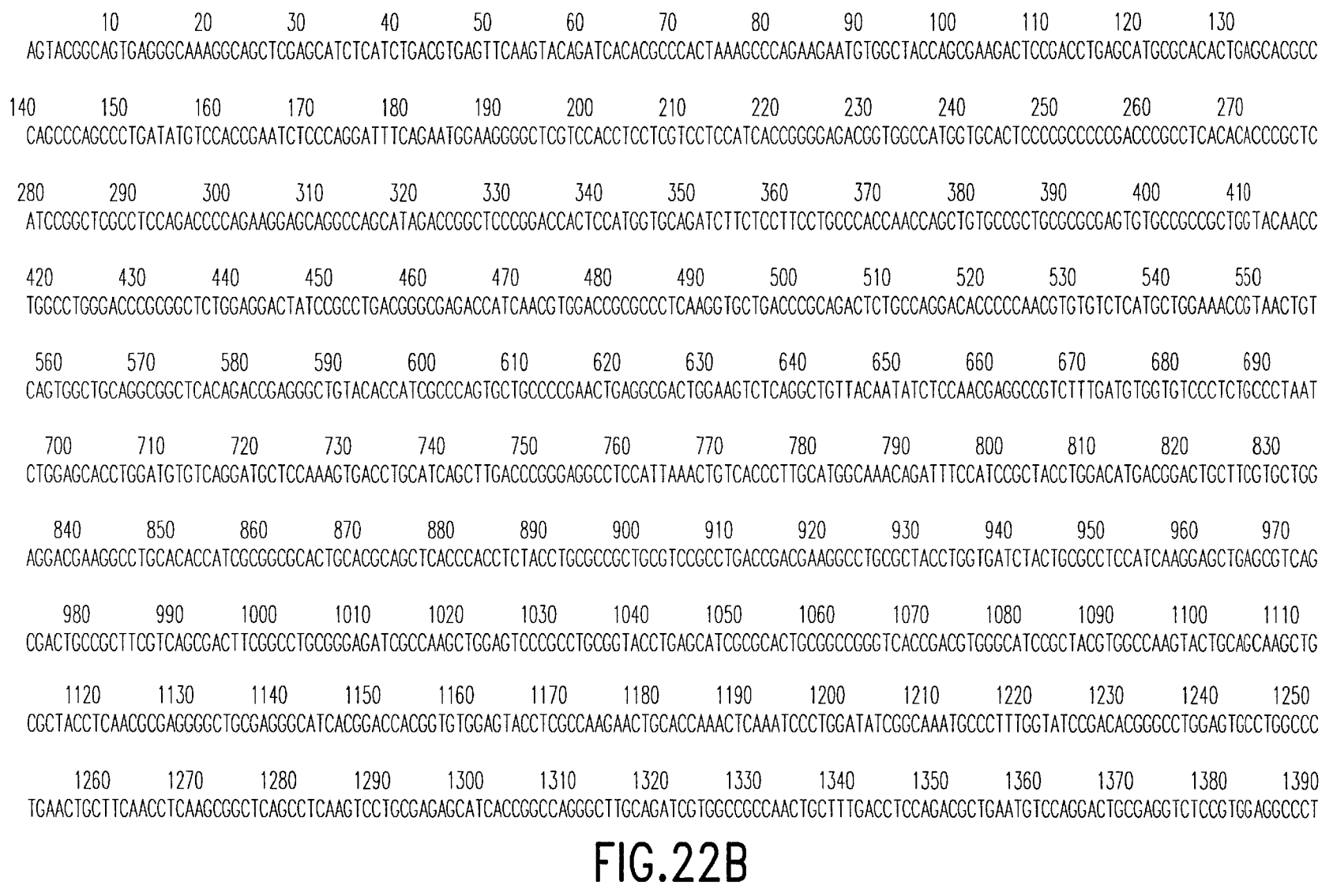
Figure 22C:
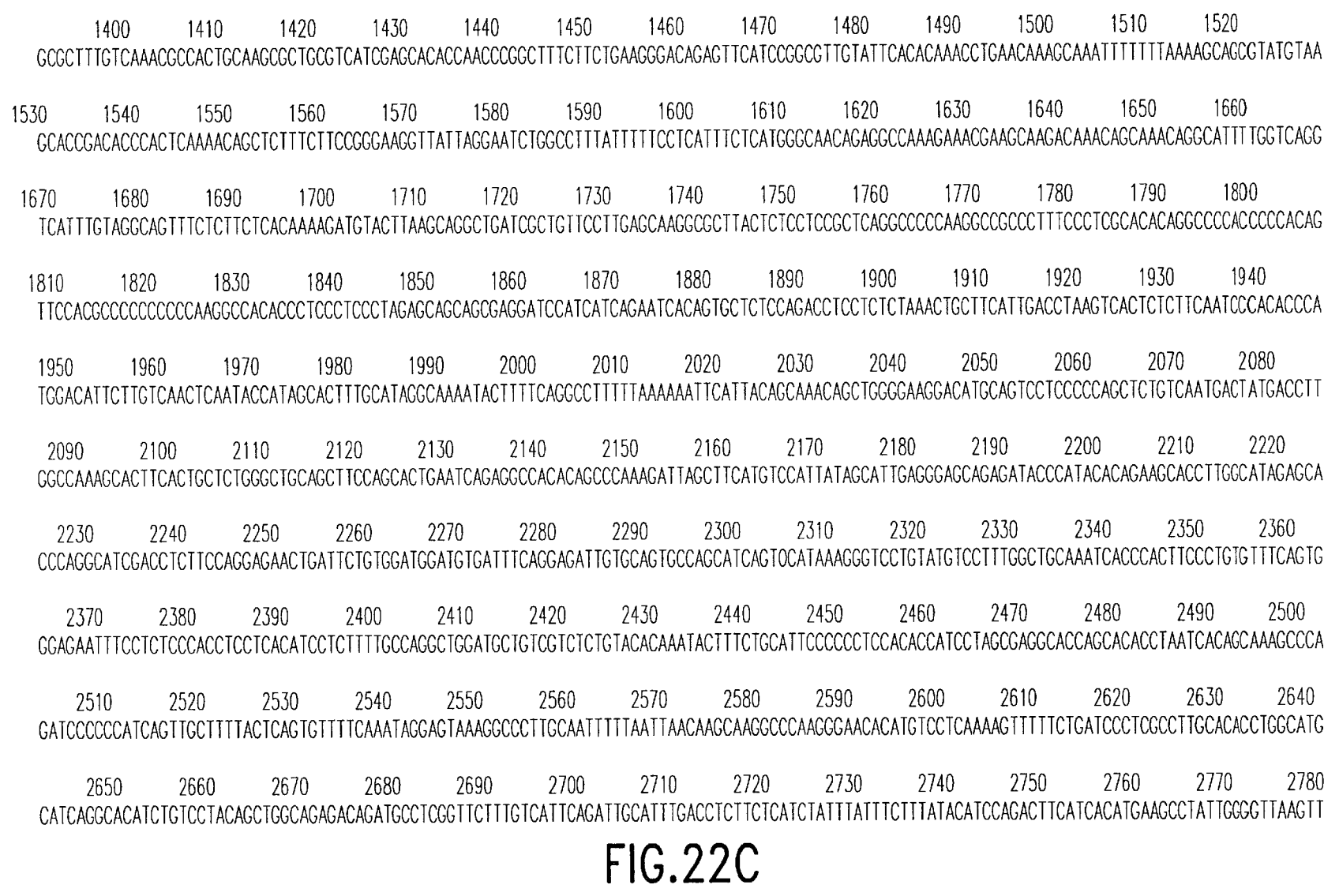

FIGS. 22A–B. A. Amino acid sequence of human F-box protein FBP19 (SEQ ID NO:48). B. Corresponding cDNA (SEQ ID NO:47).

FIGS. 23A–B. A. Amino acid sequence of human F-box protein FBP20 (SEQ ID NO:50). B. Corresponding cDNA (SEQ ID NO:49).

FIGS. 24A–B. A. Amino acid sequence of human F-box protein FBP21 (SEQ ID NO:52). B. Corresponding cDNA (SEQ ID NO:51).

FIGS. 25A–B. A. Amino acid sequence of human F-box protein FBP22 (SEQ ID NO:54). B. Corresponding cDNA (SEQ ID NO:53).

FIGS. 26A–B. A. Amino acid sequence of human F-box protein FBP23 (SEQ ID NO:56). B. Corresponding cDNA (SEQ ID NO:55).

FIGS. 27A–B. A. Amino acid sequence of human F-box protein FBP24 (SEQ ID NO:58). B. Corresponding cDNA (SEQ ID NO:57).

FIGS. 28A–B. A. Amino acid sequence of human F-box protein FBP25 (SEQ ID NO:60). B. Corresponding cDNA (SEQ ID NO:59).

Figure 29:
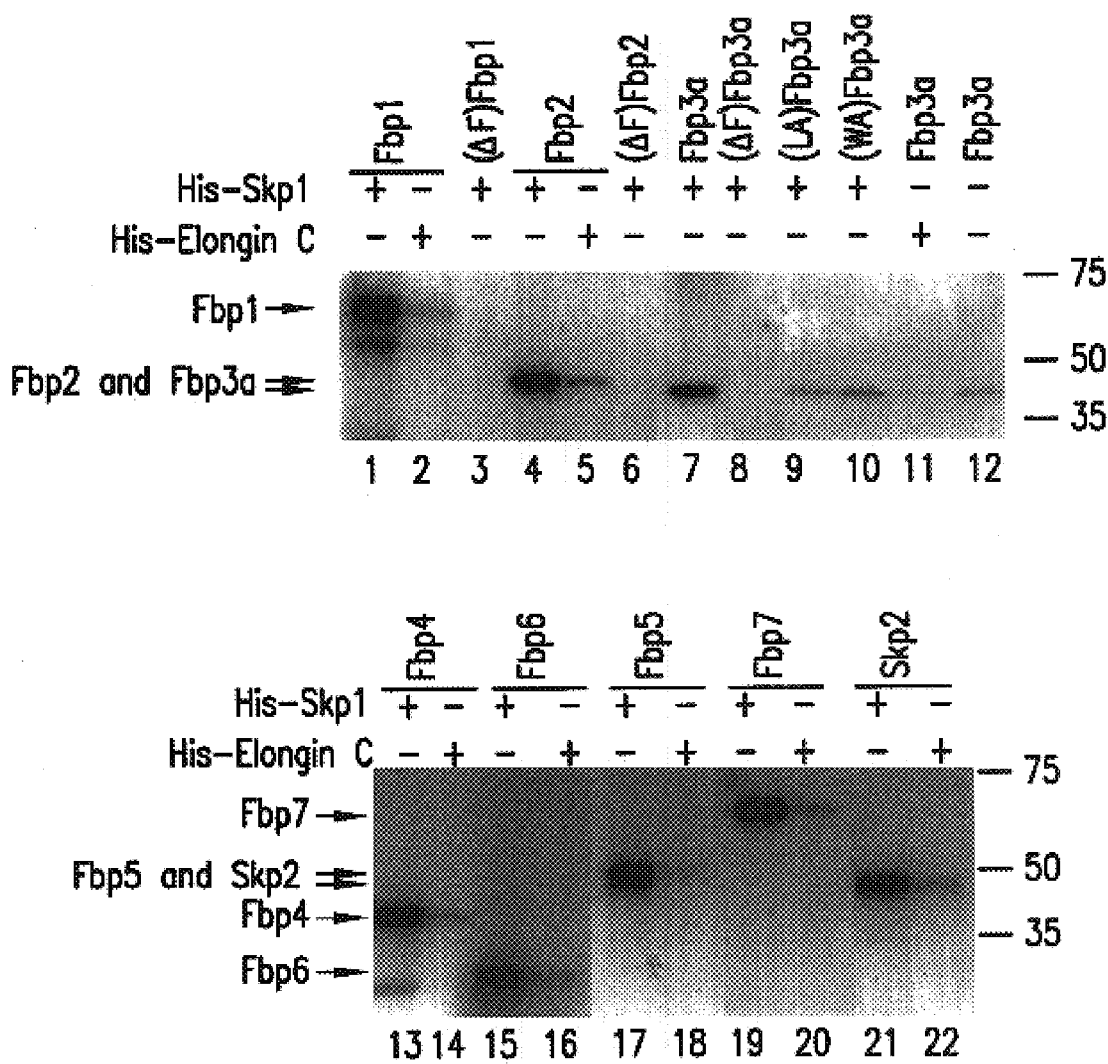

FIGS. 29. FBPs interact specifically with Skp1 through their F-box. The cDNAs of FBPs (wild type and mutants) were transcribed and translated in vitro (IVT) in the presence of 35S-methionine. Similar amounts of IVT proteins (indicated at the top of each lane) were subjected to a histidine-tagged pull-down assay using Nickel-agarose beads to which either His-tagged-Skp1 (lanes 1, 3, 4, 6–10, 12, 15, 17, 19 and 21), His-tagged-Elongin C (lanes 2, 5, 11, 14, 16, 18, 19 and 22), or His-tagged p27 (lane 12) were pre-bound. Bound IVT proteins were analyzed by SDS-PAGE and autoradiography. The arrows on the left side of the panels point to the indicated FBPs. The apparent molecular weights of the protein standards are indicated on the right side of the panels.

Figure 30:
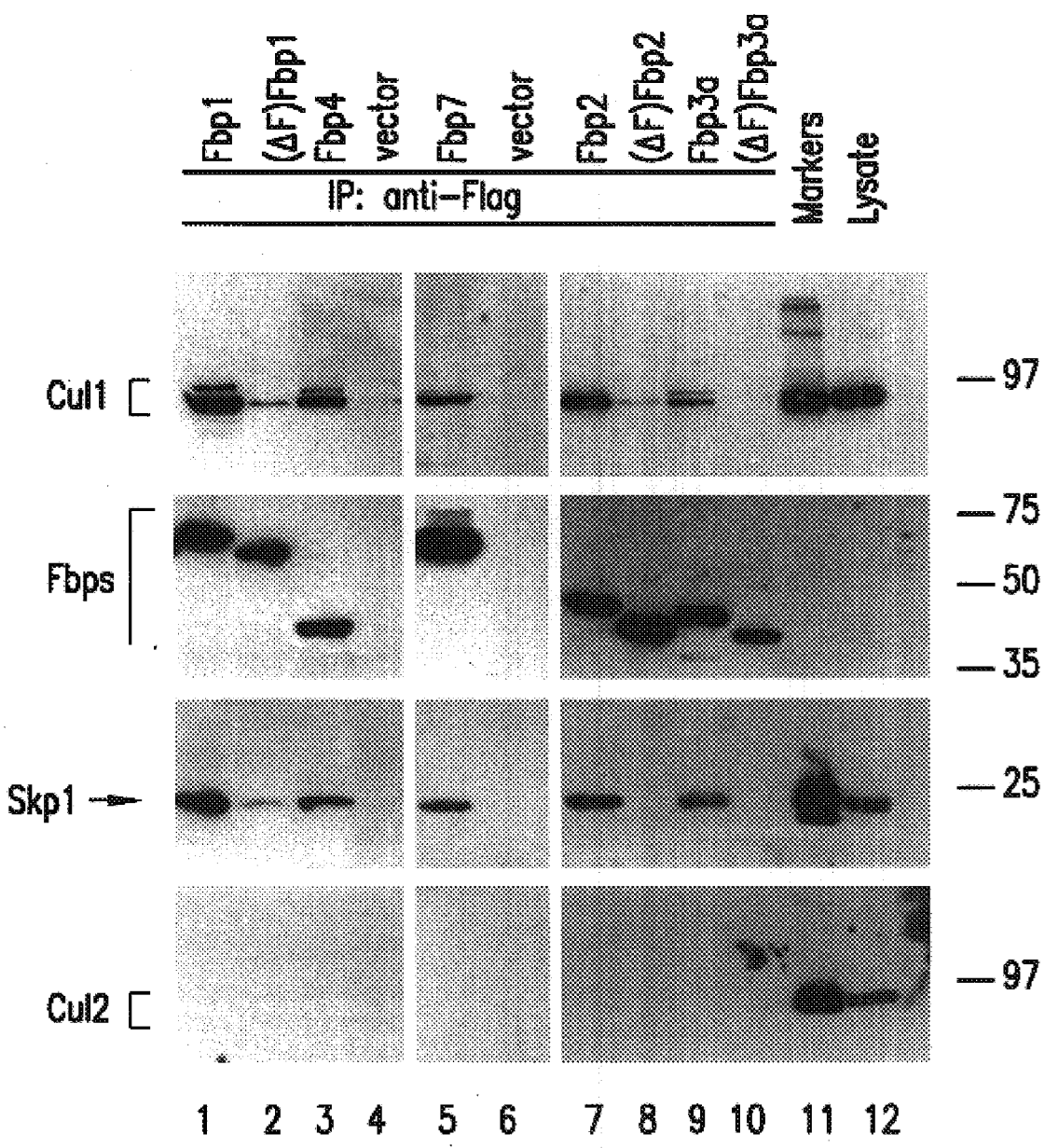

FIG. 30. FBP1, FBP2, FBP3a, FBP4 and FBP7 form novel SCFs with endogenous Skp1 and Cul1 in vivo. HeLa cells were transfected with mammalian expression plasmids encoding Flag-tagged versions of FBP1 (lane 1), (ΔF)FBP1 (lane 2), FBP4 (lane 3), FBP7 (lane 5), FBP2 (lane 7), (ΔF)FBP2 (lane 8), FBP3a (lane 9), (ΔF)FBP3a (lane 10), or with an empty vector (lanes 4 and 6). Cells were lysed and extracts were subjected to immunoprecipitation with a rabbit anti-Flag antibody (lanes 1–8). Immunoprecipitates were then immunoblotted with a mouse anti-Cul1 monoclonal antibody, a rabbit anti-Skp1 polyclonal antibody or a rabbit anti-Cul2 polyclonal antibody, as indicated. The last lane contains 25 μg of extracts from non-transfected HeLa cells; lane 9 contains recombinant Cul1, Skp1, or Cul2 proteins used as markers. The slower migrating bands detected with the antibodies to Cul1 and Cul2 are likely generated by the covalent attachment of a ubiquitin-like molecule to these two cullins, as already described for the yeast cullin Cdc53 and mammalian Cul4a.

Figure 31:
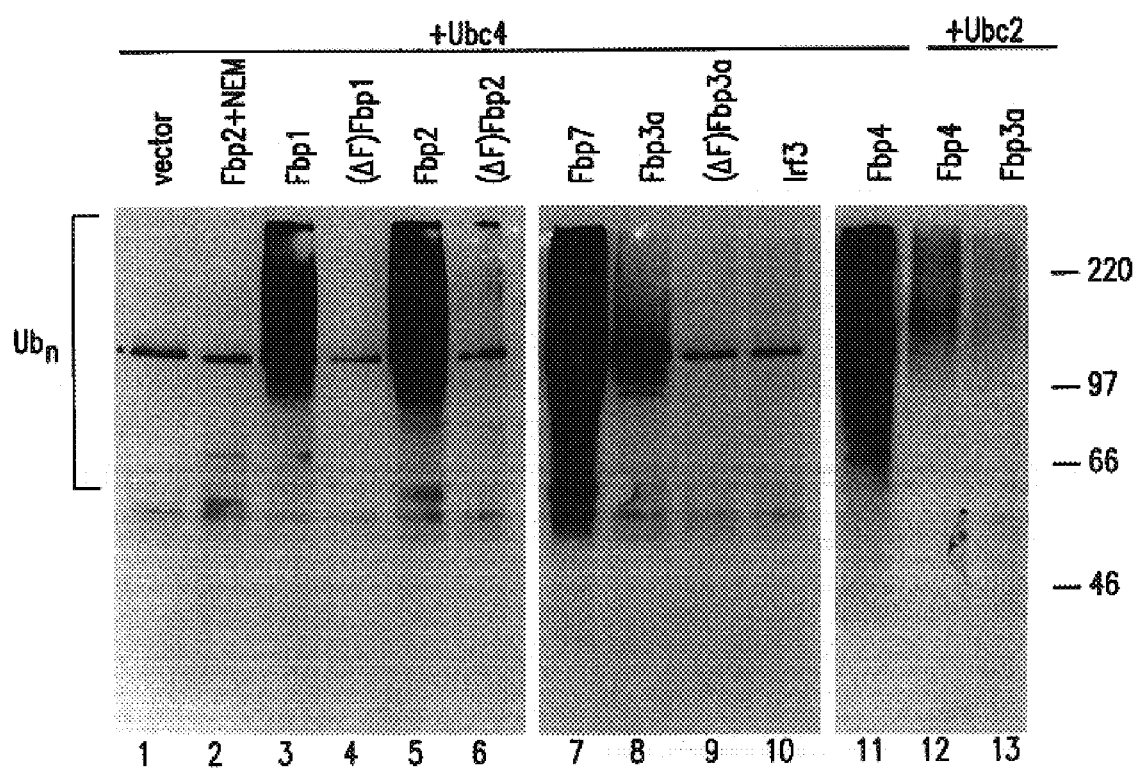

FIG. 31. FBP1, FBP2, FBP3a, FBP4 and FBP7 associate with a ubiquitin ligase activity. HeLa cells were transfected with mammalian expression plasmids encoding human Skp1, Cul1 and Flag-tagged versions of FBP1 (lane 3), (ΔF)FBP1 (lane 4), FBP2 (lanes 2 and 5), (ΔF)FBP2 (lane 6), FBP7 (lane 7), FBP3a (lanes 8 and 13), (ΔF)FBP3a (lane 9), a non relevant Flag-tagged protein (Irf3, lane 10), FBP4 (lanes 11 and 12) or with an empty vector (lane 1). Cells were lysed and extracts were subjected to immunoprecipitation with a rabbit anti-Flag antibody. Immunoprecipitates were incubated in the presence of purified recombinant E1 and Ubc4 (lanes 1–11) or Ubc2 (lanes (12 and 13) and a reaction mix containing biotynilated ubiquitin. Reaction in lane 2 contained also NEM. Ubiquitinated proteins were visualized by blotting with HRP-streptavidin. The bracket on the left side of the panels marks a smear of ubiquitinated proteins produced in the reaction, the asterisk indicates ubiquitin conjugated with E1 that were resistant to boiling.

FIG. 32. Subcellular localization of FBPs. HeLa cells were transfected with mammalian expression plasmids encoding Flag-tagged versions of FBP1 (a–b), FBP2 (c–d), FBP3a (e–f), FBP4 (g–h), (DF)FBP2 (i–j), or (ΔF)FBP3a (k–l). After 24 hours, cells were subjected to immunofluorescence with a rabbit anti-Flag antibody (a, c, e, g, i, k) to stain FBPs and bisbenzimide (b, d, f, h, j, l) to stain nuclei.

Figure 33:
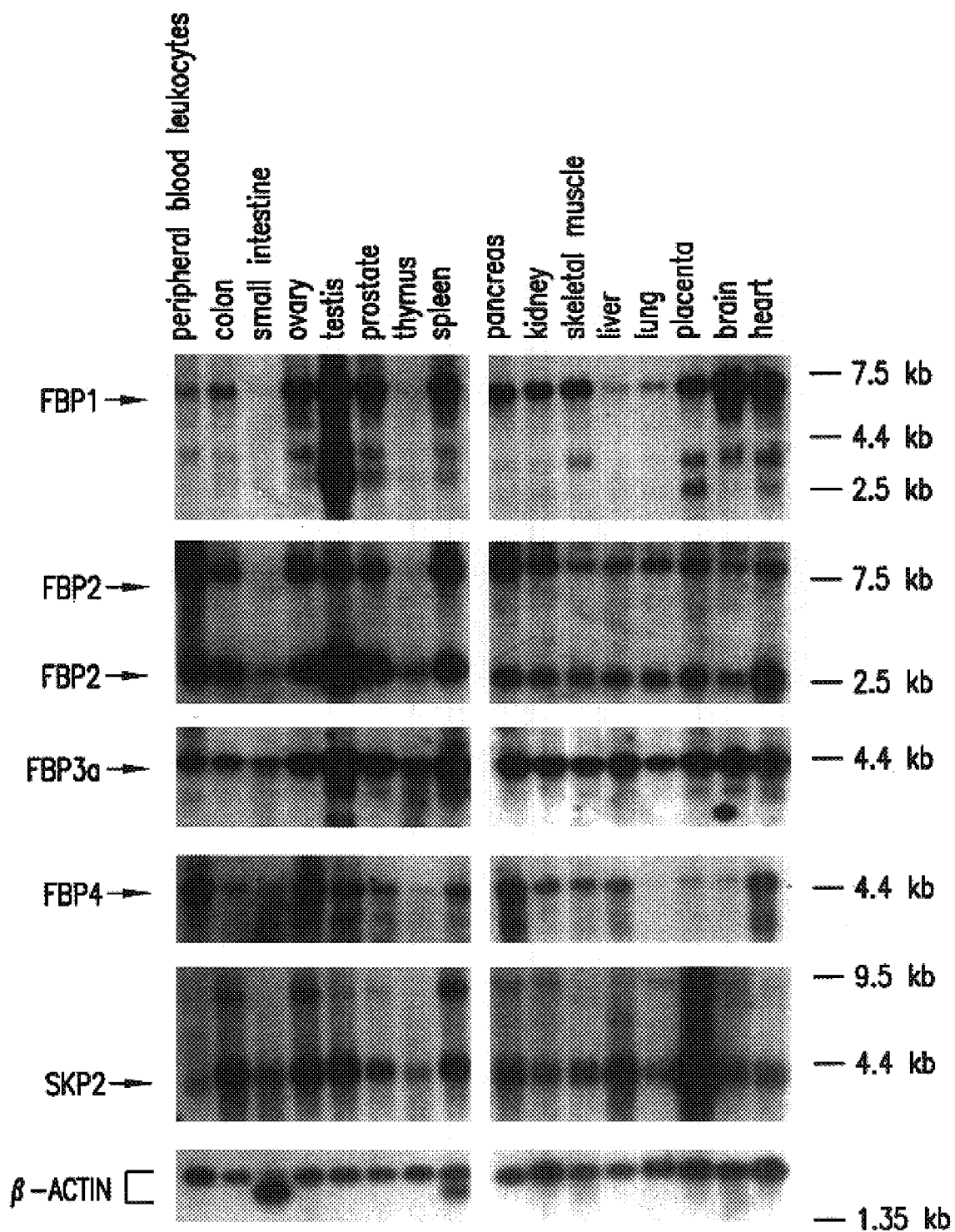

FIG. 33. Abundance of FBP transcripts in human tissues. Membranes containing electrophoretically fractionated poly (A)+ mRNA from different human tissues were hybridized with specific probes prepared form FBP1, FBP2, FBP3a, FBP4, SKP2, and β-ACTIN cDNAs. The arrows on the left side of the figure point to the major transcripts as described in the text.

FIGS. 34A–E. FISH localization of FBP genes. Purified phage DNA containing a genomic probe was labeled with digoxygenin dUTP and detected with Cy3-conjugated antibodies. The signals corresponding to the locus of the genomic probe (red) are seen against the DAPI-Actimomycin D stained normal human chromosomes (blue-white). Panel A shows localization of FBP1 to 10q24, B shows localization of FBP2 to 9q34, C shows localization of FBP3a to 13q22, D shows localization of FBP4 to 5p12, and E shows localization of FBP5 to 6q25-26. Arrows point to FBP-specific FISH signals.

Figure 35A:
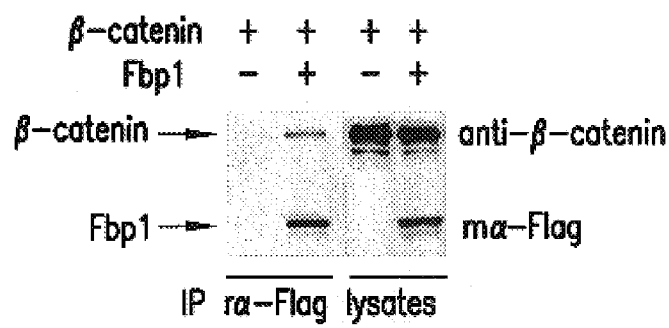
Figure 35B:
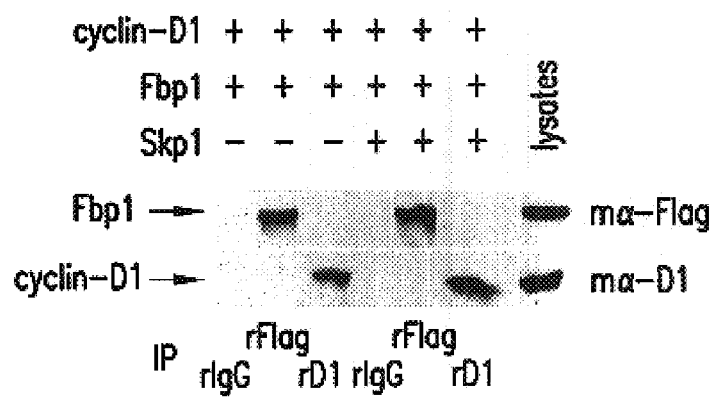
Figure 35C:
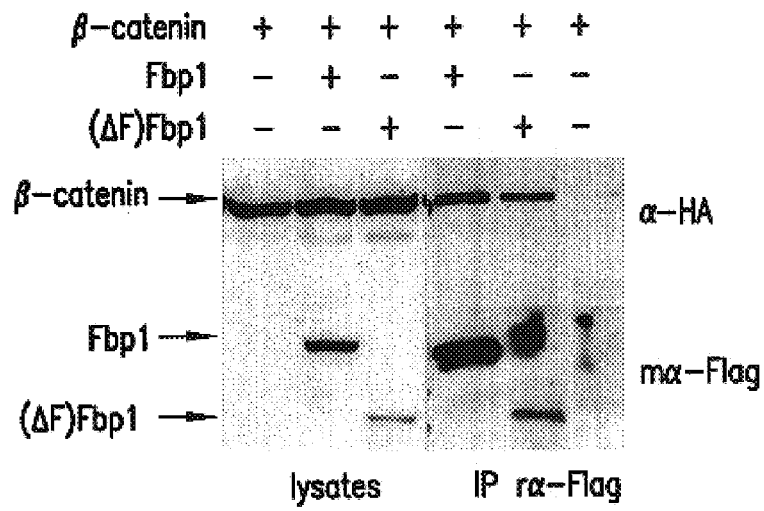

FIGS. 35A–C. FBP1 associates with β-catenin. A. Extracts from baculovirus-infected insect cells expressing either β-catenin alone (lane 1) or in combination with Flag-tagged FBP1 (lane 2) were immunoprecipitated (IP) with a rabbit anti-Flag antibody (rα-Flag), followed by immunoblotting with anti-Flag (mα-Flag) and anti-β-catenin mouse antibodies, as indicated. Lanes 3 and 4 contain 25 μg of extracts from infected insect cells immunoblotted with the same antibodies. B. Extracts from baculovirus-infected insect cells expressing cyclin D1, Flag-FBP1 in the absence (lanes 1–3) or in the presence of Skp1 (lanes 4–6) were immunoprecipitated with normal rabbit IgG (r-IgG, lanes 1 and 4), rabbit anti-Flag antibody (rα-Flag, lanes 2 and 5), or rabbit anti-cyclin D1 antibody (rα-D1, lanes 3 and 6). Immunoprecipitates were then immunoblotted with anti-Flag (mα-Flag) and cyclin D1 (mα-D1) mouse antibodies, as indicated. The last lane contains 25 μg of a representative extract from infected insect cells immunoblotted with the same antibodies. C. 293 cells were transfected with mammalian expression plasmids encoding HA-tagged β-catenin alone or in combination with either Flag-tagged FBP1 or Flag-tagged (ΔF)FBP1. Cells were lysed and extracts were subjected to immunoprecipitation with a rabbit anti-Flag antibody (rα-Flag, lanes 4–6) and immunoblotted with rat anti-HA (α-HA) and mouse anti-Flag (mα-Flag) antibodies, as indicated. The first three lanes contain 25 μg of extracts from transfected 293 cells immunoblotted with the same antibodies. Transfecting high levels of β-catenin expression vector, the associations of β-catenin with FBP1 and (ΔF)FBP1 could be determined independently of β-catenin levels.

Figure 36A:
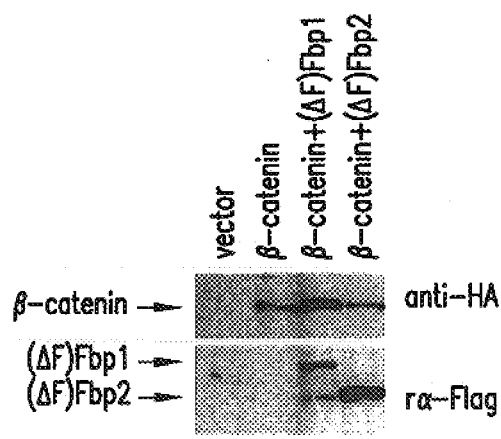
Figure 36B:
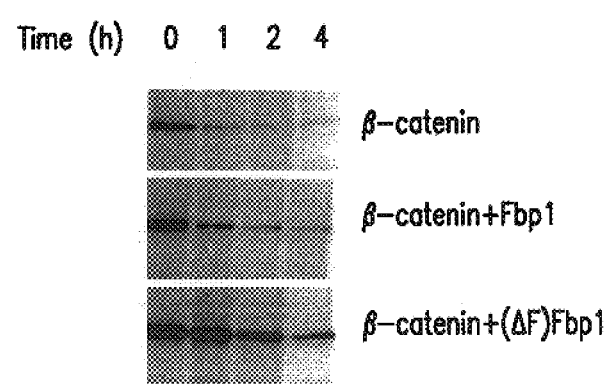

FIGS. 36A–B. Stabilization of β-catenin by a dominant negative (ΔF)FBP1 mutant. A. Human 293 cells were transfected with mammalian expression plasmids encoding HA-tagged β-catenin alone or in combination with either Flag-tagged (ΔF)FBP1 or Flag-tagged (ΔF)FBP2. Cells were lysed and extracts were subjected to immunoblotting with rat anti-HA and rabbit anti-Flag (rα-Flag) antibody, as indicated. B. Pulse chase analysis of β-catenin turnover rate. HA-tagged β-catenin in combination with either an empty vector, FBP1, or (ΔF)FBP1 was co-transfected in 293 cells. 24 hours later cells were labeled with 35S-methionine for 30 minutes and chased with medium for the indicated times. Extracts were then subjected to immunoprecipitation with a rat anti-HA antibody.

Figure 37A:
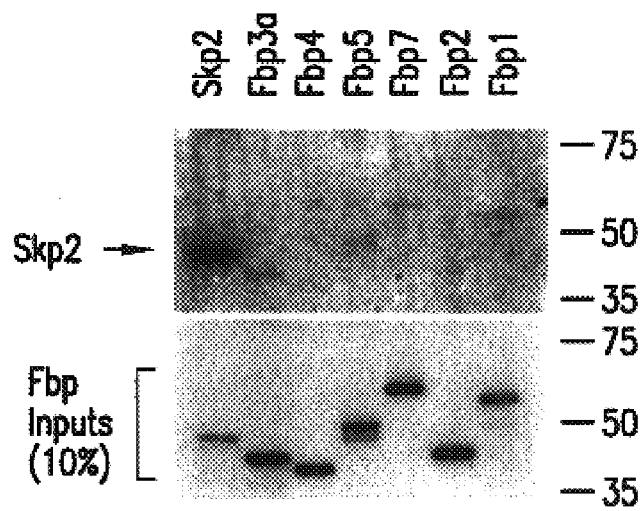
Figure 37B:
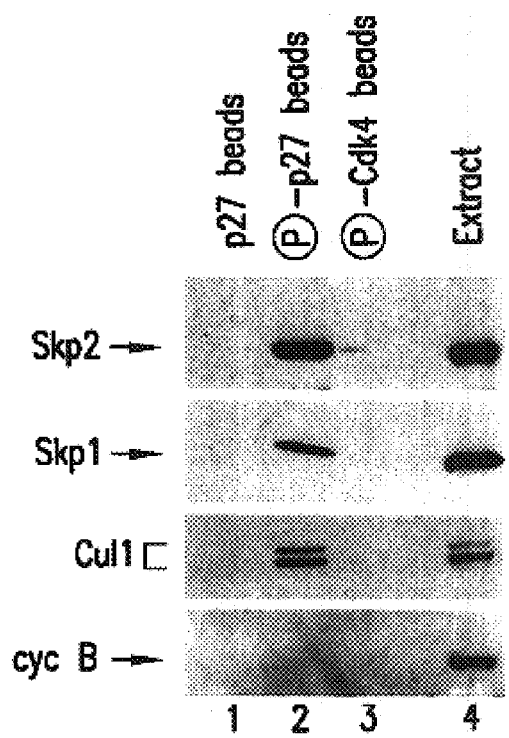
Figure 37C:
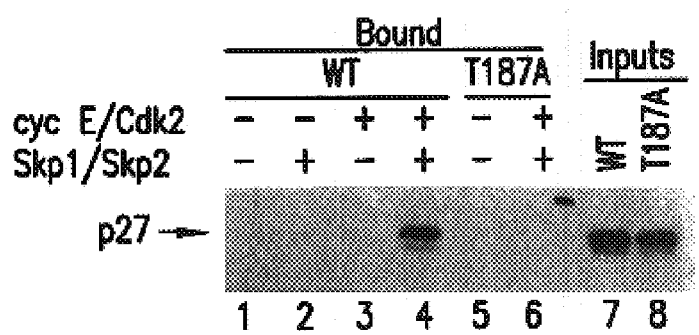

FIGS. 37A–C. Binding of phosphorylated p27 to Skp2. A. A panel of in vitro translated [35S]FBPs were used in binding reactions with beads coupled to the phospho-peptide NAGSVEQT*PKKPGLRRRQT, corresponding to the carboxy terminus of the human p27 with a phosphothreonine at position 187 (T*). Beads were washed with RIPA buffer and bound proteins were eluted and subjected to electrophoresis and autoradiography (Upper Panel). Bottom Panel: 10% of the in vitro translated [35S]FBP inputs. B. HeLa cell extracts were incubated with beads coupled to the phospho-p27 peptide (lane 2), an identical except unphosphorylated p27 peptide (lane 1) or the control phospho-peptide AEIGVGAY*GTVYKARDPHS SEQ ID NO:85, corresponding to an amino terminal peptide of human Cdk4 with a phosphotyrosine at position 17 (Y*) (lane 3). Beads were washed with RIPA buffer and bound proteins were immunoblotted with antibodies to the proteins indicated on the left of each panel. A portion of the HeLa extract (25 μg) was used as a control (lane 4). The slower migrating band in Cul1 is likely generated by the covalent attachment of a ubiquitin-like molecule, as already described for other cullins 48. C. One μl of in vitro translated [35S] wild type p27 (WT, lanes 1–4) or p27(T187A) mutant (T187A, lanes 5–6) were incubated for 30 minutes at 30¼C in 10 μl of kinase buffer. Where indicated, ~2.5 pmole of recombinant purified cyclin E/Cdk2 or ~1 pmole Skp2 (in Skp1/Skp2 complex) were added. Samples were then incubated with 6 μl of Protein-A beads to which antibodies to Skp2 had been covalently linked. Beads were washed with RIPA buffer and bound proteins subjected to electrophoresis and autoradiography. Lanes 1–6: Skp2-bound proteins; Lanes 7 and 8: 7.5% of the in vitro translated [35S] protein inputs.

Figure 38:
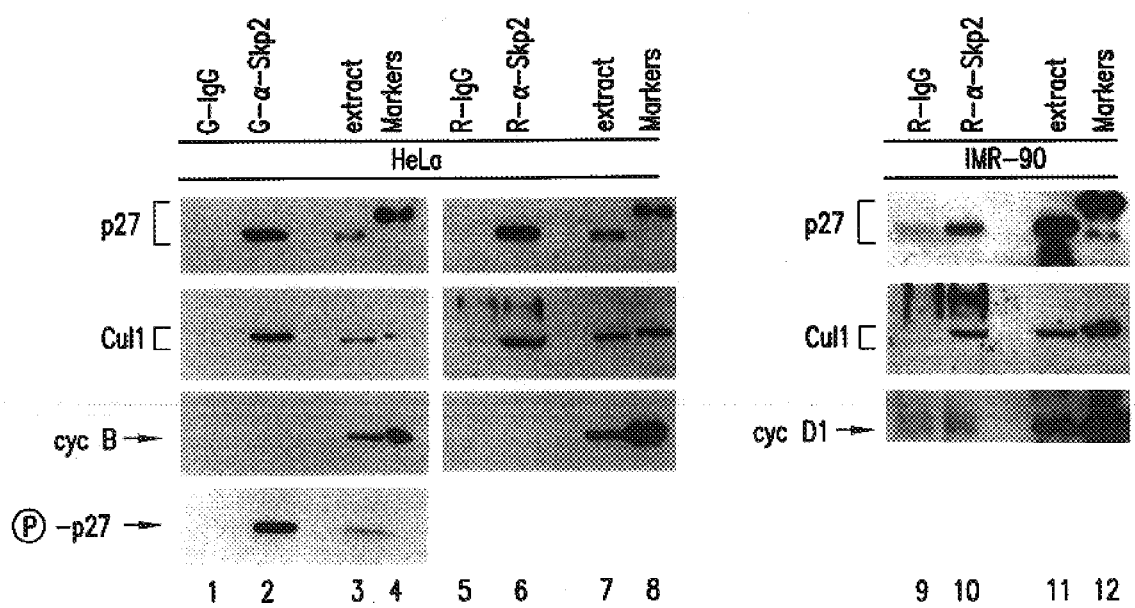

FIG. 38. In vivo binding of Skp2 to p27. Extracts from HeLa cells (lanes 1–2 and 5–6) or IMR90 fibroblasts (lanes 9–10) were immunoprecipitated with different affinity purified (AP) antibodies to Skp2 or with purified control IgG fractions. Lane 1: extract immunoprecipitated with a goat IgG (G-IgG); lane 2: with an AP goat antibody to an N-terminal Skp2 peptide (G-α-Skp2); lanes 5 and 9: with a rabbit IgG (R-IgG); lanes 6 and 10: with an AP rabbit antibody to Skp2 (R-α-Skp2). Immunoprecipitates were immunoblotted with antibodies to the proteins indicated on the left of each panel. Lanes 1–4 in the bottom panel were immunoblotted with a phospho-site p27 specific antibody. Lanes 3, 7, and 11 contain 25 μg of cell extracts; Lanes 4, 8, and 12 contain the relevant recombinant proteins used as markers. The altered migration of some markers is due to the presence of tags on the recombinant proteins.

Figures 39A, 39B:
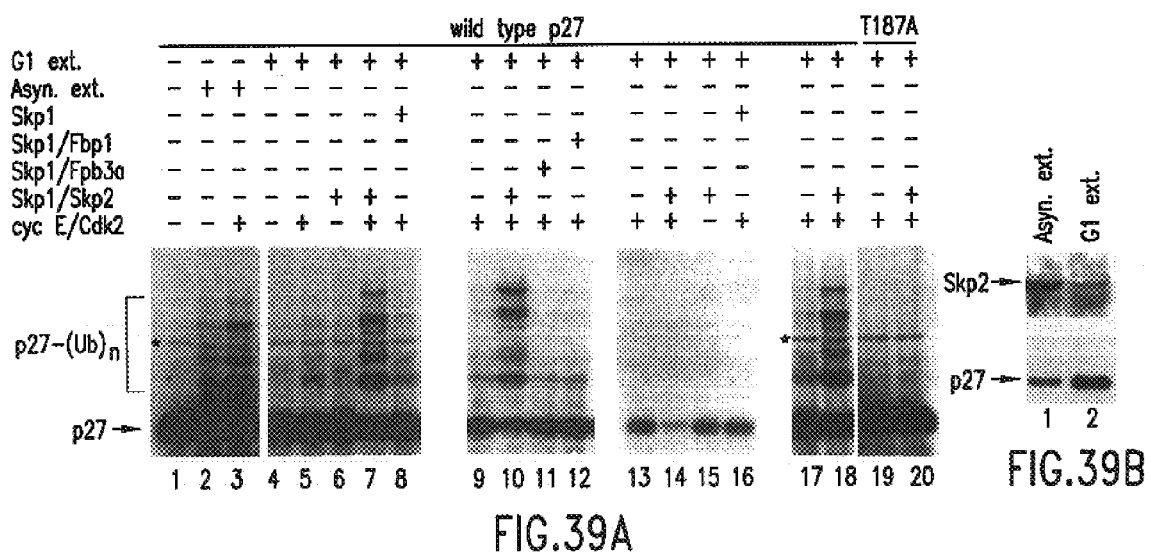

FIGS. 39A–B. Skp2 and cyclin E/Cdk2 complex are rate-limiting for p27 ubiquitination in G1 extracts. A. In vitro ubiquitin ligation (lanes 1–12 and 17–20) and degradation (lanes 13–16) of p27 were carried out with extracts from asynchronously growing (Asyn. ext., lanes 2–3) or G1-arrested (G1 ext., lanes 4–20) HeLa cells. Lane 1 contains no extract. Recombinant purified proteins were supplemented as indicated. Reactions were performed using wild-type p27 (lanes 1–18) or p27(T187A) mutant (T187A, lanes 19–20). Lanes 1–8, 9–12, and 17–20 are from three separate experiments. The bracket on the left side of the panels marks a ladder of bands >27,000 corresponding to polyubiquitinated p27. The asterisk indicates a non-specific band present in most samples. B. Immunoblot analysis of levels of Skp2 and p27 in extracts from asynchronous (lane 1) or G1-arrested (lane 2) HeLa cells.

Figure 40A:
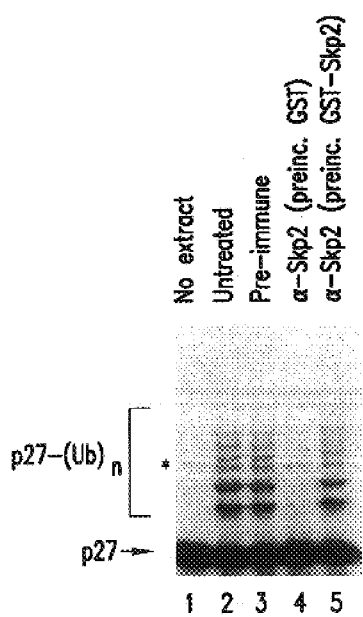
Figure 40B:
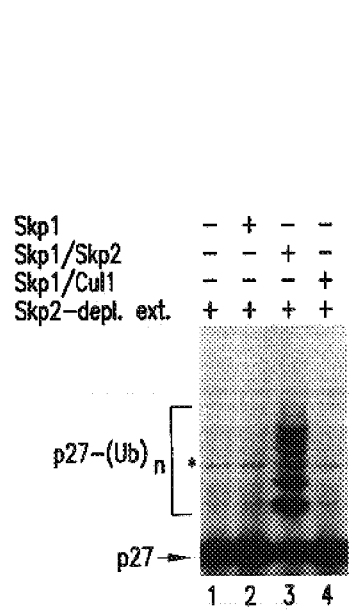
Figure 40C:
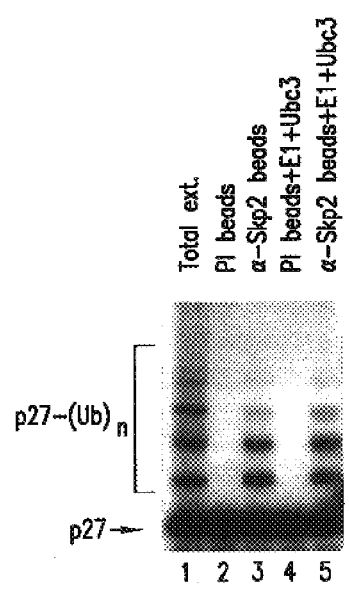

FIGS. 40A–C. Skp2 is required for p27-ubiquitin ligation activity. A. Immunodepletion. Extracts from asynchronous HeLa cells were untreated (lane 2) or immunodepleted with pre-immune serum (lane 3), anti-Skp2 antibody pre-incubated with 2 μg of purified GST (lane 4), or anti-Skp2 antibody pre-incubated with 2 μg of purified GST-Skp2 (lane 5). Lane 1 contains no extract. Samples (30 μg of protein) were assayed for p27 ubiquitination in the presence of cyclin E/Cdk2. The bracket on the left side of the panels marks a ladder of bands >27,000 corresponding to polyubiquitinated p27. The asterisk indicates a non-specific band present in all samples. B. Reconstitution. The restoration of p27 ubiquitination activity in Skp2-immunodepleted extracts was tested by the addition of the indicated purified proteins. All samples contained 30 μg of Skp2-depleted extract (Skp2-depl. ext.) and cyclin E/Cdk2. C. Immunopurification. Extracts from asynchronous HeLa cells were immunoprecipitated with a rabbit anti-Skp2 antibody (lanes 3 and 5) or pre-immune serum (PI, lanes 2 and 4). Total extract (lane 1) and immuno-beads (lanes 2–5) were added with p27, recombinant purified cyclin E/Cdk2 and ubiquitination reaction mix. Samples in lanes 4 and 5 were supplemented with recombinant purified E1 and Ubc3. All samples were then assayed for p27 ubiquitination.

Figure 41A:
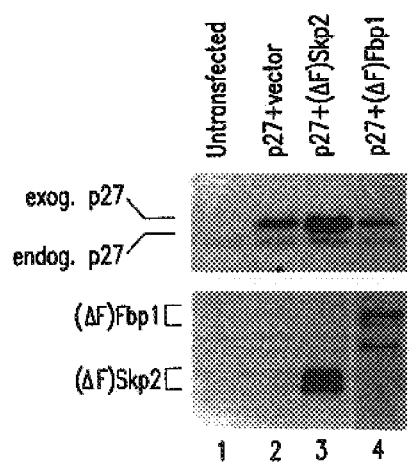
Figure 41B:
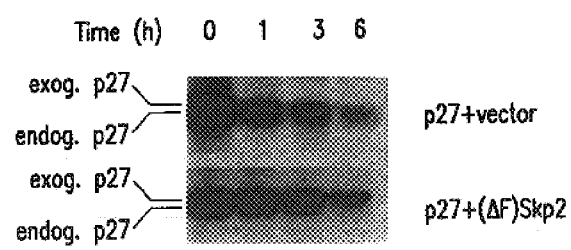

FIGS. 41A–B. In vivo role of Skp2 in p27 degradation. A. Stabilization of p27 by a dominant negative (ΔF)Skp2 mutant in vivo. NIH-3T3 cells were transfected with mammalian expression vectors encoding human p27 alone (lane 2), p27 in combination with either (ΔF)Skp2 (lane 3), or (ΔF)FBP1 (lane 4). Lane 1: untransfected cells. Cells were lysed and extracts were subjected to immunoblotting with antibodies to p27, Skp2 or Flag [to detect Flag-tagged (ΔF)FBP1]. Exogenous human p27 protein migrates more slowly than the endogenous murine p27. B. Pulse chase analysis of p27 turnover rate. Human p27 in combination with either an empty vector, or (ΔF)Skp2 was transfected in NIH-3T3 cells. Twenty-four hours later, cells were labeled with [35S]-methionine for 20 minutes and chased with medium for the indicated times. Extracts were then subjected to immunoprecipitation with a mouse anti-p27 antibody.

Figure 42:
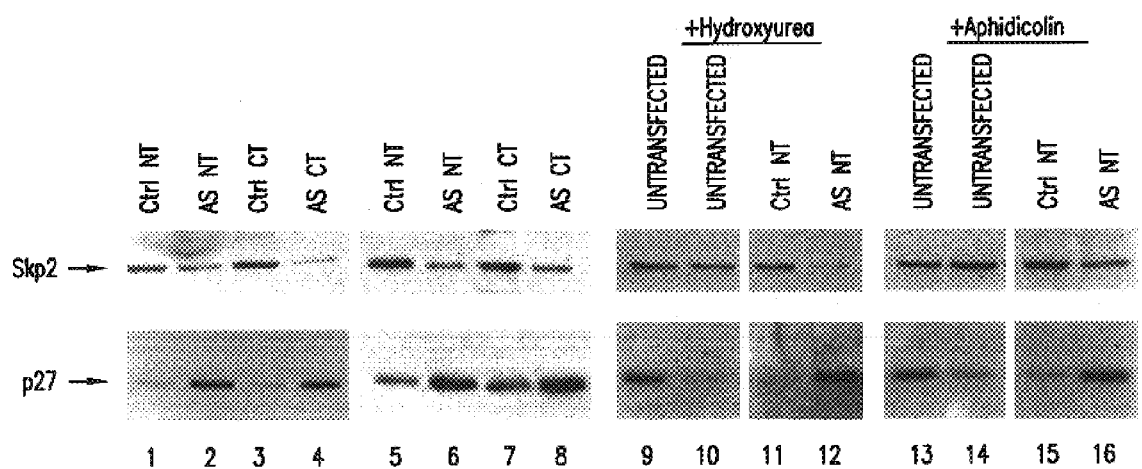

FIG. 42. Stabilization of cellular p27 by antisense oligonucleotides targeting SKP2 mRNA. HeLa cells were treated for 16–18 hours with two different anti-sense oligodeoxynucleotides (AS) targeting two different regions of SKP2 mRNA. Lanes 2, 6, 12 and 16: AS targeting the N-terminal SKP2 region (NT); Lanes 4 and 8: AS targeting the C-terminal SKP2 region (CT); Lanes 1, 3, 5, 7 11 and 15: control oligodeoxynucleotides pairs (Ctrl). Lanes 1–4, and 5–8 are from two separate experiments. Lanes 11–12 and 15–16: HeLa cells were blocked in G1/S with either Hydroxyurea or Aphidicolin treatment respectively, for 24 hours. Cells were then transfected with oligodeoxynucleotides, lysed after 12 hours (before cells had re-entered G1) and immunoblotted with antibodies to Skp2 (top panels) and p27 (bottom panels). Lanes 9 and 13: Untransfected HeLa cells; Lanes 10 and 14: Untransfected HeLa cells treated with drugs as transfected cells.

Figure 43A:
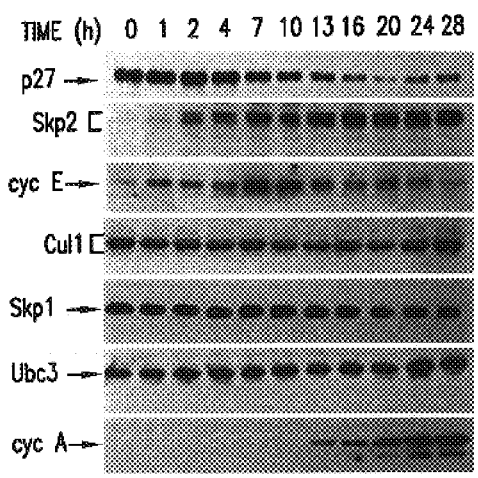
Figure 43B:
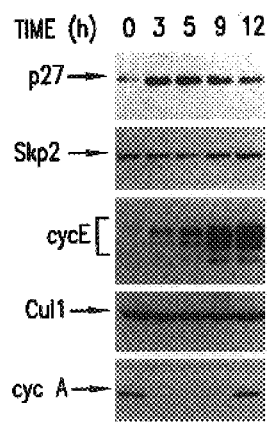
Figure 43C:
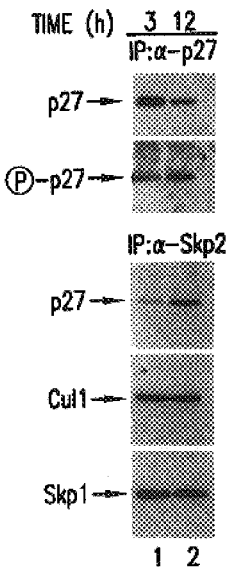

FIGS. 43A–C. Timing of Skp2 action in the process of p27 degradation. A. IMR90 fibroblasts were synchronized in G0/G1 by serum deprivation, reactivated with serum, and sampled at the indicated intervals. Protein extracts were analyzed by immunoblot with the antibodies to the indicated proteins. The Skp2 doublet was likely generated by phosphorylation since was consistently observed using a 12.5% gel only when cell lysis was performed in the presence of okadaic acid. B. HeLa cells blocked in mitosis with nocodazole were shaken off, released in fresh medium and sampled at the indicated intervals. Protein extracts were analyzed by immunoblotting with the antibodies to the indicated proteins. C. Extracts from G1 (3 hours after release from nocodazole block) (lane 1) and S-phase (12 hours after release from the nocodazole block) (lane 2) HeLa cells were either immunoprecipitated with an anti-p27 antibody (top two panels) or with an anti-Skp2 antibody (bottom three panels) and then immunoblotted with the antibodies to the indicated proteins.

Figure 44A:
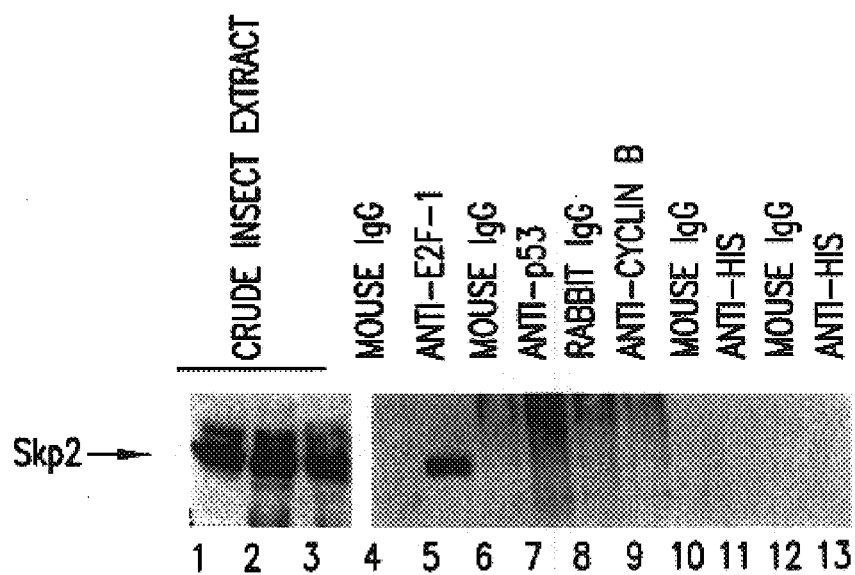
Figure 44B:
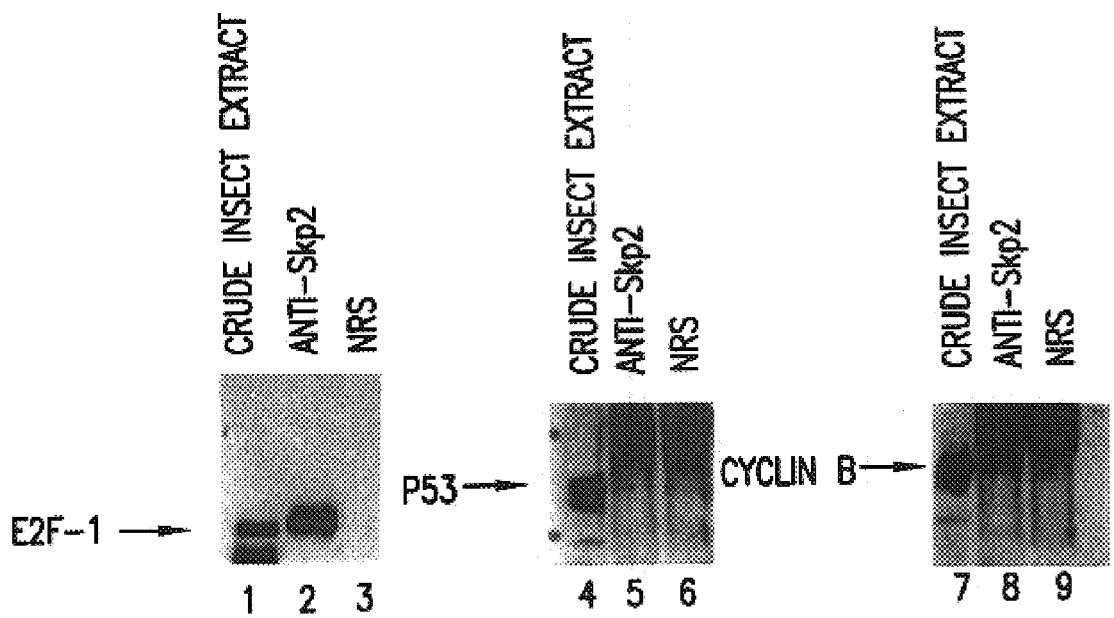
Figure 44C:
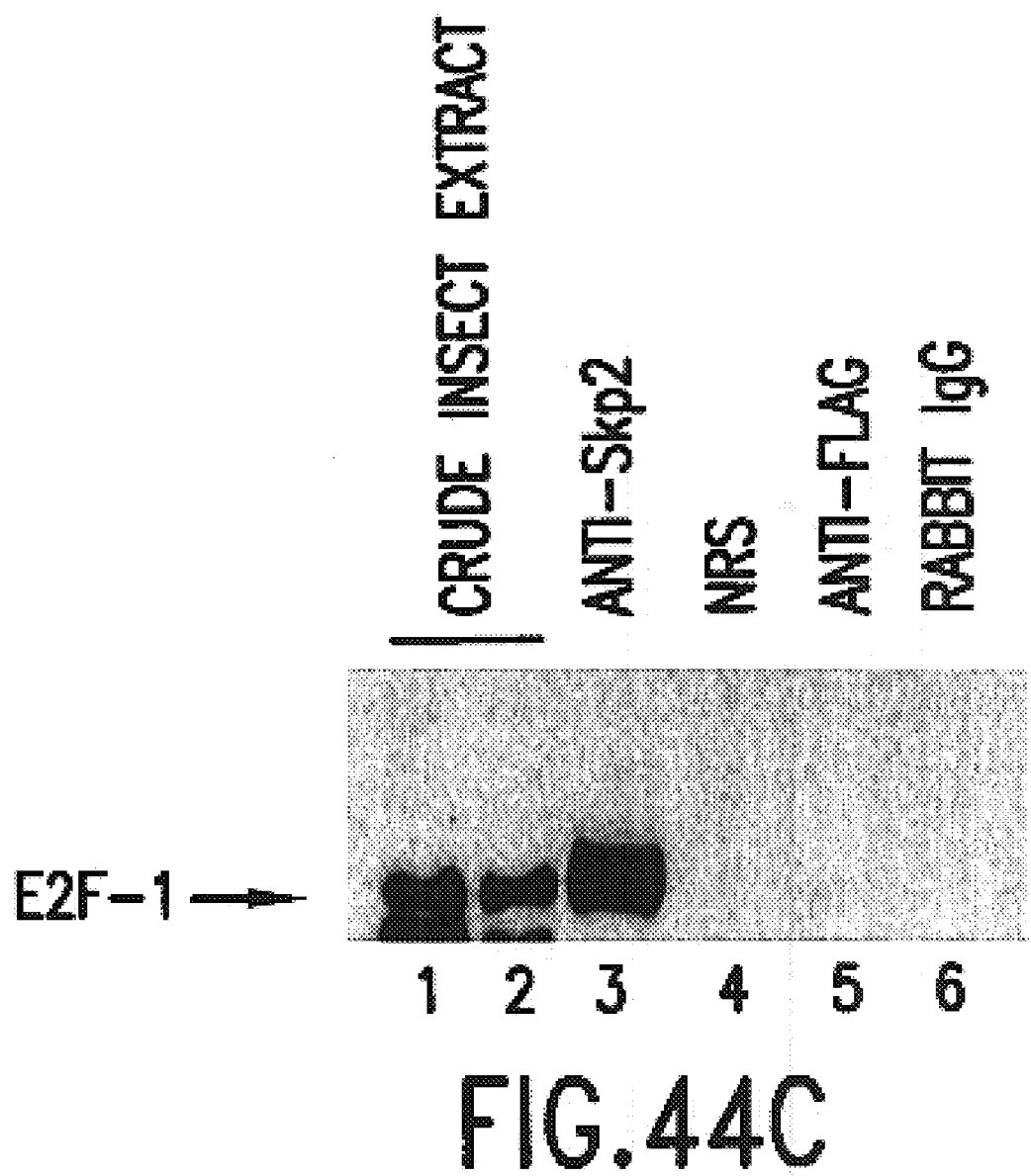

FIGS. 44A–C. Western blot analysis of Skp2/E2F interaction assay. Details of the Western Blot experiments are given in the Example in Section 9.

5. DETAILED DESCRIPTION OF THE INVENTION

The present invention relates to novel F-box proteins and to novel substrates of F-box proteins. The present invention relates to screening assays designed to identify substrates of the novel F-box proteins and to identify small molecules and compounds which modulate the interaction and/or activity of the F-box proteins and their substrates.

The present invention relates to screening assays to identify substrates of the novel F-box proteins and to identify potential therapeutic agents. The present invention further relates to screening assays based on the identification of novel substrates of both novel and known F-box proteins. The screening assays of the present invention may be used to identify potential therapeutic agents which may be used in protocols and as pharmaceutical compositions designed to target the novel ubiquitin ligases and interactions with their substrates for the treatment of proliferative disorders. In one particular embodiment the present invention relates to screening assays and potential therapeutic agents which target the interaction of FBP with novel substrates β-catenin, p27 and E2F as identified by Applicants.

The invention further encompasses the use of nucleotides encoding the novel F-box proteins, proteins and peptides, as well as antibodies to the novel ubiquitin ligases (which can, for example, act as agonists or antagonists), antagonists that inhibit ubiquitin ligase activity or expression, or agonists that activate ubiquitin ligase activity or increase its expression. In addition, nucleotides encoding the novel ubiquitin ligases and proteins are useful for the identification of compounds which regulate or mimic their activity and therefore are potentially effective in the treatment of cancer and tumorigenesis.

In particular, the invention described in the subsections below encompasses FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 polypeptides or peptides corresponding to functional domains of the novel ubiquitin ligases (e.g., the F-box motif, the substrate binding domain, and leucine-rich repeats), mutated, truncated or deleted (e.g. with one or more functional domains or portions thereof deleted), ubiquitin ligase fusion proteins, nucleotide sequences encoding such products, and host cell expression systems that can produce such ubiquitin ligase products.

The present invention provides methods of screening for peptides and proteins that interact with novel components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22. FBP23, FBP24, and FBP25 or derivatives, fragments or analogs thereof. Preferably, the method of screening is a yeast two-hybrid assay system or a variation thereof, as further described below. Derivatives (e.g., fragments) and analogs of a protein can be assayed for binding to a binding partner by any method known in the art, for example, the modified yeast two-hybrid assay system described below, immunoprecipitation with an antibody that binds to the protein in a complex followed by analysis by size fractionation of the immunoprecipitated proteins (e.g., by denaturing or nondenaturing polyacrylamide gel electrophoresis), Western analysis, non-denaturing gel electrophoresis, etc.

The present invention relates to screening assays to identify agents which modulate the activity of the novel ubiquitin ligases. The invention encompasses both in vivo and in vitro assays to screen small molecules, compounds, recombinant proteins, peptides, nucleic acids, antibodies etc. which modulate the activity of the novel ubiquitin ligases and thus, identify potential therapeutic agents for the treatment of proliferative or differentiative disorders. In one embodiment, the present invention provides methods of screening for proteins that interact with the novel ubiquitin ligases.

The invention also encompasses antibodies and anti-idiotypic antibodies, antagonists and agonists, as well as compounds or nucleotide constructs that inhibit expression of the ubiquitin ligase gene (transcription factor inhibitors, antisense and ribozyme molecules, or gene or regulatory sequence replacement constructs), or promote expression of the ubiquitin ligase (e.g., expression constructs in which ubiquitin ligase coding sequences are operatively associated with expression control elements such as promoters, promoter/enhancers, etc.). The invention also relates to host cells and animals genetically engineered to express the human (or mutants thereof) or to inhibit or "knock-out" expression of the animal's endogenous ubiquitin ligase.

Finally, the ubiquitin ligase protein products and fusion protein products, (i.e., fusions of the proteins or a domain of the protein, e.g., F-box motif), antibodies and anti-idiotypic antibodies (including Fab fragments), antagonists or agonists (including compounds that modulate the ubiquitization pathway can be used for therapy of proliferative or differentiative diseases. Thus, the invention also encompasses pharmaceutical formulations and methods for treating cancer and tumorigenesis.

Various aspects of the invention are described in greater detail in the subsections below.

5.1 FBP GENES

The invention provides nucleic acid molecules comprising seven novel nucleotide sequences, and fragments thereof, FBP1, FBP2, FBP3a, FBP4, FBP5, FBP6, and FBP7, nucleic acids which are novel genes identified by the interaction of their gene products with Skp1, a component of the ubiquitin ligase complex. The invention further provides fourteen novel nucleic acid molecules comprising the nucleotide sequences of FBP1, FBP2, FBP3a, FBP3b, FBP4, FBP5, FBP6, FBP7, FBP8, FBP11, FBP12, FBP13, FBP14, FBP15, FBP17, FBP18, FBP20, FBP21, FBP22, FBP23, FBP24, and FBP25, which Nucleic acid sequences of the identified FBP genes are described herein.

As used herein, "an FBP gene" refers to:

(a) a nucleic acid molecule containing the DNA sequences of FBP1, shown in FIG. 3 (SEQ ID NO:1), the DNA sequences of FBP2, shown in FIG. 4 (SEQ ID NO:3), the DNA sequences of FBP3a, shown in FIG. 5 (SEQ ID NO:5), the DNA sequences of FBP3b, shown in FIG. 6 (SEQ ID NO:23), the DNA sequences of FBP4, shown in FIG. 7 (SEQ ID NO:7), the DNA sequences of FBP5, shown in FIG. 8 (SEQ ID NO:9), the DNA sequences of FBP6, shown in FIG. 9 (SEQ ID NO:11), the DNA sequences of FBP7, shown in FIG. 10 (SEQ ID NO:13), the DNA sequences of FBP8, shown in FIG. 11 (SEQ ID NO:25), the DNA sequences of FBP9, shown in FIG. 12 (SEQ ID NO:27), the DNA sequences of FBP10, shown in FIG. 13 (SEQ ID NO:29), the DNA sequences of FBP11, shown in FIG. 14 (SEQ ID NO:31), the DNA sequences of FBP12, shown in FIG. 15 (SEQ ID NO:33), the DNA sequences of FBP13, shown in FIG. 16 (SEQ ID NO:35), the DNA sequences of FBP14, shown in FIG. 17 (SEQ ID NO:37), the DNA sequences of FBP15, shown in FIG. 18 (SEQ ID NO:39), the DNA sequences of FBP16, shown in FIG. 19 (SEQ ID NO:41), the DNA sequences of FBP17, shown in FIG. 20 (SEQ ID NO:43), the DNA sequences of FBP18, shown in FIG. 21 (SEQ ID NO:45), the DNA sequences of FBP19, shown in FIG. 22 (SEQ ID NO:47), the NA sequences of FBP20, shown in FIG. 23 (SEQ ID NO:49), the DNA sequences of FBP21, shown in FIG. 24 (SEQ ID NO:51), the DNA sequences of FBP22, shown in FIG. 25 (SEQ ID NO:53), the DNA sequences of FBP23, shown in FIG. 26 (SEQ ID NO:55), the DNA sequences of FBP24, shown in FIG. 27 (SEQ ID NO:57), the DNA sequences of FBP25, shown in FIG. 28 (SEQ ID NO:59).

(b) any DNA sequence that encodes a polypeptide containing: the amino acid sequence of FBP1 shown in FIG. 3A (SEQ ID NO:2), the amino acid sequence of FBP2, shown in FIG. 4A (SEQ ID NO:4), the amino acid sequence of FBP3a shown in FIG. 5A (SEQ ID NO:6), the amino acid sequence of FBP3b shown in FIG. 6A (SEQ ID NO:24), the amino acid sequence of FBP4 shown in FIG. 7A (SEQ ID NO:8), the amino acid sequence of FBP5 shown in FIG. 8A (SEQ ID NO:10), or the amino acid sequence of FBP6 shown in FIG. 9A (SEQ ID NO:12), the amino acid sequences of FBP7, shown in FIG. 10 (SEQ ID NO:14), the amino acid sequences of FBP8, shown in FIG. 11 (SEQ ID NO:26), the amino acid sequences of FBP9, shown in FIG. 12 (SEQ ID NO:28), the amino acid sequences of FBP10, shown in FIG. 13 (SEQ ID NO:30), the amino acid sequences of FBP11, shown in FIG. 14 (SEQ ID NO:32), the amino acid sequences of FBP12, shown in FIG. 15 (SEQ ID NO:34), the amino acid sequences of FBP13, shown in FIG. 16 (SEQ ID NO:36), the amino acid sequences of FBP14, shown in FIG. 17 (SEQ ID NO:38), the amino acid sequences of FBP15, shown in FIG. 18 (SEQ ID NO:40), the amino acid sequences of FBP16, shown in FIG. 19 (SEQ ID NO:42), the amino acid sequences of FBP17, shown in FIG. 20 (SEQ ID NO:44), the amino acid sequences of FBP18, shown in FIG. 21 (SEQ ID NO:46), the amino acid sequences of FBP19, shown in FIG. 22 (SEQ ID NO:48), the amino acid sequences of FBP20, shown in FIG. 23 (SEQ ID NO:50), the amino acid sequences of FBP21, shown in FIG. 24 (SEQ ID NO:52), the amino acid sequences of FBP22, shown in FIG. 25 (SEQ ID NO:54), the amino acid sequences of FBP23, shown in FIG. 26 (SEQ ID NO:56), the amino acid sequences of FBP24, shown in FIG. 27 (SEQ ID NO:58), the amino acid sequences of FBP25, shown in FIG. 28 (SEQ ID NO:60).

(c) any DNA sequence that hybridizes to the complement of the DNA sequences that encode any of the amino acid sequences of (SEQ ID NO: 2, 4, 6, 8, 10, 12 or 14) or FIG. 15 under highly stringent conditions, e.g., hybridization to filter-bound DNA in 0.5 M NaHPO4, 7% sodium dodecyl sulfate (SDS), 1 mM EDTA at 65 C, and washing in 0.1×SSC/0.1% SDS at 68 C (Ausubel F. M. et al., eds., 1989, Current Protocols in Molecular Biology, Vol. I, Green Publishing Associates, Inc., and John Wiley & sons, Inc., New York, at p. 2.10.3); and/or (d) any DNA sequence that hybridizes to the complement of the DNA sequences that encode any of the amino acid sequences in (SEQ ID NO: 2, 4, 6, 8, 10, 12 or 14) or FIG. 15, under less stringent conditions, such as moderately stringent conditions, e.g., washing in 0.2× SSC/0.1% SDS at 42 C (Ausubel et al., 1989, supra), and encodes a gene product functionally equivalent to an FBP gene product.

It is understood that the FBP gene sequences of the present invention do not encompass the previously described genes encoding other mammalian F-box proteins, Skp2, Elongin A, Cyclin F, mouse Md6, (see Pagano, 1997, supra; Zhang et al., 1995, supra; Bai et al., 1996, supra; Skowyra et al., 1997, supra). It is further understood that the nucleic acid molecules of the invention do not include nucleic acid molecules that consist solely of the nucleotide sequence in GenBank Accession Nos. AC002428, AI457595, AI05408, H66467, T47217, H38755, THC274684, AI750732, AA976979, AI571815, T57296, Z44228, Z45230, N42405, AA018063, AI751015, AI400663, T74432, AA402415, AI826000, AI590138, AF174602, Z45775, AF174599, THC288870, AI017603, AF174598, THC260994, AI475671, AA768343, AF174595, THC240016, N70417, T10511, AF174603, EST04915, AA147429, AI192344, AF174594, AI147207, AI279712, AA593015, AA644633, AA335703, N26196, AF174604, AF053356, AF174606, AA836036, AA853045, AI479142, AA772788, AA039454, AA397652, AA463756, AA007384, AA749085, AI640599, THC253263, AB020647, THC295423, AA434109, AA370939, AA215393, THC271423, AF052097, THC288182, AL049953, CAB37981, AL022395, AL031178, THC197682, and THC205131.

FBP sequences of the present invention are derived from a eukaryotic genome, preferably a mammalian genome, and more preferably a human or murine genome.

Thus, the nucleotide sequences of the present invention do not encompass those derived from yeast genomes. In a specific embodiment, the nucleotides of the present invention encompass any DNA sequence derived from a mammalian genome which hybridizes under highly stringent conditions to SEQ ID NO: 1, 3, 5, 7, 9, 11 or 13, or to DNA sequence shown in FIG. 14, encodes a gene product which contains an F-box motif and binds to Skp1. In a specific embodiment, the nucleotides of the present invention encompass any DNA sequence derived from a mammalian genome which hybridize under highly stringent conditions to SEQ ID NO: 1, 3, 5, 7, 9, 11 or 13 encodes a gene product which contains an F-box motif and another domain selected from the group comprising WD-40, leucine rich region, leucine zipper motif, or other protein-protein interaction domain, and binds to Skp-1 and is at least 300 or 400 nucleotides in length.

FBP sequences can include, for example, either eukaryotic genomic DNA (cDNA) or cDNA sequences. When referring to a nucleic acid which encodes a given amino acid sequence, therefore, it is to be understood that the nucleic acid need not only be a cDNA molecule, but can also, for example, refer to a cDNA sequence from which an mRNA species is transcribed that is processed to encode the given amino acid sequence.

As used herein, an FBP gene may also refer to degenerate variants of DNA sequences (a) through (d).

The invention also includes nucleic acid molecules derived from mammalian nucleic acids, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37 C (for 14-base oligos), 48 C (for 17-base oligos), 55 C (for 20-base oligos), and 60 C (for 23-base oligos). These nucleic acid molecules may encode or act as FBP gene antisense molecules, useful, for example, in FBP gene regulation (for and/or as antisense primers in amplification reactions of FBP gene nucleic acid sequences). With respect to FBP gene regulation, such techniques can be used to regulate, for example, an FBP-regulated pathway, in order to block cell proliferation associated with cancer. Further, such sequences may be used as part of ribozyme and/or triple helix sequences, also useful for FBP gene regulation. Still further, such molecules may be used as components of diagnostic methods whereby, for example, the presence of a particular FBP allele responsible for causing an FBP-related disorder, e.g., proliferative or differentiative disorders such as tumorigenesis or cancer, may be detected.

The invention also encompasses:
(a) DNA vectors that contain any of the foregoing FBP coding sequences and/or their complements (i.e., antisense);
(b) DNA expression vectors that contain any of the foregoing FBP coding sequences operatively associated with a regulatory element that directs the expression of the coding sequences; and
(c) genetically engineered host cells that contain any of the foregoing FBP coding sequences operatively associated with a regulatory element that directs the expression of the coding sequences in the host cell.

As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

The invention further includes fragments of any of the DNA sequences disclosed herein.

In one embodiment, the FBP gene sequences of the invention are mammalian gene sequences, with human sequences being preferred.

In yet another embodiment, the FBP gene sequences of the invention are gene sequences encoding FBP gene products containing polypeptide portions corresponding to (that is, polypeptide portions exhibiting amino acid sequence similarity to) the amino acid sequence depicted in FIGS. 2, 4–9 or 15, wherein the corresponding portion exhibits greater than about 50% amino acid identity with the depicted sequence, averaged across the FBP gene product's entire length.

In specific embodiments, F-box encoding nucleic acids comprise the cDNA sequences of SEQ ID NOs: 1, 3, 5, 23, 7, 9, 11, 13, 15, 25, 27, 29, 31, 33, 35, 37, 39, 41, 43, 45, 47, 49, 51, 53, 55, 57, or 59, nucleotide sequence of FIGS. 3B, 4B, 5B, 6B, 7B, 8B, 9B, 10B, 11B, 12B, 13B, 14B, 15B, 16B, 17B, 18B, 19B, 20B, 21B, 22B, 26B, 27B, or 28B, respectively, or the coding regions thereof, or nucleic acids encoding an F-box protein (e.g., a protein having the sequence of SEQ ID NOs: 2, 4, 6, 24, 8, 10, 12, 14, 26, 28, 30, 32, 34, 36, 38, 40, 42, 44, 46, 48, 50, 52, 54, 56, 68, or 60, or as shown in FIGS. 3A, 4A, 5A, 6A, 7A, 8A, 9A, 10A, 11A, 12A, 13A, 14A, 15A, 16A, 17A, 19A, 20A, 21A, 22A, 23A, 24A, 25A, 26A, 27A, or 28A, respectively).

The invention further provides nucleotide fragments of nucleotide sequences encoding FBP1, FBP2, FBP3a, FBP4, FBP5, FBP6, or FBP7 (SEQ ID NOs: 1, 3, 5, 7, 9, 11 and 13, respectively) of the invention. Such fragments consist of at least 8 nucleotides (i.e., a hybridizable portion) of an FBP gene sequence; in other embodiments, the nucleic acids consist of at least 25 (continuous) nucleotides, 50 nucleotides, 100 nucleotides, 150 nucleotides, or 200 nucleotides of an F-box sequence, or a full-length F-box coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of an F-box gene.

The invention further relates to the human genomic nucleotide sequences of nucleic acids. In specific embodiments, F-box encoding nucleic acids comprise the genomic sequences of SEQ ID NOs:1, 3, 5, 7, 9, 11 or 13 or the coding regions thereof, or nucleic acids encoding an FBP protein (e.g., a protein having the sequence of SEQ ID Nos: 5 2, 4, 6, 8, 10, 12 or 14). The invention provides purified nucleic acids consisting of at least 8 nucleotides (i.e., a hybridizable portion) of an FBP gene sequence; in other embodiments, the nucleic acids consist of at least 25 (continuous) nucleotides, 50 nucleotides, 100 nucleotides, 150 nucleotides, or 200 nucleotides of an FBP gene sequence or a full-length FBP gene coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of an FBP gene sequence.

In addition to the human FBP nucleotide sequences disclosed herein, other FBP gene sequences can be identified and readily isolated, without undue experimentation, by molecular biological techniques well known in the art, used in conjunction with the FBP gene sequences disclosed herein. For example, additional human FBP gene sequences at the same or at different genetic loci as those disclosed in SEQ ID Nos: 1, 3, 5, 7, 9, 11 or 13 can be isolated readily. There can exist, for example, genes at other genetic or physical loci within the human genome that encode proteins that have extensive homology to one or more domains of the FBP gene products and that encode gene products functionally equivalent to an FBP gene product. Further, homologous FBP gene sequences present in other species can be identified and isolated readily.

The FBP nucleotide sequences of the invention further include nucleotide sequences that encode polypeptides having at least 30%, 35%, 40%, 45%, 50%, 55%, 60%, 65%, 70%, 75%, 80%, 85%, 90%, 95%, 98%, or higher amino acid sequence identity to the polypeptides encoded by the FBP nucleotide sequences of SEQ ID No. 1, 3, 5, 7, 9, 11 or 13.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of overlapping positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264–2268, modified as in Karlin nd Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, 1988, *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

With respect to identification and isolation of FBP gene sequences present at the same genetic or physical locus as those sequences disclosed herein, such sequences can, for example, be obtained readily by utilizing standard sequencing and bacterial artificial chromosome (BAC) technologies.

With respect to the cloning of an FBP gene homologue in human or other species (e.g., mouse), the isolated FBP gene sequences disclosed herein may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., supra. Further, an FBP gene homologue may be isolated from, for example, human nucleic acid, by performing PCR using two degenerate oligonucleotide primer pools designed on the basis of amino acid sequences within any FBP gene product disclosed herein.

The PCR product may be subcloned and sequenced to ensure that the amplified sequences represent the sequences of an FBP gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the FBP gene, such as, for example, blood samples or brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., supra.

FBP gene sequences may additionally be used to identify mutant FBP gene alleles. Such mutant alleles may be isolated from individuals either known or proposed to have a genotype that contributes to the symptoms of an FBP gene disorder, such as proliferative or differentiative disorders involved in tumorigenesis or causing cancer, for example. Mutant alleles and mutant allele products may then be utilized in the therapeutic, diagnostic and prognostic systems described below. Additionally, such FBP gene sequences can be used to detect FBP gene regulatory (e.g., promoter) defects which can be associated with an FBP disorder, such as proliferative or differentiative disorders involved in tumorigenesis or causing cancer, for example.

FBP alleles may be identified by single strand conformational polymorphism (SSCP) mutation detection techniques, Southern blot, and/or PCR amplification techniques. Primers can routinely be designed to amplify overlapping regions of the whole FBP sequence including the promoter region. In one embodiment, primers are designed to cover the exon-intron boundaries such that, first, coding regions can be scanned for mutations. Genomic DNA isolated from lymphocytes of normal and affected individuals is used as PCR template. PCR products from normal and affected individuals are compared, either by single strand conformational polymorphism (SSCP) mutation detection techniques and/or by sequencing. SSCP analysis can be performed as follows: 100 ng of genomic DNA is amplified in a 10 $\mu$l reaction, adding 10 pmols of each primer, 0.5 U of Taq DNA polymerase (Promega), 1 $\mu$Ci of $\alpha$-[32P]dCTP (NEN; specific activity, 3000 Ci/mmol), in 2.5 $\mu$M dNTPs (Pharmacia), 10 mM Tris-HCl (pH 8.8), 50 mM KCl, 1 mM MgC12, 0.01% gelatin, final concentration. Thirty cycles of denaturation (94° C.), annealing (56° C. to 64° C., depending on primer melting temperature), and extension (72° C.) is carried out in a thermal-cycler (MJ Research, Boston, Mass., USA), followed by a 7 min final extension at 72° C. Two microliters of the reaction mixture is diluted in 0.1% SDS, 10 mM EDTA and then mixed 1:1 with a sequencing stop solution containing 20 mM NaOH. Samples are heated at 95 C for 5 min, chilled on ice for 3 min and then 3 l will be loaded onto a 6% acrylamide/TBE gel containing 5% (v/v) glycerol. Gels are run at 8 W for 12–15 h at room temperature. Autoradiography is performed by exposure to film at −70 C with intensifying screens for different periods of time. The mutations responsible for the loss or alteration of function of the mutant FBP gene product can then be ascertained.

Alternatively, a cDNA of a mutant FBP gene may be isolated, for example, using PCR. In this case, the first cDNA strand may be synthesized by hybridizing an oligo-dT oligonucleotide to mRNA isolated from tissue known or suspected to be expressed in an individual putatively carrying the mutant FBP allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant FBP allele to that of the normal FBP allele, the mutation(s) responsible for the loss or alteration of function of the mutant FBP gene product can be ascertained.

Alternatively, a genomic library can be constructed using DNA obtained from an individual suspected of or known to carry a mutant FBP allele, or a cDNA library can be constructed using RNA from a tissue known, or suspected, to express a mutant FBP allele. An unimpaired FBP gene or any suitable fragment thereof may then be labeled and used as a probe to identify the corresponding mutant FBP allele in such libraries. Clones containing the mutant FBP gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant FBP allele in an individual suspected of or known to carry such a mutant allele. In this manner, gene products made by the putatively mutant tissue may be expressed and screened using standard antibody screening techniques in conjunction with antibodies raised against the normal FBP gene product, as described, below, in Section 5.3. (For screening techniques, see, for example, Harlow and Lane, eds., 1988, "Antibodies: A Laboratory Manual", Cold Spring Harbor Press, Cold Spring Harbor.)

Nucleic acids encoding derivatives and analogs of FBP proteins, and FBP antisense nucleic acids can be isolated by the methods recited above. As used herein, a "nucleic acid encoding a fragment or portion of an F-box protein" shall be construed as referring to a nucleic acid encoding only the recited fragment or portion of the FBP and not the other contiguous portions of the FBP protein as a continuous sequence.

Fragments of FBP gene nucleic acids comprising regions conserved between (i.e., with homology to) other FBP gene nucleic acids, of the same or different species, are also provided. Nucleic acids encoding one or more FBP domains can be isolated by the methods recited above.

In cases where an FBP mutation results in an expressed gene product with altered function (e.g., as a result of a missense or a frameshift mutation), a polyclonal set of anti-FBP gene product antibodies are likely to cross-react with the mutant FBP gene product. Library clones detected via their reaction with such labeled antibodies can be purified and subjected to sequence analysis according to methods well known to those of skill in the art.

5.2 PROTEINS AND POLYPEPTIDES OF FBP GENES

The amino acid sequences depicted in FIGS. 1, 2, and parts B of FIGS. 3 to 28 represent FBP gene products. The FBP1 gene product, sometimes referred to herein as a "FBP1 protein", includes those gene products encoded by the FBP1 gene sequences described in Section 5.1, above. Likewise, the FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 gene products, referred to herein as an FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 proteins, include those gene products encoded by the FBP2, FBP3, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 genes. In accordance with the present invention, the nucleic acid sequences encoding the FBP gene products are derived from eukaryotic genomes, including mammalian genomes. In a preferred embodiment the nucleic acid sequences encoding the FBP gene products are derived from human or murine genomes.

FBP gene products, or peptide fragments thereof, can be prepared for a variety of uses. For example, such gene products, or peptide fragments thereof, can be used for the generation of antibodies, in diagnostic and prognostic assays, or for the identification of other cellular or extracellular gene products involved in the ubiquitination pathway and thereby implicated in the regulation of cell cycle and proliferative disorders.

In addition, FBP gene products of the present invention may include proteins that represent functionally equivalent (see Section 5.1 for a definition) gene products. FBP gene products of the invention do not encompass the previously identified mammalian F-box proteins Skp2, Cyclin F, Elongin A, or mouse Md6 (see Pagano, 1997, supra; Zhang et al., 1995 supra; Bai et al., 1996 supra; Skowyra et al., 1997, supra).

Functionally equivalent FBP gene products may contain deletions, including internal deletions, additions, including additions yielding fusion proteins, or substitutions of amino acid residues within and/or adjacent to the amino acid sequence encoded by the FBP gene sequences described, above, in Section 5.1, but that result in a "silent" change, in that the change produces a functionally equivalent FBP gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered FBP gene products. Such alterations can, for example, alter one or more of the biological functions of the FBP gene product. Further, such alterations can be selected so as to generate FBP gene products that are better suited for expression, scale up, etc. in the host cells chosen. For example, cysteine residues can be deleted or substituted with another amino acid residue in order to eliminate disulfide bridges.

The FBP gene products, peptide fragments thereof and fusion proteins thereof, may be produced by recombinant DNA technology using techniques well known in the art. Thus, methods for preparing the FBP gene polypeptides, peptides, fusion peptide and fusion polypeptides of the invention by expressing nucleic acid containing FBP gene sequences are described herein. Methods that are well known to those skilled in the art can be used to construct expression vectors containing FBP gene product coding sequences and appropriate transcriptional and translational control signals. These methods include, for example, in vitro recombinant DNA techniques, synthetic techniques, and in vivo genetic recombination. See, for example, the techniques described in Sambrook, et al., supra, and Ausubel, et al., supra. Alternatively, RNA capable of encoding FBP gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the FBP gene coding sequences of the invention. Such host-expression systems represent vehicles by which the coding sequences of interest may be produced and subsequently purified, but also represent cells that may, when transformed or transfected with the appropriate nucleotide coding sequences, exhibit the FBP gene product of the invention in situ. These include but are not limited to microorganisms such as bacteria (e.g., E. coli, B. subtilis) transformed with recombinant bacteriophage DNA, plasmid DNA or cosmid DNA expression vectors containing FBP gene product coding sequences; yeast (e.g., Saccharomyces, Pichia) transformed with recombinant yeast expression vectors containing the FBP gene product coding sequences; insect cell systems infected with recombinant virus expression vectors (e.g., baculovirus) containing the FBP gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing FBP gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the FBP gene product being expressed. For example, when a large quantity of such a protein is to be produced, for the generation of pharmaceutical compositions of FBP protein or for raising antibodies to FBP protein, for example, vectors that direct the expression of high levels of fusion protein products that are readily purified may be desirable. Such vectors include, but are not limited to, the *E. coli* expression vector pUR278 (Ruther et al., 1983, EMBO J. 2, 1791), in which the FBP gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhedrosis virus (AcNPV) is used as a vector to express foreign genes. The virus grows in *Spodoptera frugiperda* cells. The FBP gene coding sequence may be cloned individually into non-essential regions (for example the polyhedrin gene) of the virus and placed under control of an AcNPV promoter (for example the polyhedrin promoter). Successful insertion of FBP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the FBP gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing FBP gene product in infected hosts. (e.g., See Logan and Shenk, 1984, Proc. Natl. Acad. Sci. USA 81, 3655–3659). Specific initiation signals may also be required for efficient translation of inserted FBP gene product coding sequences. These signals include the ATG initiation codon and adjacent sequences. In cases where an entire FBP gene, including its own initiation codon and adjacent sequences, is inserted into the appropriate expression vector, no additional translational control signals may be needed. However, in cases where only a portion of the FBP gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the FBP gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the FBP gene product. Such engineered cell lines may be particularly useful in screening and evaluation of compounds that affect the endogenous activity of the FBP gene product.

A number of selection systems may be used, including but not limited to the herpes simplex virus thymidine kinase (Wigler, et al., 1977, Cell 11:223), hypoxanthineguanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk-, hgprt- or aprt-cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+ nitriloacetic acid-agarose columns and histidine-tagged proteins are selectively eluted with imidazole-containing buffers.

The FBP gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate FBP transgenic animals. The term "transgenic," as used herein, refers to animals expressing FBP gene sequences from a different species (e.g., mice expressing human FBP sequences), as well as animals that have been genetically engineered to overexpress endogenous (i.e., same species) FBP sequences or animals that have been genetically engineered to no longer express endogenous FBP gene sequences (i.e., "knock-out" animals), and their progeny.

In particular, the present invention relates to FBP1 knockout mice. The present invention also relates to transgenic mice which express human wild-type FBP1 and Skp2 gene sequences in addition to mice engineered to express human mutant FBP1 and Skp2 gene sequences deleted of their F-box domains. Any technique known in the art may be used to introduce an FBP gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229)

Any technique known in the art may be used to produce transgenic animal clones containing an FBP transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry an FBP transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. Examples of regulatory sequences that can be used to direct tissue-specific expression of an FBP transgene include, but are not limited to, the elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:42S–51S); the insulin gene control region which is active in pancreatic beta cells (Hanahan, 1985, Nature 315:115–122); immunoglobulin gene control region which is active in lymphoid cells (Grosschedl et al., 1984, Cell 38:647–658; Adams et al., 1985, Nature 318:533–538; Alexander et al., 1987, Mol. Cell. Biol. 7:1436–1444): albumin gene control region which is active in liver (Pinkert et al., 1987, Genes and Devel. 1:268–276) alpha-fetoprotein gene control region which is active in liver (Krumlauf et al., 1985, Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378). Promoters isolated from the genome of viruses that grow in mammalian cells, (e.g., vaccinia virus 7.5K, SV40, HSV, adenoviruses MLP, MMTV, LTR and CMV promoters) may be used, as well as promoters produced by recombinant DNA or synthetic techniques.

When it is desired that the FBP gene transgene be integrated into the chromosomal site of the endogenous FBP gene, gene targeting is preferred. Briefly, when such a technique is to be utilized, vectors containing some nucleotide sequences homologous to the endogenous FBP gene are designed for the purpose of integrating, via homologous recombination with chromosomal sequences, into and disrupting the function of the nucleotide sequence of the endogenous FBP gene. The transgene may also be selectively introduced into a particular cell type, thus inactivating the endogenous FBP gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant FBP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of FBP gene-expressing tissue, may also be evaluated immunocytochemically using antibodies specific for the FBP transgene product.

Transgenic mice harboring tissue-directed transgenes can be used to test the effects of FBP gene expression the intact animal. In one embodiment, transgenic mice harboring a human FBP1 transgene in the mammary gland can be used to assess the role of FBPs in mouse mammary development and tumorigenesis. In another embodiment, transgenic mice can be generated that overexpress the human FBP1 dominant negative mutant form (F-box deleted) in the mammary gland. In a specific embodiment, for example, the MMTV LTR promoter (mouse mammary tumor virus long terminal repeat) can be used to direct integration of the transgene in the mammary gland. An MMTV/FBP1 fusion gene can be constructed by fusing sequences of the MMTV LTR promoter to nucleotide sequences upstream of the first ATG of FBP1 gene. An SV40 polyadenylation region can also be fused to sequences downstream of the FBP1 coding region. Transgenic mice are generated by methods well known in the art (Gordon, 1989, Transgenic Animals, Intl. Rev. Cytol. 115, 171–229). Briefly, immature B6D2F1 female mice are superovulated and mated to CD-1 males. The following morning the females are examined for the presence of vaginal plugs, and fertilized ova are recovered and microinjected with a plasmid vector. Approximately 2000 copies of the material are microinjected into each pronucleus. Screening of founder animals is performed by extraction of DNA from spleen and Southern hybridization using the MMTV/FBP1 as a probe. Screening of offspring is performed by PCR of tail DNA. Once transgenic pedigrees are established, the expression pattern of the transgene is determined by Northern blot and RT-PCR analysis in different organs in order to correlate it with subsequent pathological changes.

The resulting transgenic animals can then be examined for the role of FBP genes in tumorigenesis. In one embodiment, for example, FBP transgenes can be constructed for use as a breast cancer model. Overexpression of FBP1 genes in such mice is expected to increase β-catenin ubiquitination and degradation, resulting in a tumor suppressor phenotype. Conversely, overexpression of the FBP1 deletion mutant is expected to result in stabilization of β-catenin and induce proliferation of mammary gland epithelium. These phenotypes can be tested in both female and male transgenic mice, by assays such as those described in Sections 5.4, 5.5 and 7.

In another specific embodiment, transgenic mice are generated that express FBP1 transgenes in T-lymphocytes. In this embodiment, a CD2/FBP1 fusion gene is constructed by fusion of the CD2 promoter, which drives expression in both CD4 positive and negative T-cells, to sequences located upstream of the first ATG of an FBP gene, e.g., the wild-type and mutant FBP1 genes. The construct can also contain an SV40 polyadenylation region downstream of the FBP gene. After generation and testing of transgenic mice, as described above, the expression of the FBP transgene is examined. The transgene is expressed in thymus and spleen. Overexpression of wild-type FBP1 is expected to result in a phenotype. For example, possible expected phenotypes of FBP1 transgenic mice include increased degradation of IKBα, increased activation of NFKB, or increased cell proliferation. Conversely, overexpression of the dominant negative mutant, FBP1, lacking the F-box domain, can be expected to have the opposite effect, for example, increased stability of IKBα, decreased activation of NFKB, or decreased cell proliferation. Such transgenic phenotypes can be tested by assays such as those used in Section 5.4 and 5.5.

In another specific embodiment, the SKP2 gene is expressed in T-lymphocytes of trangenic mice. Conversely, the F-box deletion form acts as dominant negative, stabilizing p27 and inhibiting T-cell activation. Construction of the CD2/SKP2 fusion genes and production of transgenic mice are as described above for CD2/FBP fusion genes, using wild-type and mutant SKP2 cDNA, instead of FBP1 cDNA, controlled by the CD2 promoter. Founders and their progeny are analyzed for the presence and expression of the SKP2 transgene and the mutant SKP2 transgene. Expression of the transgene in spleen and thymus is analyzed by Northern blot and RT-PCR In another specific embodiment, transgenic mice are constructed by inactivation of the FBP1 locus in mice. Inactivation of the FBP1 locus in mice by homologous recombination involves four stages: 1) the construction of the targeting vector for FBP1; 2) the generation of ES+/−cells; 3) the production of knock-out mice; and 4) the characterization of the phenotype. A 129 SV mouse genomic phage library is used to identify and isolate the mouse FBP1 gene. Bacteriophages are plated at an appropriate density and an imprint of the pattern of plaques can be obtained by gently layering a nylon membrane onto the surface of agarose dishes. Bacteriophage particles and DNA are transferred to the filter by capillary action in an exact replica of the pattern of plaques. After denaturation, the DNA is bound to the filter by baking and then hybridized with $^{32}$P-labeled-FBP1 cDNA. Excess probe is washed away and the filters were then exposed for autoradiography. Hybridizing plaques, identified by aligning the film with the original agar plate, were picked for a secondary and a tertiary screening to obtain a pure plaque preparation. Using this method, positive phage which span the region of interest, for example, the region encoding the F-box, are isolated. Using PCR, Southern hybridization, restriction mapping, subcloning and DNA sequencing the partial structure of the wild-type FBP1 gene can be determined.

To inactivate the Fbp1 locus by homologous recombination, a gene targeting vector in which exon 3 in the Fbp1 locus is replaced by a selectable marker, for example, the neoR gene, in an antisense orientation can be constructed. Exon 3 encodes the F-box motif which is known to be critical for Fbp1 interaction with Skp1. The targeting construct possesses a short and a long arm of homology flanking a selectable marker gene. One of the vector arms is relatively short (2 kb) to ensure efficient amplification since homologous recombinant ES clones will be screened by PCR. The other arm is >6 kb to maximize the frequency of homologous recombination. A thymidine kinase (tk) gene, included at the end of the long homology arm of the vector provides an additional negative selection marker (using gancylovir) against ES clones which randomly integrate the targeting vector. Since homologous recombination occurs frequently using linear DNA, the targeting vector is linearized prior to transfection of ES cells. Following electroporation and double drug selection of embryonic stem cell clones, PCR and Southern analysis is used to determine whether homologous recombination has occurred at the FBP1 locus. Screening by PCR is advantageous because a larger number of colonies can be analyzed with this method than with Southern analysis. In addition, PCR screening allows rapid elimination of negative clones thus to avoid feeding and subsequently freezing all the clones while recombinants are identified. This PCR strategy for detection of homologous recombinants is based on the use of a primer pair chosen such that one primer anneals to a sequence specific to the targeting construct, e.g., sequences of the neomycin gene or other selectable marker, and not in the endogenous locus, and the other primer anneals to a region outside the construct, but within the endogenous locus. Southern analysis is used to confirm that a homologous recombination event has occurred (both at the short arm of homology and at the long arm of homology) and that no gene duplication events have occurred during the recombination.

Such FBP1 knockout mice can be used to test the role of Fbp1 in cellular regulation and control of proliferation. In one embodiment, phenotype of such mice lacking Fbp1 is cellular hyperplasia and increased tumor formation. In another embodiment, FBP1 null mice phenotypes include, but are not limited to, increased β-catenin activity, stabilization of β-catenin, increased cellular proliferation, accumulation of IK-Ba, decreased NF-KB activity, deficient immune response, inflammation, or increased cell death or apoptotic activity. Alternatively, a deletion of the of the FBP1 gene can result in an embryonic lethality. In this case, heterozygous mice at the FBP1 allele can be tested using the above assays, and embryos of null FBP mice can be tested using the assays described above.

Transgenic mice bearing FBP transgenes can also be used to screen for compounds capable of modulating the expression of the FBP gene and/or the synthesis or activity of the FBP1 gene or gene product. Such compounds and methods for screening are described.

5.3 GENERATION OF ANTIBODIES TO F-BOX PROTEINS AND THEIR DERIVATIVES

According to the invention, F-box motif, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human FBP protein are produced. In another embodiment, antibodies to a domain (e.g., the F-box domain or the substrate-binding domain) of an FBP are produced.

Various procedures known in the art may be used for the production of polyclonal antibodies to an FBP or derivative or analog. In a particular embodiment, rabbit polyclonal antibodies to an epitope of an FBP encoded by a sequence of FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, or a subsequence thereof, can be obtained (Pagano, M., 1995, "From peptide to purified antibody", in Cell Cycle: Materials and Methods. M. Pagano, ed. Spring-Verlag. 217–281). For the production of antibody, various host animals can be immunized by injection with the native FBP, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward an FBP sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for FBP together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce FBP-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for FBPs, derivatives, or analogs.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of an FBP, one may assay generated hybridomas for a product which binds to an FBP fragment containing such domain. For selection of an antibody that specifically binds a first FBP homolog but which does not specifically bind a different FBP homolog, one can select on the basis of positive binding to the first FBP homolog and a lack of binding to the second FBP homolog.

Antibodies specific to a domain of an FBP are also provided, such as an F-box motif.

The foregoing antibodies can be used in methods known in the art relating to the localization and activity of the FBP sequences of the invention, e.g., for imaging these proteins, measuring levels thereof in appropriate physiological samples, in diagnostic methods, etc.

In another embodiment of the invention (see infra), anti-FBP antibodies and fragments thereof containing the binding domain are used as therapeutics.

5.4 SCREENING ASSAYS FOR THE IDENTIFICATION OF AGENTS THAT INTERACT WITH F-BOX PROTEINS AND/OR INTERFERE WITH THEIR ENZYMATIC ACTIVITIES

Novel components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, interact with cellular proteins to regulate cellular proliferation. One aspect of the present invention provides methods for assaying and screening fragments, derivatives and analogs of the novel components to identify polypeptides or peptides or other compounds that interact with the novel ubiquitin ligases such as potential substrates of ubiquitin ligase activity. The present invention also provides screening assays to identify compounds that modulate or inhibit the interaction of the novel FBPs with other subunits or numbers of the ubiquitin ligase complex, such as Skp1, or ubiquitinating enzymes with which the novel FBPs interact.

In yet another embodiment, the assays of the present invention may be used to identify polypeptides or peptides or other compounds which inhibit or modulate the interaction between the novel ubiquitin ligases or known (e.g., Skp1) components of the ubiquitin ligase complex with novel or known substrates. By way of example, but not by limitation, the screening assays described herein may be used to identify peptides or proteins that interfere with the interaction between known ubiquitin ligase component, Skp2, and its novel substrate, p27. In another example, compounds that interfere with the interaction between FBP1 and its novel substrate, β-catenin, are identified using the screening assay. In another example, compounds that interfere with the interaction between Skp2 and another putative substrate, E2F, are identified using the screening assay. In yet another example, compounds that interfere with the interaction between FBP1 and another putative substrate, IKBα, are identified using the screening assay.

In yet another embodiment, the assays of the present invention may be used to identify polypeptides or peptides which inhibit or activate the enzymatic activators of the novel FBPs.

5.4.1 ASSAYS FOR PROTEIN-PROTEIN INTERACTIONS

Derivatives, analogs and fragments of proteins that interact with the novel components of the ubiquitin ligase complex of the present invention can be identified by means of a yeast two hybrid assay system (Fields and Song, 1989, Nature 340:245–246 and U.S. Pat. No. 5,283,173). Because the interactions are screened for in yeast, the intermolecular protein interactions detected in this system occur under physiological conditions that mimic the conditions in mammalian cells (Chien et al., 1991, Proc. Natl. Acad. Sci. U.S.A. 88:9578–9581).

Identification of interacting proteins by the improved yeast two hybrid system is based upon the detection of expression of a reporter gene, the transcription of which is dependent upon the reconstitution of a transcriptional regulator by the interaction of two proteins, each fused to one half of the transcriptional regulator. The "bait" (i.e., the novel components of the ubiquitin ligase complex of the present invention or derivatives or analogs thereof) and "prey" (proteins to be tested for ability to interact with the bait) proteins are expressed as fusion proteins to a DNA binding domain, and to a transcriptional regulatory domain, respectively, or vice versa. In various specific embodiments, the prey has a complexity of at least about 50, about 100, about 500, about 1,000, about 5,000, about 10,000, or about 50,000; or has a complexity in the range of about 25 to about 100,000, about 100 to about 100,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence). Preferably, the prey populations are proteins encoded by DNA, e.g., cDNA or genomic DNA or synthetically-generated DNA. For example, the populations can be expressed from chimeric genes comprising cDNA sequences from an un-characterized sample of a population of cDNA from mRNA.

In a specific embodiment, recombinant biological libraries expressing random peptides can be used as the source of prey nucleic acids.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the present method of the present invention, binding of a ubiquitin ligase fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter.

Alternatively, the transcriptional activation binding site of the desired gene(s) can be deleted and replaced with GAL4 binding sites (Bartel et al., 1993, BioTechniques 14:920–924, Chasman et al., 1989, Mol. Cell. Biol. 9:4746–4749). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator).

The activation domain and DNA binding domain used in the assay can be from a wide variety of transcriptional activator proteins, as long as these transcriptional activators have separable binding and transcriptional activation domains. For example, the GAL4 protein of S. cerevisiae (Ma et al., 1987, Cell 48:847–853), the GCN4 protein of S. cerevisiae (Hope & Struhl, 1986, Cell 46:885–894), the ARD1 protein of S. cerevisiae (Thukral et al., 1989, Mol. Cell. Biol. 9:2360–2369), and the human estrogen receptor (Kumar et al., 1987, Cell 51:941–951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) comprise the activation domain.

In a preferred embodiment, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme betagalactosidase (detectable by routine chromogenic assay) upon binding of a reconstituted Ace1N transcriptional activator (see Chaudhuri et al., 1995, FEBS Letters 357:221–226). In another specific embodiment, the DNA binding domain of the human estrogen receptor is used, with a reporter gene driven by one or three estrogen receptor response elements (Le Douarin et al., 1995, Nucl. Acids. Res. 23:876–878). The DNA binding domain and the transcriptional activator/inhibitor domain each preferably has a nuclear localization signal (see Ylikomi et al., 1992, EMBO J. 11:3681–3694, Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, or insect cells, and is preferably a yeast cell. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc.

Various vectors and host strains for expression of the two fusion protein populations in yeast are known and can be used (see e.g., U.S. Pat. No. 5,1468,614; Bartel et al., 1993, "Using the two-hybrid system to detect protein-protein interactions" In: Cellular Interactions in Development, Hartley, ed., Practical Approach Series xviii, IRL Press at Oxford University Press, New York, N.Y., pp. 153–179; Fields and Sternglanz, 1994, Trends In Genetics 10:286–292).

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101:202–211).

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed using two different types of host cells, strain-type a and alpha of the yeast Saccharomyces cerevisiae. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In another embodiment, the fusion constructs are introduced directly into the yeast chromosome via homologous recombination. The homologous recombination for these purposes is mediated through yeast sequences that are not essential for vegetative growth of yeast, e.g., the MER2, MER1, ZIP1, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising (a) recombinantly expressing a novel ubiquitin ligase component of the present invention or a derivative or analog thereof in a first population of yeast cells being of a first mating type and comprising a first fusion protein containing the sequence of a novel ubiquitin ligase component of the present invention and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

5.4.2 ASSAYS TO IDENTIFY F-BOX PROTEIN INTERACTIONS WITH KNOWN PROTEINS INCLUDING POTENTIAL SUBSTRATES

The cellular abundance of cell-cycle regulatory proteins, such as members of the cyclin family or the Cki inhibitory proteins, is regulated by the ubiquitin pathway. The enzymes responsible for the ubiquitination of mammalian cell cycle regulation are not known. In yeast, SCF complexes represent the ubiquitin ligases for cell cycle regulators. The F-box component of the ubiquitin ligase complexes, such as the novel F-box proteins of the invention, determines the specificity of the target of the ubiquitin ligase complex. The invention therefore provides assays to screen known molecules for specific binding to F-box protein nucleic acids, proteins, or derivatives under conditions conducive to binding, and then molecules that specifically bind to the FBP protein are identified.

In a specific embodiment, the invention provides a method for studying the interaction between the F-box protein FBP1 and the Cul1/Skp1 complex, and its role in regulating the stability of β-catenin. Protein-protein interactions can be probed in vivo and in vitro using antibodies specific to these proteins, as described in detail in the experiments in Section 8.

In another specific embodiment, the invention provides for a method for detecting the interaction between the F-box protein Skp2 and E2F-1, a transcription factor involved in cell cycle progression. Insect cells can be infected with baculoviruses co-expressing Skp2 and E2F-1, and cell extracts can be prepared and analyzed for protein-protein interactions. As described in detail in Section 7, this assay has been used successfully to identify potential targets, such as E2F, for known F-box proteins, such as Skp2. This assay can be used to identify other Skp2 targets, as well as targets for novel F-box proteins.

In another specific embodiment, methods for detecting the interaction between Skp2 and p27, a cell cycle regulated cyclin-dependent kinase (Cdk) inhibitor, are provided. The interaction between Skp2 and p27 may be targeted to identify modulators of Skp2 activity, including its interaction with cell cycle regulators, such as p27. The ubiquitination of Skp2-specific substrates, such as p27 may be used as a means of measuring the ability of a test compound to modulate Skp2 activity. In another embodiment of the screening assays of the present invention, immunodepletion assays, as described in Section 9, can be used to identify modulators of the Skp2/p27 interaction. In particular, Section 9 describes a method for detection of ubiquitination activity in vitro using p27 as a substrate, which can also be used to identify modulators of the Skp2-dependent ubiquitination of p27. In another embodiment of the screening assays of the present invention, antisense oligonucleotides, as described in Section 5.7.1, can be used as inhibitors of the Skp2 activity. Such identified modulators of p27 ubiquitination/degradation and of the Skp2/p27 interaction can be useful in anti-cancer therapies.

The invention further provides methods for screening ubiquitin ligase complexes having novel F-box proteins (or fragments thereof) as one of their components for ubiquitin ligase activity using known cell-cycle regulatory molecules as potential substrates for ubiquitination. For example, cells engineered to express FBP nucleic acids can be used to recombinantly produce FBP proteins either wild-type or dominant negative mutants in cells that also express a putative ubiquitin-ligase substrate molecule. Such candidates for substrates of the novel FBP of the present invention include, but are not limited to, such potential substrates as IKBα, β-catenin, myc, E2F-1, p27, p21, cyclin A, cyclin B, cycD1, cyclin E and p53. Then the extracts can be used to test the association of F-box proteins with their substrates, (by Western blot immunoassays) and whether the presence of the FBP increases or decreases the level of the potential substrates.

5.5 ASSAYS FOR THE IDENTIFICATION OF COMPOUNDS THAT MODULATE THE ACTIVITY OF F-BOX PROTEINS

The present invention relates to in vitro and in vivo assay systems described in the subsections below, which can be used to identify compounds or compositions that modulate the interaction of known FBPs with novel substrates and novel components of the ubiquitin ligase complex. The screening assays of the present invention may also be used to identify compounds or compositions that modulate the interaction of novel FBPs with their identified substrates and components of the ubiquitin ligase complex.

Methods to screen potential agents for their ability to disrupt or moderate FBP expression and activity can be designed based on the Applicants' discovery of novel FBPs and their interaction with other components of the ubiquitin ligase complex as well as its known and potential substrates. For example, candidate compounds can be screened for their ability to modulate the interaction of an FBP and Skp1, or the specific interactions of Skp2 with E2F-1, Skp2 with p27, or the FBP1/Cul1/Skp1 complex with β-catenin. In principle, many methods known to those of skill in the art, can be readily adapted in designed the assays of the present invention.

The screening assays of the present invention also encompass high-throughput screens and assays to identify modulators of FBP expression and activity. In accordance with this embodiment, the systems described below may be formulated into kits. To this end, cells expressing FBP and components of the ubiquitination ligase complex and the ubiquitination pathway, or cell lysates, thereof can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

The invention provides screening methodologies useful in the identification of proteins and other compounds which bind to, or otherwise directly interact with, the FBP genes and their gene products. Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant FBP genes and FBP proteins.

Alternatively, any of a variety of exogenous compounds, both naturally occurring and/or synthetic (e.g., libraries of small molecules or peptides), may be screened for binding capacity. All of these methods comprise the step of mixing an FBP protein or fragment with test compounds, allowing time for any binding to occur, and assaying for any bound complexes. All such methods are enabled by the present disclosure of substantially pure FBP proteins, substantially pure functional domain fragments, fusion proteins, antibodies, and methods of making and using the same.

5.5.1 ASSAYS FOR F-BOX PROTEIN AGONISTS AND ANTAGONISTS

FBP nucleic acids, F-box proteins, and derivatives can be used in screening assays to detect molecules that specifically bind to FBP nucleic acids, proteins, or derivatives and thus have potential use as agonists or antagonists of FBPs, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to FBP nucleic acids, proteins, or derivatives. For example, recombinant cells expressing FBP nucleic acids can be used to recombinantly produce FBP proteins in these assays, to screen for molecules that bind to an FBP protein. Similar methods can be used to screen for molecules that bind to FBP derivatives or nucleic acids. Methods that can be used to carry out the foregoing are commonly known in the art. The assays of the present invention may be first optimized on a small scale (i.e., in test tubes), and then scaled up for high-throughput assays. The screening assays of the present may be performed in vitro, i.e. in test tubes, using purified components or cell lysates. The screening assays of the present invention may also be carried out in intact cells in culture and in animal models. In accordance with the present invention, test compounds which are shown to modulate the activity of the FBP as described herein in vitro, will further be assayed in vivo, including cultured cells and animal models to determine if the test compound has the similar effects in vivo and to determine the effects of the test compound on cell cycle progression, the accumulation or degradation of positive and negative regulators, cellular proliferation etc.

In accordance with the present invention, screening assays may be designed to detect molecules which act as agonists or antagonists of the activity of the novel F-box proteins. In accordance with this aspect of the invention, the test compound may be added to an assay system to measure its effect on the activity of the novel FBP, i.e., ubiquitination of its substrates, interaction with other components of the ubiquitin ligase complex, etc. These assays should be conducted both in the presence and absence of the test compound.

In accordance with the present invention, ubiquitination activity of a novel FBP in the presence or absence of a test compound can be measured in vitro using purified components of the ubiquitination pathway or may be measured using crude cellular extracts obtained from tissue culture cells or tissue samples. In another embodiment of the aspect of the present invention the screening may be performed by adding the test agent to in vitro translation systems such as a rabbit reticulocyte lysate (RRL) system and then proceeding with the established analysis. As another alternative, purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts of cells expressing the components of the ubiquitin ligase complex and pathway, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components of the ubiquitin ligase complex or interaction with the target substrate, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

In another embodiment, screening can be carried out by contacting the library members with an FBP protein (or nucleic acid or derivative) immobilized on a solid phase and harvesting those library members that bind to the protein (or nucleic acid or derivative). Examples of such screening methods, termed "panning" techniques are described by way of example in Parmley & Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins or peptides in yeast (Fields & Song, 1989, Nature 340:245–246; Chien et al., 1991, Proc. Natl. Acad. Sci. USA 88:9578–9582) can be used to identify molecules that specifically bind to an FBP protein or derivative.

Alternatively, test methods may rely on measurements of enzyme activity, such as ubiquitination of the target substrate. Once a substrate of a novel FBP is identified or a novel putative substrate of a known FBP is identified, such as the novel substrates of Skp2, E2F and p27, these components may be used in assays to determine the effect of a test compound on the ubiquitin ligase activity of the ubiquitin ligase complex.

In one embodiment, the screening assays may be conducted with a purified system in the presence and absence of test compound. Purified substrate is incubated together with purified ubiquitin ligase complex, ubiquitin conjugating enzymes, ubiquitin activating enzymes and ubiquitin in the presence or in the absence of test compound. Ubiquitination of the substrate is analyzed by immunoassay (see Pagano et al., 1995, Science 269:682–685). Briefly, ubiquitination of the substrate can be performed in vitro in reactions containing 50–200 ng of proteins in 50 mM Tris pH 7.5, 5 mM MgCl2, 2 mM ATPγ-S, 0.1 mM DTT and 5μM of biotinylated ubiquitin. Total reactions (30 μl) can be incubated at 25° C. for up to 3 hours in the presence or absence of test compound and then loaded on an 8% SDS gel or a 4–20% gradient gel for analysis. The gels are run and proteins are electrophoretically transferred to nitrocellulose. Ubiquitination of the substrate can be detected by immunoblotting. Ubiquitinated substrates can be visualized using Extravidin-HRP (Sigma), or by using a substrate-specific antibody, and the ECL detection system (NEN).

In another embodiment, ubiquitination of the substrate may be assayed in intact cells in culture or in animal models in the presence and absence of the test compound. For example, the test compound may be administered directly to an animal model or to crude extracts obtained from animal tissue samples to measure ubiquitination of the substrate in the presence and absence of the test compounds. For these assays, host cells to which the test compound is added may be genetically engineered to express the FBP components of the ubiquitin ligase pathway and the target substrate, the expression of which may be transient, induced or constitutive, or stable. For the purposes of the screening methods of the present invention, a wide variety of host cells may be used including, but not limited to, tissue culture cells, mammalian cells, yeast cells, and bacteria. Each cell type has its own set of advantages and drawbacks. Mammalian cells such as primary cultures of human tissue cells may be a preferred cell type in which to carry out the assays of the present invention, however these cell types are sometimes difficult to cultivate. Bacteria and yeast are relatively easy to cultivate but process proteins differently than mammalian cells. This ubiquitination assay may be conducted as follows: first, the extracts are prepared from human or animal tissue. To prepare animal tissue samples preserving ubiquitinating enzymes, 1 g of tissue can be sectioned and homogenized at 15,000 r.p.m. with a Brinkmann Polytron homogenizer (PT 3000, Westbury, N.Y.) in 1 ml of ice-cold double-distilled water. The sample is frozen and thawed 3 times. The lysate is spun down at 15,000 r.p.m. in a Beckman JA-20.1 rotor (Beckman Instruments, Palo Alto, Calif.) for 45 min at 4° C. The supernatant is retrieved and frozen at −80° C. This method of preparation of total extract preserves ubiquitinating enzymes (Loda et al. 1997, Nature Medicine 3:231–234, incorporated by reference herein in its entirety).

Purified recombinant substrate is added to the assay system and incubated at 37° C. for different times in 30 µl of ubiquitination mix containing 100 µg of protein tissue homogenates, 50 mM Tris-HCl (pH 8.0), 5 mM MgCl2, and 1 mM DTT, 2 mM ATP, 10 mM creatine phosphokinase, 10 mM creatine phosphate and 5 µM biotinylated ubiquitin. The substrate is then re-purified with antibodies or affinity chromatography. Ubiquitination of the substrate is measured by immunoassays with either antibodies specific to the substrates or with Extravidin-HRP.

In addition, Drosophila can be used as a model system in order to detect genes that phenotypically interact with FBP. For example, overexpression of FBP in Drosophila eye leads to a smaller and rougher eye. Mutagenesis of the fly genome can be performed, followed by selecting flies in which the mutagenesis has resulted in suppression or enhancement of the small rough eye phenotype; the mutated genes in such flies are likely to encode proteins that interact/bind with FBP. Active compounds identified with methods described above will be tested in cultured cells and/or animal models to test the effect of blocking in vivo FBP activity (e.g. effects on cell proliferation, accumulation of substrates, etc.).

In various other embodiments, screening the can be accomplished by one of many commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

Compounds, peptides, and small molecules can be used in screening assays to identify candidate agonists and antagonists. In one embodiment, peptide libraries may be used to screen for agonists or antagonists of the FBP of the present invention diversity libraries, such as random or combinatorial peptide or non-peptide libraries can be screened for molecules that specifically bind to FBP. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lemer, 1992, Proc. Natl. Acad. Sci. USA 89:5381–5383.

Examples of phage display libraries are described in Scott & Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of non-peptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

5.5.2 ASSAYS FOR THE IDENTIFICATION OF COMPOUNDS THAT MODULATE THE INTERACTION OF F-BOX PROTEINS WITH OTHER PROTEINS

Once a substrate or interacting protein is identified, as described in detail in Section 5.4, then one can assay for modulators of the F-box protein interaction with such a protein. The present invention provides for methods of detecting agonists and antagonists of such interactions.

In one embodiment, the invention encompasses methods to identify modulators, such as inhibitors or agonists, of the interaction between the F-box protein Skp2 and E2F-1, identified in Section 7 and FIG. 10. Such methods comprise both in vivo and in vitro assays for modulator activity. For example, in an in vivo assay, insect cells can be co-infected with baculoviruses co-expressing Skp2 and E2F-1 as well as potential modulators of the Skp2/E2F-1 interaction. The screening methods of the present invention encompass in vitro assays which measure the ability of a test compound to inhibit the enzymatic activity of Skp2 as described above in Section 5.5.1. Cell extracts can be prepared and analyzed for protein-protein interactions by gel electrophoresis and detected by immunoblotting, as described in detail in Section 7 and presented in FIG. 10. Alternatively, an in vitro protein-protein interaction assay can be used. Recombinant purified Skp2, E2F-1, and putative agonist or antagonist molecules can be incubated together, under conditions that allow binding to occur, such as 37 C for 30 minutes. Protein-protein complex formation can be detected by gel analysis, such as those described herein in Section 7. This assay can be used to identify modulators of interactions of known FBP, such as Skp2 with novel substrates.

In another embodiment, the invention provides for a method for identification of modulators of F-box protein/Skp1 interaction. Such agonist and antagonists can be identified in vivo or in vitro. For example, in an in vitro assay to identify modulators of F-box protein/Skp1 interactions, purified Skp1 and the novel FBP can be incubated together, under conditions that allow binding occur, such as 37 C for 30 minutes. In a parallel reaction, a potential agonist or antagonist, as described above in Section 5.5.1, is added either before or during the box protein/Skp1 incubation. Protein-protein interactions can be detected by gel analysis, such as those described herein in Section 7. Modulators of FBP activities and interactions with other proteins can be used as therapeutics using the methods described herein, in Section 5.7.

These assays may be carried out utilizing any of the screening methods described herein, including the following in vitro assay. The screening can be performed by adding the test agent to intact cells which express components of the ubiquitin pathway, and then examining the component of interest by whatever procedure has been established. Alternatively, the screening can be performed by adding the test agent to in vitro translation reactions and then proceeding with the established analysis. As another alternative, purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts of cells expressing the components of the ubiquitin ligase complex and pathway, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components of the ubiquitin ligase complex or interaction with the target substrate, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

5.6 METHODS AND COMPOSITIONS FOR DIAGNOSTIC USE OF F-BOX PROTEINS, DERIVATIVES, AND MODULATORS

Cell cycle regulators are the products of oncogenes (cyclins, β-catenin, etc.), or tumor suppressor genes (ckis, p53, etc.) The FBPs, part of ubiquitin ligase complexes, might therefore be products of oncogenes or tumor suppressor genes, depending on which cell cycle regulatory proteins for which they regulate cellular abundance.

FBP proteins, analogues, derivatives, and subsequences thereof, FBP nucleic acids (and sequences complementary thereto), anti-FBP antibodies, have uses in diagnostics. The FBP and FBP nucleic acids can be used in assays to detect, prognose, or diagnose proliferative or differentiative disorders, including tumorigenesis, carcinomas, adenomas etc. The novel FBP nucleic acids of the present invention are located at chromosome sites associated with karyotypic abnormalities and loss of heterozygosity. The FBP1 nucleic acid of the present invention is mapped and localized to chromosome position 10q24, the loss of which has been demonstrated in 10% of human prostate tumors and small cell lung carcinomas (SCLC), suggesting the presence of a tumor suppressor gene at this location. In addition, up to 7% of childhood acute T-cell leukemia is accompanied by a translocation involving 10q24 as a breakpoint, either t(10;14)(q24;q11) or t(7;10)(q35;q24). 9q34 region (where FBP2 is located) has been shown to be a site of loss of heterozygosity (LOH) in human ovarian and bladder cancers. The FBP2 nucleic acid of the present invention is mapped and localized to chromosome position 9q34 which has been shown to be a site of loss of heterozygosity (LOH) in human ovarian and bladder cancers. The FBP3 nucleic acid of the present invention is mapped and localized to chromosome position 1 3q22, a region known to contain a putative tumor suppressor gene with loss of heterozygosity in approx. 75% of human SCLC. The FBP4 nucleic acid of the present invention is mapped and localized to chromosome position 5p12, a region shown to be a site of karyotypic abnormalities in a variety of tumors, including human breast cancer and nasopharyngeal carcinomas. The FBP5 nucleic acid of the present invention is mapped and localized to chromosome position 6q25-26, a region shown to be a site of loss of heterozygosity in human ovarian, breast and gastric cancers hepatocarcinomas, Burkitt's lymphomas, gliomas, and parathyroid adenomas. The FBP7 nucleic acid of the present invention is mapped and localized to chromosome position 15q15 a region which contains a tumor suppressor gene associated with progression to a metastatic stage in breast and colon cancers and a loss of heterozygosity in parathyroid adenomas.

The molecules of the present invention can be used in assays, such as immunoassays, to detect, prognose, diagnose, or monitor various conditions, diseases, and disorders affecting FBP expression, or monitor the treatment thereof. In particular, such an immunoassay is carried out by a method comprising contacting a sample derived from a patient with an anti-FBP antibody under conditions such that immunospecific binding can occur, and detecting or measuring the amount of any immunospecific binding by the antibody. In a specific aspect, such binding of antibody, in tissue sections, can be used to detect aberrant FBP localization or aberrant (e.g., low or absent) levels of FBP. In a specific embodiment, antibody to FBP can be used to assay a patient tissue or serum sample for the presence of FBP where an aberrant level of FBP is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

FBP genes and related nucleic acid sequences and subsequences, including complementary sequences, can also be used in hybridization assays. FBP nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in FBP expression and/or activity as described supra. In particular, such a hybridization assay is carried out by a method comprising contacting a sample containing nucleic acid with a nucleic acid probe capable of hybridizing to FBP DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting decreased levels of FBP protein, FBP RNA, or FBP functional activity (e.g., ubiquitin ligase target binding activity, F-box domain binding activity, ubiquitin ligase activity etc.), or by detecting mutations in FBP RNA, DNA or FBP protein.(e.g., translocations in FBP nucleic acids, truncations in the FBP gene or protein, changes in nucleotide or amino acid sequence relative to wild-type FBP) that cause decreased expression or activity of FBP. Such diseases and disorders include but are not limited to those described in Section 5.7.3. By way of example, levels of FBP protein can be detected by immunoassay, levels of FBP RNA can be detected by hybridization assays (e.g., Northern blots, in situ-hybridization), FBP activity can be assayed by measuring ubiquitin ligase activity in E3 ubiquitin ligase complexes formed in vivo or in vitro, F-box domain binding activity can be assayed by measuring binding to Skp1 protein by binding assays commonly known in the art, translocations, deletions and point mutations in FBP nucleic acids can be detected by Southern blotting, FISH, RFLP analysis, SSCP, PCR using primers that preferably generate a fragment spanning at least most of the FBP gene, sequencing of FBP genomic DNA or cDNA obtained from the patient, etc.

In a preferred embodiment, levels of FBP mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting increased levels of FBP protein, FBP RNA, or FBP functional activity (e.g., ubiquitin ligase activity, Skp1 binding activity, etc.), or by detecting mutations in FBP RNA, DNA or protein (e.g., translocations in FBP nucleic acids, truncations in the gene or protein, changes in nucleotide or amino acid sequence relative to wild-type FBP) that cause increased expression or activity of FBP. Such diseases and disorders include but are not limited to those described in Section 5.7.3. By way of example, levels of FBP protein, levels of FBP RNA, ubiquitin ligase activity, FBP binding activity, and the presence of translocations or point mutations can be determined as described above.

In a specific embodiment, levels of FBP mRNA or protein in a patient sample are detected or measured, in which increased levels indicate that the subject has, or has a predisposition to developing, a growth deficiency or degenerative or hypoproliferative disorder; in which the increased levels are relative to the levels present in an analogous sample from a portion of the body or from a subject not having the growth deficiency, degenerative, or hypoproliferative disorder, as the case may be.

Kits for diagnostic use are also provided, that comprise in one or more containers an anti-FBP antibody, and, optionally, a labeled binding partner to the antibody. Alternatively, the anti-FBP antibody can be labeled (with a detectable marker, e.g., a chemiluminescent, enzymatic, fluorescent, or radioactive moiety). A kit is also provided that comprises in one or more containers a nucleic acid probe capable of hybridizing to FBP RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Q replicase, cyclic probe reaction, or other methods known in the art]

under appropriate reaction conditions of at least a portion of a FBP nucleic acid. A kit can optionally further comprise in a container a predetermined amount of a purified FBP protein or nucleic acid, e.g., for use as a standard or control.

5.7 METHODS AND COMPOSITIONS FOR THERAPEUTIC USE OF F-BOX PROTEINS, DERIVATIVES, AND MODULATORS

Described below are methods and compositions for the use of F-box proteins in the treatment of proliferative disorders and oncogenic disease symptoms may be ameliorated by compounds that activate or enhance FBP activity, and whereby proliferative disorders and cancer may be ameliorated.

In certain instances, compounds and methods that increase or enhance the activity of an FBP can be used to treat proliferative and oncogenic disease symptoms. Such a case may involve, for example, a proliferative disorder that is brought about, at least in part, by a reduced level of FBP gene expression, or an aberrant level of an FBP gene product's activity. For example, decreased activity or under-expression of an FBP component of a ubiquitin ligase complex whose substrate is a positive cell-cycle regulator, such as a member of the Cyclin family, will result in increased cell proliferation. As such, an increase in the level of gene expression and/or the activity of such FBP gene products would bring about the amelioration of proliferative disease symptoms.

In another instance, compounds that increase or enhance the activity of an FBP can be used to treat proliferative and oncogenic disease symptoms resulting from defects in the expression or activity of other genes and gene products involved in cell cycle control, such as FBP substrate molecules. For example, an increase in the expression or activity of a positive cell-cycle positive molecule, such as a member of the Cyclin family, may result in its over-activity and thereby lead to increased cell proliferation. Compounds that increase the expression or activity of the FBP component of a ubiquitin ligase complex whose substrate is such a cell-cycle positive regulator will lead to ubiquitination of the defective molecule, and thereby result in an increase in its degradation. Disease symptoms resulting from such a defect may be ameliorated by compounds that compensate the disorder by increased FBP activity. Techniques for increasing FBP gene expression levels or gene product activity levels are discussed in Section 5.7, below.

Alternatively, compounds and methods that reduce or inactivate FBP activity may be used therapeutically to ameliorate proliferative and oncogenic disease symptoms. For example, a proliferative disorder may be caused, at least in part, by a defective FBP gene or gene product that leads to its overactivity. Where such a defective gene product is a component of a ubiquitin ligase complex whose target is a cell-cycle inhibitor molecule, such as a Cki, an overactive FBP will lead to a decrease in the level of cell-cycle molecule and therefore an increase in cell proliferation. In such an instance, compounds and methods that reduce or inactivate FBP function may be used to treat the disease symptoms.

In another instance, compounds and methods that reduce the activity of an FBP can be used to treat disorders resulting from defects in the expression or activity of other genes and gene products involved in cell cycle control, such as FBP substrate molecules. For example, a defect in the expression or activity of a cell-cycle negative regulatory molecule, such as a Cki, may lead to its under-activity and thereby result in increased cell proliferation. Reduction in the level and/or activity of an FBP component whose substrate was such molecule would decrease the ubiquitination and thereby increase the level of such a defective molecule. Therefore, compounds and methods aimed at reducing the expression and/or activity of such FBP molecules could thereby be used in the treatment of disease symptoms by compensating for the defective gene or gene product.

Techniques for the reduction of target gene expression levels or target gene product activity levels are discussed in Section 5.7 below.

5.7.1 THERAPEUTIC USE OF INHIBITORY ANTISENSE, RIBOZYME AND TRIPLE HELIX MOLECULES AND IDENTIFIED AGONISTS AND ANTAGONISTS

In another embodiment, symptoms of certain FBP disorders, such as such as proliferative or differentiative disorders causing tumorigenesis or cancer, may be ameliorated by decreasing the level of FBP gene expression and/or FBP gene product activity by using FBP gene sequences in conjunction with well-known antisense, gene "knock-out" ribozyme and/or triple helix methods to decrease the level of FBP gene expression. Among the compounds that may exhibit the ability to modulate the activity, expression or synthesis of the FBP gene, including the ability to ameliorate the symptoms of an FBP disorder, such as cancer, are antisense, ribozyme, and triple helix molecules. Such molecules may be designed to reduce or inhibit either unimpaired, or if appropriate, mutant target gene activity. Techniques for the production and use of such molecules are well known to those of skill in the art. For example, antisense targeting SKP2 mRNA stabilize the Skp2-substrate p27, as described in Section X (Figure X).

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the FBP gene could be used in an antisense approach to inhibit translation of endogenous FBP mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In an embodiment of the present invention, oligonucleotides complementary to the nucleic acids encoding the F-box motif as indicated in FIGS. 2 and 4–9.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate (S-ODNs), a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an -anomeric oligonucleotide. An anomeric oligonucle-otide forms specific double-stranded hybrids with complementary RNA in which, contrary to the usual -units, the strands run parallel to each other (Gautier, et al., 1987, Nucl. Acids Res. 15, 6625–6641). The oligonucleotide is a 2-0-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

In one embodiment of the present invention, gene expression downregulation is achieved because specific target mRNAs are digested by RNAse H after they have hybridized with the antisense phosphorothioate oligonucleotides (S-ODNs). Since no rules exist to predict which antisense S-ODNs will be more successful, the best strategy is completely empirical and consists of trying several antisense S-ODNs. Antisense phosphorothioate oligonucleotides (S-ODNs) will be designed to target specific regions of mRNAs of interest. Control S-ODNs consisting of scrambled sequences of the antisense S-ODNs will also be designed to assure identical nucleotide content and minimize differences potentially attributable to nucleic acid content. All S-ODNs will be synthesized by Oligos Etc. (Wilsonville, Oreg.). In order to test the effectiveness of the antisense molecules when applied to cells in culture, such as assays for research purposes or ex vivo gene therapy protocols, cells will be grown to 60–80% confluence on 100 mm tissue culture plates, rinsed with PBS and overlaid with lipofection mix consisting of 8 ml Opti-MEM, 52.8 l Lipofectin, and a final concentration of 200 nM S-ODNs. Lipofections will be carried out using Lipofectin Reagent and Opti-MEM (Gibco BRL). Cells will be incubated in the presence of the lipofection mix for 5 hours. Following incubation the medium will be replaced with complete DMEM. Cells will be harvested at different time points post-lipofection and protein levels will be analyzed by Western blot.

Antisense molecules should be targeted to cells that express the target gene, either directly to the subject in vivo or to cells in culture, such as in ex vivo gene therapy protocols. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290, 304–310), the promoter contained in the 3 long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product (see, e.g., PCT International Publication WO90/11364, published Oct. 4, 1990; Sarver, et al., 1990, Science 247, 1222–1225). In an embodiment of the present invention, oligonucleotides which hybridize to the FBP gene are designed to be complementary to the nucleic acids encoding the F-box motif as indicated in FIGS. 2 and 4–9.

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff & Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been & Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas & Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited modifications to ES (embryonic stem) cells can be used to generate animal offspring with an inactive target gene (e.g., see Thomas & Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.7.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.7.2 GENE REPLACEMENT THERAPY

With respect to an increase in the level of normal FBP gene expression and/or FBP gene product activity, FBP gene nucleic acid sequences, described, above, in Section 5.1 can, for example, be utilized for the treatment of proliferative disorders such as cancer. Such treatment can be administered, for example, in the form of gene replacement therapy. Specifically, one or more copies of a normal FBP gene or a portion of the FBP gene that directs the production of an FBP gene product exhibiting normal FBP gene function, may be inserted into the appropriate cells within a patient, using vectors that include, but are not limited to adenovirus, adeno-associated virus, and retrovirus vectors, in addition to other particles that introduce DNA into cells, such as liposomes.

For FBP genes that are expressed in all tissues or are preferentially expressed, such as FBP1 gene is expressed preferably in the brain, such gene replacement therapy techniques should be capable delivering FBP gene sequences to these cell types within patients. Thus, in one embodiment, techniques that are well known to those of skill in the art (see, e.g., PCT Publication No. WO89/10134, published Apr. 25, 1988) can be used to enable FBP gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such FBP gene sequences to the site of the cells in which the FBP gene sequences are to be expressed.

Additional methods that may be utilized to increase the overall level of FBP gene expression and/or FBP gene product activity include the introduction of appropriate FBP-expressing cells, preferably autologous cells, into a patient at positions and in numbers that are sufficient to ameliorate the symptoms of an FBP disorder. Such cells may be either recombinant or non-recombinant.

Among the cells that can be administered to increase the overall level of FBP gene expression in a patient are cells that normally express the FBP gene.

Alternatively, cells, preferably autologous cells, can be engineered to express FBP gene sequences, and may then be introduced into a patient in positions appropriate for the amelioration of the symptoms of an FBP disorder or a proliferative or differentiative disorders, e.g., cancer and tumorigenesis. Alternately, cells that express an unimpaired FBP gene and that are from a MHC matched individual can be utilized, and may include, for example, brain cells. The expression of the FBP gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399, 349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.5, that are capable of modulating FBP gene product activity can be administered using standard techniques that are well known to those of skill in the art. In instances in which the compounds to be administered are to involve an interaction with brain cells, the administration techniques should include well known ones that allow for a crossing of the blood-brain barrier.

5.7.3 TARGET PROLIFERATIVE CELL DISORDERS

With respect to specific proliferative and oncogenic disease associated with ubiquitin ligase activity, the diseases that can be treated or prevented by the methods of the present invention include but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

Diseases and disorders involving a deficiency in cell proliferation or in which cell proliferation is desired for treatment or prevention, and that can be treated or prevented by inhibiting FBP function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

5.8 PHARMACEUTICAL PREPARATIONS AND METHODS OF ADMINISTRATION

The compounds that are determined to affect FBP gene expression or gene product activity can be administered to a patient at therapeutically effective doses to treat or ameliorate a cell proliferative disorder. A therapeutically effective dose refers to that amount of the compound sufficient to result in amelioration of symptoms of such a disorder.

5.8.1 EFFECTIVE DOSE

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.8.2 FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE: IDENTIFICATION AND CHARACTERIZATION OF NOVEL UBIQUITIN LIGASE F-BOX PROTEINS AND GENES

The following studies were carried out to identify novel F-box proteins which may act to recruit novel specific substrates to the ubiquitination pathways. Studies involving several organisms have shown that some FBPs play a crucial role in the controlled degradation of important cellular regulatory proteins (e.g., cyclins, cdk-inhibitors, β-catenin, IKBa, etc.). These FBPs are subunits of ubiquitin protein SCF ligases formed by three basic subunits: a cullin subunit (called Cdc53 in S. cerevisiae and Cul1 in humans); Skp1; and one of many FBPs. SCF ligases target ubiquitin conjugating enzymes (either Ubc3 or Ubc4) to specific substrates which are recruited by different FBPs. Schematically, the Ubc is bound to the ligase through the cullin subunit while the substrate interacts with the FBP subunit. Although FBPs can bind the cullin subunit directly, the presence of fourth subunit, Skp1, which simultaneously can bind the cullin N-terminus and the F-box of the FBP, stabilizes the complex. Thus, the substrate specificity of the ubiquitin ligase complex is provided by the F-box subunit.

6.1 MATERIALS AND METHODS USED FOR THE IDENTIFICATION AND CHARACTERIZATION OF NOVEL F-BOX GENES

Yeast Two-Hybrid Screening In order to clone the human genes encoding F-box proteins, proteins associated with Skp1 were identified using a modified yeast 2-hybrid system (Vidal et al., 1996, Proc. Nat. Acad. Sci., 93:10315–20; Vidal et al., 1996, Proc. Nat. Acad. Sci., 93:10321–26). This modified system takes advantage of using three reporter genes expressed from three different Gal4 binding site promoters, thereby decreasing the number of false positive interactions. This multiple reporter gene assay facilitates identification of true interactors.

Human Skp1 was used as a bait to search for proteins that interact with Skp1, such as novel F-box proteins and the putative human homolog of Cdc4. The plasmids pPC97-CYH2 and pPC86 plasmids, encoding the DNA binding domain (DB, aa 1–147) and the transcriptional activation domain (AD, aa 768–881) of yeast GAL4, and containing LEU2 and TRP1 as selectable markers, respectively, were used (Chevray and Nathans, 1992, Proc. Nat. Acad. Sci., 89:5789–93; Vidal et al., supra).

An in-frame fusion between Skp1 and DB was obtained by homologous recombination of the PCR product described below. The following 2 oligonucleotides were designed and obtained as purified primers from Gene Link Inc.: 5'-AGT-AGT-AAC-AAA-GGT-CAA-AGA-CAG-TTG-ACT-GTA-TCG-TCG-AGG-ATG-CCT-TCA-ATT-AAG-TT (SEQ ID NO: 80); 3'-GCG-GTT-ACT-TAC-TTA-GAG-CTC-GAC-GTC-TTA-CTT-ACT-TAG-CTC-ACT-TCT-CTT-CAC-ACC-A (SEQ ID NO: 81). The 5' primer corresponds to a sequence located in the DB of the pPC97-CYH2 plasmid (underlined) flanked by the 5' sequence of the skp1 gene. The 3' primer corresponds to a sequence located by polylinker of the pPC97-CYH2 plasmid (underlined) flanked by the 3' sequence of the skp1 gene. These primers were used in a PCR reaction containing the following components: 100 ng DNA template (skp1 pET plasmid), 1 µM of each primer, 0.2 mM dNTP, 2 mM $MgCl_2$, 10 mM KCl, 20 mM TrisCl pH 8.0, 0.1% Triton X-100, 6 mM $(NH_4)_2SO_4$, 10 µg/ml nuclease-free BSA, 1 unit of Pfu DNA polymerase (4' at 94° C., 1' at 50 C, 10' at 72° C. for 28 cycles). Approximately 100 ng of PCR product were transformed into yeast cells (MaV103 strain; Vidal et al., 1996, Proc. Natl. Acad. Sci. U.S.A. 93:10315–10320; Vidal et al., 1996, Proc. Natl. Acad. Sci. U.S.A. 93:10321–10326) in the presence or in the absence of 100 ng of pPC97-CYH2 plasmid previously digested with BglII and SalI. As a result of the homologous recombination, only yeast cells containing the pPC97-CYH2 plasmid homologously recombined with skp1 cDNA, grew in the absence of leucine. Six colonies were isolated and analyzed by immunoblotting for the expression of Skp1, as described (Vidal et al., supra). All 6 colonies, but not control colonies, expressed a Mr 36,000 fusion-protein that was recognized by our affinity purified anti-Skp1 antibody.

The AD fusions were generated by cloning cDNA fragments in the frame downstream of the AD domains and constructs were confirmed by sequencing, immunoblot, and interaction with Skp1. The pPC86-Skp2s (pPC86) include: pPC86-Skp2, and pPC86-Skp2-CT (aa 181–435 of Skp2). The first fusion represents our positive control since Skp2 is a known interactor of Skp1 (Zhang, et al, 1995, Cell, 82: 915–25); the latter fusion was used as a negative control since it lacked the F-box required for the interaction with Skp1.

MaV103 strain harboring the DB-skp1 fusions was transformed with an activated T-cell cDNA library (Alala 2; Hu, et al., Genes & Dev. 11: 2701–14) in pPC86 using the standard lithium acetate method. Transformants were first plated onto synthetic complete (SC)-Leu-Trp plates, followed by replica plating onto (SC)-Leu-Trp-His plates containing 20 mM 3-aminotriazole (3-AT) after 2 days. Yeast colonies grown out after additional 3–4 days of incubation were picked as primary positives and further tested in three reporter assays: i) growth on SC-Leu-Trp-His plates supplemented with 20 mM 3-AT; ii) -galactosidase activity; and iii) URA3 activation on SC-Leu-Trp plates containing 0.2% 5-fluoroortic acid, as a counterselection method. Of the $3 \times 10^6$ yeast transformants screened AD plasmids were rescued from the fifteen selected positive colonies after all three. MaV103 cells were re-transformed with either rescued AD plasmids and the DBskp1fusion or rescued AD plasmid and the pPC97-CYH2vector without a cDNA insert as control. Eleven AD plasmids from colonies that repeatedly tested positive in all three reporter assays (very strong interactors) and four additional AD plasmids from clones that were positive on some but not all three reporter assays (strong interactors) were recovered and sequenced with the automated ABI 373 DNA sequencing system.

Cloning of full length FBPs Two of the clones encoding FBP4 and FBP5 appeared to be full-length, while full length clones of 4 other cDNAs encoding FBP1, FBP2, FBP3 and FBP7 were obtained with RACE using Marathon-Ready cDNA libraries (Clonthec, cat. #7406, 7445, 7402) according to the manufacturer's instructions. A full-length clone encoding FBP6 was not obtained. Criteria for full length clones included at least two of the following: i) the identification of an ORF yielding a sequence related to known F-box proteins; ii) the presence of a consensus Kozak translation initiation sequence at a putative initiator methionine codon; iii) the identification of a stop codon in the same reading frame but upstream of the putative initiation codon; iv) the inability to further increase the size of the clone by RACE using three different cDNA libraries.

Analysis by Immunoblotting of Protein from Yeast Extracts Yeast cells were grown to mid-logarithmic phase, harvested, washed and resuspended in buffer (50 mM Tris pH 8.0, 20% glycerol, 1 mM EDTA, 0.1% Triton X-100, 5 mM MgCl2, 10 mM β-mercaptoethanol, 1 mM PMSF, 1 mg/ml Leupeptin, 1 mg/ml Pepstatin) at a cell density of about 109 cells/ml. Cells were disrupted by vortexing in the presence of glass beads for 10 min at 40 C. Debris was pelleted by centrifugation at 12,000 RPM for 15 min at 40 C. Approximately 50 g of proteins were subjected to immunoblot analysis as described (Vidal et al., 1996a, supra; Vidal et al., 1996b, supra).

DNA database searches and analysis of protein motifs ESTs (expressed sequence tags) with homology to FBP genes were identified using BLAST, PSI-BLAST (http://www.ncbi.nlm.nih.gov/BLAST/) and TGI Sequence Search (http://www.tigr.org/cgi-bin/BlastSearch/blast_tgi.cgi). ESTs that overlapped more than 95% in at least 100 bps were assembled into novel contiguous ORFs using Sequencher 3.0. Protein domains were identified with ProfileScan Server (http://www.isrec.isb-sib.ch/software/PFSCAN_form.html), BLOCKS Sercher (http://www.blocks.fhcrc.org/blocks_search.html) and IMB Jena (http://genome.imb-jena.de/cgi-bin/GDEWWW/menu.cgi).

Construction of F-box mutants Delta-F-box mutants [(ΔF) FBP1, residues 32–179; (ΔF)FBP2, residues 60–101; (ΔF) FBP3a, residues 40–76; (ΔF)FBP4, residues 55–98] were obtained by deletion with the appropriate restriction enzymes with conservation of the reading frame. (ΔF)Skp2 mutant was obtained by removing a DNA fragment (nucleotides 338–997) with BspEI and XbaI restriction enzymes, and replacing it with a PCR fragment containing nucleotides 457 to 997. The final construct encoded a protein lacking residues 113–152. The leucine 51-to-alanine FBP3a mutant [FBP3a(L51A)] and the tryptophan 76-to-alanine FBP3a mutant [FBP3a(W76A)] were generated by oligonucleotide-directed mutagenesis using the polymerase chain reaction of the QuikChange site-directed mutagenesis kit (Stratagene). All mutants were sequenced in their entirety.

Recombinant proteins cDNA fragments encoding the following human proteins: Flag-tagged FBP1, Flag-tagged (ΔF)FBP1, Flag-tagged FBP3a, Skp2, HA-tagged Cul1, HA-tagged Cul2, (β-catenin, His-tagged cyclin D1, Skp1, His-tagged Skp1, His-tagged Elongin C were inserted into the baculovirus expression vector pBacpak-8 (Clonetech) and cotransfected into Sf9 cells with linearized baculovirus DNA using the BaculoGold transfection kit (Pharmingen). Recombinant viruses were used to infect 5B cells and assayed for expression of their encoded protein by immunoblotting as described above. His-proteins were purified with Nickel-agarose (Invitrogen) according to the manufacturer's instructions.

Antibodies. Anti-Cul1 antibodies was generated by injecting rabbits and mice with the following amino acid peptide: (C)DGEKDTYSYLA (SEQ ID NO: 82). This peptide corresponds to the carboxy-terminus of human Cul1 and is not conserved in other cullins. Anti-Cul2 antibodies was generated by injecting rabbits with the following amino acid peptide: (C)ESSFSLNMNFSSKRTKFKITTSMQ (SEQ ID NO: 83). This peptide is located 87 amino acids from the carboxy-terminus of human Cul2 and is not conserved in other cullins. The anti-Skp1 antibody was generated by injecting rabbits with the peptide (C)EEAQVRKENQW (SEQ ID NO: 84), corresponding to the carboxy-terminus of human Skp1. The cysteine residues (C) were added in order to couple the peptides to keyhole limpet hemocyanin (KLH). All of the antibodies were generated, affinity-purified (AP) and characterized as described (Pagano, M., ed., 1995, "From Peptide to Purified Antibody", in Cell Cycle: Materials and Methods, Spring-Verlag, 217–281). Briefly, peptides whose sequence showed high antigenic index (high hydrophilicity, good surface probability, good flexibility, and good secondary structure) were chosen. Rabbits and mice were injected with peptide-KLH mixed with complete Freund's adjuvant. Subsequently they were injected with the peptide in incomplete Freund's adjuvant, every 2 weeks, until a significant immunoreactivity was detected by immunoprecipitation of 35S-methionine labeled HeLa extract. These antisera recognized bands at the predicted size in both human extracts and a extracts containing recombinant proteins.

Monoclonal antibody (Mab) to Ubc3 was generated and characterized in collaboration with Zymed Inc. Mab to cyclin B (cat #sc-245) was from Santa Cruz; Mabs to p21 (cat #C24420) and p27 (cat #K25020) from Transduction lab. (Mabs) cyclin E, (Faha, 1993, J. of Virology 67: 2456); AP rabbit antibodies to human p27, Skp2, Cdk2 (Pagano, 1992, EMBO J. 11: 761), and cyclin A (Pagano, 1992, EMBO J. 11: 761), and phospho-site p27 specific antibody, were obtained or generated by standard methods. Where indicated, an AP goat antibody to an N-terminal Skp2 peptide (Santa Cruz, cat #sc-1567) was used. Rat anti-HA antibody was from Boehringer Mannheim (cat. #1867423), rabbit anti-HA antibody was from Santa Cruz (cat. #sc-805), mouse anti-Flag antibody was from Kodak (cat. #IB13010), rabbit anti-Flag antibody was from Zymed (cat. #71-5400), anti-Skp1 and anti-(β-catenin mouse antibodies were from Transduction Laboratories (cat. #C19220 and P46020, respectively). The preparation, purification and characterization of a Mab to human cyclin D1 (clone AM29, cat. #33-2500) was performed in collaboration with Zymed Inc. Antiserum to human cyclin D1 was produced as described (Ohtsubo et al., 1995, Mol Cell Biol, 15, 2612–2624).

Extract preparation and cell synchronization Protein extraction was performed as previously described (Pagano, 1993, J. Cell Biol. 121: 101) with the only difference that 1 μm okadaic acid was present in the lysis buffer. Human lung fibroblasts IMR-90 were synchronized in G0/G1 by serum starvation for 48 hours and the restimulated to re-enter the cell cycle by serum readdition. HeLa cells were synchronized by mitotic shake-off as described (Pagano, 1992, EMBO J. 11: 761). Synchronization was monitored by flow cytometry. For in vitro ubiquitination and degradation assays, G1 HeLa cells were obtained with a 48-hour lovastatin treatment and protein extraction performed as described below.

Immunoprecipitation and Immunoblotting. Cell extracts were prepared by addition of 3–5 volumes of standard lysis buffers (Pagano et al., 1992, Science 255, 1144–1147), and conditions for immunoprecipitation were as described (Jenkins and Xiong, 1995; Pagano et al., 1992a Science 255-1144–1147). Proteins were transferred from gel to a nitrocellulose membrane (Novex) by wet blotting as described (Tam et al., 1994 Oncogene 9, 2663). Filters were subjected to immunoblotting using a chemiluminescence (DuPont-NEN) detection system according to the manufacturer's instructions Protein extraction for in vitro ubiquitination assay Logarithmically growing, HeLa-S3 cells were collected at a density of $6 \times 10^5$ cells/ml. Approx. 4 ml of HeLa S3 cell pellet were suspended in 6 ml of ice-cold buffer consisting of 20 mM Tris-HCl (pH 7.2), 2 mM DTT, 0.25 mM EDTA, 10 μg/ml leupeptin, and 10 μg/ml pepstatin. The suspension was transferred to a cell nitrogen-disruption bomb (Parr, Moline, Ill., cat #4639) that had been rinsed thoroughly and chilled on ice before use. The bomb chamber was connected to a nitrogen tank and the pressure was brought slowly to 1000 psi. The chamber was left on ice under the same pressure for 30 minutes and then the pressure was released slowly. The material was transferred to an Eppendorf tube and centrifuged in a microcentrifuge at 10,000 g for 10 minutes. The supernatant (S-10) was divided into smaller samples and frozen at −800 C.

In vitro ubiquitination The ubiquitination assay was performed as described (Lyapina, 1998, Proc Natl Acad Sci U S A, 95: 7451). Briefly, immuno-beads containing Flag-tagged. FBPs immunoprecipitated with anti-Flag antibody were added with purified recombinant human E1 and E2 enzymes (Ubc2, Ubc3 or Ubc4) to a reaction mix containing biotinylated-ubiquitin. Samples were then analyzed by blotting with HRP-streptavidin. E1 and E2 enzymes and biotinylated-ubiquitin were produced as described (Pagano, 1995, Science 269: 682).

Transient transfections cDNA fragments encoding the following human proteins: FBP1, (ΔF)FBP1, FBP2, (ΔF)FBP2, FBP3a, (ΔF)FBP3a, FBP3a(L51A), FBP3a(W76A), FBP4, (ΔF)FBP4, Skp2, (ΔF)Skp2, HA-tagged β-catenin, untagged β-catenin, Skp1, cyclin D1 were inserted into the mammalian expression vector pcDNA3 (Invitrogen) in frame with a Flag-tag at their C-terminus. Cells were transfected with FuGENE transfection reagent (Boehringer, cat. #1-814-443) according to the manufacture's instruction.

Immunofluorescence Transfected cell monolayers growing on glass coverslips were rinsed in PBS and fixed with 4% paraformaldehyde in PBS for 10 minutes at 4° C. followed by permeabilization for 10 minutes with 0.25% Triton X-100 in PBS. Other fixation protocols gave comparable results. Immunofluorescence stainings were performed using 1 μg/ml rabbit anti-Flag antibody as described (Pagano, 1994, Genes & Dev., 8:1627).

Northern Blot Analysis Northern blots were performed using human multiple-tissue mRNAs from Clontech Inc. Probes were radiolabeled with [alpha-32P] dCTP (Amersham Inc.) using a random primer DNA labeling kit (Gibco BRL) ($2 \times 10^6$ cpm/ml). Washes were performed with 0.2×SSC, 0.1% SDS, at 55–60° C. FBP1 and FBP3a probes were two HindIII restriction fragments (nucleotides 1–571 and 1–450, respectively), FBP2, FBP4, and FBP1 probes were their respective full-length cDNAs, and β-ACTIN probe was from Clontech Inc.

Fluorescence in situ hybridixation (FISH) Genomic clones were isolated by high-stringency screening (65° C., 0.2×SSC, 0.1% SDS wash) of a λFLX II placenta human genomic library (Stratagene) with cDNA probes obtained from the 2-hybrid screening. Phage clones were confirmed by high-stringency Southern hybridization and partial sequence analysis. Purified whole phage DNA was labeled and FISH was performed as described (M. Pagano., ed., 1994, in Cell Cycle: Materials and Methods, 29).

6.2 RESULTS 6.2.1 CHARACTERIZATION OF NOVEL F-BOX PROTEINS AND THEIR ACTIVITY IN VIVO

An improved version of the yeast two-hybrid system was used to search for interactors of human Skp1. The MaV103 yeast strain harboring the Gal4 DB-Skp1 fusion protein as bait was transformed with an activated T-cell cDNA library expressing Gal4 AD fusion proteins as prey. After initial selection and re-transformation steps, 3 different reporter assays were used to obtain 13 positive clones that specifically interact with human Skp1. After sequence analysis, the 13 rescued cDNAs were found to be derived from 7 different open reading frames all encoding FBPs. These novel FBPs were named as follows: FBP1, shown in FIG. 3 (SEQ ID NO:1); FBP2, shown in FIG. 4 (SEQ ID NO:3), FBP3a, shown in FIG. 5 (SEQ ID NO:5), FBP4, shown in FIG. 7 (SEQ ID NO:7), FBP5, shown in FIG. 8 (SEQ ID NO:9), FBP6, shown in FIG. 9 (SEQ ID NO:11), FBP7, shown in FIG. 10 (SEQ ID NO:13). One of the seven FBPs, FBP1 (SEQ ID NO:1) was also identified by others while our screen was in progress (Margottin et al., 1998, Molecular Cell, 1:565–74).

BLAST programs were used to search for predicted human proteins containing an F-box in databases available through the National Center for Biotechnology Information and The Institute for Genomic Research. The alignment of the F-box motifs from these predicted human FBPs is shown in FIG. 1. Nineteen previously uncharacterized human FBPs were identified by aligning available sequences (GenBank Accession Nos. AC002428, AI457595, AI105408, H66467, T47217, H38755, THC274684, AI750732, AA976979, AI571815, T57296, Z44228, Z45230, N42405, AA018063, AI751015, AI400663, T74432, AA402415, AI826000, AI590138, AF174602, Z45775, AF174599, THC288870, AI017603, AF174598, THC260994, AI475671, AA768343, AF174595, THC240016, N70417, T10511, AF174603, EST04915, AA147429, AI192344, AF174594, AI147207, AI279712, AA593015, AA644633, AA335703, N26196, AF174604, AF053356, AF174606, AA836036, AA853045, AI479142, AA772788, AA039454, AA397652, AA463756, AA007384, AA749085, AI640599, THC253263, AB020647, THC295423, AA434109, AA370939, AA215393, THC271423, AF052097, THC288182, AL049953, CAB37981, AL022395, AL031178, THC197682, and THC205131), with the nucleotide sequences derived from the F-box proteins disclosed above.

The nineteen previously uncharacterized FBP nucleotide sequences thus identified were named as follows: FBP3b, shown in FIG. 6 (SEQ ID NO:23); FBP8, shown in FIG. 11 (SEQ ID NO:25); FBP9, shown in FIG. 12 (SEQ ID NO:27); FBP10, shown in FIG. 13 (SEQ ID NO:29); FBP11, shown in FIG. 14 (SEQ ID NO:31); FBP12, shown in FIG. 15 (SEQ ID NO:33); FBP13, shown in FIG. 16 (SEQ ID NO:35); FBP14, shown in FIG. 17 (SEQ ID NO:37); FBP15, shown in FIG. 18 (SEQ ID NO:39); FBP16, shown in FIG. 19 (SEQ ID NO:41); FBP17, shown in FIG. 20 (SEQ ID NO:43); FBP18, shown in FIG. 21 (SEQ ID NO:45); FBP19, shown in FIG. 22 (SEQ ID NO:47); FBP20, shown in FIG. 23 (SEQ ID NO:49); FBP21, shown in FIG. 24 (SEQ ID NO:51); FBP22, shown in FIG. 25 (SEQ ID NO:53); FBP23, shown in FIG. 26 (SEQ ID NO:55); FBP24, shown in FIG. 27 (SEQ ID NO:57); and FBP25, shown in FIG. 28 (SEQ ID NO:59). The alignment of the F-box motifs from these predicted human FBPs is shown in FIG. 1A. Of these sequences, the nucleotide sequences of fourteen identified FBPs, FBP3b (SEQ ID NO:23), FBP8 (SEQ ID NO:25), FBP11 (SEQ ID NO:31), FBP12 (SEQ ID NO:33), FBP13 (SEQ ID NO:35), FBP14 (SEQ ID NO:37), FBP15 (SEQ ID NO:39), FBP17 (SEQ ID NO:43), FBP18 (SEQ ID NO:45), FBP20 (SEQ ID NO:49), FBP21 (SEQ ID NO:51), FBP22 (SEQ ID NO:53), FBP23 (SEQ ID NO:55), and FBP25 (SEQ ID NO:59) were not previously assembled and represent novel nucleic acid molecules. The five remaining sequences, FBP9 (SEQ ID NO:27), FBP10 (SEQ ID NO:29), FBP16 (SEQ ID NO:41), FBP19 (SEQ ID NO:47), and FBP24 (SEQ ID NO:57) were previously assembled and disclosed in the database, but were not previously recognized as F-box proteins.

Computer analysis of human FBPs revealed several interesting features (see the schematic representation of FBPs in FIG. 2. Three FBPs contain WD-40 domains; seven FBPs contain LRRs, and six FBPs contain other potential protein-protein interaction modules not yet identified in FBPs, such as leucine zippers, ring fingers, helix-loop-helix domains, proline rich motifs and SH2 domains.

As examples of the human FBP family, a more detailed characterization of some FBPs was performed. To confirm the specificity of interaction between the novel FBPs and human Skp1, eight in vitro translated FBPs were tested for binding to His-tagged-Skp1 pre-bound to Nickel-agarose beads. As a control Elongin C was used, the only known human Skp1 homolog. All 7 FBPs were able to bind His-Skp1 beads but not to His-tagged-Elongin C beads (FIG. 29). The small amount of FBPs that bound to His-tagged-Elongin C beads very likely represents non-specific binding since it was also present when a non-relevant protein (His-tagged-p27) bound to Nickel-agarose beads was used in pull-down assays (see as an example, FIG. 29, lane 12).

F-box deletion mutants, (ΔF)FBP1, (ΔF)FBP2, (ΔF)FBP3a, and mutants containing single point mutations in conserved amino acid residues of the F-box, FBP3a(L51A) and FBP3a(W76A) were constructed. Mutants lacking the F-box and those with point mutations lost their ability to bind Skp1 (FIG. 29), confirming that human FBPs require the integrity of their F-box to specifically bind Skp1.

In order to determine whether FBP1, FBP2, FBP3a, FBP4 and FBP7 interact with human Skp1 and Cul1 in vivo (as Skp2 is known to do), flag-tagged-FBP1, -(ΔF)FBP1, -FBP2, -(ΔF)FBP2, -FBP3a, -(ΔF)FBP3a, -FBP4 and -FBP7 were expressed in HeLa cells from which cell extracts were made and subjected to immunoprecipitation with an anti-Flag antibody. As detected in immunoblots with specific antibodies to Cul1, Cul2 (another human cullin), and Skp1, the anti-Flag antibody co-precipitated Cul1 and Skp1, but not Cul2, exclusively in extracts from cells expressing wild-type FBPs (FIG. 29 and data not shown). These data indicate that as in yeast, the human Skp1/cullin complex forms a scaffold for many FBPs.

The binding of FBPs to the Skp1/Cul1 complex is consistent with the possibility that FBPs associate with a ubiquitin ligation activity. To test this possibility, Flag-tagged were expressed in HeLa cells, FBPs together with human Skp1 and Cul1. Extracts were subjected to immunoprecipitation with an anti-Flag antibody and assayed for ubiquitin ligase activity in the presence of the human ubiquitin-activating enzyme (E1) and a human Ubc. All of the wild type FBPs tested, but not FBP mutants, associated with a ubiquitin ligase activity which produced a high molecular weight smear characteristic of ubiquitinated proteins (FIG. 31). The ligase activity was N-ethylmaleimide (NEM) sensitive (FIG. 31, lane 2) and required the presence of both Ubc4 and E1. Results similar to those with Ubc4 were obtained using human Ubc3, whereas Ubc2 was unable to sustain the ubiquitin ligase activity of these SCFs (FIG. 31, lanes 12, 13).

Using indirect immunofluorescence techniques, the subcellular distribution of FBP1, FBP2, FBP3a, FBP4 and FBP7 was studied in human cells. Flag-tagged-versions of these proteins were expressed in HeLa, U2OS, and 293T cells and subjected to immunofluorescent staining with an anti-Flag antibody. FBP1, FBP4 and FBP7 were found to be distributed both in the cytoplasm and in the nucleus, while FBP2 was detected mainly in the cytoplasm and FBP3a mainly in the nucleus. FIG. 32 shows, as an example, the subcellular localization of FBP1, FBP2, FBP3a, FBP4 observed in HeLa cells. The localization of (ΔF)FBP1, (ΔF)FBP2, (ΔF)FBP3a mutants was identical to those of the respective wild-type proteins (FIG. 32) demonstrating that the F-box and the F-box-dependent binding to Skp1 do not determine the subcellular localization of FBPs. Immunofluorescence stainings were in agreement with the results of biochemical subcellular fractionation.

6.2.2 NORTHERN BLOT ANALYSIS OF NOVEL UBIQUITIN LIGASE GENE TRANSCRIPTS

RNA blot analysis was performed on poly(A)+ mRNA from multiple normal human tissues (heart, brain, placenta, lung, liver, skeletal, muscle, kidney, pancreas, spleen, thymus, prostate, testis, ovary, small intestine, colon, peripheral blood leukocytes, see FIG. 33). FBP1 mRNA transcripts (a major band of ~7-kb and two minor bands of ~3.5 and ~2.5 kb) were expressed in all of the 16 human tissues tested but were more prevalent in brain and testis. Testis was the only tissue expressing the smaller FBP1 mRNA forms in amounts equal to, if not in excess of, the 7 kb form. FBP2 transcripts (~7.7-kb and ~2.4-kb) were expressed in all tissues tested, yet the ratio of the FBP2 transcripts displayed some tissue differences. An approximately 4 kb FBP3a transcript was present in all tissues tested and two minor FBP3a forms of approximately 3 kb and 2 kb became visible, upon longer exposure, especially in the testis. An approximately 4.8 kb FBP4 transcript was expressed in all normal human tissues tested, but was particularly abundant in heart and pancreas. Finally, the pattern of expression of the new FBPs was compared to that of FBP1 whose mRNA species (a major band ~4 kb and a minor band of ~8.5 kb) were found in all tissues but was particularly abundant in placenta.

6.2.3 CHROMOSOMAL LOCALIZATION OF THE HUMAN FBP GENES

Figure 34A:
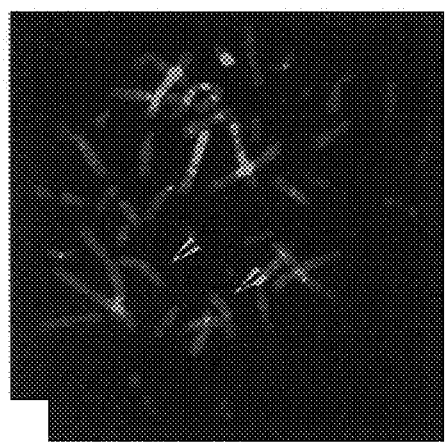
Figure 34B:
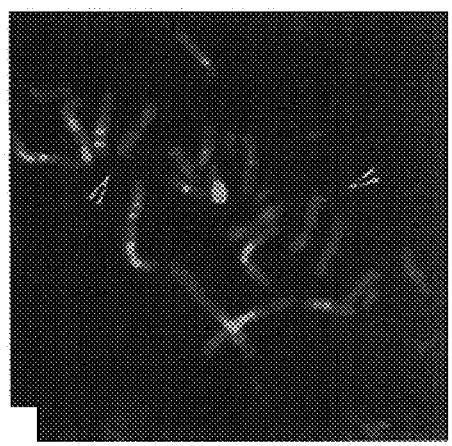
Figure 34C:
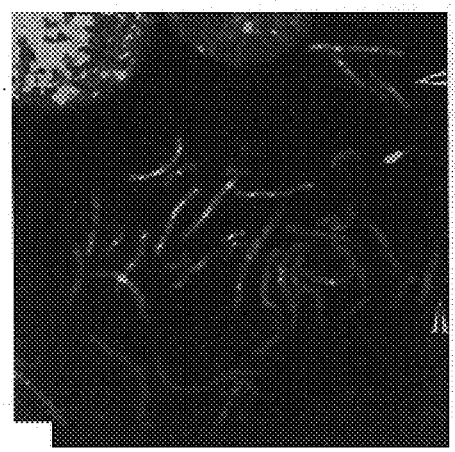
Figure 34D:
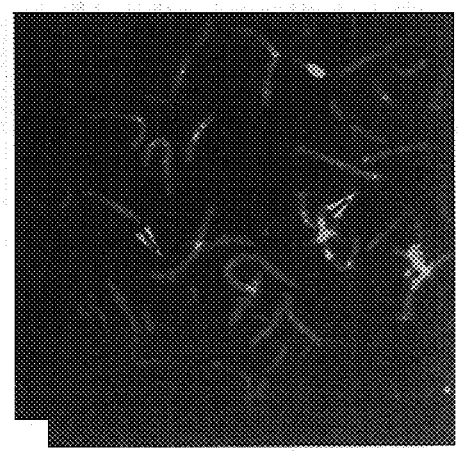
Figure 34E:
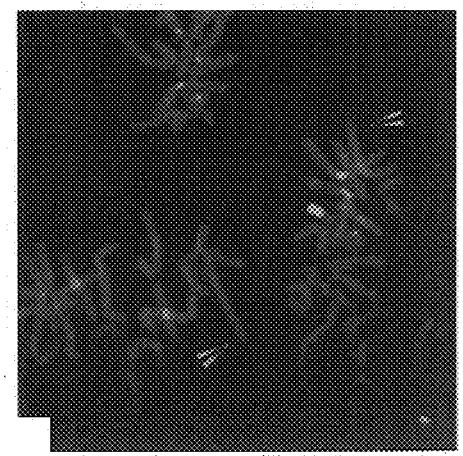

Unchecked degradation of cellular regulatory proteins (e.g., p53, p27, β-catenin) has been observed in certain tumors, suggesting the hypothesis that deregulated ubiquitin ligases play a role in this altered degradation (reviewed in A. Ciechanover, 1998, Embo J, 17: 7151). A well understood example is that of MDM2, a proto-oncogene encoding a ubiquitin ligase whose overexpression destabilize its substrate, the tumor suppressor p53 (reviewed by Brown and Pagano, 1997, Biochim Biophys Acta, 1332: 1, 1998). To map the chromosomal localization of the human FBP genes and to determine if these positions coincided with loci known to be altered in tumors or in inherited disease, fluorescence in situ hybridization (FISH) was used. The FBP1 gene was mapped and localized to 10q24 (FIG. 34A), FBP2 to 9q34 (FIG. 34B), FBP3a to 13q22 (FIG. 34C), FBP4 to 5p12 (FIG. 34D) and FBP5 to 6q25-26 (FIG. 34E). FBP genes (particularly FBP1, FBP3a, and FBP5) are localized to chromosomal loci frequently altered in tumors (for references and details see Online Mendelian Inheritance in Man database, http://www3.ncbi.nlm.nih.gov/omim/). In particular, loss of 10q24 (where FBP1 is located) has been demonstrated in approx. 10% of human prostate tumors and small cell lung carcinomas (SCLC), suggesting the presence of a tumor suppressor gene at this location. In addition, up to 7% of childhood acute T-cell leukemia is accompanied by a translocation involving 10q24 as a breakpoint, either t(10;14)(q24;q11) or t(7;10)(q35;q24). Although rarely, the 9q34 region (where FBP2 is located) has been shown to be a site of loss of heterozygosity (LOH) in human ovarian and bladder cancers. LOH is also observed in the region. Finally, 6q25-26 (where FBP5 is located) has been shown to be a site of loss of heterozygosity in human ovarian, breast and gastric cancers hepatocarcinomas, Burkitt's lymphomas, and parathyroid adenomas.

7. EXAMPLE: FBP1 REGULATES THE STABILITY OF β-CATENIN

Deregulation of β-catenin proteolysis is associated with malignant transformation. Xenopus Slimb and Drosophila FBP1 negatively regulate the Wnt/β-catenin signaling pathway (Jiang and Struhl, 1998, supra; Marikawa and Elinson, 1998). Since ubiquitin ligase complexes physically associate with their substrates, the studies in this Example were designed to determine whether FBP1 can interact with β-catenin. The results show that FBP1 forms a novel ubiquitin ligase complex that regulates the in vivo stability of β-catenin. Thus, the identification of FBP1 as a component of the novel ubiquitin ligase complex that ubiquitinates β-catenin, provides new targets that can be used in screens for agonists, antagonists, ligands, and novel substrates using the methods of the present invention. Molecules identified by these assays are potentially useful drugs as therapeutic agents against cancer and proliferative disorders.

7.1 MATERIALS AND METHODS FOR IDENTIFICATION OF FBP1 FUNCTION

Recombinant proteins, Construction of F-box mutants, Antibodies, Transient transfections, Immunoprecipitation, Immunoblotting, Cell culture and Extract preparation Details of the methods are described in Section 6.1, supra.

7.2 RESULTS

7.2.1 HUMAN FBP1 INTERACTS WITH β-CATENIN

Flag-tagged FBP1 and β-catenin viruses were used to co-infect insect cells, and extracts were analyzed by immunoprecipitation followed by immunoblotting. β-catenin was co-immunoprecipitated by an anti-Flag antibody (FIG. 35A), indicating that in intact cells β-catenin and FBP1 physically interact. It has been shown that binding of the yeast FBP Cdc4 to its substrate Sic1 is stabilized by the presence of Skp1 (Skowyra et al., 1997, Cell, 91, 209–219). Simultaneous expression of human Skp1 had no effect on the strength of the interaction between FBP1 and β-catenin. To test the specificity of the FBP1/β-catenin interaction, cells were co-infected with human cyclin D1 and FBP1 viruses. The choice of this cyclin was dictated by the fact that human cyclin D1 can form a complex with the Skp2 ubiquitin ligase complex (Skp1-Cul1-Skp2; Yu et al., 1998, Proc. Natl. Acad. Sci. U.S.A, 95:11324–9). Under the same conditions used to demonstrate the formation of the FBP1/β-catenin complex, cyclin D1 could not be co-immunoprecipitated with Flag-tagged FBP1, and anti-cyclin D1 antibodies were unable to co-immunoprecipitate FBP1 (FIG. 35B, lanes 1–3). Co-expression of Skp1 (FIG. 35B, lanes 4–6) or Cdk4 with FBP1 and cyclin D1 did not stimulate the association of cyclin D1 with FBP1.

Mammalian expression plasmids carrying HA-tagged β-catenin and Flag-tagged FBP1 (wild type or mutant) were then co-transfected in human 293 cells. β-catenin was detected in anti-Flag immunoprecipitates when co-expressed with either wild type or (ΔF)FBP1 mutant (FIG. 35C, lanes 4–6), confirming the presence of a complex formed between β-catenin and FBP1 in human cells.

7.2.2 F-BOX DELETED FBP1 MUTANT STABILIZES β-CATENIN IN VIVO

The association of (ΔF)FBP1 to β-catenin suggested that (ΔF)FBP1 might act as a dominant negative mutant in vivo by being unable to bind Skp1/Cul1 complex, on the one hand, while retaining the ability to bind β-catenin, on the other. HA-tagged β-catenin was co-expressed together with Flag-tagged (ΔF)FBP1 or with another F-box deleted FBP, (ΔF)FBP2. FBP2 was also obtained with our screening for Skp1-interactors; and, like FBP1, contains several WD-40 domains. The presence of (ΔF)FBP1 specifically led to the accumulation of higher quantities of β-catenin (FIG. 36A). To determine whether this accumulation was due to an increase in β-catenin stability, we measured the half-life of β-catenin using pulse chase analysis. Human 293 cells were transfected with HA-tagged β-catenin alone or in combination with the wild type or mutant FBP1. While wild type Fpb1 had little effect on the degradation of β-catenin, the F-box deletion mutant prolonged the half life of β-catenin from 1 to 4 hours (FIG. 36B).

FBP1 is also involved in CD4 degradation induced by the HIV-I Vpu protein (Margottin et al., supra). It has been shown that Vpu recruits FBP1 to DC4 and (ΔF) FBP1 inhibits Vpu-mediated CD4 regulation. In addition, FBP1-ubiquitin ligase complex also controls the stability of IKBαa (Yaron et al., 1998, Nature, 396: 590). Thus, the interactions between FBP1 and β-catenin, Vpu protein, CD4, and IKBαa are potential targets that can be used to screen for agonists, antagonists, ligands, and novel substrates using the methods of the present invention.

8. EXAMPLE: METHODS FOR IDENTIFYING p27 AS A SUBSTRATE OF THE FBP SKP2

Degradation of the mammalian G1 cyclin-dependent kinase (Cdk) inhibitor p27 is required for the cellular transition from quiescence to the proliferative state. The ubiquitination and degradation of p27 depend upon its phosphorylation by cyclin/Cdk complexes. Skp2, an F-box protein essential for entry into S phase, specifically recognizes p27 in a phosphorylation-dependent manner. Furthermore, both in vivo and in vitro, Skp2 is a rate-limiting component of the machinery that ubiquitinates and degrades phosphorylated p27. Thus, p27 degradation is subject to dual control by the accumulation of both Skp2 and cyclins following mitogenic stimulation.

This Example discloses novel assays that have been used to identify the interaction of Skp2 and p27 in vitro. First, an in vitro ubiquitination assay performed using p27 as a substrate is described. Second, Skp2 is depleted from cell extracts using anti-Skp2 antibody, and the effect on p27 ubiquitin ligase activity is assayed. Purified Skp2 is added back to such immunodepleted extracts to restore p27 ubiquitination and degradation. Also disclosed is the use of a dominant negative mutant, (ΔF)Skp2, which interferes with p27 ubiquitination and degradation.

The assays described herein can be used to test for compounds that inhibit cell proliferation. The assays can be carried out in the presence or absence of molecules, compounds, peptides, or other agents described in Section 5.5. Agents that either enhance or inhibit the interactions or the ubiquitination activity can be identified by an increase or decrease the formation of a final product are identified. Such agents can be used, for example, to inhibit Skp2-regulated p27 ubiquitination and degradation in vivo. Molecules identified by these assays are potentially useful drugs as therapeutic agents against cancer and proliferative disorders.

Dominant negative mutants, for example the mutant (ΔF) Skp2, and antisense oligos targeting SKP2, mRNA interfere with p27 ubiquitination and degradation, and can be used in gene therapies against cancer. The assays described herein can also be used to identify novel substrates of the novel FBP proteins, as well as modulators of novel ubiquitin ligase complex-substrate interactions and activities.

8.1 MATERIALS AND METHODS FOR IDENTIFICATION OF p27 AS A SKP2 SUBSTRATE

Protein extraction for in vitro ubiquitination assay Approx. 4 ml of HeLa S3 cell pellet were suspended in 6 ml of ice-cold buffer consisting of 20 mM Tris-HCl (pH 7.2), 2 mM DTT, 0.25 mM EDTA, 10 µg/ml leupeptin, and 10 µg/ml pepstatin. The suspension was transferred to a cell nitrogen-disruption bomb (Parr, Moline, Ill., cat #4639) that had been rinsed thoroughly and chilled on ice before use. The bomb chamber was connected to a nitrogen tank and the pressure was brought slowly to 1000 psi. The chamber was left on ice under the same pressure for 30 minutes and then the pressure was released slowly. The material was transferred to an Eppendorf tube and centrifuged in a microcentrifuge at 10,000 g for 10 minutes. The supernatant (S-10) was divided into smaller samples and frozen at −80° C. . This method of extract preparation based on the use of a cell nitrogen-disruption bomb extract preserves the activity to in vitro ubiquitinate p27 better than the method previously described (Pagano et al., 1995, Science 269:682–685).

Reagents and antibodies Ubiquitin aldehyde (Hershko & Rose, 1987, Proc. Natl. Acad. Sci. USA 84:1829–33), methyl-ubiquitin (Hershko & Heller, 1985, Biochem. Biophys. Res. Commun. 128:1079–86) and p13 beads (Brizuela et al., 1987, EMBO J. 6:3507–3514) were prepared as described. β, γ-imidoadenosine-50-triphosphate (AMP-PNP), staurosporine, hexokinase, and deoxy-glucose were from Sigma; lovastatine obtained from Merck; flavopiridol obtained from Hoechst Marion Roussel. The phospho-site p27 specific antibody was generated in collaboration with Zymed Inc. by injecting rabbits with the phospho-peptide NAGSVEQT*PKKPGLRRRQT (SEQ ID NO: 85), corresponding to the carboxy terminus of the human p27 with a phosphothreonine at position 187 (T*). The antibody was then purified from serum with two rounds of affinity chromatography using both phospho- and nonphospho-peptide chromatography. All the other antibodies are described in Section 6.1.

Immunodepletion Assays For immunodepletion assays, 3 µl of an Skp2 antiserum was adsorbed to 15 µl Affi-Prep Protein-A beads (BioRad), at 4° C. for 90 min. The beads were washed and then mixed (4° C., 2 hours) with 40 µl of HeLa extract (approximately 400 µg of protein). Beads were removed by centrifugation and supernatants were filtered through a 0.45-µ Microspin filter (Millipore). Immunoprecipitations and immunoblots were performed as described (M. Pagano, et al., 1995, supra. Rabbit polyclonal antibody against purified GST-Skp2 was generated, affinity-purified (AP) and characterized as described (M. Pagano, in Cell Cycle-Materials and Methods, M. Pagano Ed. (Springer, N.Y., 1995), chap. 24; E. Harlow and D. Lane, in Using antibodies. A Laboratory Manual (Cold Spring Harbor Laboratory, Cold Spring Harbor, N.Y., 1998), in collaboration with Zymed Inc. (cat #51-1900). Monoclonal antibodies (Mabs) to human Cul1, and cyclin E, (Faha et al., 1993, J. of Virology 67:2456); AP rabbit antibodies to human p27, Skp1 (Latres et al., 1999, Oncogene 18:849), Cdk2 (Pagano, et al., 1992, Science 255:1144) and phospho-site p27 specific antibody. Mab to cyclin B was from Santa Cruz (cat #sc-245); Mabs to p21 (cat #C24420) and p27 (cat #K25020) Transduction lab; anti-Flag rabbit antibody from Zymed (cat #71-5400). An AP goat antibody to an N-terminal Skp2 peptide (Santa Cruz, cat #sc-1567) was used.

Construction of Skp2 F-box mutant (ΔF)Skp2 mutant was obtained by removing a DNA fragment (nucleotides 338–997) with BspEI and XbaI restriction enzymes, and replacing it with a PCR fragment containing nucleotides 457 to 997. The final construct encoded a protein lacking residues 113–152.

Recombinant proteins cDNA fragments encoding the following human proteins: Flag-tagged FBP1, Flag-tagged (ΔF)FBP1, Flag-tagged FBP3a, Skp2, HA-tagged Cul1, HA-tagged Cul2, β-catenin, His-tagged cyclin D1, Skp1, His-tagged Skp1, His-tagged Elongin C were inserted into the baculovirus expression vector pBacpak-8 (Clonetech) and cotransfected into Sf9 cells with linearized baculovirus DNA using the BaculoGold transfection kit (Pharningen). Baculoviruses expressing human His-tagged cyclin E and HA-tagged Cdk2 were supplied by D. Morgan (Desai, 1992, Molecular Biology of the Cell 3: 571). Recombinant viruses were used to infect 5B cells and assayed for expression of their encoded protein by immunoblotting as described above. His-proteins were purified with Nickel-agarose (Invitrogen) according to the manufacturer's instructions. The different complexes were formed by co-expression of the appropriate baculoviruses and purified by nickel-agarose chromatography, using the His tag at the 5' of Skp1 and cyclin E. Unless otherwise stated, recombinant proteins were added to incubations at the following amounts: cyclin E/Cdk2, ~0.5 pmol; Skp1, ~0.5 pmol; Skp2, ~0.1 pmol; FBP1, ~0.1 pmol; FBP3a, ~0.1 pmol, Cul1, ~0.1 pmol. The molar ratio of Skp1/Skp2, Skp1/FBP1, Skp1/FBP3a, and Skp1/Cul1 in the purified preparations was ~5.

Extract preparation and cell synchronization. Transient transfections, Immunoprecipitation and Immunoblotting Methods were carried out as described in Section 6.1, supra.

8.2 RESULTS 8.2.1 p27 IN VITRO UBIQUITINATION ASSAY

In an exemplary in vitro ubiquitination assay, logarithmically growing, HeLa-S3 cells were collected at a density of $6 \times 10^5$ cells/ml. Cells are arrested in G1 by 48-hour treatment with 70 µM lovastatin as described (O'Connor &. Jackman, 1995 in Cell Cycle-Materials and Methods, M. Pagano, ed., Springer, N.Y., chap. 6). 1 µl of in vitro translated [35S]p27 is incubated at 30° C. for different times (0–75 minutes) in 10 µl of ubiquitination mix containing: 40 mM Tris pH 7.6, 5 mM $MgCl_2$, 1 mM DTT, 10% glycerol, 1 µM ubiquitin aldehyde, 1 mg/ml methyl ubiquitin, 10 mM creatine phosphate, 0.1 mg/ml creatine phosphokinase, 0.5 mM ATP, 1 µM okadaic acid, 20–30 µg HeLa cell extract. Ubiquitin aldehyde can be added to the ubiquitination reaction to inhibit the isopeptidases that would remove the chains of ubiquitin from p27. Addition of methyl ubiquitin competes with the ubiquitin present in the cellular extracts and terminates p27 ubiquitin chains. Such chains appear as discrete bands instead of a high molecular smear. These shorter polyubiquitin chains have lower affinity for the proteasome and therefore are more stable. Reactions are terminated with Laemmli sample buffer containing β-mercaptoethanol and the products can be analyzed on protein gels under denaturing conditions.

Polyubiquitinated p27 forms are identified by autoradiography. p27 degradation assay is performed in a similar manner, except that (i) Methylated ubiquitin and ubiquitin aldehyde were omitted; (ii) The concentration of HeLa extract is approximately 7 µg/µl; (iii) Extracts are prepared by hypotonic lysis (Pagano et al., 1995, Science 269:682), which preserves proteasome activity better than the nitrogen bomb disruption procedure. In the absence of methyl ubiquitin, p27 degradation activity, instead of p27 ubiquitination activity, can be measured.

The samples are immunoprecipited with an antibody to p27 followed by a subsequent immunoprecipitation with an anti-ubiquitin antibody and run on an 8% SDS gel. The high molecular species as determined by this assay are ubiquitinated. As a control, a p27 mutant lacking all 13 lysines was used. This mutant form of p27 is not ubiquitinated and runs at higher molecular weight on the 8% SDS gel.

8.2.2 p27-SKP2 INTERACTION ASSAYS AND p27-SKP2 IMMUNODEPLETION ASSAY

The recruitment of specific substrates by yeast and human FBPs to Skp1/cullin complexes is phosphorylation-dependent. Accordingly, peptides derived from IKBα and β-catenin bind to FBP1 specifically and in a phosphorylation-dependent manner (Yaron, 1998, Nature 396: 590; Winston et al., 1999, Genes Dev. 13: 270). A p27 phospho-peptide with a phosphothreonine at position 187 was assayed for its ability to bind to human FBPs, including Skp2 and the FBP1, FBP2, FBP3a, FBP4, FBP5, FBP6, and FBP7, isolated by using a 2-hybrid screen using Skp1 as bait, as described in Section 6, above. Four of these FBPs contain potential substrate interaction domains, such as WD-40 domains in FBP1 and FBP2, and leucine-rich repeats in Skp2 and FBP3a. The phospho-p27 peptide was immobilized to Sepharose beads and incubated with these seven in vitro translated FBPs (FIG. 37A). Only one FBP, Skp2, was able to bind to the phospho-T187 p27 peptide. Then, beads linked to p27 peptides (in either phosphorylated or unphosphorylated forms) or with an unrelated phospho-peptide were incubated with HeLa cell extracts. Proteins stably associated with the beads were examined by immunoblotting. Skp2 and its associated proteins, Skp1 and Cul1, were readily detected as proteins bound to the phospho-p27 peptide but not to control peptides (FIG. 37B).

To further study p27 association to Skp2, in vitro translated p27 was incubated with either Skp1/Skp2 complex, cyclin E/Cdk2 complex, or the combination of both complexes under conditions in which p27 is phosphorylated on T187 by cyclin E/Cdk2 (Montagnoli, A., et al., 1999, Genes & Dev 13: 1181). Samples were then immunoprecipitated with an anti-Skp2 antibody. p27 was co-immunoprecipitated with Skp2 only in the presence of cyclin E/Cdk2 complex (FIG. 37C). Notably, under the same conditions, a T187-to-alanine p27 mutant, p27(T187A), was not co-immunoprecipitated by the anti-Skp2 antibody. Finally, we tested Skp2 and p27 association in vivo. Extracts from HeLa cells and IMR90 human diploid fibroblasts were subjected to immunoprecipitation with two different antibodies to Skp2 and then immunoblotted. p27 and Cul1, but not cyclin D1 and cyclin B1, were specifically detected in Skp2 immunoprecipitates (FIG. 38). Importantly, using a phospho-T187 site p27 specific antibody we demonstrated that the Skp2-bound p27 was phosphorylated on T187 (FIG. 38, lane 2, bottom panel). Furthermore, an anti-peptide p27 antibody specifically co-immunoprecipitated Skp2. These results indicate that the stable interaction of p27 with Skp2 was highly specific and dependent upon phosphorylation of p27 on T187.

A cell-free assay for p27 ubiquitination which faithfully reproduced the cell cycle stage-specific ubiquitination and degradation of p27 has been developed (Montagnoli et al., supra). Using this assay, a p27-ubiquitin ligation activity is higher in extracts from asynchronously growing cells than in those from G1-arrested cells (FIG. 39A, lanes 2 and 4). In accordance with previous findings (Montagnoli, A., et al., supra), the addition of cyclin E/Cdk2 stimulated the ubiquitination of p27 in both types of extracts (FIG. 39A, lanes 3 and 5). However, this stimulation was much lower in extracts from G1-arrested cells than in those from growing cells, suggesting that in addition to cyclin E/Cdk2, some other component of the p27-ubiquitin ligation system is rate-limiting in G1. This component could be Skp2 since, in contrast to other SCF subunits, its levels are lower in extracts from G1 cells than in those from asynchronous cells and are inversely correlated with levels of p27 (FIGS. 39B and 43). Skp2 was thus tested to determine if it is a rate-limiting component of a p27 ubiquitin ligase activity. The addition of recombinant purified Skp1/Skp2 complex alone to G1 extracts did not stimulate p27 ubiquitination significantly (FIG. 39A, lane 6). In contrast, the combined addition of Skp1/Skp2 and cyclin E/Cdk2 complexes strongly stimulated p27 ubiquitination in G1 extracts (FIG. 39A, lane 7). Similarly, the combined addition of Skp1/Skp2 and cyclin E/Cdk2 strongly stimulated p27 proteolysis as measured by a degradation assay (FIG. 39A, lanes 13–16). Since the Skp1/Skp2 complex used for these experiments was isolated from insect cells co-expressing baculovirus His-tagged-Skp1 and Skp2 (and co-purified by nickel-agarose chromatography), it was possible that an insect-derived F-box protein co-purified with His-Skp1 and was responsible for the stimulation of p27 ubiquitination in G1 extracts. This possibility was eliminated by showing that the addition of a similar amount of His-tagged-Skp1, expressed in the absence of Skp2 in insect cells and purified by the same procedure, did not stimulate p27 ubiquitination in the presence of cyclin E/Cdk2 (FIG. 39A, lane 8). Furthermore, we found that neither FBP1 nor FBP3a could replace Skp2 for the stimulation of p27-ubiquitin ligation in G1 extracts (FIG. 39A, lanes 9–12). Stimulation of p27-ubiquitination in G1 extracts by the combined addition of Skp1/Skp2 and cyclin E/Cdk2 could be observed only with wild-type p27, but not with the p27(T187A) mutant (lanes 17–20), indicating that phosphorylation of p27 on T187 is required for the Skp2-mediated ubiquitination of p27. These findings indicated that both cyclin E/Cdk2 and Skp1/Skp2 30 complexes are rate-limiting for p27 ubiquitination and degradation in the G1 phase.

To further investigate the requirement of Skp2 for p27 ubiquitin ligation, Skp2 was specifically removed from extracts of asynchronously growing cells by immunodepletion with an antibody to Skp2. The immunodepletion procedure efficiently removed most of Skp2 from these extracts and caused a drastic reduction of p27-ubiquitin ligation activity (FIG. 40A, lane 4) as well as of p27 degradation activity. This effect was specific as shown by the following observations: (i) Similar treatment with pre-immune serum did not inhibit p27-ubiquitination (FIG. 40A, lane 3); (ii) Pre-incubation of anti-Skp2 antibody with recombinant GST-Skp2 (lane 5), but not with a control protein (lane 4), prevented the immunodepletion of p27-ubiquitination activity from extracts; (iii) p27-ubiquitinating activity could be restored in Skp2-depleted extracts by the addition of His-Skp1/Skp2 complex (FIG. 40B, lane 3) but not His-Skp1 (lane 2), His-Skp1/Cul1complex (lane 4), or His-Skp1/FBP1.

We then immunoprecipitated Skp2 from HeLa extracts and tested whether this immunoprecipitate contained a p27 ubiquitinating activity. The anti-Skp2 beads, but not a immunoprecipitate made with a pre-immune (PI) serum, was able to induce p27 ubiquitination in the presence of cyclin E/Cdk2 (FIG. 40C, lanes 2 and 3). The addition of purified recombinant E1 ubiquitin-activating enzyme, and purified recombinant Ubc3 did not greatly increase the ability of the Skp2 immunoprecipitate to sustain p27 ubiquitination, (FIG. 40C, lane 5), likely due to the presence of both proteins in the rabbit reticulocyte lysate used for p27 in vitro translation.

8.2.3 F-BOX DELETED SKP2 MUTANT STABILIZES p27 IN VIVO

Skp2 also targets p27 for ubiquitin-mediated degradation in vivo. The F-box-deleted FBP1 mutant, (ΔF)FBP1, acts in vivo as a dominant negative mutant, most likely because without the F-box is unable to bind Skp1/Cul1 complex but retains the ability to bind its substrates. Therefore, once expressed in cells, (ΔF)Fb sequesters β-catenin and IKBα and causes their stabilization. An F-box deleted Skp2 mutant, (ΔF)Skp2, was constructed. p27 was expressed in murine cells either alone or in combination with (ΔF)Skp2 or (ΔF)FBP1 (see FIG. 41). The presence of (ΔF)Skp2 led to the accumulation of higher quantities of p27. To determine whether this accumulation was due to an increase in p27 stability, the half-life of p27 was measured using pulse chase analysis (for details, see Section 8, above). Indeed, (ΔF) Skp2 prolonged p27 half-life from less than 1 hour to ~3 hours. Since in these experiments the efficiency of transfection was approximately 10%, (ΔF)Skp2 affected only the stability of co-expressed human exogenous p27, but not of murine endogenous p27.

8.2.4 SKP2 ANTISENSE EXPERIMENTS

SKP2 mRNA was targeted with antisense oligonucleotides to determine whether a decrease in Skp2 levels would influence the abundance of endogenous p27. Two different antisense oligos, but not control oligodeoxynucleotides induced a decrease in Skp2 protein levels (FIG. 42). Concomitant with the Skp2 decrease, there was a substantial increase in the level of endogenous p27 protein. Similar results were obtained with cells blocked at the G1/S transition with hydroxyurea or aphidicolin treatment (lanes 9–16). Thus, the effect of the SKP2 antisense oligos on p27 was not a secondary consequence of a possible block in G1 due to the decrease in Skp2 levels.

Antisense experiments were performed as described in (Yu, 1998, Proc. Natl. Acad. Sci. U.S.A. 95: 11324). Briefly, four oligodeoxynucleotides that contain a phosphorothioate backbone and C-5 propyne pyrimidines were synthesized (Keck Biotechnology Resource Laboratory at Yale University): (1) 5'-CCTGGGGGATGTTCTCA-3' (SEQ ID NO: 86) (the antisense direction of human Skp2 cDNA nucleotides 180–196); (2) 5'-GGCTTCCGGGCATTTAG-3' (SEQ ID NO: 87) [the scrambled control of (1)]; (3) 5'-CATCTGGCACGATTCCA-3' (SEQ ID NO: 88) (the antisense direction of Skp2 cDNA nucleotides 1137–1153); (4) 5'-CCGCTCATCGTATGACA-3' (89) [the scrambled control for (3)]. The oligonucleotides were delivered into HeLa cells using Cytofectin GS (Glen Research) according to the manufacturers instructions. The cells were then harvested between 16 and 18 hours postransfection.

9. EXAMPLE: ASSAY TO IDENTIFY AN FBP INTERACTION WITH A CELL CYCLE REGULATORY PROTEIN (e.g., SKP2 WITH E2F)

The following study was conducted to identify novel substrates of the known FBP, Skp2.

As shown in FIG. 44, E2F-1, but not other substrates of the ubiquitin pathway assayed, including p53 and Cyclin B, physically associates with Skp2. Extracts of insect cells infected with baculoviruses co-expressing Skp2 and E2F-1, (lanes 1, 4 and 5), or Skp2 and hexa-histidine p53 (His-p53) (lanes 2, 6, 7, 10 and 11), or Skp2 and His-Cyclin B (lanes 3, 8, 9, 12, and 13) were either directly immunoblotted with an anti-serum to Skp2 (lanes 1–3) or first subjected to immunoblotted with an anti-serum to Skp2 (lanes 1–3) or first subjected to immunoprecipitation with the indicated antibodies and then immunoblotted with an anti-serum to Skp2 (lanes 4–13). Antibodies used in the immunoprecipitations are: normal purified mouse immunoglobulins (IgG) (lane 4, 6, 10 and 12), purified mouse monoclonal anti-E2F-1 antibody (KH-95, from Santa Cruz) (lane 5), purified mouse monoclonal anti-p53 antibody (DO-1, from Oncogene Science) (lane 7), purified rabbit IgG (lane 8), purified rabbit polyclonal anti-Cyclin B antibody (lane 9), purified mouse monoclonal anti-His antibody (clone 34660, from Qiagen) (lanes 11 and 13).

As shown in FIG. 44B, Skp2 physically associates with E2F-1 but not with other substrates of the ubiquitin pathway (p53 and Cyclin B). Extracts of insect cells infected with baculoviruses co-expressing Skp2 and E2F-1 (lanes 1–3), or Skp2 and His-p53 (lanes 4–6), or Skp2 and His-Cyclin B (lanes 7–9) were either directly immunoblotted with antibodies to the indicated proteins (lanes 1, 4 and 7) or first subjected to immunoprecipitation with the indicated antisera and then immunoblotted with antibodies to the indicated proteins (lanes 2, 3, 5, 6, 8 and 9). Anti-sera used in the immunoprecipitations are: anti-Skp2 serum (lanes 2, 5 and 8), and normal rabbit serum (NRS) (lane 3,6 and 9).

As shown in FIG. 44C, E2F-1 physically associates with Skp2 but not with another F-box protein (FBP1). Extracts of insect cells infected with baculoviruses co-expressing Skp2 and E2F-1 (lanes 1, 3 and 4), or Flag-tagged-FBP1 and E2F-1 (lanes 2, 5 and 6) were either directly immunoblotted with a mouse monoclonal anti-E2F-1 antibody (lanes 1 and 2) or first subjected to immunoprecipitation with the indicated antibodies and then immunoblotted with a mouse monoclonal anti-E2F-1 antibody (lanes 3–6). Antibodies used in the immunoprecipitations are: anti-Skp2 serum (lanes 3), NRS (lane 4), purified rabbit polyclonal anti-Flag (lane 5), purified rabbit IgG (lane 6).

The methodology used in this example can also be applied to identify novel substrates of any FBP, including, but not limited to, the FBPs of the invention, such as FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated herein by reference for all purposes.

What is claimed is:

1. An isolated nucleic acid molecule comprising the nucleotide sequence of SEQ ID NO:5.

2. An isolated nucleic acid molecule comprising a nucleotide sequence which encodes a polypeptide comprising the amino acid sequence of SEQ ID NO:6.

3. An isolated nucleic acid molecule comprising a contiguous open reading frame which encodes a polypeptide which 1) binds to Skp1 and 2) comprises an amino acid sequence at least 95% identical to the amino acid sequence of SEQ ID NO:6 over the entire length of SEQ ID NO:6, or a complement of a coding or non-coding strand thereof, wherein said polypeptide has ubiquitination activity.

4. An isolated nucleic acid molecule comprising a nucleotide sequence which 1) encodes a polypeptide which binds to Skp1, and 2) hybridizes contiguously over its full length to a second nucleic acid molecule consisting of the nucleotide sequence of SEQ ID NO:5, under conditions of incubation at 65° C. in 0.5 M NaHPO$_4$, 7% sodium dodecyl sulfate (SDS), 1 mM EDTA followed by washing in 0.1× SSC/0.1% SDS at 65° C., wherein said polypeptide has ubiquitination activity, and has at least 95% sequence identity to SEQ ID NO:6.

5. The isolated nucleic acid molecule of any one of claims 1, 2, 3, and 4 which is derived from a mammalian genome.

6. A method for detecting the presence of a nucleic acid molecule comprising the contiguous nucleotide sequence of SEQ ID NO:5 in a sample, said method comprising the steps of:

a) contacting the sample with a nucleic acid probe or primer which selectively hybridizes over its full length to a nucleic acid molecule consisting of a nucleotide sequence of SEQ ID NO:5; and b) determining whether the nucleic acid probe or primer binds to a nucleic acid molecule in the sample, wherein if the nucleic acid probe or primer binds to the nucleic acid in the sample, then the nucleic acid molecule is present in the sample.

7. The method of claim 6, wherein the sample comprises mRNA molecules and is contacted with a nucleic acid probe.

8. An isolated nucleic acid molecule comprising a nucleotide sequence which encodes a fusion polypeptide comprising a contiguous amino acid sequence encoded by the nucleotide sequence of SEQ ID NO:5.

9. The isolated nucleic acid molecule of any one of claims 1, 2, 3, 4, and 8, further comprising a heterologous nucleic acid sequence.

10. A nucleotide vector comprising the nucleic acid molecule of any one of claims 1, 2, 3, 4, and 8.

11. An expression vector comprising the nucleic acid molecule of any one of claims 1, 2, 3, 4, and 8, wherein the nucleic acid sequence is operatively associated with a nucleotide regulatory sequence that controls expression of the nucleotide sequence in a host cell.

12. An isolated host cell comprising the nucleotide sequence of any one of claims 1, 2, 3, 4, and 8, wherein the nucleic acid sequence is operatively associated with a nucleotide regulatory sequence that controls expression of the nucleotide sequence in a the host cell.

* * * * *

SEQUENCE LISTING

<160> NUMBER OF SEQ ID NOS: 90

<210> SEQ ID NO 1
<211> LENGTH: 2151
<212> TYPE: DNA
<213> ORGANISM: Homo sapiens

<400> SEQUENCE: 1

| | | | | | |
|---|---|---|---|---|---|
| tgcgttggct | gcggcctggc | accaaagggg | cggccccggc | ggagagcgga | cccagtggcc | 60 |
| tcggcgatta | tggacccggc | cgaggcggtg | ctgcaagaga | aggcactcaa | gtttatgaat | 120 |
| tcctcagaga | gagaagactg | taataatggc | gaaccccta | ggaagataat | accagagaag | 180 |
| aattcactta | gacagacata | caacagctgt | gccagactct | gcttaaacca | agaaacagta | 240 |
| tgtttagcaa | gcactgctat | gaagactgag | aattgtgtgg | ccaaaacaaa | acttgccaat | 300 |
| ggcacttcca | gtatgattgt | gcccaagcaa | cggaaactct | cagcaagcta | tgaaaaggaa | 360 |
| aaggaactgt | gtgtcaaata | ctttgagcag | tggtcagagt | cagatcaagt | ggaatttgtg | 420 |
| gaacatctta | tatcccaaat | gtgtcattac | caacatgggc | acataaactc | gtatcttaaa | 480 |
| cctatgttgc | agagagattt | cataactgct | ctgccagctc | ggggattgga | tcatatcgct | 540 |
| gagaacattc | tgtcatacct | ggatgccaaa | tcactatgtg | ctgctgaact | tgtgtgcaag | 600 |
| gaatggtacc | gagtgacctc | tgatggcatg | ctgtggaaga | agcttatcga | gagaatggtc | 660 |
| aggacagatt | ctctgtggag | aggcctggca | gaacgaaagg | gatggggaca | gtatttattc | 720 |
| aaaaacaaac | ctcctgacgg | gaatgctcct | cccaactctt | tttatagagc | actttatcct | 780 |
| aaaattatac | aagacattga | gacaatagaa | tctaattgga | gatgtggaag | acatagttta | 840 |
| cagagaattc | actgccgaag | tgaaacaagc | aaaggagttt | actgtttaca | gtatgatgat | 900 |
| cagaaaatag | taagcggcct | tcgagacaac | acaatcaaga | tctgggataa | aaacacattg | 960 |
| gaatgcaagc | gaattctcac | aggccataca | ggttcagtcc | tctgtctcca | gtatgatgag | 1020 |
| agagtgatca | taacaggatc | atcggattcc | acggtcagag | tgtgggatgt | aaatacaggt | 1080 |
| gaaatgctaa | acacgttgat | tcaccattgt | gaagcagttc | tgcacttgcg | tttcaataat | 1140 |
| ggcatgatgg | tgacctgctc | caaagatcgt | tccattgctg | tatgggatat | ggcctcccca | 1200 |
| actgacatta | ccctccggag | ggtgctggtc | ggacaccgag | ctgctgtcaa | tgttgtagac | 1260 |
| tttgatgaca | agtacattgt | ttctgcatct | ggggatagaa | ctataaaggt | atggaacaca | 1320 |
| agtacttgtg | aatttgtaag | gaccttaaat | ggacacaaac | gaggcattgc | ctgtttgcag | 1380 |
| tacagggaca | ggctggtagt | gagtggctca | tctgacaaca | ctatcagatt | atgggacata | 1440 |
| gaatgtggtg | catgtttacg | agtgttagaa | ggccatgagg | aattggtgcg | ttgtattcga | 1500 |
| tttgataaca | agaggatagt | cagtgggggcc | tatgatggaa | aaattaaagt | gtgggatctt | 1560 |
| gtggctgctt | tggaccccg | tgctcctgca | gggacactct | gtctacggac | ccttgtggag | 1620 |
| cattccggaa | gagttttcg | actacagttt | gatgaattcc | agattgtcag | tagttcacat | 1680 |
| gatgacacaa | tcctcatctg | ggacttccta | aatgatccag | ctgcccaagc | tgaacccccc | 1740 |
| cgttcccctt | ctcgaacata | cacctacatc | tccagataaa | taaccataca | ctgacctcat | 1800 |
| acttgcccag | gacccattaa | agttgcggta | tttaacgtat | ctgccaatac | caggatgagc | 1860 |
| aacaacagta | acaatcaaac | tactgcccag | tttccctgga | ctagccgagg | agcagggctt | 1920 |
| tgagactcct | gttgggacac | agttggtctg | cagtcggccc | aggacggtct | actcagcaca | 1980 |
| actgactgct | tcagtgctgc | tatcagaaga | tgtcttctat | caattgtgaa | tgattggaac | 2040 |

```
tttttaaacct ccccctcctct cctcctttca cctctgcacc tagtttttc ccattggttc      2100 cagacaaagg tgacttataa atatatttag tgttttgcca gaaaaaaaaa a                2151
```

<210> SEQ ID NO 2
<211> LENGTH: 569
<212> TYPE: PRT
<213> ORGANISM: Homo sapiens

<400> SEQUENCE: 2

```
Met Asp Pro Ala Glu Ala Val Leu Gln Glu Lys Ala Leu Lys Phe Met
 1               5                  10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285

Ile Lys Ile Trp Asp Lys Asn Thr Leu Glu Cys Lys Arg Ile Leu Thr
    290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350
```

Leu Arg Phe Asn Asn Gly Met Met Val Thr Cys Ser Lys Asp Arg Ser
            355                 360                 365

Ile Ala Val Trp Asp Met Ala Ser Pro Thr Asp Ile Thr Leu Arg Arg
        370                 375                 380

Val Leu Val Gly His Arg Ala Ala Val Asn Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
            420                 425                 430

Ile Ala Cys Leu Gln Tyr Arg Asp Arg Leu Val Val Ser Gly Ser Ser
        435                 440                 445

Asp Asn Thr Ile Arg Leu Trp Asp Ile Glu Cys Gly Ala Cys Leu Arg
    450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
            500                 505                 510

Arg Thr Leu Val Glu His Ser Gly Arg Val Phe Arg Leu Gln Phe Asp
        515                 520                 525

Glu Phe Gln Ile Val Ser Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 3
<211> LENGTH: 1476
<212> TYPE: DNA
<213> ORGANISM: Homo sapiens

<400> SEQUENCE: 3
atggagagaa aggactttga dacatggctt gataacattt ctgttacatt tctttctctg      60
acggacttgc agaaaaatga aactctggat cacctgatta gtctgagtgg ggcagtccag     120
ctcaggcatc tctccaataa cctagagact tcctcaagc gggacttcct caaactcctt     180
cccctggagc tcagttttta tttgttaaaa tggctcgatc ctcagacttt actcacatgc     240
tgcctcgtct ctaaacagtg gaataaggtg ataagtgcct gtacagaggt gtggcagact     300
gcatgtaaaa atttgggctg cagatagat gattctgttc aggacgcttt gcactggaag     360
aaggtttatt tgaaggctat tttgagaatg aagcaactgg aggaccatga agcctttgaa     420
acctcgtcat taattggaca cagtgccaga gtgtatgcac tttactacaa agatggactt     480
ctctgtacag ggtcagatga cttgtctgca aagctgtggg atgtgagcac agggcagtgc     540
gtttatggca tccagaccca cacttgtgca gcggtgaagt tgatgaaca gaagcttgtg     600 acaggctcct ttgacaacac tgtggcttgc tgggaatgga gttccggagc caggacccag     660
cactttcggg ggcacacggg ggcggtattt agcgtggact acaatgatga actggatatc     720
ttggtgagcg gctctgcaga cttcactgtg aaagtatggg ctttatctgc tgggacatgc     780
ctgaacacac tcaccgggca cacggaatgg gtcaccaagg tagttttgca gaagtgcaaa     840
gtcaagtctc tcttgcacag tcctggagac tacatcctct aagtgcaga caaatatgag     900

```
attaagattt ggccaattgg gagagaaatc aactgtaagt gcttaaagac attgtctgtc    960
tctgaggata gaagtatctg cctgcagcca agacttcatt ttgatggcaa atacattgtc   1020
tgtagttcag cacttggtct ctaccagtgg gactttgcca gttatgatat tctcagggtc   1080
atcaagactc ctgagatagc aaacttggcc ttgcttggct ttggagatat ctttgccctg   1140
ctgtttgaca accgctacct gtacatcatg gacttgcgga cagagagcct gattagtcgc   1200
tggcctctgc cagagtacag ggaatcaaag agaggctcaa gcttcctggc aggcgaacat   1260
cctggctgaa tggactggat gggcacaatg cacgggctt ggtctttgcc accagcatgc   1320
ctgaccacag tattcacctg gtgttgtgga aggagcacgg ctgacaccat gagccaccac   1380
cgctgactga ctttgggtgc cggggctgcg ggttttgggt gcacctctgc ggcacgcgac   1440
tgcatgaacc aaagttctca cctaatggta tcatca                             1476
```

<210> SEQ ID NO 4
<211> LENGTH: 422
<212> TYPE: PRT
<213> ORGANISM: Homo sapiens

<400> SEQUENCE: 4

```
Met Glu Arg Lys Asp Phe Glu Thr Trp Leu Asp Asn Ile Ser Val Thr
 1               5                  10                  15

Phe Leu Ser Leu Thr Asp Leu Gln Lys Asn Glu Thr Leu Asp His Leu
                20                  25                  30

Ile Ser Leu Ser Gly Ala Val Gln Leu Arg His Leu Ser Asn Asn Leu
            35                  40                  45

Glu Thr Leu Leu Lys Arg Asp Phe Leu Lys Leu Pro Leu Glu Leu
    50                  55                  60

Ser Phe Tyr Leu Leu Lys Trp Leu Asp Pro Gln Thr Leu Leu Thr Cys
 65                  70                  75                  80

Cys Leu Val Ser Lys Gln Trp Asn Lys Val Ile Ser Ala Cys Thr Glu
                85                  90                  95

Val Trp Gln Thr Ala Cys Lys Asn Leu Gly Trp Gln Ile Asp Asp Ser
            100                 105                 110

Val Gln Asp Ala Leu His Trp Lys Lys Val Tyr Leu Lys Ala Ile Leu
        115                 120                 125

Arg Met Lys Gln Leu Glu Asp His Glu Ala Phe Glu Thr Ser Ser Leu
    130                 135                 140

Ile Gly His Ser Ala Arg Val Tyr Ala Leu Tyr Tyr Lys Asp Gly Leu
145                 150                 155                 160

Leu Cys Thr Gly Ser Asp Asp Leu Ser Ala Lys Leu Trp Asp Val Ser
                165                 170                 175

Thr Gly Gln Cys Val Tyr Gly Ile Gln Thr His Thr Cys Ala Ala Val
            180                 185                 190

Lys Phe Asp Glu Gln Lys Leu Val Thr Gly Ser Phe Asp Asn Thr Val
        195                 200                 205

Ala Cys Trp Glu Trp Ser Ser Gly Ala Arg Thr Gln His Phe Arg Gly
    210                 215                 220

His Thr Gly Ala Val Phe Ser Val Asp Tyr Asn Asp Glu Leu Asp Ile
225                 230                 235                 240

Leu Val Ser Gly Ser Ala Asp Phe Thr Val Lys Val Trp Ala Leu Ser
                245                 250                 255

Ala Gly Thr Cys Leu Asn Thr Leu Thr Gly His Thr Glu Trp Val Thr
            260                 265                 270
```

-continued

```
Lys Val Val Leu Gln Lys Cys Lys Val Lys Ser Leu Leu His Ser Pro
            275                 280                 285
Gly Asp Tyr Ile Leu Leu Ser Ala Asp Lys Tyr Glu Ile Lys Ile Trp
        290                 295                 300
Pro Ile Gly Arg Glu Ile Asn Cys Lys Cys Leu Lys Thr Leu Ser Val
305                 310                 315                 320
Ser Glu Asp Arg Ser Ile Cys Leu Gln Pro Arg Leu His Phe Asp Gly
                325                 330                 335
Lys Tyr Ile Val Cys Ser Ser Ala Leu Gly Leu Tyr Gln Trp Asp Phe
            340                 345                 350
Ala Ser Tyr Asp Ile Leu Arg Val Ile Lys Thr Pro Glu Ile Ala Asn
        355                 360                 365
Leu Ala Leu Leu Gly Phe Gly Asp Ile Phe Ala Leu Leu Phe Asp Asn
    370                 375                 380
Arg Tyr Leu Tyr Ile Met Asp Leu Arg Thr Glu Ser Leu Ile Ser Arg
385                 390                 395                 400
Trp Pro Leu Pro Glu Tyr Arg Glu Ser Lys Arg Gly Ser Ser Phe Leu
                405                 410                 415
Ala Gly Glu His Pro Gly
            420

<210> SEQ ID NO 5
<211> LENGTH: 1407
<212> TYPE: DNA
<213> ORGANISM: Homo sapiens

<400> SEQUENCE: 5
cggggtggtg tgtgggggaa gccgccccg  gcagcaggat gaaacgagga ggaagagata      60
gtgaccgtaa ttcatcagaa gaaggaactg cagagaaatc caagaaactg aggactacaa    120
atgagcattc tcagacttgt gattggggta atctccttca ggacattatt ctccaagtat    180
ttaaatattt gcctcttctt gaccgggctc atgcttcaca gtttgccgc  aactggaacc    240
aggtatttca catgcctgac ttgtggagat gttttgaatt tgaactgaat cagccagcta    300
catcttattt gaaagctacc catccagagc tgatcaaaca gattattaaa agacattcaa    360
accatctaca atatgtcagc ttcaaggtgg acagcagcaa ggaatcagct gaagcagctt    420
gtgatatact atcgcaactt gtgaattgct ctttaaaaac acttggactt atttcaactg    480
ctcgaccaag ctttatggat ttaccaaagt ctcactttat ctctgcactg acagttgtgt    540
tcgtaaactc caaatccctg tcttcgctta agatagatga tactccagta gatgatccat    600
ctctcaaagt actagtggcc aacaatagtg atacactcaa gctgttgaaa atgagcagct    660
gtcctcatgt ctctccagca ggtatccttt gtgtggctga tcagtgtcac ggcttaagag    720
aactagccct gaactaccac ttattgagtg atgagttgtt acttgcattg tcttctgaaa    780
aacatgttcg attagaacat ttgcgcattg atgtagtcag tgagaatcct ggacagacac    840
acttccatac tattcagaag agtagctggg atgctttcat cagacattca cccaaagtga    900
acttagtgat gtattttttt ttatatgaag aagaatttga ccccttcttt cgctatgaaa    960
tacctgccac ccatctgtac tttgggagat cagtaagcaa agatgtgctt ggccgtgtgg   1020
gaatgacatg ccctagactg gttgaactag tagtgtgtgc aaatggatta cggccacttg   1080
atgaagagtg aattcgcatt gcagaacgtt gcaaaaattt gtcagctatt ggactagggg   1140
aatgtgaagt ctcatgtagt gcctttgttg agtttgtgaa gatgtgtggt ggccgcctat   1200
```

```
ctcaattatc cattatggaa gaagtactaa ttcctgacca aaagtatagt ttggagcaga   1260
ttcactggga agtgtccaag catcttggta gggtgtggtt tcccgacatg atgcccactt   1320
ggtaaaaact gcatgatgaa tagcaccta atttcaagca aatgtattat aattaaagtt    1380
ttatttgctg taaaaaaaaa aaaaaaa                                       1407
```

<210> SEQ ID NO 6
<211> LENGTH: 428
<212> TYPE: PRT
<213> ORGANISM: Homo sapiens

<400> SEQUENCE: 6

```
Met Lys Arg Gly Gly Arg Asp Ser Asp Arg Asn Ser Ser Glu Glu Gly
 1               5                   10                  15

Thr Ala Glu Lys Ser Lys Lys Leu Arg Thr Thr Asn Glu His Ser Gln
            20                  25                  30

Thr Cys Asp Trp Gly Asn Leu Leu Gln Asp Ile Ile Leu Gln Val Phe
        35                  40                  45

Lys Tyr Leu Pro Leu Leu Asp Arg Ala His Ala Ser Gln Val Cys Arg
    50                  55                  60

Asn Trp Asn Gln Val Phe His Met Pro Asp Leu Trp Arg Cys Phe Glu
65                  70                  75                  80

Phe Glu Leu Asn Gln Pro Ala Thr Ser Tyr Leu Lys Ala Thr His Pro
                85                  90                  95

Glu Leu Ile Lys Gln Ile Lys Arg His Ser Asn His Leu Gln Tyr
            100                 105                 110

Val Ser Phe Lys Val Asp Ser Ser Lys Glu Ser Ala Glu Ala Ala Cys
        115                 120                 125

Asp Ile Leu Ser Gln Leu Val Asn Cys Ser Leu Lys Thr Leu Gly Leu
    130                 135                 140

Ile Ser Thr Ala Arg Pro Ser Phe Met Asp Leu Pro Lys Ser His Phe
145                 150                 155                 160

Ile Ser Ala Leu Thr Val Val Phe Val Asn Ser Lys Ser Leu Ser Ser
                165                 170                 175

Leu Lys Ile Asp Asp Thr Pro Val Asp Asp Pro Ser Leu Lys Val Leu
            180                 185                 190

Val Ala Asn Asn Ser Asp Thr Leu Lys Leu Leu Lys Met Ser Ser Cys
        195                 200                 205

Pro His Val Ser Pro Ala Gly Ile Leu Cys Val Ala Asp Gln Cys His
    210                 215                 220

Gly Leu Arg Glu Leu Ala Leu Asn Tyr His Leu Leu Ser Asp Glu Leu
225                 230                 235                 240

Leu Leu Ala Leu Ser Ser Glu Lys His Val Arg Leu Glu His Leu Arg
                245                 250                 255

Ile Asp Val Val Ser Glu Asn Pro Gly Gln Thr His Phe His Thr Ile
            260                 265                 270

Gln Lys Ser Ser Trp Asp Ala Phe Ile Arg His Ser Pro Lys Val Asn
        275                 280                 285

Leu Val Met Tyr Phe Phe Leu Tyr Glu Glu Glu Phe Asp Pro Phe Phe
    290                 295                 300

Arg Tyr Glu Ile Pro Ala Thr His Leu Tyr Phe Gly Arg Ser Val Ser
305                 310                 315                 320

Lys Asp Val Leu Gly Arg Val Gly Met Thr Cys Pro Arg Leu Val Glu
                325                 330                 335
```

```
Leu Val Val Cys Ala Asn Gly Leu Arg Pro Leu Asp Glu Glu Leu Ile
            340                 345                 350

Arg Ile Ala Glu Arg Cys Lys Asn Leu Ser Ala Ile Gly Leu Gly Glu
        355                 360                 365

Cys Glu Val Ser Cys Ser Ala Phe Val Glu Phe Val Lys Met Cys Gly
        370                 375                 380

Gly Arg Leu Ser Gln Leu Ser Ile Met Glu Val Leu Ile Pro Asp
385                 390                 395                 400

Gln Lys Tyr Ser Leu Glu Gln Ile His Trp Glu Val Ser Lys His Leu
                405                 410                 415

Gly Arg Val Trp Phe Pro Asp Met Met Pro Thr Trp
                420                 425
```

<210> SEQ ID NO 7
<211> LENGTH: 1444
<212> TYPE: DNA
<213> ORGANISM: Homo sapiens

<400> SEQUENCE: 7

```
atggcgggaa gcgagccgcg cagcggaaca aattcgccgc cgccgccctt cagcgactgg      60
ggccgcctgg aggcggccat cctcagcggc tggaagacct tctggcagtc agtgagcaag     120
gataggtgg cgcgtacgac ctcccggag gaggtggatg aggcggccag caccctgacg      180
cggctgccga ttgatgtaca gctatatatt ttgtcctttc tttcacctca tgatctgtgt     240
cagttgggaa gtacaaatca ttattggaat gaaactgtaa gaaatccaat tctgtggaga     300
tactttttgt tgagggatct tccttcttgg tcttctgttg actggaagtc tcttccatat     360
ctacaaatct taaaaaagcc tatatctgag gtctctgatg gtgcattttt tgactacatg     420
gcagtctatc taatgtgctg tccatacaca agaagagctt caaaatccag ccgtcctatg     480
tatggagctg tcacttcttt tttacactcc ctgatcattc ccaatgaacc tcgatttgct     540
ctgtttggac cacgtttgga acaattgaat acctctttgg tgttgagctt gctgtcttca     600
gaggaacttt gcccaacagc tggtttgcct cagaggcaga ttgatggtat tggatcagga     660
gtcaattttc agttgaacaa ccaacataaa ttcaacattc taatcttata ttcaactacc     720
agaaaggaaa gagatagagc aagggaagag catacaagtg cagttaacaa gatgttcagt     780
cgacacaatg aaggtgatga tcgaccagga agccggtaca gtgtgattcc acagattcaa     840
aaactgtgtg aagttgtaga tgggttcatc tatgttgcaa atgctgaagc tcataaaaga     900
catgaatggc aagatgaatt ttctcatatt atggcaatga cagatccagc ctttgggtct     960
tcgggaagac cattgttggt tttatcttgt atttctcaag gggatgtaaa agaatgccc    1020
tgtttttatt tggctcatga gctgcatctg aatcttctaa atcacccatg gctggtccag    1080
gatacagagg ctgaaactct gactggtttt ttgaatggca ttgagtggat tcttgaagaa    1140
gtggaatcta agcgtgcaag atgattctct tttcagatct tgggaactga aaccatttga    1200
aatttattac taaggtcgtg atgtgaatat ttgctcagtc agcccacctt gtcctgcctt    1260
tttgcagata ggctttcatt tggacagcta taactgctgt gtttttata ttatttttac    1320
tttttaccat aaatcaatta caagaaaaga gtttcagtcc tagtatttag ccccaaaatg    1380
aacctttaaa cattttttttg gtaattttta tattttctgt cttttaaaa atattaaatt    1440
ttgg                                                               1444
```

<210> SEQ ID NO 8
<211> LENGTH: 472

-continued

```
<212> TYPE: PRT
<213> ORGANISM: Homo sapiens

<400> SEQUENCE: 8

Met Ala Gly Ser Glu Pro Arg Ser Gly Thr Asn Ser Pro Pro Pro
  1               5                  10                  15

Phe Ser Asp Trp Gly Arg Leu Glu Ala Ala Ile Leu Ser Gly Trp Lys
             20                  25                  30

Thr Phe Trp Gln Ser Val Ser Lys Asp Arg Val Ala Arg Thr Thr Ser
         35                  40                  45

Arg Glu Glu Val Asp Glu Ala Ala Ser Thr Leu Thr Arg Leu Pro Ile
     50                  55                  60

Asp Val Gln Leu Tyr Ile Leu Ser Phe Leu Ser Pro His Asp Leu Cys
 65                  70                  75                  80

Gln Leu Gly Ser Thr Asn His Tyr Trp Asn Glu Thr Val Arg Asn Pro
                 85                  90                  95

Ile Leu Trp Arg Tyr Phe Leu Leu Arg Asp Leu Pro Ser Trp Ser Ser
                100                 105                 110

Val Asp Trp Lys Ser Leu Pro Tyr Leu Gln Ile Leu Lys Lys Pro Ile
            115                 120                 125

Ser Glu Val Ser Asp Gly Ala Phe Phe Asp Tyr Met Ala Val Tyr Leu
    130                 135                 140

Met Cys Cys Pro Tyr Thr Arg Arg Ala Ser Lys Ser Ser Arg Pro Met
145                 150                 155                 160

Tyr Gly Ala Val Thr Ser Phe Leu His Ser Leu Ile Ile Pro Asn Glu
                165                 170                 175

Pro Arg Phe Ala Leu Phe Gly Pro Arg Leu Glu Gln Leu Asn Thr Ser
            180                 185                 190

Leu Val Leu Ser Leu Leu Ser Ser Glu Glu Leu Cys Pro Thr Ala Gly
        195                 200                 205

Leu Pro Gln Arg Gln Ile Asp Gly Ile Gly Ser Gly Val Asn Phe Gln
    210                 215                 220

Leu Asn Asn Gln His Lys Phe Asn Ile Leu Ile Leu Tyr Ser Thr Thr
225                 230                 235                 240

Arg Lys Glu Arg Asp Arg Ala Arg Glu Glu His Thr Ser Ala Val Asn
                245                 250                 255

Lys Met Phe Ser Arg His Asn Glu Gly Asp Asp Arg Pro Gly Ser Arg
            260                 265                 270

Tyr Ser Val Ile Pro Gln Ile Gln Lys Leu Cys Glu Val Val Asp Gly
        275                 280                 285

Phe Ile Tyr Val Ala Asn Ala Glu Ala His Lys Arg His Glu Trp Gln
    290                 295                 300

Asp Glu Phe Ser His Ile Met Ala Met Thr Asp Pro Ala Phe Gly Ser
305                 310                 315                 320

Ser Gly Arg Pro Leu Leu Val Leu Ser Cys Ile Ser Gln Gly Asp Val
                325                 330                 335

Lys Arg Met Pro Cys Phe Tyr Leu Ala His Glu Leu His Leu Asn Leu
            340                 345                 350

Leu Asn His Pro Trp Leu Val Gln Asp Thr Glu Ala Glu Thr Leu Thr
        355                 360                 365

Gly Phe Leu Asn Gly Ile Glu Trp Ile Leu Glu Glu Val Glu Ser Lys
    370                 375                 380

Arg Ala Arg Phe Ser Phe Gln Ile Leu Gly Thr Glu Thr Ile Asn Leu
385                 390                 395                 400
```

```
Leu Leu Arg Ser Cys Glu Tyr Leu Leu Ser Gln Pro Thr Leu Ser Cys
            405                 410                 415

Leu Phe Ala Asp Arg Leu Ser Phe Gly Gln Leu Leu Leu Cys Phe Leu
        420                 425                 430

Tyr Tyr Phe Tyr Phe Leu Pro Ile Asn Tyr Lys Lys Arg Val Ser Val
            435                 440                 445

Leu Val Phe Ser Pro Lys Met Asn Leu Thr Phe Phe Trp Phe Leu Tyr
        450                 455                 460

Phe Leu Ser Phe Lys Tyr Ile Leu
465                 470

<210> SEQ ID NO 9
<211> LENGTH: 2076
<212> TYPE: DNA
<213> ORGANISM: Homo sapiens

<400> SEQUENCE: 9
aggttgctca gctgcccccg gagcggttcc tccacctgag gcagacacca cctcggttgg      60
catgagccgg cgccctgca gctgcgccct acggccaccc cgctgctcct gcagcgccag     120
ccccagcgca gtgacagccg ccgggcgccc tcgaccctcg gatagttgta aagaagaaag     180
ttctacccct tctgtcaaaa tgaagtgtga ttttaattgt aaccatgttc attccggact     240
taaactggta aaacctgatg acattggaag actagtttcc tacaccctg catatctgga      300 aggttcctgt aaagactgca ttaaagacta tgaaaggctg tcatgtattg ggtcaccgat     360
tgtgagccct aggattgtac aacttgaaac tgaaagcaag cgcttgcata caaggaaaa      420 tcaacatgtg caacagacac ttaatagtac aaatgaaata gaagcactag agaccagtag     480
actttatgaa gacagtggct attcctcatt ttctctacaa gtggcctca gtgaacatga      540 agaaggtagc ctcctggagg agaatttcgg tgacagtcta caatcctgcc tgctacaaat     600
acaaagccca gaccaatatc ccaacaaaaa cttgctgcca gttcttcatt ttgaaaagt      660 ggtttgttca acattaaaaa agaatgcaaa acgaatcct aaagtagatc gggagatgct      720
gaaggaaatt atagccagag gaaattttag actgcagaat ataattggca gaaaatggg      780 cctagaatgt gtagatattc tcagcgaact ctttcgaagg ggactcagac atgtcttagc     840
aactatttta gcacaactca gtgacatgga cttaatcaat gtgtctaaag tgagcacaac     900
ttggaagaag atcctagaag atgataaggg ggcattccag ttgtacagta aagcaataca     960
aagagttacc gaaaacaaca ataaattttc acctcatgct tcaaccagag aatatgttat    1020
gttcagaacc ccactggctt ctgttcgaa atcagcagcc cagacttctc tcaaaaaaga    1080
tgctcaaacc aagttatcca atcaaggtga tcagaaaggt tctacttata gtcgacacaa    1140
tgaattctct gaggttgcca agacattgaa aaagaacgaa agcctcaaag cctgtattcg    1200
ctgtaattca cctgcaaaat atgattgcta tttacaacgg gcaacctgca acgagaagg     1260 ctgtggattt gattattgta cgaagtgtct ctgtaattat catactacta agactgttc      1320 agatggcaag ctcctcaaag ccagttgtaa aataggtccc ctgcctggta caagaaaag    1380 caaaaagaat ttcgaagat tgtgatctct tattaaatca attgttactg atcatgaatg     1440
ttagttagaa aatgttaggt tttaacttaa aaaaattgt attgtgattt tcaattttat      1500
gttgaaatcg tgtagtatc ctgaggttttt ttcccccca gaagataaag aggatagaca     1560
acctcttaaa atattttac aatttaatga gaaaagtttt aaaattctca atacaaatca     1620
aacaatttaa atattttaag aaaaaaggaa aagtagatag tgatactgag ggtaaaaaaa     1680
```

-continued

```
aaattgattc aattttatgg taaaggaaac ccatgcaatt ttacctagac agtcttaaat    1740
atgtctggtt ttccatctgt tagcatttca gacattttat gttcctctta ctcaattgat    1800
accaacagaa atatcaactt ctggagtcta ttaaatgtgt tgtcacctt ctaaagcttt     1860 ttttcattgt gtgtatttcc caagaaagta tcctttgtaa aaacttgctt gttttcctta    1920
tttctgaaat ctgttttaat attttgtat acatgtaaat atttctgtat tttttatatg     1980
tcaaagaata tgtctcttgt atgtacatat aaaaataaat tttgctcaat aaaattgtaa    2040
gcttaaaaaa aaaaaaaaa aactcgagac tagtgc                               2076
```

<210> SEQ ID NO 10
<211> LENGTH: 447
<212> TYPE: PRT
<213> ORGANISM: Homo sapiens

<400> SEQUENCE: 10

```
Met Ser Arg Arg Pro Cys Ser Cys Ala Leu Arg Pro Pro Arg Cys Ser
  1               5                  10                  15

Cys Ser Ala Ser Pro Ser Ala Val Thr Ala Ala Gly Arg Pro Arg Pro
             20                  25                  30

Ser Asp Ser Cys Lys Glu Glu Ser Ser Thr Leu Ser Val Lys Met Lys
         35                  40                  45

Cys Asp Phe Asn Cys Asn His Val His Ser Gly Leu Lys Leu Val Lys
     50                  55                  60

Pro Asp Asp Ile Gly Arg Leu Val Ser Tyr Thr Pro Ala Tyr Leu Glu
 65                  70                  75                  80

Gly Ser Cys Lys Asp Cys Ile Lys Asp Tyr Glu Arg Leu Ser Cys Ile
                 85                  90                  95

Gly Ser Pro Ile Val Ser Pro Arg Ile Val Gln Leu Glu Thr Glu Ser
            100                 105                 110

Lys Arg Leu His Asn Lys Glu Asn Gln His Val Gln Gln Thr Leu Asn
        115                 120                 125

Ser Thr Asn Glu Ile Glu Ala Leu Glu Thr Ser Arg Leu Tyr Glu Asp
    130                 135                 140

Ser Gly Tyr Ser Ser Phe Ser Leu Gln Ser Gly Leu Ser Glu His Glu
145                 150                 155                 160

Glu Gly Ser Leu Leu Glu Glu Asn Phe Gly Asp Ser Leu Gln Ser Cys
                165                 170                 175

Leu Leu Gln Ile Gln Ser Pro Asp Gln Tyr Pro Asn Lys Asn Leu Leu
            180                 185                 190

Pro Val Leu His Phe Glu Lys Val Val Cys Ser Thr Leu Lys Lys Asn
        195                 200                 205

Ala Lys Arg Asn Pro Lys Val Asp Arg Glu Met Leu Lys Glu Ile Ile
    210                 215                 220

Ala Arg Gly Asn Phe Arg Leu Gln Asn Ile Ile Gly Arg Lys Met Gly
225                 230                 235                 240

Leu Glu Cys Val Asp Ile Leu Ser Glu Leu Phe Arg Arg Gly Leu Arg
                245                 250                 255

His Val Leu Ala Thr Ile Leu Ala Gln Leu Ser Asp Met Asp Leu Ile
            260                 265                 270

Asn Val Ser Lys Val Ser Thr Thr Trp Lys Lys Ile Leu Glu Asp Asp
        275                 280                 285

Lys Gly Ala Phe Gln Leu Tyr Ser Lys Ala Ile Gln Arg Val Thr Glu
    290                 295                 300
```

Asn Asn Asn Lys Phe Ser Pro His Ala Ser Thr Arg Glu Tyr Val Met
305                 310                 315                 320

Phe Arg Thr Pro Leu Ala Ser Val Gln Lys Ser Ala Ala Gln Thr Ser
            325                 330                 335

Leu Lys Lys Asp Ala Gln Thr Lys Leu Ser Asn Gln Gly Asp Gln Lys
        340                 345                 350

Gly Ser Thr Tyr Ser Arg His Asn Glu Phe Ser Glu Val Ala Lys Thr
    355                 360                 365

Leu Lys Lys Asn Glu Ser Leu Lys Ala Cys Ile Arg Cys Asn Ser Pro
370                 375                 380

Ala Lys Tyr Asp Cys Tyr Leu Gln Arg Ala Thr Cys Lys Arg Glu Gly
385                 390                 395                 400

Cys Gly Phe Asp Tyr Cys Thr Lys Cys Leu Cys Asn Tyr His Thr Thr
            405                 410                 415

Lys Asp Cys Ser Asp Gly Lys Leu Leu Lys Ala Ser Cys Lys Ile Gly
        420                 425                 430

Pro Leu Pro Gly Thr Lys Lys Ser Lys Lys Asn Leu Arg Arg Leu
    435                 440                 445

<210> SEQ ID NO 11
<211> LENGTH: 1535
<212> TYPE: DNA
<213> ORGANISM: Homo sapiens

<400> SEQUENCE: 11

| | | | | | |
|---|---|---|---|---|---|
| gcgcgttcgg | gagcttcggc | cctgcgtagg | aggcgggtgc | aggtgtgggt | gctgagccgc | 60 |
| ccgccgcctg | gagggggaga | cagcttcagg | acacgcaggc | cgcagcgagg | gcccgggccc | 120 |
| gggggatccc | aggccatgga | cgctcccac | tccaaagcag | ccctggacag | cattaacgag | 180 |
| ctgcccgata | acatcctgct | ggagctgttc | acgcacgtgc | ccgccgcca | gctgctgctg | 240 |
| aactgccgcc | tggtctgcag | cctctggcgg | gacctcatcg | acctcctgac | cctctggaaa | 300 |
| cgcaagtgcc | tgcgaaaggg | cttcatcacc | aaggactggg | accagcccgt | ggccgactgg | 360 |
| aaaatcttct | acttcctacg | gagcctgcat | aggaacctcc | tgcgcaaccc | cgtgtgctga | 420 |
| aacgatatgt | ttgcatggca | aattgatttc | aatggtgggg | accgctggaa | ggtggatagc | 480 |
| ctccctggag | cccacgggac | agaatttcct | gaccccaaag | tcaagaagtc | ttttgtcaca | 540 |
| tcctacgaac | tgtgcctcaa | gtgggagctg | gtggaccttc | tagccgaccg | ctactgggag | 600 |
| gagctactag | acacattccg | gccggacatc | gtggttaagg | actggtttgc | tgccagagcc | 660 |
| gactgtggct | gcacctacca | actcaaagtg | cagctggcct | cggctgacta | cttcgtgttg | 720 |
| gcctccttcg | agcccccacc | tgtgaccatc | aacagtggaa | acaatgccac | atggacagag | 780 |
| gtctcctaca | ccttctcaga | ctaccccgg | ggtgtccgct | acatcctctt | ccagcatggg | 840 |
| ggcagggaca | cccagtactg | ggcaggctgg | tatgggcccc | gagtcaccaa | cagcagcatt | 900 |
| gtcgtcagcc | ccaagatgac | caggaaccag | gcctcgtccg | aggctcagcc | tgggcagaag | 960 |
| catggacagg | aggaggctgc | ccaatcgccc | tacggagctg | ttgtccagat | tttctgacag | 1020 |
| ctgtccatcc | tgtgtctggg | tcagccagag | gttcctccag | gcaggagctg | agcatggggt | 1080 |
| gggcagtgag | gtccctgtac | cagcgactcc | tgccccggtt | caaccctacc | agcttgtggt | 1140 |
| aacttactgt | cacatagctc | tgacgttttg | ttgtaataaa | tgttttcagg | ccgggcactg | 1200 |
| tggctcacgc | ctgtaatccc | agcactttgg | gagaccgagg | caggtggatc | acgaggtcag | 1260 |
| gagacagaga | ccatcctggc | caacacggtg | aaaccctgtc | tctactaaaa | atacaaaaaa | 1320 |

```
ttagccgggc gtggtggcgg gcgcctgtag tcccagctac tcgggaggct gatgcagaag   1380
aatggcgtga acccggaagg cagagcttgc agtgagccga gatcacgcca ctgcactcca   1440
gcctgggtga cagagcgaga ctctggctca taaaataata ataataataa ataaataaaa   1500
aataaatggt tttcagtaaa aaaaaaaaaa aaaaa                              1535
```

<210> SEQ ID NO 12
<211> LENGTH: 338
<212> TYPE: PRT
<213> ORGANISM: Homo sapiens

<400> SEQUENCE: 12

```
Ala Arg Ser Gly Ala Ser Ala Leu Arg Arg Arg Val Gln Val Trp
 1               5                  10                  15

Val Leu Ser Arg Pro Pro Gly Gly Gly Asp Ser Phe Arg Thr Arg
                20                  25                  30

Arg Pro Gln Arg Gly Pro Gly Pro Gly Ser Gln Ala Met Asp Ala
            35                  40                  45

Pro His Ser Lys Ala Ala Leu Asp Ser Ile Asn Glu Leu Pro Asp Asn
 50                  55                  60

Ile Leu Leu Glu Leu Phe Thr His Val Pro Ala Arg Gln Leu Leu Leu
65                  70                  75                  80

Asn Cys Arg Leu Val Cys Ser Leu Trp Arg Asp Leu Ile Asp Leu Leu
                85                  90                  95

Thr Leu Trp Lys Arg Lys Cys Leu Arg Lys Gly Phe Ile Thr Lys Asp
            100                 105                 110

Trp Asp Gln Pro Val Ala Asp Trp Lys Ile Phe Tyr Phe Leu Arg Ser
        115                 120                 125

Leu His Arg Asn Leu Leu Arg Asn Pro Cys Ala Glu Asn Asp Met Phe
    130                 135                 140

Ala Trp Gln Ile Asp Phe Asn Gly Gly Asp Arg Trp Lys Val Asp Ser
145                 150                 155                 160

Leu Pro Gly Ala His Gly Thr Glu Phe Pro Asp Pro Lys Val Lys Lys
                165                 170                 175

Ser Phe Val Thr Ser Tyr Glu Leu Cys Leu Lys Trp Glu Leu Val Asp
            180                 185                 190

Leu Leu Ala Asp Arg Tyr Trp Glu Glu Leu Leu Asp Thr Phe Arg Pro
        195                 200                 205

Asp Ile Val Val Lys Asp Trp Phe Ala Ala Arg Ala Asp Cys Gly Cys
    210                 215                 220

Thr Tyr Gln Leu Lys Val Gln Leu Ala Ser Ala Asp Tyr Phe Val Leu
225                 230                 235                 240

Ala Ser Phe Glu Pro Pro Val Thr Ile Gln Gln Trp Asn Asn Ala
                245                 250                 255

Thr Trp Thr Glu Val Ser Tyr Thr Phe Ser Asp Tyr Pro Arg Gly Val
            260                 265                 270

Arg Tyr Ile Leu Phe Gln His Gly Gly Arg Asp Thr Gln Tyr Trp Ala
        275                 280                 285

Gly Trp Tyr Gly Pro Arg Val Thr Asn Ser Ser Ile Val Val Ser Pro
    290                 295                 300

Lys Met Thr Arg Asn Gln Ala Ser Ser Glu Ala Gln Pro Gly Gln Lys
305                 310                 315                 320

His Gly Gln Glu Glu Ala Ala Gln Ser Pro Tyr Gly Ala Val Val Gln
                325                 330                 335
```

Ile Phe

<210> SEQ ID NO 13
<211> LENGTH: 1763
<212> TYPE: DNA
<213> ORGANISM: Homo sapiens

<400> SEQUENCE: 13

| | | | | | |
|---|---|---|---|---|---|
| tggaattccc | atggaccatg | tctaatacccc | gatttacaat | tacattgaac | tacaaggatc | 60 |
| ccctcactgg | agatgaagag | accttggctt | catatgggat | tgtttctggg | gacttgatat | 120 |
| gtttgattct | tcacgatgac | attccaccgc | ctaatatacc | ttcatccaca | gattcagagc | 180 |
| attcttcact | ccagaacaat | gagcaaccct | ctttggccac | cagctccaat | cagactagca | 240 |
| tacaggatga | caaccaagt | gattcattcc | aaggacaggc | agcccagtct | ggtgtttgga | 300 |
| atgacgacag | tatgttaggg | cctagtcaaa | attttgaagc | tgagtcaatt | caagataatg | 360 |
| cgcatatggc | agagggcaca | ggtttctatc | cctcagaacc | cctgctctgt | agtgaatcgg | 420 |
| tggaagggca | agtgccacat | tcattagaga | ccttgtatca | atcagctgac | tgttctgatg | 480 |
| ccaatgatgc | gttgatagtg | ttgatacatc | ttctcatgtt | ggagtcaggt | tacatacctc | 540 |
| agggcaccga | agccaaagca | ctgtccctgc | cggagaagtg | gaagttgagc | ggggtgtata | 600 |
| agctgcagta | catgcatcat | ctctgcgagg | gcagctccgc | tactctcacc | tgtgtgcctt | 660 |
| tgggaaacct | gattgttgta | aatgctacac | taaaaatcaa | caatgagatt | agaagtgtga | 720 |
| aaagattgca | gctgctacca | gaatctttta | tttgcaaaga | gaaactaggg | gaaaatgtag | 780 |
| ccaacatata | caaagatctt | cagaaactct | ctcgcctctt | taaagaccag | ctggtgtatc | 840 |
| ctcttctggc | ttttacccga | caagcactga | acctaccaaa | tgtatttggg | ttggtcgtcc | 900 |
| tcccattgga | actgaaacta | cggatcttcc | gacttctgga | tgttcgttcc | gtcttgtctt | 960 |
| tgtctgcggt | ttgtcgtgac | ctctttactg | cttcaaatga | cccactcctg | tggaggtttt | 1020 |
| tatatctgcg | tgattttcga | gacaatactg | tcagagttca | agacacagat | tggaaagaac | 1080 |
| tgtacaggaa | gaggcacata | caaagaaaag | aatccccgaa | agggcggttt | gtgctgctcc | 1140 |
| tgccatcgtc | aacccacacc | attccattct | atcccaaccc | cttgcaccct | aggccatttc | 1200 |
| ctagctcccg | ccttcctcca | ggaattatcg | ggggtgaata | tgaccaaaga | ccaacacttc | 1260 |
| cctatgttgg | agacccaatc | agttcactca | ttcctggtcc | tggggagacg | cccagccagt | 1320 |
| tacctccact | gagaccacgc | tttgatccag | ttggcccact | tccaggacct | aaccccatct | 1380 |
| tgccagggcg | aggcggcccc | aatgacagat | ttcccttag | acccagcagg | ggtcggccaa | 1440 |
| ctgatggccg | cctgtcattc | atgtgattga | tttgtaattt | catttctgga | gctccatttg | 1500 |
| tttttgtttc | taaactacag | atgtcactcc | ttggggtgct | gatctcgagt | gttattttct | 1560 |
| gattgtggtg | ttgagagttg | cactcccaga | aaccttttaa | gagatacatt | tatagcccta | 1620 |
| ggggtggtat | gacccaaagg | ttcctctgtg | acaaggttgg | ccttgggaat | agttggctgc | 1680 |
| caatctcccg | gctcttggtt | ctcctctaga | ttgaagtttg | ttttctgatg | ctgttcttac | 1740 |
| cagattaaaa | aaaagtgtaa | att | | | | 1763 |

<210> SEQ ID NO 14
<211> LENGTH: 482
<212> TYPE: PRT
<213> ORGANISM: Homo sapiens

<400> SEQUENCE: 14

```
Met Ser Asn Thr Arg Phe Thr Ile Thr Leu Asn Tyr Lys Asp Pro Leu
  1               5                  10                  15

Thr Gly Asp Glu Glu Thr Leu Ala Ser Tyr Gly Ile Val Ser Gly Asp
             20                  25                  30

Leu Ile Cys Leu Ile Leu His Asp Asp Ile Pro Pro Asn Ile Pro
         35                  40                  45

Ser Ser Thr Asp Ser Glu His Ser Ser Leu Gln Asn Asn Glu Gln Pro
 50                  55                  60

Ser Leu Ala Thr Ser Ser Asn Gln Thr Ser Ile Gln Asp Glu Gln Pro
 65                  70                  75                  80

Ser Asp Ser Phe Gln Gly Gln Ala Ala Gln Ser Gly Val Trp Asn Asp
                 85                  90                  95

Asp Ser Met Leu Gly Pro Ser Gln Asn Phe Glu Ala Glu Ser Ile Gln
            100                 105                 110

Asp Asn Ala His Met Ala Glu Gly Thr Gly Phe Tyr Pro Ser Glu Pro
            115                 120                 125

Leu Leu Cys Ser Glu Ser Val Glu Gly Gln Val Pro His Ser Leu Glu
        130                 135                 140

Thr Leu Tyr Gln Ser Ala Asp Cys Ser Asp Ala Asn Asp Ala Leu Ile
145                 150                 155                 160

Val Leu Ile His Leu Leu Met Leu Glu Ser Gly Tyr Ile Pro Gln Gly
                165                 170                 175

Thr Glu Ala Lys Ala Leu Ser Leu Pro Glu Lys Trp Lys Leu Ser Gly
            180                 185                 190

Val Tyr Lys Leu Gln Tyr Met His His Leu Cys Glu Gly Ser Ser Ala
        195                 200                 205

Thr Leu Thr Cys Val Pro Leu Gly Asn Leu Ile Val Val Asn Ala Thr
210                 215                 220

Leu Lys Ile Asn Asn Glu Ile Arg Ser Val Lys Arg Leu Gln Leu Leu
225                 230                 235                 240

Pro Glu Ser Phe Ile Cys Lys Glu Lys Leu Gly Glu Asn Val Ala Asn
                245                 250                 255

Ile Tyr Lys Asp Leu Gln Lys Leu Ser Arg Leu Phe Lys Asp Gln Leu
        260                 265                 270

Val Tyr Pro Leu Leu Ala Phe Thr Arg Gln Ala Leu Asn Leu Pro Asn
        275                 280                 285

Val Phe Gly Leu Val Val Leu Pro Leu Glu Leu Lys Leu Arg Ile Phe
        290                 295                 300

Arg Leu Leu Asp Val Arg Ser Val Leu Ser Leu Ser Ala Val Cys Arg
305                 310                 315                 320

Asp Leu Phe Thr Ala Ser Asn Asp Pro Leu Leu Trp Arg Phe Leu Tyr
            325                 330                 335

Leu Arg Asp Phe Arg Asp Asn Thr Val Arg Val Gln Asp Thr Asp Trp
            340                 345                 350

Lys Glu Leu Tyr Arg Lys Arg His Ile Gln Arg Lys Glu Ser Pro Lys
            355                 360                 365

Gly Arg Phe Val Leu Leu Pro Ser Ser Thr His Thr Ile Pro Phe
370                 375                 380

Tyr Pro Asn Pro Leu His Pro Arg Pro Phe Pro Ser Ser Arg Leu Pro
385                 390                 395                 400

Pro Gly Ile Ile Gly Gly Glu Tyr Asp Gln Arg Pro Thr Leu Pro Tyr
            405                 410                 415

Val Gly Asp Pro Ile Ser Ser Leu Ile Pro Gly Pro Gly Glu Thr Pro
```

-continued

```
                420                 425                 430
Ser Gln Leu Pro Pro Leu Arg Pro Arg Phe Asp Pro Val Gly Pro Leu
                435                 440                 445

Pro Gly Pro Asn Pro Ile Leu Pro Gly Arg Gly Pro Asn Asp Arg
        450                 455                 460

Phe Pro Phe Arg Pro Ser Arg Gly Arg Pro Thr Asp Gly Arg Leu Ser
465                 470                 475                 480

Phe Met
```

<210> SEQ ID NO 15
<211> LENGTH: 43
<212> TYPE: PRT
<213> ORGANISM: Homo sapiens

<400> SEQUENCE: 15

```
Leu Pro Ala Arg Gly Leu Asp His Ile Ala Glu Asn Ile Leu Ser Tyr
1               5                   10                  15

Leu Asp Ala Lys Ser Leu Cys Ala Ala Glu Leu Val Cys Lys Glu Trp
            20                  25                  30

Tyr Arg Val Thr Ser Asp Gly Met Leu Trp Lys
        35                  40
```

<210> SEQ ID NO 16
<211> LENGTH: 40
<212> TYPE: PRT
<213> ORGANISM: Homo sapiens

<400> SEQUENCE: 16

```
Leu Pro Leu Glu Leu Ser Phe Tyr Leu Leu Lys Trp Leu Asp Pro Gln
1               5                   10                  15

Thr Leu Leu Thr Cys Cys Leu Val Ser Lys Gln Trp Asn Lys Val Ile
            20                  25                  30

Ser Ala Cys Thr Glu Val Trp Gln
        35                  40
```

<210> SEQ ID NO 17
<211> LENGTH: 39
<212> TYPE: PRT
<213> ORGANISM: Homo sapiens

<400> SEQUENCE: 17

```
Leu Leu Gln Asp Ile Ile Leu Gln Val Phe Lys Tyr Leu Pro Leu Leu
1               5                   10                  15

Asp Arg Ala His Ala Ser Gln Val Cys Arg Asn Trp Asn Gln Val Phe
            20                  25                  30

His Met Pro Asp Leu Trp Arg
        35
```

<210> SEQ ID NO 18
<211> LENGTH: 39
<212> TYPE: PRT
<213> ORGANISM: Homo sapiens

<400> SEQUENCE: 18

```
Leu Pro Ile Asp Val Gln Leu Tyr Ile Leu Ser Phe Leu Ser Pro His
1               5                   10                  15

Asp Leu Cys Gln Leu Gly Ser Thr Asn His Tyr Trp Asn Glu Thr Val
            20                  25                  30

Arg Asn Pro Ile Leu Trp Arg
        35
```

35

<210> SEQ ID NO 19
<211> LENGTH: 39
<212> TYPE: PRT
<213> ORGANISM: Homo sapiens

<400> SEQUENCE: 19

Leu Arg His Val Leu Ala Thr Ile Leu Ala Gln Leu Ser Asp Met Asp
  1               5                  10                  15

Leu Ile Asn Val Ser Lys Val Ser Thr Thr Trp Lys Lys Ile Leu Glu
             20                  25                  30

Asp Asp Lys Gly Ala Phe Gln
             35

<210> SEQ ID NO 20
<211> LENGTH: 40
<212> TYPE: PRT
<213> ORGANISM: Homo sapiens

<400> SEQUENCE: 20

Leu Pro Asp Asn Ile Leu Leu Glu Leu Phe Thr His Val Pro Ala Arg
  1               5                  10                  15

Gln Leu Leu Leu Asn Cys Arg Leu Val Cys Ser Leu Trp Arg Asp Leu
             20                  25                  30

Ile Asp Leu Leu Thr Leu Trp Lys
             35                  40

<210> SEQ ID NO 21
<211> LENGTH: 39
<212> TYPE: PRT
<213> ORGANISM: Homo sapiens

<400> SEQUENCE: 21

Leu Pro Leu Glu Leu Lys Leu Arg Ile Phe Arg Leu Leu Asp Val Arg
  1               5                  10                  15

Ser Val Leu Ser Leu Ser Ala Val Cys Arg Asp Leu Phe Thr Ala Ser
             20                  25                  30

Asn Asp Pro Leu Leu Trp Arg
             35

<210> SEQ ID NO 22
<211> LENGTH: 39
<212> TYPE: PRT
<213> ORGANISM: Homo sapiens

<400> SEQUENCE: 22

Leu Pro Asp Glu Leu Leu Leu Gly Ile Phe Ser Cys Leu Cys Leu Pro
  1               5                  10                  15

Glu Leu Leu Lys Val Ser Gly Val Cys Lys Arg Trp Tyr Arg Leu Ala
             20                  25                  30

Ser Asp Glu Ser Leu Trp Gln
             35

<210> SEQ ID NO 23
<211> LENGTH: 1323
<212> TYPE: DNA
<213> ORGANISM: Homo sapiens

<400> SEQUENCE: 23
acattttcta atgtttacag aatgaagagg aacagtttat ctgttgagaa taaaattgtc      60

-continued

```
cagttgtcag gagcagcgaa acagccaaaa gttgggttct actcttctct caaccagact    120
catacacaca cggttcttct agactggggg agtttgcctc accatgtagt attacaaatt    180
tttcagtatc ttcctttact agatcgggcc tgtgcatctt ctgtatgtag gaggtggaat    240 gaagttttc atatttctga cctttggaga agtttgaat ttgaactgaa ccagtcagct     300
acttcatctt ttaagtccac tcatcctgat ctcattcagc agatcattaa aaagcatttt    360
gctcatcttc agtatgtcag ctttaaggtt gacagtagcg ctgagtcagc agaagctgcc    420
tgtgatatac tctctcagct ggtaaattgt tccatccaga ccttgggctt gatttcaaca    480
gccaagccaa gtttcatgaa tgtgtcggag tctcattttg tgtcagcact tacagttgtt    540
tttatcaact caaaatcatt atcatcaatc aaaattgaag atacaccagt ggatgatcct    600
tcattgaaga ttcttgtggc aataatagt gacactctaa gactcccaaa gatgagtagc    660
tgtcctcatg tttcatctga tggaattctt tgtgtagctg accgttgtca aggccttaga    720
gaactggcgt tgaattatta catcctaact gatgaacttt tccttgcact ctcaagcgag    780
actcatgtta accttgaaca tcttcgaatt gatgttgtga gtgaaaatcc tggacagatt    840
aaatttcatg ctgttaaaaa acacagttgg gatgcactta ttaaacattc ccctagagtt    900
aatgttgtta tgcacttctt tctatatgaa gaggaattcg agacgttctt caaagaagaa    960 accctgtta ctcacctta ttttggtcgt tcagtcagca agtggttt aggacgggta      1020 ggtctcaact gtcctcgact gattgagtta gtggtgtgtg ctaatgatct tcagcctctt    1080
gataatgaac ttatttgtat tgctgaacac tgtacaaacc taacagcctt gggcctcagc    1140
aaatgtgaag ttagctgcag tgccttcatc aggtttgtaa gactgtgtga gagaaggtta    1200
acacagctct ctgtaatgga ggaagtttg atccctgatg aggattatag cctagatgaa    1260
attcacactg aagtctccaa ataccggga agagtatggt tccctgatgt gatgcctctc    1320
tgg                                                                  1323
```

<210> SEQ ID NO 24
<211> LENGTH: 434
<212> TYPE: PRT
<213> ORGANISM: Homo sapiens

<400> SEQUENCE: 24

```
Met Lys Arg Asn Ser Leu Ser Val Glu Asn Lys Ile Val Gln Leu Ser
 1               5                  10                  15

Gly Ala Ala Lys Gln Pro Lys Val Gly Phe Tyr Ser Ser Leu Asn Gln
             20                  25                  30

Thr His Thr His Thr Val Leu Leu Asp Trp Gly Ser Leu Pro His His
         35                  40                  45

Val Val Leu Gln Ile Phe Gln Tyr Leu Pro Leu Leu Asp Arg Ala Cys
     50                  55                  60

Ala Ser Ser Val Cys Arg Arg Trp Asn Glu Val Phe His Ile Ser Asp
 65                  70                  75                  80

Leu Trp Arg Lys Phe Glu Phe Glu Leu Asn Gln Ser Ala Thr Ser Ser
                 85                  90                  95

Phe Lys Ser Thr His Pro Asp Leu Ile Gln Gln Ile Ile Lys Lys His
            100                 105                 110

Phe Ala His Leu Gln Tyr Val Ser Phe Lys Val Asp Ser Ser Ala Glu
        115                 120                 125

Ser Ala Glu Ala Ala Cys Asp Ile Leu Ser Gln Leu Val Asn Cys Ser
    130                 135                 140
```

```
Ile Gln Thr Leu Gly Leu Ile Ser Thr Ala Lys Pro Ser Phe Met Asn
145                 150                 155                 160

Val Ser Glu Ser His Phe Val Ser Ala Leu Thr Val Phe Ile Asn
            165                 170                 175

Ser Lys Ser Leu Ser Ser Ile Lys Ile Glu Asp Thr Pro Val Asp Asp
            180                 185                 190

Pro Ser Leu Lys Ile Leu Val Ala Asn Asn Ser Asp Thr Leu Arg Leu
            195                 200                 205

Pro Lys Met Ser Ser Cys Pro His Val Ser Ser Asp Gly Ile Leu Cys
        210                 215                 220

Val Ala Asp Arg Cys Gln Gly Leu Arg Glu Leu Ala Leu Asn Tyr Tyr
225                 230                 235                 240

Ile Leu Thr Asp Glu Leu Phe Leu Ala Leu Ser Ser Glu Thr His Val
                245                 250                 255

Asn Leu Glu His Leu Arg Ile Asp Val Val Ser Glu Asn Pro Gly Gln
                260                 265                 270

Ile Lys Phe His Ala Val Lys Lys His Ser Trp Asp Ala Leu Ile Lys
            275                 280                 285

His Ser Pro Arg Val Asn Val Val Met His Phe Phe Leu Tyr Glu Glu
        290                 295                 300

Glu Phe Glu Thr Phe Phe Lys Glu Glu Thr Pro Val Thr His Leu Tyr
305                 310                 315                 320

Phe Gly Arg Ser Val Ser Lys Val Val Leu Gly Arg Val Gly Leu Asn
                325                 330                 335

Cys Pro Arg Leu Ile Glu Leu Val Val Cys Ala Asn Asp Leu Gln Pro
                340                 345                 350

Leu Asp Asn Glu Leu Ile Cys Ile Ala Glu His Cys Thr Asn Leu Thr
            355                 360                 365

Ala Leu Gly Leu Ser Lys Cys Glu Val Ser Cys Ser Ala Phe Ile Arg
            370                 375                 380

Phe Val Arg Leu Cys Glu Arg Arg Leu Thr Gln Leu Ser Val Met Glu
385                 390                 395                 400

Glu Val Leu Ile Pro Asp Glu Asp Tyr Ser Leu Asp Glu Ile His Thr
                405                 410                 415

Glu Val Ser Lys Tyr Leu Gly Arg Val Trp Phe Pro Asp Val Met Pro
            420                 425                 430

Leu Trp

<210> SEQ ID NO 25
<211> LENGTH: 1970
<212> TYPE: DNA
<213> ORGANISM: Homo sapiens

<400> SEQUENCE: 25
ggaaacgtca aaattgggat agtcggcagt tctggcccct gcagctggag gtaccctgag    60
ttctgagggt cgtagtgctg tttctggtat tctcatcgcg gtcacctcta ccggtgtgga   120
caagtaaagt ttgaatcagc ttctccatgg cctgggcacc agttcccggc tgagccattt   180
tccttttggc taaagtccc cgcccagagg ccaattcgtc gcggcggcgg tggagatcgc   240
aggtcgctca ggcttgcaga tgggtcaagg gttgtggaga gtggtcagaa accagcagct   300
gcaacaagaa ggctacagtg agcaaggcta cctcaccaga gagcagagca ggagaatggc   360
tgcgagcaac atttctaaca ccaatcatcg taaacaagtc caaggaggca ttgacatata   420
```

-continued

```
tcatctttg aaggcaagga aatcgaaaga acaggaagga ttcattaatt tggaaatgtt     480
gcctcctgag ctaagcttta ccatcttgtc ctacctgaat gcaactgacc tttgcttggc    540
ttcatgtgtt tggcaggacc ttgcgaatga tgaacttctc tggcaagggt gtgcaaatc     600 cacttggggt cactgttcca tatacaataa gaacccacct ttaggatttt cttttagaaa    660
aktgtatatg cagctggatg aaggcagcct cacctttaat gccaacccag atgagggagt    720
gaactacttt atgtccaagg gtatcctgga tgattcgcca aaggaaatag caaagtttat    780
cttctgtaca agaacactaa attggaaaaa actgagaatc tatcttgatg aaggagaga    840 tgtcttggat gaccttgtaa cattgcataa ttttagaaat cagttcttgc caaatgcact    900
gagagaattt tttcgtcata tccatgcccc tgaagagcgt ggagagtatc ttgaaactct    960
tataacaaag ttctcacata gattctgtgc ttgcaaccct gatttaatgc gagaacttgg   1020
ccttagtcct gatgctgtct atgtactgtg ctactctttg attctacttt ccattgacct   1080
cactagccct catgtgaaga ataaaatgtc aaaaagggaa tttattcgaa atacccgtcg   1140
cgctgctcaa aatattagtg aagattttgt agggcatctt tatgacaata tctaccttat   1200
tggccatgtg gctgcataaa aagcacaatt gctaggactt cagtttttac ttcagactaa   1260
agctacccaa ggacttagca gatatggggg ttacatcagt gctggtcatt gtagcctgag   1320
tatacaatca agcttcagtg tgcaaccttt ttttctttg ccattttcta ttttagtaat    1380
ttccttgggg aactaaataa ttttgcagaa ttttccctaa ttttgtttat cacgttttgc   1440
acaaagcaga gccactgtct aacacagctg ttaacgaatg ataaactgac attatactct   1500
aaaagatggt gtatttgtgc attagatttg cctgaaaaac tttatccatt tccattcttt   1560
atacaaatac catgtaatgt gtacatattt aactaaagag atttatagtc ataattattt   1620
tattgtaaag attttaacta aagttttttcc ttttctctca aactgagttc tgaaatttat   1680
ttgattctga tctgaaacta ttgtctycgt aaaagttaga tctgacttca grcagaaacc   1740
aataccagct tccttttcct ttaaactttg aagagtgttg atttgttact atattactat   1800
gcaaaactgg cagttatttt tataatataa atttataatt tgattttta ttttaaaaac    1860 tgggttaatc aagtctcggt aagtccttta aaccatttag gattttaaa acatcaaaat    1920 ttatgattta cattcatagg aataaaataa aatatyatta gaactctggt              1970
```

<210> SEQ ID NO 26
<211> LENGTH: 634
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 26

```
Glu Thr Ser Lys Leu Gly Ser Ala Val Leu Ala Pro Ala Ala Gly Gly
 1               5                  10                  15

Thr Leu Ser Ser Glu Gly Arg Ser Ala Val Ser Gly Ile Leu Ile Ala
            20                  25                  30

Val Thr Ser Thr Gly Val Asp Lys Ser Leu Asn Gln Leu Leu His Gly
        35                  40                  45

Leu Gly Thr Ser Ser Arg Leu Ser His Phe Pro Phe Gly Lys Ser Pro
    50                  55                  60

Pro Arg Gly Gln Phe Val Ala Ala Val Glu Ile Ala Gly Arg Ser
65                  70                  75                  80
```

```
Gly Leu Gln Met Gly Gln Gly Leu Trp Arg Val Val Arg Asn Gln Gln
                85                  90                  95

Leu Gln Gln Glu Gly Tyr Ser Glu Gln Gly Tyr Leu Thr Arg Glu Gln
            100                 105                 110

Ser Arg Arg Met Ala Ala Ser Asn Ile Ser Asn Thr Asn His Arg Lys
        115                 120                 125

Gln Val Gln Gly Gly Ile Asp Ile Tyr His Leu Leu Lys Ala Arg Lys
    130                 135                 140

Ser Lys Glu Gln Glu Gly Phe Ile Asn Leu Glu Met Leu Pro Pro Glu
145                 150                 155                 160

Leu Ser Phe Thr Ile Leu Ser Tyr Leu Asn Ala Thr Asp Leu Cys Leu
                165                 170                 175

Ala Ser Cys Val Trp Gln Asp Leu Ala Asn Asp Glu Leu Leu Trp Gln
            180                 185                 190

Gly Leu Cys Lys Ser Thr Trp Gly His Cys Ser Ile Tyr Asn Lys Asn
        195                 200                 205

Pro Pro Leu Gly Phe Ser Phe Arg Lys Xaa Tyr Met Gln Leu Asp Glu
    210                 215                 220

Gly Ser Leu Thr Phe Asn Ala Asn Pro Asp Glu Gly Val Asn Tyr Phe
225                 230                 235                 240

Met Ser Lys Gly Ile Leu Asp Asp Ser Pro Lys Glu Ile Ala Lys Phe
                245                 250                 255

Ile Phe Cys Thr Arg Thr Leu Asn Trp Lys Lys Leu Arg Ile Tyr Leu
            260                 265                 270

Asp Glu Arg Arg Asp Val Leu Asp Asp Leu Val Thr Leu His Asn Phe
        275                 280                 285

Arg Asn Gln Phe Leu Pro Asn Ala Leu Arg Glu Phe Phe Arg His Ile
    290                 295                 300

His Ala Pro Glu Glu Arg Gly Glu Tyr Leu Glu Thr Leu Ile Thr Lys
305                 310                 315                 320

Phe Ser His Arg Phe Cys Ala Cys Asn Pro Asp Leu Met Arg Glu Leu
                325                 330                 335

Gly Leu Ser Pro Asp Ala Val Tyr Val Leu Cys Tyr Ser Leu Ile Leu
            340                 345                 350

Leu Ser Ile Asp Leu Thr Ser Pro His Val Lys Asn Lys Met Ser Lys
        355                 360                 365

Arg Glu Phe Ile Arg Asn Thr Arg Arg Ala Ala Gln Asn Ile Ser Glu
    370                 375                 380

Asp Phe Val Gly His Leu Tyr Asp Asn Ile Tyr Leu Ile Gly His Val
385                 390                 395                 400

Ala Ala Lys Ala Gln Leu Leu Gly Leu Gln Phe Leu Leu Gln Thr Lys
                405                 410                 415

Ala Thr Gln Gly Leu Ser Arg Tyr Gly Gly Tyr Ile Ser Ala Gly His
            420                 425                 430

Cys Ser Leu Ser Ile Gln Ser Ser Phe Ser Val Gln Pro Phe Phe Leu
        435                 440                 445

Leu Pro Phe Ser Ile Leu Val Ile Ser Leu Gly Asn Ile Ile Leu Gln
    450                 455                 460

Asn Phe Ser Phe Cys Leu Ser Arg Phe Ala Gln Ser Arg Ala Thr Val
465                 470                 475                 480

His Ser Cys Arg Met Ile Asn His Tyr Thr Leu Lys Asp Gly Val Phe
                485                 490                 495

Val His Ile Cys Leu Lys Asn Phe Ile His Phe His Ser Leu Tyr Lys
```

-continued

```
            500             505             510
Tyr His Val Met Cys Thr Tyr Leu Thr Lys Glu Ile Tyr Ser His Asn
            515             520             525
Tyr Phe Ile Val Lys Ile Leu Thr Lys Val Phe Pro Phe Leu Ser Asn
            530             535             540
Val Leu Lys Phe Ile Phe Ser Glu Thr Ile Val Xaa Val Lys Val Arg
545             550             555             560
Ser Asp Phe Arg Gln Lys Pro Ile Pro Ala Ser Phe Ser Phe Lys Leu
            565             570             575
Arg Val Leu Ile Cys Tyr Tyr Ile Thr Met Gln Asn Trp Gln Leu Phe
            580             585             590
Leu Tyr Lys Phe Ile Ile Phe Ile Leu Lys Thr Gly Leu Ile Lys
            595             600             605
Ser Arg Val Leu Thr Ile Asp Phe Asn Ile Lys Ile Tyr Asp Leu His
            610             615             620
Ser Glu Asn Lys Ile Xaa Leu Glu Leu Trp
625             630
```

<210> SEQ ID NO 27
<211> LENGTH: 4168
<212> TYPE: DNA
<213> ORGANISM: Homo sapiens

<400> SEQUENCE: 27

```
gatggcggcg gcagcagtcg acagcgcgat ggaggtggtg ccggcgctgg cggaggaggc     60
cgcgccggag gtagcgggcc tcagctgcct cgtcaacctg ccgggtgagg tgctggagta    120
catcctgtgc tgcggctcgc tgacggccgc cgacatcggc cgtgtctcca gcacctgccg    180
gcggctgcgc gagctgtgcc agagcagcgg gaaggtgtgg aaggagcagt tccgggtgag    240
gtggccttcc cttatgaaac actacagccc caccgactac gtcaattggt tggaagagta    300
taaagttcgg caaaaagctg ggttagaagc gcggaagatt gtagcctcgt tctcaaagag    360
gttcttttca gagcacgttc cttgtaatgg cttcagtgac attgagaacc ttgaaggacc    420
agagattttt tttgaggatg aactggtgtg tatcctaaat atggaaggaa gaaaagcttt    480
gacctggaaa tactacgcaa aaaaattct ttactacctg cggcaacaga gatcttaaa     540
taatcttaag gcctttcttc agcagccaga tgactatgag tcgtatcttg aaggtgctgt    600
atatattgac cagtactgca atcctctctc gacatcagc ctcaaagaca tccaggccca    660
aattgacagc atcgtggagc ttgtttgcaa aacccttcgg ggcataaaca gtcgccaccc    720
cagcttggcc ttcaaggcag gtgaatcatc catgataatg gaaatagaac tccagagcca    780
ggtgctggat gccatgaact atgtccttta cgaccaactg aagttcaagg ggaatcgaat    840
ggattactat aatgccctca acttatatat gcatcaggtt ttgattcgca gaacaggaat    900
cccaatcagc atgtctctgc tctatttgac aattgctcgg cagttgggag tcccactgga    960
gcctgtcaac ttcccaagtc acttcttatt aaggtggtgc caaggcgcag aaggggcgac   1020
cctggacatc tttgactaca tctacataga tgctttggg aaaggcaagc agctgacagt   1080
gaaagaatgc gagtacttga tcggccagca cgtgactgca gcactgtatg ggtggtcaa   1140
tgtcaagaag gtgttacaga gaatggtggg aaacctgtta agcctgggga gcgggaagg   1200
catcgaccag tcataccagc tcctgagaga ctcgctggat ctctatctgg caatgtaccc   1260
ggaccaggtg cagcttctcc tcctccaagc caggctttac ttccacctgg gaatctggcc   1320
agagaaggtg cttgacatcc tccagcacat ccaaacccta gacccggggc agcacggggc   1380
```

-continued

```
ggtgggctac ctggtgcagc acactctaga gcacattgag cgcaaaaagg aggaggtggg    1440
cgtagaggtg aagctgcgct ccgatgagaa gcacagagat gtctgctact ccatcgggct    1500
cattatgaag cataagaggt atggctataa ctgtgtgatc tacggctggg accccacctg    1560
catgatggga cacgagtgga tccggaacat gaacgtccac agcctgccgc acggccacca    1620
ccagcctttc tataacgtgc tggtggagga cggctcctgt cgatacgcag cccaagaaaa    1680
cttggaatat aacgtggagc tcaagaaaat ctcacaccct gacgtgggac gctatttctc    1740
agagtttact ggcactcact acatcccaaa cgcagagctg gagatccggt atccagaaga    1800
tctggagttt gtctatgaaa cggtgcagaa tatttacagt gcaaagaaag agaacataga    1860
tgagtaaagt ctagagagga cattgcacct ttgctgctgc tgctatcttc caagagaacg    1920
ggactccgga agaagacgtc tccacggagc cctcgggacc tgctgcacca ggaaagccac    1980
tccaccagta gtgctggttg cctcctacta agtttaaata ccgtgtgctc ttccccagct    2040
gcaaagacaa tgttgctctc cgcctacact agtgaattaa tctgaaaggc actgtgtcag    2100
tggcatggct tgtatgcttg tcctgtggtg acagtttgtg acattctgtc ttcatgaggt    2160
ctcacagtcg acgctcctgt aatcattctt tgtattcact ccattcccct gtctgtctgc    2220
atttgtctca gaacatttcc ttggctggac agatgggggtt atgcatttgc ataatttcc    2280 ttctgatttc tctgtggaac gtgttcggtc ccgagtgagg actgtgtgtc tttttaccct    2340
gaagttagtt gcatattcag aggtaaagtt gtgtgctatc ttggcagcat cttagagatg    2400
gagacattaa caagctaatg gtaattagaa tcatttgaat ttattttttt ctaatatgtg    2460
aaacacagat ttcaagtgtt ttatctttt tttttaaatt taaatgggaa ataacacag    2520 ttttcccttc catattcctc tcttgagttt atgcacatct ctataaatca ttagtttct    2580 attttattac ataaaattct tttagaaaat gcaaatagtg aactttgtga atggattttt    2640
ccatactcat ctacaattcc tccattttaa atgactactt ttatttttta atttaaaaaa    2700
tctacttcag tatcatgagt aggtcttaca tcagtgatgg gttctttttg tagtgagaca    2760
tacaaatctg atgttaatgt ttgctcttag aagtcatact ccatggtctt caaagaccaa    2820
aaaatgaggt tttgccttgg taatcaggaa aaaaaaaaat taatgaacct taaaaaaaaa    2880
aaaaaaggtt ttgaagggaa aaaagtggt ttcacacctc ttgttattcc ttagagtcac    2940
ttcaaggcct gttgaatgt ggcaggttag aaagagagag aatgtctttc atttgaagag    3000
tgttggactt gtgtgaaagg agatgtgcgt gttggaatct gcttttccaa gccgccaggg    3060
tcctgacggc agcaggacga agcctgttgt ggcgtcttct gggaaagcct gaccgtgtgt    3120
tcggacggca ctggctcctt tccgaagttc tcagtaactg agcccagagt aactgcacgc    3180
ctttgtgcag ctctggagct ccaccaactc tcggcctgcc agttctcaag cgagctaatc    3240
ttgtcattaa tcgatagaag ctaacttccg aagttaggac ctagttactt tgctctcaac    3300
atttaaaata atgcagttgc tctagtgaat ggggcgttag gggcctgtct ctgcacctgt    3360
ctgtccatct gcatgcagta ttctcaccca tgttgaatgc ctgctgcttg tttacccttt    3420
ggaaaccctg gggtgaccaa ggtttggaaa gccacctgag accacttcat agcaagggaa    3480
ggctttaagc agttactaga aagagatggg gatttggccc ctggctcctc cagcctgaat    3540
gagctattta atccactgtc catgttcctc atcagtcaaa tccaaagtca aggatttga    3600 acctgcatct ggaaacgtaa ccactcacag cacctggccc gccaaggttg ggaggattgt    3660
acactacttt catttaaagg ggaaagtttg ataatacgga attaattaat atgaatgaga    3720
```

```
tgcattaata agaacctgag catgctgaga gttgcaattg ttggttttct ggtttgattg    3780 atttccttt  ttcttagaca catcaaagtc aagaaagatg gttttacctt tactgaccca   3840
gctgtacata tgtatctaga ctgttttta atgtctttct tcatgaatgc ttcatggggc    3900
tccaggaagc ctgtatcacc tgtgtaagtt ggtatttggg cactttatat ttttctaaaa  3960
acgtgttttg gatcctgtac tctaataaat cataagtttc ttttaaaaa ttttccaaaa   4020 cttttctcca ttttaaaaag ccctgttata aacgttgaac tttcacaatg ttaaaatgtt  4080
aaatatttgg atatagcaac ttcttttctc ttcaaatgaa tgccaagatt ttttgtaca   4140 atgattaata aatggaactt atccagag                                      4168
```

<210> SEQ ID NO 28
<211> LENGTH: 621
<212> TYPE: PRT
<213> ORGANISM: Homo sapiens

<400> SEQUENCE: 28

```
Met Ala Ala Ala Ala Val Asp Ser Ala Met Glu Val Val Pro Ala Leu
  1               5                  10                  15

Ala Glu Glu Ala Ala Pro Glu Val Ala Gly Leu Ser Cys Leu Val Asn
             20                  25                  30

Leu Pro Gly Glu Val Leu Glu Tyr Ile Leu Cys Cys Gly Ser Leu Thr
         35                  40                  45

Ala Ala Asp Ile Gly Arg Val Ser Ser Thr Cys Arg Arg Leu Arg Glu
     50                  55                  60

Leu Cys Gln Ser Ser Gly Lys Val Trp Lys Glu Gln Phe Arg Val Arg
 65                  70                  75                  80

Trp Pro Ser Leu Met Lys His Tyr Ser Pro Thr Asp Tyr Val Asn Trp
                 85                  90                  95

Leu Glu Glu Tyr Lys Val Arg Gln Lys Ala Gly Leu Glu Ala Arg Lys
            100                 105                 110

Ile Val Ala Ser Phe Ser Lys Arg Phe Phe Ser Glu His Val Pro Cys
        115                 120                 125

Asn Gly Phe Ser Asp Ile Glu Asn Leu Glu Gly Pro Glu Ile Phe Phe
    130                 135                 140

Glu Asp Glu Leu Val Cys Ile Leu Asn Met Glu Gly Arg Lys Ala Leu
145                 150                 155                 160

Thr Trp Lys Tyr Tyr Ala Lys Lys Ile Leu Tyr Tyr Leu Arg Gln Gln
                165                 170                 175

Lys Ile Leu Asn Asn Leu Lys Ala Phe Leu Gln Gln Pro Asp Asp Tyr
            180                 185                 190

Glu Ser Tyr Leu Glu Gly Ala Val Tyr Ile Asp Gln Tyr Cys Asn Pro
        195                 200                 205

Leu Ser Asp Ile Ser Leu Lys Asp Ile Gln Ala Gln Ile Asp Ser Ile
    210                 215                 220

Val Glu Leu Val Cys Lys Thr Leu Arg Gly Ile Asn Ser Arg His Pro
225                 230                 235                 240

Ser Leu Ala Phe Lys Ala Gly Glu Ser Ser Met Ile Met Glu Ile Glu
                245                 250                 255

Leu Gln Ser Gln Val Leu Asp Ala Met Asn Tyr Val Leu Tyr Asp Gln
            260                 265                 270

Leu Lys Phe Lys Gly Asn Arg Met Asp Tyr Tyr Asn Ala Leu Asn Leu
        275                 280                 285

Tyr Met His Gln Val Leu Ile Arg Arg Thr Gly Ile Pro Ile Ser Met
```

```
                290                 295                 300
Ser Leu Leu Tyr Leu Thr Ile Ala Arg Gln Leu Gly Val Pro Leu Glu
305                 310                 315                 320

Pro Val Asn Phe Pro Ser His Phe Leu Leu Arg Trp Cys Gln Gly Ala
                325                 330                 335

Glu Gly Ala Thr Leu Asp Ile Phe Asp Tyr Ile Tyr Ile Asp Ala Phe
                340                 345                 350

Gly Lys Gly Lys Gln Leu Thr Val Lys Glu Cys Glu Tyr Leu Ile Gly
                355                 360                 365

Gln His Val Thr Ala Ala Leu Tyr Gly Val Val Asn Val Lys Lys Val
        370                 375                 380

Leu Gln Arg Met Val Gly Asn Leu Leu Ser Leu Gly Lys Arg Glu Gly
385                 390                 395                 400

Ile Asp Gln Ser Tyr Gln Leu Leu Arg Asp Ser Leu Asp Leu Tyr Leu
                405                 410                 415

Ala Met Tyr Pro Asp Gln Val Gln Leu Leu Leu Gln Ala Arg Leu
                420                 425                 430

Tyr Phe His Leu Gly Ile Trp Pro Glu Lys Val Leu Asp Ile Leu Gln
                435                 440                 445

His Ile Gln Thr Leu Asp Pro Gly Gln His Gly Ala Val Gly Tyr Leu
        450                 455                 460

Val Gln His Thr Leu Glu His Ile Glu Arg Lys Lys Glu Val Gly
465                 470                 475                 480

Val Glu Val Lys Leu Arg Ser Asp Glu Lys His Arg Asp Val Cys Tyr
                485                 490                 495

Ser Ile Gly Leu Ile Met Lys His Lys Arg Tyr Gly Tyr Asn Cys Val
                500                 505                 510

Ile Tyr Gly Trp Asp Pro Thr Cys Met Met Gly His Glu Trp Ile Arg
                515                 520                 525

Asn Met Asn Val His Ser Leu Pro His Gly His His Gln Pro Phe Tyr
530                 535                 540

Asn Val Leu Val Glu Asp Gly Ser Cys Arg Tyr Ala Ala Gln Glu Asn
545                 550                 555                 560

Leu Glu Tyr Asn Val Glu Pro Gln Glu Ile Ser His Pro Asp Val Gly
                565                 570                 575

Arg Tyr Phe Ser Glu Phe Thr Gly Thr His Tyr Ile Pro Asn Ala Glu
                580                 585                 590

Leu Glu Ile Arg Tyr Pro Glu Asp Leu Glu Phe Val Tyr Glu Thr Val
                595                 600                 605

Gln Asn Ile Tyr Ser Ala Lys Lys Glu Asn Ile Asp Glu
    610                 615                 620

<210> SEQ ID NO 29
<211> LENGTH: 278
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 29
ccgtagtact ggnttccggc gggctggtga ggaatggagc cggtagntgc ttgcggcgag      60
tcccgggntc ctccgtagac ccgcgganac cttcgtgttg agtaacctgg cggaggtggt    120
ggagcgtgtg ctcaccttcc tgcccgccaa ggcgttgctg cgggtggcct gcgtgtgccg    180
```

```
cttatggagg gagtgtgtgc gcagagtatt gcggacccat cggagcgtaa cctggatctc      240
cgcaggcctg gcggaggccg gccacctggn ggggcatt                              278
```

<210> SEQ ID NO 30
<211> LENGTH: 91
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 30

```
Arg Ser Thr Gly Phe Arg Arg Ala Gly Glu Glu Trp Ser Arg Xaa Leu
 1               5                  10                  15

Ala Ala Ser Pro Gly Xaa Leu Arg Arg Pro Ala Xaa Thr Phe Val Leu
             20                  25                  30

Ser Asn Leu Ala Glu Val Val Glu Arg Val Leu Thr Phe Leu Pro Ala
         35                  40                  45

Lys Ala Leu Leu Arg Val Ala Cys Val Cys Arg Leu Trp Arg Glu Cys
     50                  55                  60

Val Arg Arg Val Leu Arg Thr His Arg Ser Val Thr Trp Ile Ser Ala
 65                  70                  75                  80

Gly Leu Ala Glu Ala Gly His Leu Xaa Gly His
                 85                  90
```

<210> SEQ ID NO 31
<211> LENGTH: 592
<212> TYPE: DNA
<213> ORGANISM: Homo sapiens

<400> SEQUENCE: 31

```
gcggccgcgc ccggtgcagc aacagcagca gcagccccg cagcagccgc cgccgcagcc      60
gccccagcag cagccgcccc agcagcagcc tccgccgccg ccgcagcagc agcagcagca     120
gcagcctccg ccgccgccac cgccgcctcc gccgctgcct caggagcgga caacgtcgg     180 cgagcgggat gatgatgtgc ctgcagatat ggttgcagaa gaatcaggtc ctggtgcaca     240
aaatagtcca taccaacttc gtagaaaaac tcttttgccg aaaagaacag cgtgtcccac     300
aaagaacagt atggagggcg cctcaacttc aactacagaa actttggtc atcgtgcaaa     360 acgtgcaaga gtgtctggaa atcacaaga tctatcagca gcacctgctg aacagtatct     420
tcaggagaaa ctgccagatg aagtggttct aaaaatcttc tcttacttgc tggaacagga     480
tctttgtaga gcagcttgtg tatgtaaacg cttcagtgaa cttgctaatg atcccaattt     540
gtggaaacga ttatatatgg aagtatttga atatactcgc cctatgatgc at            592
```

<210> SEQ ID NO 32
<211> LENGTH: 197
<212> TYPE: PRT
<213> ORGANISM: Homo sapiens

<400> SEQUENCE: 32

```
Arg Pro Arg Pro Val Gln Gln Gln Gln Gln Pro Pro Gln Gln Pro
 1               5                  10                  15

Pro Pro Gln Pro Pro Gln Gln Gln Pro Pro Gln Gln Gln Pro Pro Pro
             20                  25                  30

Pro Pro Gln Gln Gln Gln Gln Gln Pro Pro Pro Pro Pro Pro
         35                  40                  45
```

```
Pro Pro Pro Leu Pro Gln Glu Arg Asn Asn Val Gly Glu Arg Asp Asp
        50                  55                  60

Asp Val Pro Ala Asp Met Val Ala Glu Glu Ser Gly Pro Gly Ala Gln
 65                  70                  75                  80

Asn Ser Pro Tyr Gln Leu Arg Arg Lys Thr Leu Leu Pro Lys Arg Thr
                 85                  90                  95

Ala Cys Pro Thr Lys Asn Ser Met Glu Gly Ala Ser Thr Ser Thr Thr
                100                 105                 110

Glu Asn Phe Gly His Arg Ala Lys Arg Ala Arg Val Ser Gly Lys Ser
            115                 120                 125

Gln Asp Leu Ser Ala Ala Pro Ala Glu Gln Tyr Leu Gln Glu Lys Leu
    130                 135                 140

Pro Asp Glu Val Val Leu Lys Ile Phe Ser Tyr Leu Leu Glu Gln Asp
145                 150                 155                 160

Leu Cys Arg Ala Ala Cys Val Cys Lys Arg Phe Ser Glu Leu Ala Asn
                165                 170                 175

Asp Pro Asn Leu Trp Lys Arg Leu Tyr Met Glu Val Phe Glu Tyr Thr
                180                 185                 190

Arg Pro Met Met His
            195
```

<210> SEQ ID NO 33
<211> LENGTH: 537
<212> TYPE: DNA
<213> ORGANISM: Homo sapiens

<400> SEQUENCE: 33

```
gcggccgcgg cccggactcc gcggtgggcg agcgccctgt gaggtgacca tggaggctgg    60
tggcctcccc ttggagctgt ggcgcatgat cttagcctac ttgcaccttc ccgacctggg   120
ccgctgcagc ctggtatgca gggcctggta tgaactgatc ctcagtctcg acagcacccg   180
ctggcggcag ctgtgtctgg gttgcaccga gtgccgccat cccaattggc caaccagcc   240
agatgtggag cctgagtctt ggagagaagc cttcaagcag cattaccttg catccaagac   300
atggaccaag aatgccttgg acttggagtc ttccatctgc ttttctctat tccgccggag   360
gagggaacga cgtaccctga gtgttgggcc aggccgtgag tttgacagcc tgggcagtgc   420
cttggccatg ccagcctgt atgaccgaat tgtgctcttc ccaggtgtgt acgaagagca    480
aggtgaaatc atcttgaagg tgcctgtgga gattgtaggg caggggaagt tgggtga      537
```

<210> SEQ ID NO 34
<211> LENGTH: 178
<212> TYPE: PRT
<213> ORGANISM: Homo sapiens

<400> SEQUENCE: 34

```
Arg Pro Arg Pro Gly Leu Arg Gly Gly Arg Ala Pro Cys Glu Val Thr
  1               5                  10                  15

Met Glu Ala Gly Gly Leu Pro Leu Glu Leu Trp Arg Met Ile Leu Ala
             20                  25                  30

Tyr Leu His Leu Pro Asp Leu Gly Arg Cys Ser Leu Val Cys Arg Ala
         35                  40                  45

Trp Tyr Glu Leu Ile Leu Ser Leu Asp Ser Thr Arg Trp Arg Gln Leu
     50                  55                  60

Cys Leu Gly Cys Thr Glu Cys Arg His Pro Asn Trp Pro Asn Gln Pro
 65                  70                  75                  80
```

Asp Val Glu Pro Glu Ser Trp Arg Glu Ala Phe Lys Gln His Tyr Leu
              85                  90                  95

Ala Ser Lys Thr Trp Thr Lys Asn Ala Leu Asp Leu Glu Ser Ser Ile
            100                 105                 110

Cys Phe Ser Leu Phe Arg Arg Arg Glu Arg Arg Thr Leu Ser Val
            115                 120                 125

Gly Pro Gly Arg Glu Phe Asp Ser Leu Gly Ser Ala Leu Ala Met Ala
            130                 135                 140

Ser Leu Tyr Asp Arg Ile Val Leu Phe Pro Gly Val Tyr Glu Glu Gln
145                 150                 155                 160

Gly Glu Ile Ile Leu Lys Val Pro Val Glu Ile Val Gly Gln Gly Lys
                165                 170                 175

Leu Gly

<210> SEQ ID NO 35
<211> LENGTH: 751
<212> TYPE: DNA
<213> ORGANISM: Homo sapiens

<400> SEQUENCE: 35
gagaccgaga cggcgccgct gaccctagag tcgctgccca ccgatcccct gctcctcatc      60
ttatcctttt tggactatcg ggatctaatc aactgttgtt atgtcagtcg aagattaagc     120
cagctatcaa gtcatgatcc gctgtggaga agacattgca aaaaatactg ctgatatct     180
gaggaagaga aaacacagaa gaatcagtgt tggaaatctc tcttcataga tacttactct     240
gatgtaggaa gatacattga ccattatgct gctattaaaa aggcctcggg aatgatctca     300
agaaatattt ggagcccagg tgtcctcgga tgggttttat ctctgaaaga ggggtgctcg     360
agaggaagac ctcgatgctg tggaagcgca gattgggctg caagtttcct ggacgattat     420
cgatgttcat accgaattca caatggacag aagttagttg gttcctgggg ttattgggaa     480
gcatggcact gtctaatcac tatcgttctg aagatttgtt agacgtcgat acagctgccg     540
gagattccag cagagacagg gactgaaata ctgtctccct ttaacttttg catacatact     600
ggtttgagtc agtacatagc agtggaagct gcagagggtt gaaacaaaaa tgaagttttc     660
taccaatgtc agacagtaga acgtgtgttt aaatatggca ttaagatgtg ttctgatggt     720
tgtataaatg gcatgcatta ggtattttca g                                    751

<210> SEQ ID NO 36
<211> LENGTH: 247
<212> TYPE: PRT
<213> ORGANISM: Homo sapiens

<400> SEQUENCE: 36

Glu Thr Glu Thr Ala Pro Leu Thr Leu Glu Ser Leu Pro Thr Asp Pro
1               5                   10                  15

Leu Leu Leu Ile Leu Ser Phe Leu Asp Tyr Arg Asp Leu Ile Asn Cys
                20                  25                  30

Cys Tyr Val Ser Arg Arg Leu Ser Gln Leu Ser Ser His Asp Pro Leu
            35                  40                  45

Trp Arg Arg His Cys Lys Lys Tyr Trp Leu Ile Ser Glu Glu Lys
        50                  55                  60

Thr Gln Lys Asn Gln Cys Trp Lys Ser Leu Phe Ile Asp Thr Tyr Ser
65                  70                  75                  80

Asp Val Gly Arg Tyr Ile Asp His Tyr Ala Ala Ile Lys Lys Ala Ser

```
                        85                  90                  95
Gly Met Ile Ser Arg Asn Ile Trp Ser Pro Gly Val Leu Gly Trp Val
                100                 105                 110

Leu Ser Leu Lys Glu Gly Cys Ser Arg Gly Arg Pro Arg Cys Cys Gly
            115                 120                 125

Ser Ala Asp Trp Ala Ala Ser Phe Leu Asp Asp Tyr Arg Cys Ser Tyr
        130                 135                 140

Arg Ile His Asn Gly Gln Lys Leu Val Gly Ser Trp Gly Tyr Trp Glu
145                 150                 155                 160

Ala Trp His Cys Leu Ile Thr Ile Val Leu Lys Ile Cys Thr Ser Ile
                165                 170                 175

Gln Leu Pro Glu Ile Pro Ala Glu Thr Gly Thr Glu Ile Leu Ser Pro
            180                 185                 190

Phe Asn Phe Cys Ile His Thr Gly Leu Ser Gln Tyr Ile Ala Val Glu
        195                 200                 205

Ala Ala Glu Gly Asn Lys Asn Glu Val Phe Tyr Gln Cys Gln Thr Val
    210                 215                 220

Glu Arg Val Phe Lys Tyr Gly Ile Lys Met Cys Ser Asp Gly Cys Ile
225                 230                 235                 240

Asn Gly Met His Val Phe Ser
                245

<210> SEQ ID NO 37
<211> LENGTH: 368
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 37
ggctccggtt tccgggccgg cgggtggccg ctcaccatgc ccggnaagca ccagcatttc     60
caggaacctg aggtcggctg ctgcgggaaa tacttcctgt ttggcttcaa cattgtcttc    120
tgggtgctgg agccctgtt cctggctatc ggcctctggg cctggggtga agggcgtt      180 ctctcgaaca tctcagcgct gacagatctg ggaggccttg accccgtgtg gcttgtttgt    240
ggtagttgga ggcgtcatgt cggtgctggg ctttgctggg ctgcaattgg ggccctccgg    300
gagaacacct tcctgctcaa gttttctnc gngttcctcg gtctcatctt cttcctggag    360
ctggcaac                                                              368

<210> SEQ ID NO 38
<211> LENGTH: 122
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 38

Gly Ser Gly Phe Arg Ala Gly Gly Trp Pro Leu Thr Met Pro Gly Lys
1               5                   10                  15

His Gln His Phe Gln Glu Pro Glu Val Gly Cys Cys Gly Lys Tyr Phe
            20                  25                  30

Leu Phe Gly Phe Asn Ile Val Phe Trp Val Leu Gly Ala Leu Phe Leu
        35                  40                  45
```

```
Ala Ile Gly Leu Trp Ala Trp Gly Glu Lys Gly Val Leu Ser Asn Ile
        50                  55                  60

Ser Ala Leu Thr Asp Leu Gly Gly Leu Asp Pro Val Trp Leu Val Cys
 65                  70                  75                  80

Gly Ser Trp Arg Arg His Val Gly Ala Gly Leu Cys Trp Ala Ala Ile
                 85                  90                  95

Gly Ala Leu Arg Glu Asn Thr Phe Leu Leu Lys Phe Phe Xaa Xaa Phe
                100                 105                 110

Leu Gly Leu Ile Phe Phe Leu Glu Leu Ala
            115                 120
```

<210> SEQ ID NO 39
<211> LENGTH: 774
<212> TYPE: DNA
<213> ORGANISM: Homo sapiens

<400> SEQUENCE: 39

```
gcggcggccg ccgccgcgta cctggacgag ctgcccgagc cgctgctgct gcgcgtgctg    60
gccgcactgc cggccgccga gctggtgcag gcctgccgcc tggtgtgcct cgctggaag   120
gagctggtgg acggcgcccc gctgtggctg ctcaagtgcc agcaggaggg gctggtgccc   180
gagggcggcg tggaggagga cgcgaccac tggcagcagt tctacttcct gagcaagcgg   240
cgccgcaacc ttctgcgtaa cccgtgtggg gaagaggact ggaaggctg tgtgacgtg   300
gagcatggtg gggacggctg gagggtggag gagctgcctg gagacagtgg ggtggagttc   360
acccacgatg agagcgtcaa gaagtacttc gcctcctcct ttgagtggtg tcgcaaagca   420
caggtcattg acctgcaggc tgagggctac tgggaggagc tgctggacac gactcagccg   480
gccatcgtgg tgaaggactg gtactcgggc cgcagcgacg ctggttgcct ctacgagctc   540
accgttaagc tactgtccga gcacgagaac gtgctggctg agttcagcag cgggcaggtg   600
gcagtgcccc aagacagtga cggcgggggc tggatggaga tctcccacac cttcaccgac   660
tacgggccgg gcgtccgctt cgtccgcttc gagcacgggg ggcagggctc cgtctactgg   720
aagggctggt tcggggcccg ggtgaccaac agcagcgtgt gggtagaacc ctga         774
```

<210> SEQ ID NO 40
<211> LENGTH: 257
<212> TYPE: PRT
<213> ORGANISM: Homo sapiens

<400> SEQUENCE: 40

```
Ala Ala Ala Ala Ala Tyr Leu Asp Glu Leu Pro Glu Pro Leu Leu
  1               5                  10                  15

Leu Arg Val Leu Ala Ala Leu Pro Ala Ala Glu Leu Val Gln Ala Cys
                 20                  25                  30

Arg Leu Val Cys Leu Arg Trp Lys Glu Leu Val Asp Gly Ala Pro Leu
             35                  40                  45

Trp Leu Leu Lys Cys Gln Gln Glu Gly Leu Val Pro Glu Gly Gly Val
         50                  55                  60

Glu Glu Glu Arg Asp His Trp Gln Gln Phe Tyr Phe Leu Ser Lys Arg
 65                  70                  75                  80

Arg Arg Asn Leu Leu Arg Asn Pro Cys Gly Glu Glu Asp Leu Glu Gly
                 85                  90                  95

Trp Cys Asp Val Glu His Gly Gly Asp Gly Trp Arg Val Glu Glu Leu
                100                 105                 110

Pro Gly Asp Ser Gly Val Glu Phe Thr His Asp Glu Ser Val Lys Lys
```

```
                    115                 120                 125
Tyr Phe Ala Ser Ser Phe Glu Trp Cys Arg Lys Ala Gln Val Ile Asp
        130                 135                 140

Leu Gln Ala Glu Gly Tyr Trp Glu Glu Leu Leu Asp Thr Thr Gln Pro
145                 150                 155                 160

Ala Ile Val Val Lys Asp Trp Tyr Ser Gly Arg Ser Asp Ala Gly Cys
                165                 170                 175

Leu Tyr Glu Leu Thr Val Lys Leu Leu Ser Glu His Glu Asn Val Leu
            180                 185                 190

Ala Glu Phe Ser Ser Gly Gln Val Ala Val Pro Gln Asp Ser Asp Gly
        195                 200                 205

Gly Gly Trp Met Glu Ile Ser His Thr Phe Thr Asp Tyr Gly Pro Gly
210                 215                 220

Val Arg Phe Val Arg Phe Glu His Gly Gly Gln Gly Ser Val Tyr Trp
225                 230                 235                 240

Lys Gly Trp Phe Gly Ala Arg Val Thr Asn Ser Ser Val Trp Val Glu
                245                 250                 255

Pro

<210> SEQ ID NO 41
<211> LENGTH: 957
<212> TYPE: DNA
<213> ORGANISM: Homo sapiens

<400> SEQUENCE: 41
atgggcgaga aggcggtccc tttgctaagg aggaggcggg tgaagagaag ctgcccttct     60
tgtggctcgg agcttggggt tgaagagaag aggggaaag gaaatccgat ttccatccag    120
ttgttccccc cagagctggt ggagcatatc atctcattcc tcccagtcag agaccttgtt    180
gccctcggcc agacctgccg ctacttccac gaagtgtgcg atggggaagg cgtgtggaga    240
cgcatctgtc gcagactcag tccgcgcctc caagatcagg acacgaaggg cctgtatttc    300
caggcatttg gaggccgccg ccgatgtctc agcaagagcg tggcccccct gctagcccac    360
ggctaccgcc gcttcttgcc caccaaggat cacgtcttca ttcttgacta cgtggggacc    420
ctcttcttcc tcaaaaatgc cctggtctcc accctcggcc agatgcagtg gaagcgggcc    480
tgtcgctatg ttgtgttgtg tcgtggagcc aaggattttg cctcggaccc aaggtgtgac    540
acagtttacc gtaaatacct ctacgtcttg gccactcggg agccgcagga agtggtgggt    600
accaccagca gccgggcctg tgactgtgtt gaggtctatc tgcagtctag tgggcagcgg    660
gtcttcaaga tgacattcca ccactcaatg accttcaagc agatcgtgct ggttggtcag    720
gagacccagc gggctctact gctcctcaca gaggaaggaa agatctactc tttggtagtg    780
aatgagaccc agcttgacca gccacgctcc tacacggttc agctggccct gaggaaggtg    840
tcccactacc tgcctcacct gcgcgtggcc tgcatgactt ccaaccagag cagcaccctc    900
tacgtcacag atcctattct gtgctcttgg ctacaaccac cttggcctgg tggatga      957

<210> SEQ ID NO 42
<211> LENGTH: 318
<212> TYPE: PRT
<213> ORGANISM: Homo sapiens

<400> SEQUENCE: 42

Met Gly Glu Lys Ala Val Pro Leu Leu Arg Arg Arg Val Lys Arg
  1               5                  10                  15
```

```
Ser Cys Pro Ser Cys Gly Ser Glu Leu Gly Val Glu Glu Lys Arg Gly
             20                  25                  30

Lys Gly Asn Pro Ile Ser Ile Gln Leu Phe Pro Glu Leu Val Glu
         35                  40                  45

His Ile Ile Ser Phe Leu Pro Val Arg Asp Leu Val Ala Leu Gly Gln
     50                  55                  60

Thr Cys Arg Tyr Phe His Glu Val Cys Asp Gly Glu Gly Val Trp Arg
 65                  70                  75                  80

Arg Ile Cys Arg Arg Leu Ser Pro Arg Leu Gln Asp Gln Asp Thr Lys
                 85                  90                  95

Gly Leu Tyr Phe Gln Ala Phe Gly Arg Arg Arg Cys Leu Ser Lys
             100                 105                 110

Ser Val Ala Pro Leu Leu Ala His Gly Tyr Arg Arg Phe Leu Pro Thr
             115                 120                 125

Lys Asp His Val Phe Ile Leu Asp Tyr Val Gly Thr Leu Phe Phe Leu
         130                 135                 140

Lys Asn Ala Leu Val Ser Thr Leu Gly Gln Met Gln Trp Lys Arg Ala
145                 150                 155                 160

Cys Arg Tyr Val Val Leu Cys Arg Gly Ala Lys Asp Phe Ala Ser Asp
                 165                 170                 175

Pro Arg Cys Asp Thr Val Tyr Arg Lys Tyr Leu Tyr Val Leu Ala Thr
             180                 185                 190

Arg Glu Pro Gln Glu Val Gly Thr Thr Ser Ser Arg Ala Cys Asp
         195                 200                 205

Cys Val Glu Val Tyr Leu Gln Ser Ser Gly Gln Arg Val Phe Lys Met
     210                 215                 220

Thr Phe His His Ser Met Thr Phe Lys Gln Ile Val Leu Val Gly Gln
225                 230                 235                 240

Glu Thr Gln Arg Ala Leu Leu Leu Leu Thr Glu Glu Gly Lys Ile Tyr
                 245                 250                 255

Ser Leu Val Val Asn Glu Thr Gln Leu Asp Gln Pro Arg Ser Tyr Thr
             260                 265                 270

Val Gln Leu Ala Leu Arg Lys Val Ser His Tyr Leu Pro His Leu Arg
         275                 280                 285

Val Ala Cys Met Thr Ser Asn Gln Ser Ser Thr Leu Tyr Val Thr Asp
     290                 295                 300

Pro Ile Leu Cys Ser Trp Leu Gln Pro Pro Trp Pro Gly Gly
305                 310                 315

<210> SEQ ID NO 43
<211> LENGTH: 1590
<212> TYPE: DNA
<213> ORGANISM: Homo sapiens

<400> SEQUENCE: 43
cgagggggaa gcgaaggaag gggaagagga agggaaaagc gagcgagagg ggcaaggcgg     60
aagaggaagc agggcggaag ggaagcccgg gccgcagacg gcgaaggagg cagcgggccg    120
ggggctgagg cgggagcgag gacacgccca agagaggaag cagagggagg cggaagcgtg    180
gaggaagggg cgagaggcat catcaaagga gatgagggga gcgtagggc cgggaaagag    240 gcacaaggaa gaaagtatgg gaaggaggaa tggagggtca gggctaggcg gcgggagggc    300
gccaggccgg gaagagtaca aggacaagga ggtcaggttt gggcctacat cccggggaca    360
ggggcggcca tggcggcggc agccaggag gaggaggagg aggcggctcg ggagtcagcc    420
```

-continued

```
gcctgcccgg ctgcggggcc agcgctctgg cgcctgccgg aagtgctgct gctgcacatg      480
tgctcctacc tcgacatgcg ggccctcggc cgcctggccc aggtgtaccg ctggctgtgg      540
cacttcacca actgcgacct gctccggcgc cagatagcct gggcctcgct caactccggc      600
ttcacgcggc tcggcaccaa cctgatgacc agtgtcccag tgaaggtgtc tcagaactgg      660
atagtggggt gctgccgaga ggggattctg ctgaagtgga gatgcagtca gatgccctgg      720
atgcagctag aggatgatgc tttgtacata tcccaggcta atttcatcct ggcctaccag      780
ttccgtccag atggtgccag cttgaaccgt cagcctctgg gagtctctgc tgggcatgat      840
gaggacgttt gccactttgt gctggccacc tcgcatattg tcagtgcagg aggagatggg      900
aagattggcc ttggtaagat tcacagcacc ttcgctgcca agtactgggc tcatgaacag      960
gaggtgaact gtgtggattg caaaggggc atcatatcat ttggctccag ggacaggacg     1020
gccaaggtgt ggcctttggc ctcaggccag ctggggcagt gtttatacac catccagact     1080
gaagaccaaa tctggtctgt tgctatcagg ccattactca gctcttttgt gacagggacg     1140
gcttgttgtg ggcacttctc acccctgaaa atctgggacc tcaacagtgg gcagctgatg     1200
acacacttgg acagagactt tcccccaagg gctggggtgc tggatgtcat atatgagtcc     1260
cctttcgcac tgctctcctg tggctatgac acctatgttc gctactggga ctgccgcacc     1320
agtgtccgga aatgtgtcat ggagtgggag gagccccaca acagcaccct gtactgcctg     1380
cagacagatg caaccactt gcttgccaca ggttcctcct tctatagcgt tgtacggctg     1440
tgggaccgga accaaagggc ctgcccgcac accttcccgc tgacgtcgac ccgcctcggc     1500
agccctgtgt actgcctgca tctcaccacc aagcatctct atgctgcgct gtcttacaac     1560
ctccacgtcc tggatattca aaacccgtga                                      1590
```

<210> SEQ ID NO 44
<211> LENGTH: 529
<212> TYPE: PRT
<213> ORGANISM: Homo sapiens

<400> SEQUENCE: 44

```
Arg Gly Gly Ser Glu Gly Arg Gly Arg Gly Arg Glu Lys Arg Ala Arg
  1               5                  10                  15

Gly Ala Arg Arg Lys Arg Lys Gln Gly Gly Arg Glu Ala Arg Ala Ala
             20                  25                  30

Asp Gly Glu Gly Gly Ser Gly Pro Gly Ala Glu Ala Gly Ala Arg Thr
         35                  40                  45

Arg Pro Arg Glu Glu Ala Glu Gly Gly Ser Val Glu Glu Gly Ala
     50                  55                  60

Arg Gly Ile Ile Lys Gly Asp Glu Gly Ser Val Gly Ala Gly Lys Glu
 65                  70                  75                  80

Ala Gln Gly Arg Lys Tyr Gly Lys Glu Glu Trp Arg Val Arg Ala Arg
                 85                  90                  95

Arg Arg Glu Gly Ala Arg Pro Gly Arg Val Gln Gly Gln Gly Gly Gln
            100                 105                 110

Val Trp Ala Tyr Ile Pro Gly Thr Gly Ala Ala Met Ala Ala Ala Ala
        115                 120                 125

Arg Glu Glu Glu Glu Ala Ala Arg Glu Ser Ala Ala Cys Pro Ala
    130                 135                 140

Ala Gly Pro Ala Leu Trp Arg Leu Pro Glu Val Leu Leu His Met
145                 150                 155                 160

Cys Ser Tyr Leu Asp Met Arg Ala Leu Gly Arg Leu Ala Gln Val Tyr
```

```
                       165                 170                 175
Arg Trp Leu Trp His Phe Thr Asn Cys Asp Leu Leu Arg Arg Gln Ile
            180                 185                 190
Ala Trp Ala Ser Leu Asn Ser Gly Phe Thr Arg Leu Gly Thr Asn Leu
        195                 200                 205
Met Thr Ser Val Pro Val Lys Val Ser Gln Asn Trp Ile Val Gly Cys
    210                 215                 220
Cys Arg Glu Gly Ile Leu Leu Lys Trp Arg Cys Ser Gln Met Pro Trp
225                 230                 235                 240
Met Gln Leu Glu Asp Asp Ala Leu Tyr Ile Ser Gln Ala Asn Phe Ile
                245                 250                 255
Leu Ala Tyr Gln Phe Arg Pro Asp Gly Ala Ser Leu Asn Arg Gln Pro
            260                 265                 270
Leu Gly Val Ser Ala Gly His Asp Glu Asp Val Cys His Phe Val Leu
        275                 280                 285
Ala Thr Ser His Ile Val Ser Ala Gly Gly Asp Gly Lys Ile Gly Leu
    290                 295                 300
Gly Lys Ile His Ser Thr Phe Ala Ala Lys Tyr Trp Ala His Glu Gln
305                 310                 315                 320
Glu Val Asn Cys Val Asp Cys Lys Gly Gly Ile Ile Ser Phe Gly Ser
                325                 330                 335
Arg Asp Arg Thr Ala Lys Val Trp Pro Leu Ala Ser Gly Gln Leu Gly
            340                 345                 350
Gln Cys Leu Tyr Thr Ile Gln Thr Glu Asp Gln Ile Trp Ser Val Ala
        355                 360                 365
Ile Arg Pro Leu Leu Ser Ser Phe Val Thr Gly Thr Ala Cys Cys Gly
    370                 375                 380
His Phe Ser Pro Leu Lys Ile Trp Asp Leu Asn Ser Gly Gln Leu Met
385                 390                 395                 400
Thr His Leu Asp Arg Asp Phe Pro Pro Arg Ala Gly Val Leu Asp Val
                405                 410                 415
Ile Tyr Glu Ser Pro Phe Ala Leu Leu Ser Cys Gly Tyr Asp Thr Tyr
            420                 425                 430
Val Arg Tyr Trp Asp Cys Arg Thr Ser Val Arg Lys Cys Val Met Glu
        435                 440                 445
Trp Glu Glu Pro His Asn Ser Thr Leu Tyr Cys Leu Gln Thr Asp Gly
    450                 455                 460
Asn His Leu Leu Ala Thr Gly Ser Ser Phe Tyr Ser Val Val Arg Leu
465                 470                 475                 480
Trp Asp Arg His Gln Arg Ala Cys Pro His Thr Phe Pro Leu Thr Ser
                485                 490                 495
Thr Arg Leu Gly Ser Pro Val Tyr Cys Leu His Leu Thr Thr Lys His
            500                 505                 510
Leu Tyr Ala Ala Leu Ser Tyr Asn Leu His Val Leu Asp Ile Gln Asn
        515                 520                 525
Pro
```

<210> SEQ ID NO 45
<211> LENGTH: 1214
<212> TYPE: DNA
<213> ORGANISM: Homo sapiens

<400> SEQUENCE: 45
gcattgctat aattttacta tactctcatc taaatctaaa atcagtcttc aaaataaaaa    60

```
caaattgtcc tttgccaaaa attttttaa tcgcacaatt aattgacatt aactgccaat     120
tcttttggc taattgacta attttaactt ctgtgttgct tttccagagg catggctatt     180
gcaccttggg agaagccttt aatcggttag acttctcaag tgcaattcaa gatatccgaa    240
cgttcaatta tgtggtcaaa ctgttgcagc taattgcaaa atcccagtta acttcattga    300
gtggcgtggc acagaagaat tacttcaaca ttttggataa aatcgttcaa aaggttcttg    360
atgaccacca caatcctcgc ttaatcaaag atcttctgca agacctaagc tctaccctct    420
gcattcttat tagaggagta gggaagtctg tattagtggg aaacatcaat atttggattt    480
gccgattaga aactattctc gcctggcaac aacagctaca ggatcttcag atgactaagc    540
aagtgaacaa tggcctcacc ctcagtgacc ttcctctgca catgctgaac aacatcctat    600
accggttctc agacggatgg gacatcatca ccttaggcca ggtgaccccc acgttgtata    660
tgcttagtga agacagacag ctgtggaaga agctttgtca gtaccatttt gctgaaaagc    720
agttttgtag acatttgatc ctttcagaaa aaggtcatat tgaatggaag ttgatgtact    780
ttgcacttca gaaacattac ccagcgaagg agcagtacgg agacacactg catttctgtc    840
ggcactgcag cattctcttt tggaaggact caggacaccc ctgcacggcg ccgacccctg    900
acagctgctt cacgcctgtg tctccgcagc acttcatcga cctcttcaag ttttaagggc    960
tgcccctgcc atccctattg agattgtgaa atcctgctgt ctgtgcaggg ctcatagtga   1020
gtgttctgtg aggtgggtgg agactcctcg gaagcccctg cttccagaaa gcctgggaag   1080
aactgcccct ctgcaaaggg gggactgcat ggttgcattt tcatcactga aagtcagagg   1140
ccaaggaaat catttctact tctttaaaaa ctccttctaa gcatattaaa atgtgaaatt   1200
ttgcgtactc tctc                                                     1214
```

<210> SEQ ID NO 46
<211> LENGTH: 272
<212> TYPE: PRT
<213> ORGANISM: Homo sapiens

<400> SEQUENCE: 46

```
Leu Ile Leu Thr Ser Val Leu Leu Phe Gln Arg His Gly Tyr Cys Thr
  1               5                  10                  15

Leu Gly Glu Ala Phe Asn Arg Leu Asp Phe Ser Ser Ala Ile Gln Asp
             20                  25                  30

Ile Arg Thr Phe Asn Tyr Val Val Lys Leu Leu Gln Leu Ile Ala Lys
         35                  40                  45

Ser Gln Leu Thr Ser Leu Ser Gly Val Ala Gln Lys Asn Tyr Phe Asn
     50                  55                  60

Ile Leu Asp Lys Ile Val Gln Lys Val Leu Asp Asp His His Asn Pro
 65                  70                  75                  80

Arg Leu Ile Lys Asp Leu Leu Gln Asp Leu Ser Ser Thr Leu Cys Ile
                 85                  90                  95

Leu Ile Arg Gly Val Gly Lys Ser Val Leu Val Gly Asn Ile Asn Ile
            100                 105                 110

Trp Ile Cys Arg Leu Glu Thr Ile Leu Ala Trp Gln Gln Gln Leu Gln
        115                 120                 125

Asp Leu Gln Met Thr Lys Gln Val Asn Asn Gly Leu Thr Leu Ser Asp
    130                 135                 140

Leu Pro Leu His Met Leu Asn Asn Ile Leu Tyr Arg Phe Ser Asp Gly
145                 150                 155                 160
```

```
Trp Asp Ile Ile Thr Leu Gly Gln Val Thr Pro Thr Leu Tyr Met Leu
                165                 170                 175

Ser Glu Asp Arg Gln Leu Trp Lys Lys Leu Cys Gln Tyr His Phe Ala
            180                 185                 190

Glu Lys Gln Phe Cys Arg His Leu Ile Leu Ser Glu Lys Gly His Ile
        195                 200                 205

Glu Trp Lys Leu Met Tyr Phe Ala Leu Gln Lys His Tyr Pro Ala Lys
    210                 215                 220

Glu Gln Tyr Gly Asp Thr Leu His Phe Cys Arg His Cys Ser Ile Leu
225                 230                 235                 240

Phe Trp Lys Asp Ser Gly His Pro Cys Thr Ala Ala Asp Pro Asp Ser
                245                 250                 255

Cys Phe Thr Pro Val Ser Pro Gln His Phe Ile Asp Leu Phe Lys Phe
            260                 265                 270
```

<210> SEQ ID NO 47
<211> LENGTH: 4059
<212> TYPE: DNA
<213> ORGANISM: Homo sapiens

<400> SEQUENCE: 47

| | |
|---|---|
| agtacggcag tgagggcaaa ggcagctcga gcatctcatc tgacgtgagt tcaagtacag | 60 |
| atcacacgcc cactaaagcc cagaagaatg tggctaccag cgaagactcc gacctgagca | 120 |
| tgcgcacact gagcacgccc agcccagccc tgatatgtcc accgaatctc ccaggatttc | 180 |
| agaatggaag gggctcgtcc acctcctcgt cctccatcac cggggagacg gtggccatgg | 240 |
| tgcactcccc gccccgacc cgcctcacac acccgctcat ccggctcgcc tccagacccc | 300 |
| agaaggagca ggccagcata gaccggctcc cggaccactc catggtgcag atcttctcct | 360 |
| tcctgcccac caaccagctg tgccgctgcg cgcgagtgtg ccgccgctgg tacaacctgg | 420 |
| cctgggaccc gcggctctgg aggactatcc gcctgacggg cgagaccatc aacgtggacc | 480 |
| gcgccctcaa ggtgctgacc cgcagactct gccaggacac ccccaacgtg tgtctcatgc | 540 |
| tggaaaccgt aactgtcagt ggctgcaggc ggctcacaga ccgagggctg tacaccatcg | 600 |
| cccagtgctg ccccgaactg aggcgactgg aagtctcagg ctgttacaat atctccaacg | 660 |
| aggccgtctt tgatgtggtg tccctctgcc ctaatctgga gcacctggat gtgtcaggat | 720 |
| gctccaaagt gacctgcatc agcttgaccc gggaggcctc cattaaactg tcacccttgc | 780 |
| atggcaaaca gatttccatc cgctacctgg acatgacgga ctgcttcgtg ctggaggacg | 840 |
| aaggcctgca caccatcgcg gcgcactgca cgcagctcac ccacctctac ctgcgccgct | 900 |
| gcgtccgcct gaccgacgaa ggcctgcgct acctggtgat ctactgcgcc tccatcaagg | 960 |
| agctgagcgt cagcgactgc cgcttcgtca gcgacttcgg cctgcgggag atcgccaagc | 1020 |
| tggagtcccg cctgcggtac ctgagcatcg cgcactgcgg ccgggtcacc gacgtgggca | 1080 |
| tccgctacgt ggccaagtac tgcagcaagc tgcgctacct caacgcgagg ggctgcgagg | 1140 |
| gcatcacgga ccacggtgtg gagtacctcg ccaagaactg caccaaactc aaatccctgg | 1200 |
| atatcggcaa atgcccttg gtatccgaca cgggcctgga gtgcctggcc ctgaactgct | 1260 |
| tcaacctcaa gcggctcagc ctcaagtcct gcgagagcat caccggccag ggcttgcaga | 1320 |
| tcgtggccgc caactgcttt gacctccaga cgctgaatgt ccaggactgc gaggtctccg | 1380 |
| tggaggccct gcgctttgtc aaacgccact gcaagcgctg cgtcatcgag cacaccaacc | 1440 |
| cggctttctt ctgaagggac agagttcatc cggcgttgta ttcacacaaa cctgaacaaa | 1500 |

-continued

```
gcaaattttt ttaaaagcag cgtatgtaag caccgacacc cactcaaaac agctctttct    1560
tccgggaagg ttattaggaa tctggccttt attttcctc atttctcatg ggcaacagag    1620
gccaaagaaa cgaagcaaga caaacagcaa acaggcattt tggtcaggtc atttgtaggc    1680
agtttctctt ctcacaaaag atgtacttaa gcaggctgat cgctgttcct tgagcaaggc    1740
gcttactctc ctccgctcag gcccccaagg ccgccctttc cctcgcacac aggcccacc    1800 cccacagttc cacgccccc ccccaaggcc acccctccc tccctagagc agcagcgagg    1860
atccatcatc agaatcacag tgctctccag acctcctctc taaactgctt cattgaccta    1920
agtcactctc ttcaatccca cacccatgga cattcttgtc aactcaatac catagcactt    1980
tgcataggca aaatactttt caggccttt taaaaaattc attacagcaa acagctgggg    2040
aaggacatgc agtcctcccc cagctctgtc aatgactatg accttggcca agcacttca    2100 ctgctctggg ctgcagcttc cagcactgaa tcagaggcca cacagcccaa agattagctt    2160
catgtccatt atagcattga gggagcagag atacccatac acagaagcac cttggcatag    2220
agcacccagg catcgacctc ttccaggaga actgattctg tggatggatg tgatttcagg    2280
agattgtgca gtgccagcat cagtgcataa agggtcctgt atgtcctttg gctgcaaatc    2340
acccacttcc ctgtgtttca gtgggagaat ttcctctccc acctcctcac atcctctttt    2400
gccaggctgg atgctgtcgt ctctgtacac aaatactttc tgcattcccc cctccacacc    2460
atcctagcga ggcaccagca cacctaatca cagcaaagcc cagatccccc catcagttgc    2520
ttttactcag tgttttcaaa taggagtaaa ggcccttgca attttaatt aacaagcaag    2580 gcccaaggga acacatgtcc tcaaaagttt ttctgatccc tcgccttgca cacctggcat    2640
gcatcaggca catctgtcct acagctgcca gagacagatg cctcggttct ttgtcattca    2700
gattgcattt gacctcttct catctattta tttctttata catccagact tcatcacatg    2760
aagcctattg gggttaagtt tgtaagtgtt taattgtgca aattgccacc ctgtgtacct    2820
cctccatgtc tgtctgcgtg ttttccacca aagaatgcaa agcagacttc caggtgttta    2880
aattctgttc actcaacaat gccagatgaa tggaagaggg aacacactga gatgacttag    2940
actctggtcc accaaccaga cccttggaaa ggaatactaa aatcattaca aggtatggat    3000
tttaaatgga tgaaacttca aattatctta tttggataga agtctatatt ctagcctcat    3060
ttgcatgaag tcagatagcc agaagaaatt ccattgctgg ttttcacgaa attcacttgt    3120
cttttgctaa taaacacatg gcccttcc agattattct ctagccaagc ccaccctttg    3180
ttacgttgaa atccctcatt tatttcttc tcaaaatgcc cattatccaa atgcagaacc    3240
tctgcatctc caagccagtt atgctgaatt tgtcaaactt agacacccct tgacaactgca    3300 ctcctactgt aggctcctgt gcatactgtc gtcttctgtg ggggatggag aggttagtgt    3360
gatgaggtgg tgtctgccca ggaggtttct ttcaaacatc atggcctccc atccaatcaa    3420
catcatcaaa ttacatgtgt aatcaaggct ctgtgccatg ggggaaatga atcatttagc    3480
taggccagga tctagtgaaa gccacagagt ttaaaaccat gaaagaagtt gaaggcagca    3540
ttcctcagct ctgtgacttg tgaccctatt tgaagtttca ggatttgggt gtcacaaagg    3600 attgtccta atccttggcc ctgggtctt ccgagtgagc tggtttaata ctctgagaat    3660
gagcagggag atcagagaa tgaatccctg accgcatcac ctaaactgtc ttccaaacat    3720
gagacaaagc tgactgttca cactgattgc ccagcacata ccgtcttgcc agtttcttct    3780
tttctcccag tctcctgttc atccattctg ttctcccttg gggtgggaat ctatgatgga    3840
ggttactggg gaaacagctc agcagatttt tggagaccaa accaaaggtc tcactaggaa    3900
```

```
atttatctgt tttaaaacat tgcttccttc ctggctctgc taaattgaat gctcattgtt   3960
tgttgttgtt gttttttaat tctaatgttc aaatcactgc gtgctgtatg aatctagaaa   4020
gccttaattt actaccaaga aataaagcaa tatgttcgt                           4059
```

<210> SEQ ID NO 48
<211> LENGTH: 483
<212> TYPE: PRT
<213> ORGANISM: Homo sapiens

<400> SEQUENCE: 48

```
Tyr Gly Ser Glu Gly Lys Gly Ser Ser Ile Ser Ser Asp Val Ser
 1               5                  10                  15

Ser Ser Thr Asp His Thr Pro Thr Lys Ala Gln Lys Asn Val Ala Thr
                20                  25                  30

Ser Glu Asp Ser Asp Leu Ser Met Arg Thr Leu Ser Thr Pro Ser Pro
            35                  40                  45

Ala Leu Ile Cys Pro Pro Asn Leu Pro Gly Phe Gln Asn Gly Arg Gly
        50                  55                  60

Ser Ser Thr Ser Ser Ser Ile Thr Gly Glu Thr Val Ala Met Val
65                  70                  75                  80

His Ser Pro Pro Thr Arg Leu Thr His Pro Leu Ile Arg Leu Ala
                85                  90                  95

Ser Arg Pro Gln Lys Glu Gln Ala Ser Ile Asp Arg Leu Pro Asp His
            100                 105                 110

Ser Met Val Gln Ile Phe Ser Phe Leu Pro Thr Asn Gln Leu Cys Arg
        115                 120                 125

Cys Ala Arg Val Cys Arg Arg Trp Tyr Asn Leu Ala Trp Asp Pro Arg
    130                 135                 140

Leu Trp Arg Thr Ile Arg Leu Thr Gly Glu Thr Ile Asn Val Asp Arg
145                 150                 155                 160

Ala Leu Lys Val Leu Thr Arg Arg Leu Cys Gln Asp Thr Pro Asn Val
                165                 170                 175

Cys Leu Met Leu Glu Thr Val Thr Val Ser Gly Cys Arg Arg Leu Thr
            180                 185                 190

Asp Arg Gly Leu Tyr Thr Ile Ala Gln Cys Cys Pro Glu Leu Arg Arg
        195                 200                 205

Leu Glu Val Ser Gly Cys Tyr Asn Ile Ser Asn Glu Ala Val Phe Asp
    210                 215                 220

Val Val Ser Leu Cys Pro Asn Leu Glu His Leu Asp Val Ser Gly Cys
225                 230                 235                 240

Ser Lys Val Thr Cys Ile Ser Leu Thr Arg Glu Ala Ser Ile Lys Leu
                245                 250                 255

Ser Pro Leu His Gly Lys Gln Ile Ser Ile Arg Tyr Leu Asp Met Thr
            260                 265                 270

Asp Cys Phe Val Leu Glu Asp Glu Gly Leu His Thr Ile Ala Ala His
        275                 280                 285

Cys Thr Gln Leu Thr His Leu Tyr Leu Arg Arg Cys Val Arg Leu Thr
    290                 295                 300

Asp Glu Gly Leu Arg Tyr Leu Val Ile Tyr Cys Ala Ser Ile Lys Glu
305                 310                 315                 320

Leu Ser Val Ser Asp Cys Arg Phe Val Ser Asp Phe Gly Leu Arg Glu
                325                 330                 335

Ile Ala Lys Leu Glu Ser Arg Leu Arg Tyr Leu Ser Ile Ala His Cys
```

```
                        340             345                 350
Gly Arg Val Thr Asp Val Gly Ile Arg Tyr Val Ala Lys Tyr Cys Ser
                355                 360                 365
Lys Leu Arg Tyr Leu Asn Ala Arg Gly Cys Glu Gly Ile Thr Asp His
        370                 375                 380
Gly Val Glu Tyr Leu Ala Lys Asn Cys Thr Lys Leu Lys Ser Leu Asp
385                 390                 395                 400
Ile Gly Lys Cys Pro Leu Val Ser Asp Thr Gly Leu Glu Cys Leu Ala
                405                 410                 415
Leu Asn Cys Phe Asn Leu Lys Arg Leu Ser Leu Lys Ser Cys Glu Ser
                420                 425                 430
Ile Thr Gly Gln Gly Leu Gln Ile Val Ala Ala Asn Cys Phe Asp Leu
            435                 440                 445
Gln Thr Leu Asn Val Gln Asp Cys Glu Val Ser Val Glu Ala Leu Arg
        450                 455                 460
Phe Val Lys Arg His Cys Lys Arg Cys Val Ile Glu His Thr Asn Pro
465                 470                 475                 480
Ala Phe Phe

<210> SEQ ID NO 49
<211> LENGTH: 850
<212> TYPE: DNA
<213> ORGANISM: Homo sapiens

<400> SEQUENCE: 49
tgcggccgcg cccgcacccg caccggcacc cacgcccacg cccgaggaag ggcccgacgc      60
gggctgggga gaccgcattc ccttggaaat cctggtgcag attttcgggt tgttggtggc     120
ggcggacggc cccatgccct tcctgggcag ggctgcgcgc gtgtgccgcc gctggcagga     180
ggccgcttcc caacccgcgc tctggcacac cgtgaccctg tcgtcccgc tggtcggccg      240
gcctgccaag ggcggggtca aggcggagaa gaagctcctt gcttccctgg agtggcttat     300
gcccaatcgg ttttcacagc tccagaggct gaccctcatc cactggaagt ctcaggtaca     360
ccccgtgttg aagctggtag gtgagtgctg tcctcggctc actttcctca agctctccgg     420
ctgccacggt gtgactgctg acgctctggt catgctagcc aaagcctgct gccagctcca     480
tagcctggac ctacagcact ccatggtgga gtccacagct gtggtgagct tcttggagga     540
ggcagggtcc cgaatgcgca agttgtggct gacctacagc tcccagacga cagccatcct     600
gggcgcattg ctgggcagct gctgccccca gctccaggtc ctggaggtga gcaccggcat     660
caaccgtaat agcattcccc ttcagctgcc tgtcgaggct ctgcagaaag gctgccctca     720
gctccaggtg ctgcggctgt tgaacctgat gtggctgccc aagcctccgg gacgaggggt     780
ggctcccgga ccaggcttcc ctagcctaga ggagctctgc ctggcgagct caacctgcaa     840
ctttgtgagc                                                           850

<210> SEQ ID NO 50
<211> LENGTH: 283
<212> TYPE: PRT
<213> ORGANISM: Homo sapiens

<400> SEQUENCE: 50

Ala Ala Ala Pro Ala Pro Ala Pro Ala Pro Thr Pro Thr Pro Glu Glu
1               5                   10                  15
Gly Pro Asp Ala Gly Trp Gly Asp Arg Ile Pro Leu Glu Ile Leu Val
                20                  25                  30
```

```
Gln Ile Phe Gly Leu Leu Val Ala Ala Asp Gly Pro Met Pro Phe Leu
         35                  40                  45
Gly Arg Ala Ala Arg Val Cys Arg Arg Trp Gln Glu Ala Ala Ser Gln
 50                  55                  60
Pro Ala Leu Trp His Thr Val Thr Leu Ser Ser Pro Leu Val Gly Arg
 65                  70                  75                  80
Pro Ala Lys Gly Gly Val Lys Ala Glu Lys Lys Leu Leu Ala Ser Leu
                 85                  90                  95
Glu Trp Leu Met Pro Asn Arg Phe Ser Gln Leu Gln Arg Leu Thr Leu
             100                 105                 110
Ile His Trp Lys Ser Gln Val His Pro Val Leu Lys Leu Val Gly Glu
             115                 120                 125
Cys Cys Pro Arg Leu Thr Phe Leu Lys Leu Ser Gly Cys His Gly Val
        130                 135                 140
Thr Ala Asp Ala Leu Val Met Leu Ala Lys Ala Cys Cys Gln Leu His
145                 150                 155                 160
Ser Leu Asp Leu Gln His Ser Met Val Glu Ser Thr Ala Val Val Ser
                 165                 170                 175
Phe Leu Glu Glu Ala Gly Ser Arg Met Arg Lys Leu Trp Leu Thr Tyr
             180                 185                 190
Ser Ser Gln Thr Thr Ala Ile Leu Gly Ala Leu Leu Gly Ser Cys Cys
             195                 200                 205
Pro Gln Leu Gln Val Leu Glu Val Ser Thr Gly Ile Asn Arg Asn Ser
        210                 215                 220
Ile Pro Leu Gln Leu Pro Val Glu Ala Leu Gln Lys Gly Cys Pro Gln
225                 230                 235                 240
Leu Gln Val Leu Arg Leu Leu Asn Leu Met Trp Leu Pro Lys Pro Pro
                 245                 250                 255
Gly Arg Gly Val Ala Pro Gly Pro Gly Phe Pro Ser Leu Glu Glu Leu
             260                 265                 270
Cys Leu Ala Ser Ser Thr Cys Asn Phe Val Ser
             275                 280
```

<210> SEQ ID NO 51
<211> LENGTH: 1777
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 51

```
acaacactgc tctcagaagg atactgcaga actccttaga ggtcttagcc tatggaatca    60
tgctgaagag cgacagaart tttttaaata ttccgtggat gaaagtcag ataaagaagc    120
agaagtgtca gaacactcca caggtataac ccatcttcct cctgaggtaa tgctgtcaat    180
tttcagctat cttaatcctc aagagttatg tcgatgcagt caagtaagca tgaaatggtc    240
tcagctgaca aaaacgggat cgctttggaa acatctttac cctgttcatt gggccagagg    300
tgactggtat agtggtcccg caactgaact tgatactgaa cctgatgatg aatgggtgaa    360
aaataggaaa gatgaaagtc gtgcttttca tgagtgggat gaagatgctg acattgatga    420
atctgaagag tctgcggagg aatcaattgc tatcagcatt gcacaaatgg aaaaacgttt    480
actccatggc ttaattcata cgttctacc atatgttggt acttctgtaa aaaccttagt    540
```

```
attagcatac agctctgcag tttccagcaa aatggttagg cagattttag agctttgtcc      600
taacctggag catctggatc ttacccagac tgacatttca gattctgcat tgacagttg      660 gtcttggctt ggttgctgcc agagtcttcg gcatcttgat ctgtctggtt gtgagaaaat      720
cacagatgtg gccctagaga agatttccag agctcttgga attctgacat ctcatcaaag      780
tggctttttg aaaacatcta caagcaaaat tacttcaact gcgtggaaaa ataaagacat      840
taccatgcag tccaccaagc agtatgcctg tttgcacgat ttaactaaca agggcattgg      900
agaagaaata gataatgaac acccctggac taagcctgtt tcttctgaga atttcacttc      960
tccttatgtg tggatgttag atgctgaaga tttggctgat attgaagata ctgtggaatg     1020
gagacataga aatgttgaaa gtctttgtgt aatggaaaca gcatccaact ttagttgttc     1080
cacctctggt tgttttagta aggacattgt tggactaagg actagtgtct gttggcagca     1140
gcattgtgct ctccagcct ttgcgtattg tggtcactca ttttgttgta caggaacagc      1200
tttaagaact atgtcatcac tcccagaatc ttctgcaatg tgtagaaaag cagcaaggac     1260
tagattgcct aggggaaaag acttaattta ctttgggagt gaaaaatctg atcaagagac     1320
tggacgtgta cttctgtttc tcagtttatc tggatgttat cagatcacag accatggtct     1380
cagggttttg actctgggag gagggctgcc ttatttggag caccttaatc tctctggttg     1440
tcttactata actggtgcag gcctgcagga tttggtttca gcatgtcctt ctctgaatga     1500
tgaatacttt tactactgtg acaacattaa cggtcctcat gctgataccg ccagtggatg     1560
ccagaatttg cagtgtggtt ttcgagcctg ctgccgctct ggcgaatgac ccttgacttc     1620
tgatctttgt ctacttcatt tagctgagca ggctttcttt catgcacttt actcatagca     1680
catttcttgt gttaaccatc ccttttgag cgtgacttgt tttgggccca ttnyttacaa      1740
cttcagaaat cttaattacc agtgrattgt aatgttg                              1777
```

<210> SEQ ID NO 52
<211> LENGTH: 590
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 52

```
Gln His Cys Ser Gln Lys Asp Thr Ala Glu Leu Leu Arg Gly Leu Ser
  1               5                  10                  15

Leu Trp Asn His Ala Glu Glu Arg Gln Lys Phe Phe Lys Tyr Ser Val
             20                  25                  30

Asp Glu Lys Ser Asp Lys Glu Ala Glu Val Ser Glu His Ser Thr Gly
         35                  40                  45

Ile Thr His Leu Pro Pro Glu Val Met Leu Ser Ile Phe Ser Tyr Leu
     50                  55                  60

Asn Pro Gln Glu Leu Cys Arg Cys Ser Gln Val Ser Met Lys Trp Ser
 65                  70                  75                  80

Gln Leu Thr Lys Thr Gly Ser Leu Trp Lys His Leu Tyr Pro Val His
                 85                  90                  95

Trp Ala Arg Gly Asp Trp Tyr Ser Gly Pro Ala Thr Glu Leu Asp Thr
            100                 105                 110

Glu Pro Asp Asp Glu Trp Val Lys Asn Arg Lys Asp Glu Ser Arg Ala
        115                 120                 125

Phe His Glu Trp Asp Glu Asp Ala Asp Ile Asp Glu Ser Glu Glu Ser
```

```
            130                 135                 140
Ala Glu Glu Ser Ile Ala Ile Ser Ile Ala Gln Met Glu Lys Arg Leu
145                 150                 155                 160

Leu His Gly Leu Ile His Asn Val Leu Pro Tyr Val Gly Thr Ser Val
                165                 170                 175

Lys Thr Leu Val Leu Ala Tyr Ser Ser Ala Val Ser Ser Lys Met Val
                180                 185                 190

Arg Gln Ile Leu Glu Leu Cys Pro Asn Leu Glu His Leu Asp Leu Thr
                195                 200                 205

Gln Thr Asp Ile Ser Asp Ser Ala Phe Asp Ser Trp Ser Trp Leu Gly
        210                 215                 220

Cys Cys Gln Ser Leu Arg His Leu Asp Leu Ser Gly Cys Glu Lys Ile
225                 230                 235                 240

Thr Asp Val Ala Leu Glu Lys Ile Ser Arg Ala Leu Gly Ile Leu Thr
                245                 250                 255

Ser His Gln Ser Gly Phe Leu Lys Thr Ser Thr Ser Lys Ile Thr Ser
                260                 265                 270

Thr Ala Trp Lys Asn Lys Asp Ile Thr Met Gln Ser Thr Lys Gln Tyr
        275                 280                 285

Ala Cys Leu His Asp Leu Thr Asn Lys Gly Ile Gly Glu Glu Ile Asp
        290                 295                 300

Asn Glu His Pro Trp Thr Lys Pro Val Ser Ser Glu Asn Phe Thr Ser
305                 310                 315                 320

Pro Tyr Val Trp Met Leu Asp Ala Glu Asp Leu Ala Asp Ile Glu Asp
                325                 330                 335

Thr Val Glu Trp Arg His Arg Asn Val Glu Ser Leu Cys Val Met Glu
                340                 345                 350

Thr Ala Ser Asn Phe Ser Cys Ser Thr Ser Gly Cys Phe Ser Lys Asp
        355                 360                 365

Ile Val Gly Leu Arg Thr Ser Val Cys Trp Gln Gln His Cys Ala Ser
        370                 375                 380

Pro Ala Phe Ala Tyr Cys Gly His Ser Phe Cys Cys Thr Gly Thr Ala
385                 390                 395                 400

Leu Arg Thr Met Ser Ser Leu Pro Glu Ser Ser Ala Met Cys Arg Lys
                405                 410                 415

Ala Ala Arg Thr Arg Leu Pro Arg Gly Lys Asp Leu Ile Tyr Phe Gly
                420                 425                 430

Ser Glu Lys Ser Asp Gln Glu Thr Gly Arg Val Leu Leu Phe Leu Ser
        435                 440                 445

Leu Ser Gly Cys Tyr Gln Ile Thr Asp His Gly Leu Arg Val Leu Thr
        450                 455                 460

Leu Gly Gly Gly Leu Pro Tyr Leu Glu His Leu Asn Leu Ser Gly Cys
465                 470                 475                 480

Leu Thr Ile Thr Gly Ala Gly Leu Gln Asp Leu Val Ser Ala Cys Pro
                485                 490                 495

Ser Leu Asn Asp Glu Tyr Phe Tyr Tyr Cys Asp Asn Ile Asn Gly Pro
                500                 505                 510

His Ala Asp Thr Ala Ser Gly Cys Gln Asn Leu Gln Cys Gly Phe Arg
                515                 520                 525

Ala Cys Cys Arg Ser Gly Glu Pro Leu Thr Ser Asp Leu Cys Leu Leu
        530                 535                 540

His Leu Ala Glu Gln Ala Phe Phe His Ala Leu Tyr Ser His Ile Ser
545                 550                 555                 560
```

```
Cys Val Asn His Pro Phe Leu Ser Val Thr Cys Phe Gly Pro Ile Xaa
            565                 570                 575

Tyr Asn Phe Arg Asn Leu Asn Tyr Gln Xaa Ile Val Met Leu
            580                 585                 590
```

<210> SEQ ID NO 53
<211> LENGTH: 1681
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 53

```
ttttactgta cacagttgat gtattttgat gctgggcctg tctggtctgt cttgaggatt      60
attaaccttt agaggtatca gagaagcaaa tgggtactgg tgaggctgct cattagggaa     120
gagggcaaaa ggagcactag ctaggtcaga gccatgtttc aggtcacaat gtgatgtcag     180
atgttgctta taaatccttt cttgtcttcg ccattcttaa atcttgatag gtgcctgttg     240
ggaaactgta aatgcctttc ccaatggaga atcaacagat tgggtgatgg tggagtcggt     300
caggaagact caggtcttct agaggaaagg atgcctcatc accccttngg cccaggcagc     360
tgctgtcaga gaatgacaca gcacctgcac agtcgctgtc cacttcctgc cactgctgtc     420
ggtggggtga cgggagcaaa gtaggcgtgg actttgacat gagggagctg agcccgcatc     480
cgcttgatgc ctgcacgggt aacctgctgg cagtcgtaca gctcgaggcg ctccaggcct     540
cggcagttct ctaggtgtyc cagggccaca tcagtgatga ggaggcagtt gtccaactcc     600
agtacccgca gcctctcatg gccacaggta ctgttgctca ggtgcaggat cccatcatct     660
gkgatgagtt cacagtggga caggctcagg gcttgcagtt taggacagtg aatggagagc     720
tggatgagtg tgctgtcggt tatcaggatg cawtcttcaa gatccatctt ctccaattcg     780
tggcaattcc gagctaaaag tgtaaaacct gcgtcagtca aatgggagca tcgggcagcc     840
tccaaaattt gcagtcgcgg acagttcaaa cccagggctg taagagaggc atctgtgagg     900
ttgctgcaac ccgaaaggca gagagcctgt agccggtgac agcccctgca tatctgcacc     960
acaccttcat ccgtgatacg tgagcaggac tgcaagttga ggctcacaag ctcatggcag    1020
taattctgaa tgtgtttcag agcttcatct tctaactgtg tgcagcccct caggagcagg    1080
gctttcaggc ctcgacaacc tcgcaccagt gcctcgatgc catccttcgt gatctgatca    1140
caccaagaga ggttcaggta ctccaggttt cggcagccct cactgatccc cttcaaggag    1200
ctgtttgtaa tagacacaca ggaggtcaga wccagatgtt tcagcttgga acagaatctg    1260
ctaaggctat aacacgtgct gtcagtgatt tttgtgcatc cattgaggtt caaatgttca    1320
atgtttcggc agttctgtgc aaaggtcttc aaggaggaat ccccaacacc aatgcagcct    1380
cgcaagctga gcttcctcag gaatccaacg catcgcttcg agatattttc caccactcga    1440
ccctctacat ctatttgaaa gttaaaaaga tctattcttt gccagttgct tccatccagg    1500
gctaagatgt tccaagcctt ggaaatctgt gcacatcggc acaaagttac tatatccaag    1560
aaggaaaata ttcttaacag aagttctttg ggtaacttt tgttaataag gccttcatca    1620
ttgtttgaga aaaccatggc cgaagagccg cgagcgagcc cacagcccga agtcacacgg    1680
c                                                                    1681
```

<210> SEQ ID NO 54

-continued

<211> LENGTH: 437
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 54

Arg Val Thr Ser Gly Cys Gly Leu Ala Arg Gly Ser Ser Ala Met Val
 1               5                  10                  15

Phe Ser Asn Asn Asp Glu Gly Leu Ile Asn Lys Lys Leu Pro Lys Glu
                20                  25                  30

Leu Leu Leu Arg Ile Phe Ser Phe Leu Asp Ile Val Thr Leu Cys Arg
            35                  40                  45

Cys Ala Gln Ile Ser Lys Ala Trp Asn Ile Leu Ala Leu Asp Gly Ser
        50                  55                  60

Asn Trp Gln Arg Ile Asp Leu Phe Asn Phe Gln Ile Asp Val Glu Gly
65                  70                  75                  80

Arg Val Val Glu Asn Ile Ser Lys Arg Cys Val Gly Phe Leu Arg Lys
                85                  90                  95

Leu Ser Leu Arg Gly Cys Ile Gly Val Gly Asp Ser Ser Leu Lys Thr
            100                 105                 110

Phe Ala Gln Asn Cys Arg Asn Ile Glu His Leu Asn Leu Asn Gly Cys
        115                 120                 125

Thr Lys Ile Thr Asp Ser Thr Cys Tyr Ser Leu Ser Arg Phe Cys Ser
    130                 135                 140

Lys Leu Lys His Leu Xaa Leu Thr Ser Cys Val Ser Ile Thr Asn Ser
145                 150                 155                 160

Ser Leu Lys Gly Ile Ser Glu Gly Cys Arg Asn Leu Glu Tyr Leu Asn
                165                 170                 175

Leu Ser Trp Cys Asp Gln Ile Thr Lys Asp Gly Ile Glu Ala Leu Val
            180                 185                 190

Arg Gly Cys Arg Gly Leu Lys Ala Leu Leu Leu Arg Gly Cys Thr Gln
        195                 200                 205

Leu Glu Asp Glu Ala Leu Lys His Ile Gln Asn Tyr Cys His Glu Leu
    210                 215                 220

Val Ser Leu Asn Leu Gln Ser Cys Ser Arg Ile Thr Asp Glu Gly Val
225                 230                 235                 240

Val Gln Ile Cys Arg Gly Cys His Arg Leu Gln Ala Leu Cys Leu Ser
                245                 250                 255

Gly Cys Ser Asn Leu Thr Asp Ala Ser Leu Thr Ala Leu Gly Leu Asn
            260                 265                 270

Cys Pro Arg Leu Gln Ile Leu Glu Ala Ala Arg Cys Ser His Leu Thr
        275                 280                 285

Asp Ala Gly Phe Thr Leu Leu Ala Arg Asn Cys His Glu Leu Glu Lys
    290                 295                 300

Met Asp Leu Glu Xaa Cys Ile Leu Ile Thr Asp Ser Thr Leu Ile Gln
305                 310                 315                 320

Leu Ser Ile His Cys Pro Lys Leu Gln Ala Leu Ser Leu Ser His Cys
                325                 330                 335

Glu Leu Ile Xaa Asp Asp Gly Ile Leu His Leu Ser Asn Ser Thr Cys
            340                 345                 350

Gly His Glu Arg Leu Arg Val Leu Glu Leu Asp Asn Cys Leu Leu Ile
        355                 360                 365

```
Thr Asp Val Ala Leu Xaa His Leu Glu Asn Cys Arg Gly Leu Glu Arg
        370                 375                 380

Leu Glu Leu Tyr Asp Cys Gln Gln Val Thr Arg Ala Gly Ile Lys Arg
385                 390                 395                 400

Met Arg Ala Gln Leu Pro His Val Lys Val His Ala Tyr Phe Ala Pro
                405                 410                 415

Val Thr Pro Pro Thr Ala Val Ala Gly Ser Gly Gln Arg Leu Cys Arg
            420                 425                 430

Cys Cys Val Ile Leu
        435

<210> SEQ ID NO 55
<211> LENGTH: 1866
<212> TYPE: DNA
<213> ORGANISM: Homo sapiens

<400> SEQUENCE: 55
```

| | | | | | |
|---|---|---|---|---|---|
| atgtcaccgg | tctttcccat | gttaacagtt | ctgaccatgt | tttattatat | atgccttcgg | 60 |
| cgccgagcca | ggacagctac | aagaggagaa | atgatgaaca | cccatagagc | tatagaatca | 120 |
| aacagccaga | cttcccctct | caatgcagag | gtagtccagt | atgccaaaga | agtagtggat | 180 |
| ttcagttccc | attatggaag | tgagaatagt | atgtcctata | ctatgtggaa | tttggctggt | 240 |
| gtaccaaatg | tattcccaag | ttctggtgac | tttactcaga | cagctgtgtt | tcgaacttat | 300 |
| gggacatggt | gggatcagtg | tcctagtgct | tccttgccat | tcaagaggac | gcccacctaa | 360 |
| tttcagagcc | aggactatgt | ggaacttact | tttgaacaac | aggtgtatcc | tacagctgta | 420 |
| catgttctag | aaacctatca | tcccggagca | gtcattagaa | ttctcgcttg | ttctgcaaat | 480 |
| ccttattccc | caaatccacc | agctgaagta | agatgggaga | ttctttggtc | agagagacct | 540 |
| acgaaggtga | atgcttccca | agctcgccag | tttaaacctt | gtattaagca | gataaatttc | 600 |
| cccacaaatc | ttatacgact | ggaagtaaat | agttctcttc | tggaatatta | cactgaatta | 660 |
| gatgcagttg | tgctacatgg | tgtgaaggac | aagccagtgc | tttctctcaa | gacttcactt | 720 |
| attgacatga | atgatataga | agatgatgcc | tatgcagaaa | aggatggttg | tggaatggac | 780 |
| agtcttaaca | aaagtttag | cagtgctgtc | ctcggggaag | ggccaaataa | tgggtatttt | 840 |
| gataaactac | cttatgagct | tattcagctg | attctgaatc | atcttacact | accagacctg | 900 |
| tgtagattag | cacagacttg | caaactactg | agccagcatt | gctgtgatcc | tctgcaatac | 960 |
| atccacctca | atctgcaacc | atactgggca | aaactagatg | acacttctct | ggaatttcta | 1020 |
| cagtctcgct | gcactcttgt | ccagtggctt | aatttatctt | ggactggcaa | tagaggcttc | 1080 |
| atctctgttg | caggatttag | caggtttctg | aaggtttgtg | gatccgaatt | agtacgcctt | 1140 |
| gaattgtctt | gcagccactt | tcttaatgaa | acttgcttag | aagttatttc | tgagatgtgt | 1200 |
| ccaaatctac | aggccttaaa | tctctcctcc | tgtgataagc | taccacctca | agctttcaac | 1260 |
| cacattgcca | gttatgcag | ccttaaacga | cttgttctct | atcgaacaaa | agtagagcaa | 1320 |
| acagcactgc | tcagcatttt | gaacttctgt | tcagagcttc | agcacctcag | tttaggcagt | 1380 |
| tgtgtcatga | ttgaagacta | tgatgtgata | gctagcatga | taggagccaa | gtgtaaaaaa | 1440 |
| ctccggaccc | tggatctgtg | gagatgtaag | aatattactg | agaatggaat | agcagaactg | 1500 |
| gcttctgggt | gtccactact | ggaggagctt | gaccttggct | ggtgcccaac | tctgcagagc | 1560 |
| agcaccgggt | gcttcaccag | actggcacac | cagctcccaa | acttgcaaaa | actctttctt | 1620 |
| acagctaata | gatctgtgtg | tgacacagac | attgatgaat | tggcatgtaa | ttgtaccagg | 1680 |

-continued

```
ttacagcagc tggacatatt aggaacaaga atggtaagtc cggcatcctt aagaaaactc    1740
ctggaatctt gtaaagatct ttctttactt gatgtgtcct tctgttcgca gattgataac    1800
agagctgtgc tagaactgaa tgcaagcttt ccaaaagtgt tcataaaaaa gagctttact    1860
cagtga                                                                1866
```

<210> SEQ ID NO 56
<211> LENGTH: 621
<212> TYPE: PRT
<213> ORGANISM: Homo sapiens

<400> SEQUENCE: 56

```
Met Ser Pro Val Phe Pro Met Leu Thr Val Leu Thr Met Phe Tyr Tyr
 1               5                  10                  15

Ile Cys Leu Arg Arg Ala Arg Thr Ala Arg Gly Glu Met Met
                20                  25                  30

Asn Thr His Arg Ala Ile Glu Ser Asn Ser Gln Thr Ser Pro Leu Asn
            35                  40                  45

Ala Glu Val Val Gln Tyr Ala Lys Glu Val Val Asp Phe Ser Ser His
        50                  55                  60

Tyr Gly Ser Glu Asn Ser Met Ser Tyr Thr Met Trp Asn Leu Ala Gly
 65                  70                  75                  80

Val Pro Asn Val Phe Pro Ser Ser Gly Asp Phe Thr Gln Thr Ala Val
                85                  90                  95

Phe Arg Thr Tyr Gly Thr Trp Trp Asp Gln Cys Pro Ser Ala Ser Leu
            100                 105                 110

Pro Phe Lys Arg Thr Pro Pro Asn Phe Gln Ser Gln Asp Tyr Val Glu
        115                 120                 125

Leu Thr Phe Glu Gln Gln Val Tyr Pro Thr Ala Val His Val Leu Glu
    130                 135                 140

Thr Tyr His Pro Gly Ala Val Ile Arg Ile Leu Ala Cys Ser Ala Asn
145                 150                 155                 160

Pro Tyr Ser Pro Asn Pro Pro Ala Glu Val Arg Trp Glu Ile Leu Trp
                165                 170                 175

Ser Glu Arg Pro Thr Lys Val Asn Ala Ser Gln Ala Arg Gln Phe Lys
            180                 185                 190

Pro Cys Ile Lys Gln Ile Asn Phe Pro Thr Asn Leu Ile Arg Leu Glu
        195                 200                 205

Val Asn Ser Ser Leu Leu Glu Tyr Tyr Thr Glu Leu Asp Ala Val Val
    210                 215                 220

Leu His Gly Val Lys Asp Lys Pro Val Leu Ser Leu Lys Thr Ser Leu
225                 230                 235                 240

Ile Asp Met Asn Asp Ile Glu Asp Ala Tyr Ala Glu Lys Asp Gly
                245                 250                 255

Cys Gly Met Asp Ser Leu Asn Lys Lys Phe Ser Ser Ala Val Leu Gly
            260                 265                 270

Glu Gly Pro Asn Asn Gly Tyr Phe Asp Lys Leu Pro Tyr Glu Leu Ile
        275                 280                 285

Gln Leu Ile Leu Asn His Leu Thr Leu Pro Asp Leu Cys Arg Leu Ala
    290                 295                 300

Gln Thr Cys Lys Leu Leu Ser Gln His Cys Cys Asp Pro Leu Gln Tyr
305                 310                 315                 320

Ile His Leu Asn Leu Gln Pro Tyr Trp Ala Lys Leu Asp Asp Thr Ser
                325                 330                 335
```

```
Leu Glu Phe Leu Gln Ser Arg Cys Thr Leu Val Gln Trp Leu Asn Leu
                340                 345                 350
Ser Trp Thr Gly Asn Arg Gly Phe Ile Ser Val Ala Gly Phe Ser Arg
            355                 360                 365
Phe Leu Lys Val Cys Gly Ser Glu Leu Val Arg Leu Glu Leu Ser Cys
        370                 375                 380
Ser His Phe Leu Asn Glu Thr Cys Leu Glu Val Ile Ser Glu Met Cys
385                 390                 395                 400
Pro Asn Leu Gln Ala Leu Asn Leu Ser Ser Cys Asp Lys Leu Pro Pro
                405                 410                 415
Gln Ala Phe Asn His Ile Ala Lys Leu Cys Ser Leu Lys Arg Leu Val
            420                 425                 430
Leu Tyr Arg Thr Lys Val Glu Gln Thr Ala Leu Leu Ser Ile Leu Asn
        435                 440                 445
Phe Cys Ser Glu Leu Gln His Leu Ser Leu Gly Ser Cys Val Met Ile
        450                 455                 460
Glu Asp Tyr Asp Val Ile Ala Ser Met Ile Gly Ala Lys Cys Lys Lys
465                 470                 475                 480
Leu Arg Thr Leu Asp Leu Trp Arg Cys Lys Asn Ile Thr Glu Asn Gly
                485                 490                 495
Ile Ala Glu Leu Ala Ser Gly Cys Pro Leu Leu Glu Glu Leu Asp Leu
            500                 505                 510
Gly Trp Cys Pro Thr Leu Gln Ser Ser Thr Gly Cys Phe Thr Arg Leu
        515                 520                 525
Ala His Gln Leu Pro Asn Leu Gln Lys Leu Phe Leu Thr Ala Asn Arg
        530                 535                 540
Ser Val Cys Asp Thr Asp Ile Asp Glu Leu Ala Cys Asn Cys Thr Arg
545                 550                 555                 560
Leu Gln Gln Leu Asp Ile Leu Gly Thr Arg Met Val Ser Pro Ala Ser
                565                 570                 575
Leu Arg Lys Leu Leu Glu Ser Cys Lys Asp Leu Ser Leu Leu Asp Val
            580                 585                 590
Ser Phe Cys Ser Gln Ile Asp Asn Arg Ala Val Leu Glu Leu Asn Ala
        595                 600                 605
Ser Phe Pro Lys Val Phe Ile Lys Ser Phe Thr Gln
        610                 615                 620

<210> SEQ ID NO 57
<211> LENGTH: 984
<212> TYPE: DNA
<213> ORGANISM: Homo sapiens

<400> SEQUENCE: 57
atgcaacttg tacctgatat agagttcaag attacttata cccggtctcc agatggtgat      60
ggcgttggaa acagctacat tgaagataat gatgatgaca gcaaaatggc agatctcttg     120
tcctacttcc agcagcaact cacatttcag gagtctgtgc ttaaactgtg tcagcctgag     180
cttgagagca gtcagattca catatcagtg ctgccaatgg aggtcctgat gtacatcttc     240
cgatgggtgg tgtctagtga cttggacctc agatcattgg agcagttgtc gctggtgtgc     300
agaggattct acatctgtgc cagagaccct gaaatatggc gtctggcctg cttgaaagtt     360
tggggcagaa gctgtattaa acttgttccg tacacgtcct ggagagagat gttttagaa      420 cggcctcgtg ttcggtttga tggcgtgtat atcagtaaaa ccacatatat tcgtcaaggg     480
gaacagtctc ttgatggttt ctatagagcc tggcaccaag tggaatatta caggtacata     540
```

```
agattctttc ctgatggcca tgtgatgatg ttgacaaccc ctgaagagcc tcagtccatt    600
gttccacgtt taagaactag gaataccagg actgatgcaa ttctactggg tcactatcgc    660
ttgtcacaag acacagacaa tcagaccaaa gtatttgctg taataactaa gaaaaaagaa    720
gaaaaaccac ttgactataa atacagatat tttcgtcgtg tccctgtaca agaagcagat    780
cagagttttc atgtggggct acagctatgt tccagtggtc accagaggtt caacaaactc    840
atctggatac atcattcttg tcacattact tacaaatcaa ctggtgagac tgcagtcagt    900
gcttttgaga ttgacaagat gtaccccccc ttgttcttcg ccagagtaag gagctacaca    960
gctttctcag aaaggcctct gtag                                            984
```

<210> SEQ ID NO 58
<211> LENGTH: 327
<212> TYPE: PRT
<213> ORGANISM: Homo sapiens

<400> SEQUENCE: 58

```
Met Gln Leu Val Pro Asp Ile Glu Phe Lys Ile Thr Tyr Thr Arg Ser
  1               5                  10                  15

Pro Asp Gly Asp Gly Val Gly Asn Ser Tyr Ile Glu Asp Asn Asp Asp
                 20                  25                  30

Asp Ser Lys Met Ala Asp Leu Leu Ser Tyr Phe Gln Gln Gln Leu Thr
             35                  40                  45

Phe Gln Glu Ser Val Leu Lys Leu Cys Gln Pro Glu Leu Glu Ser Ser
         50                  55                  60

Gln Ile His Ile Ser Val Leu Pro Met Glu Val Leu Met Tyr Ile Phe
     65                  70                  75                  80

Arg Trp Val Val Ser Ser Asp Leu Asp Leu Arg Ser Leu Glu Gln Leu
                 85                  90                  95

Ser Leu Val Cys Arg Gly Phe Tyr Ile Cys Ala Arg Asp Pro Glu Ile
                100                 105                 110

Trp Arg Leu Ala Cys Leu Lys Val Trp Gly Arg Ser Cys Ile Lys Leu
            115                 120                 125

Val Pro Tyr Thr Ser Trp Arg Glu Met Phe Leu Glu Arg Pro Arg Val
        130                 135                 140

Arg Phe Asp Gly Val Tyr Ile Ser Lys Thr Thr Tyr Ile Arg Gln Gly
145                 150                 155                 160

Glu Gln Ser Leu Asp Gly Phe Tyr Arg Ala Trp His Gln Val Glu Tyr
                165                 170                 175

Tyr Arg Tyr Ile Arg Phe Phe Pro Asp Gly His Val Met Met Leu Thr
            180                 185                 190

Thr Pro Glu Glu Pro Gln Ser Ile Val Pro Arg Leu Arg Thr Arg Asn
        195                 200                 205

Thr Arg Thr Asp Ala Ile Leu Leu Gly His Tyr Arg Leu Ser Gln Asp
    210                 215                 220

Thr Asp Asn Gln Thr Lys Val Phe Ala Val Ile Thr Lys Lys Lys Glu
225                 230                 235                 240

Glu Lys Pro Leu Asp Tyr Lys Tyr Arg Tyr Phe Arg Arg Val Pro Val
                245                 250                 255

Gln Glu Ala Asp Gln Ser Phe His Val Gly Leu Gln Leu Cys Ser Ser
            260                 265                 270

Gly His Gln Arg Phe Asn Lys Leu Ile Trp Ile His His Ser Cys His
        275                 280                 285
```

```
Ile Thr Tyr Lys Ser Thr Gly Glu Thr Ala Val Ser Ala Phe Glu Ile
        290                 295                 300

Asp Lys Met Tyr Thr Pro Leu Phe Phe Ala Arg Val Arg Ser Tyr Thr
305                 310                 315                 320

Ala Phe Ser Glu Arg Pro Leu
                325
```

<210> SEQ ID NO 59
<211> LENGTH: 765
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 59

```
gcagccctgg atcctgactt agagaatgat gatttctttg tcagaaagac tggggctttc      60
catgcaaatc catatgttct ccgagctttt gaagacttta gaagttctc tgagcaagat     120
gattctgtag agcgagatat aattttacag tgtagaaag gtgaacttgt acttccggat     180
ttggaaaaag atgatatgat tgttcgccga atcccagcac agaagaaaga agtgccgctg     240
tctgggccc cagatagata ccacccagtc ccttttcccg aaccctggac tcttcctcca     300
gaaattcaag caaaatttct ctgtgtactt gaaaggacat gcccatccaa agaaaaagt     360
aatagctgta gaatattagt tccttcatat cggcagaaga agatgacat gctgacacgt     420
aagattcagt cctggaaact gggaactacc gtgcctccca tcagtttcac ncctggcccc     480
tgcagtgagc tgacttgaa gagatgggag gccatccggg aggccagcag actcaggcac     540
aagaaaggc tgatggtgga gagactcttt caaaagattt atggtgagaa tgggagtaag     600
tccatgagtg atgtcagcgc agaagatgtt caaaacttgc gtcagctgcg ttacgaggag     660
atgcagaaaa taaaatcaca attaaaagaa caagatcaga aatggcagga tgaccttgca     720
aaatggaaag atcgtcgaaa aagttacact tcagatctgc agaag                    765
```

<210> SEQ ID NO 60
<211> LENGTH: 255
<212> TYPE: PRT
<213> ORGANISM: Homo sapiens

<400> SEQUENCE: 60

```
Ala Ala Leu Asp Pro Asp Leu Glu Asn Asp Asp Phe Phe Val Arg Lys
  1               5                  10                  15

Thr Gly Ala Phe His Ala Asn Pro Tyr Val Leu Arg Ala Phe Glu Asp
                 20                  25                  30

Phe Arg Lys Phe Ser Glu Gln Asp Asp Ser Val Glu Arg Asp Ile Ile
             35                  40                  45

Leu Gln Cys Arg Glu Gly Glu Leu Val Leu Pro Asp Leu Glu Lys Asp
         50                  55                  60

Asp Met Ile Val Arg Arg Ile Pro Ala Gln Lys Lys Glu Val Pro Leu
 65                  70                  75                  80

Ser Gly Ala Pro Asp Arg Tyr His Pro Val Pro Phe Pro Glu Pro Trp
                 85                  90                  95

Thr Leu Pro Pro Glu Ile Gln Ala Lys Phe Leu Cys Val Leu Glu Arg
                100                 105                 110

Thr Cys Pro Ser Lys Glu Lys Ser Asn Ser Cys Arg Ile Leu Val Pro
            115                 120                 125
```

-continued

```
Ser Tyr Arg Gln Lys Lys Asp Asp Met Leu Thr Arg Lys Ile Gln Ser
    130                 135                 140

Trp Lys Leu Gly Thr Thr Val Pro Pro Ile Ser Phe Thr Pro Gly Pro
145                 150                 155                 160

Cys Ser Glu Ala Asp Leu Lys Arg Trp Glu Ala Ile Arg Glu Ala Ser
                165                 170                 175

Arg Leu Arg His Lys Lys Arg Leu Met Val Glu Arg Leu Phe Gln Lys
            180                 185                 190

Ile Tyr Gly Glu Asn Gly Ser Lys Ser Met Ser Asp Val Ser Ala Glu
        195                 200                 205

Asp Val Gln Asn Leu Arg Gln Leu Arg Tyr Glu Glu Met Gln Lys Ile
    210                 215                 220

Lys Ser Gln Leu Lys Glu Gln Asp Gln Lys Trp Gln Asp Asp Leu Ala
225                 230                 235                 240

Lys Trp Lys Asp Arg Arg Lys Ser Tyr Thr Ser Asp Leu Gln Lys
                245                 250                 255

<210> SEQ ID NO 61
<211> LENGTH: 36
<212> TYPE: PRT
<213> ORGANISM: Homo sapiens

<400> SEQUENCE: 61

Leu Pro Pro Glu Leu Ser Phe Thr Ile Leu Ser Tyr Leu Asn Ala Thr
1               5                   10                  15

Asp Leu Cys Leu Ala Ser Cys Val Trp Gln Asp Leu Ala Asn Asp Glu
                20                  25                  30

Leu Leu Trp Gln
        35

<210> SEQ ID NO 62
<211> LENGTH: 42
<212> TYPE: PRT
<213> ORGANISM: Homo sapiens

<400> SEQUENCE: 62

Leu Pro Gly Glu Val Leu Glu Tyr Ile Leu Cys Cys Gly Ser Leu Thr
1               5                   10                  15

Ala Ala Asp Ile Gly Arg Val Ser Ser Thr Cys Arg Arg Leu Arg Glu
                20                  25                  30

Leu Cys Gln Ser Ser Gly Lys Val Trp Lys
        35                  40

<210> SEQ ID NO 63
<211> LENGTH: 44
<212> TYPE: PRT
<213> ORGANISM: Homo sapiens

<400> SEQUENCE: 63

Leu Ala Glu Val Val Glu Arg Val Leu Thr Phe Leu Pro Ala Lys Ala
1               5                   10                  15

Leu Leu Arg Val Ala Cys Val Cys Arg Leu Trp Arg Glu Cys Val Arg
                20                  25                  30

Arg Val Leu Arg Thr His Arg Ser Val Thr Trp Ile
        35                  40

<210> SEQ ID NO 64
<211> LENGTH: 39
<212> TYPE: PRT
```

```
<213> ORGANISM: Homo sapiens

<400> SEQUENCE: 64

Leu Pro Asp Glu Val Val Leu Lys Ile Phe Ser Tyr Leu Leu Glu Gln
 1               5                  10                  15

Asp Leu Cys Arg Ala Ala Cys Val Cys Lys Arg Phe Ser Glu Leu Ala
            20                  25                  30

Asn Asp Pro Asn Leu Trp Lys
            35

<210> SEQ ID NO 65
<211> LENGTH: 41
<212> TYPE: PRT
<213> ORGANISM: Homo sapiens

<400> SEQUENCE: 65

Leu Pro Leu Glu Leu Trp Arg Met Ile Leu Ala Tyr Leu His Leu Pro
 1               5                  10                  15

Asp Leu Gly Arg Cys Ser Leu Val Cys Arg Ala Trp Tyr Glu Leu Ile
            20                  25                  30

Leu Ser Leu Asp Ser Thr Arg Trp Arg
            35                  40

<210> SEQ ID NO 66
<211> LENGTH: 39
<212> TYPE: PRT
<213> ORGANISM: Homo sapiens

<400> SEQUENCE: 66

Leu Pro Thr Asp Pro Leu Leu Leu Ile Leu Ser Phe Leu Asp Tyr Arg
 1               5                  10                  15

Asp Leu Ile Asn Cys Cys Tyr Val Ser Arg Arg Leu Ser Gln Leu Ser
            20                  25                  30

Ser His Asp Pro Leu Trp Arg
            35

<210> SEQ ID NO 67
<211> LENGTH: 40
<212> TYPE: PRT
<213> ORGANISM: Homo sapiens

<400> SEQUENCE: 67

Leu Pro Glu Pro Leu Leu Leu Arg Val Leu Ala Ala Leu Pro Ala Ala
 1               5                  10                  15

Glu Leu Val Gln Ala Cys Arg Leu Val Cys Leu Arg Trp Lys Glu Leu
            20                  25                  30

Val Asp Gly Ala Pro Leu Trp Leu
            35                  40

<210> SEQ ID NO 68
<211> LENGTH: 40
<212> TYPE: PRT
<213> ORGANISM: Homo sapiens

<400> SEQUENCE: 68

Leu Phe Pro Pro Glu Leu Val Glu His Ile Ile Ser Phe Leu Pro Val
 1               5                  10                  15

Arg Asp Leu Val Ala Leu Gly Gln Thr Cys Arg Tyr Phe His Glu Val
            20                  25                  30

Cys Asp Gly Glu Gly Val Trp Arg
```

-continued

```
                 35                  40

<210> SEQ ID NO 69
<211> LENGTH: 44
<212> TYPE: PRT
<213> ORGANISM: Homo sapiens

<400> SEQUENCE: 69

Leu Pro Glu Val Leu Leu His Met Cys Ser Tyr Leu Asp Met Arg
 1               5                  10                  15

Ala Leu Gly Arg Leu Ala Gln Val Tyr Arg Trp Leu Trp His Phe Thr
                20                  25                  30

Asn Cys Asp Leu Leu Arg Arg Gln Ile Ala Trp Ala
             35                  40

<210> SEQ ID NO 70
<211> LENGTH: 40
<212> TYPE: PRT
<213> ORGANISM: Homo sapiens

<400> SEQUENCE: 70

Leu Pro Leu His Met Leu Asn Asn Ile Leu Tyr Arg Phe Ser Asp Gly
 1               5                  10                  15

Trp Asp Ile Ile Thr Leu Gly Gln Val Thr Pro Thr Leu Tyr Met Leu
                20                  25                  30

Ser Glu Asp Arg Gln Leu Trp Lys
             35                  40

<210> SEQ ID NO 71
<211> LENGTH: 39
<212> TYPE: PRT
<213> ORGANISM: Homo sapiens

<400> SEQUENCE: 71

Leu Pro Asp His Ser Met Val Gln Ile Phe Ser Phe Leu Pro Thr Asn
 1               5                  10                  15

Gln Leu Cys Arg Cys Ala Arg Val Cys Arg Arg Trp Tyr Asn Leu Ala
                20                  25                  30

Trp Asp Pro Arg Leu Trp Arg
             35

<210> SEQ ID NO 72
<211> LENGTH: 44
<212> TYPE: PRT
<213> ORGANISM: Homo sapiens

<400> SEQUENCE: 72

Ile Pro Leu Glu Ile Leu Val Gln Ile Phe Gly Leu Leu Val Ala Ala
 1               5                  10                  15

Asp Gly Pro Met Pro Phe Leu Gly Arg Ala Ala Arg Val Cys Arg Arg
                20                  25                  30

Trp Gln Glu Ala Ala Ser Gln Pro Ala Leu Trp His
             35                  40

<210> SEQ ID NO 73
<211> LENGTH: 39
<212> TYPE: PRT
<213> ORGANISM: Homo sapiens

<400> SEQUENCE: 73

Leu Pro Pro Glu Val Met Leu Ser Ile Phe Ser Tyr Leu Asn Pro Gln
```

-continued

```
                1               5                  10                 15
          Glu Leu Cys Arg Cys Ser Gln Val Ser Met Lys Trp Ser Gln Leu Thr
                          20                  25                 30

Lys Thr Gly Ser Leu Trp Lys
                      35

<210> SEQ ID NO 74
<211> LENGTH: 39
<212> TYPE: PRT
<213> ORGANISM: Homo sapiens

<400> SEQUENCE: 74

Leu Pro Lys Glu Leu Leu Leu Arg Ile Phe Ser Phe Leu Asp Ile Val
           1               5                  10                 15

Thr Leu Cys Arg Cys Ala Gln Ile Ser Lys Ala Trp Asn Ile Leu Ala
                          20                  25                 30

Leu Asp Gly Ser Asn Trp Gln
                      35

<210> SEQ ID NO 75
<211> LENGTH: 48
<212> TYPE: PRT
<213> ORGANISM: Homo sapiens

<400> SEQUENCE: 75

Leu Pro Tyr Glu Leu Ile Gln Leu Ile Leu Asn His Leu Thr Leu Pro
           1               5                  10                 15

Asp Leu Cys Arg Leu Ala Gln Thr Cys Lys Leu Leu Ser Gln His Cys
                          20                  25                 30

Cys Asp Pro Leu Gln Tyr Ile His Leu Asn Leu Gln Pro Tyr Trp Ala
                      35                  40                  45

<210> SEQ ID NO 76
<211> LENGTH: 44
<212> TYPE: PRT
<213> ORGANISM: Homo sapiens

<400> SEQUENCE: 76

Leu Pro Met Glu Val Leu Met Tyr Ile Phe Arg Trp Val Val Ser Ser
           1               5                  10                 15

Asp Leu Asp Leu Arg Ser Leu Glu Gln Leu Ser Leu Val Cys Arg Gly
                          20                  25                 30

Phe Tyr Ile Cys Ala Arg Asp Pro Glu Ile Trp Arg
                      35                  40

<210> SEQ ID NO 77
<211> LENGTH: 49
<212> TYPE: PRT
<213> ORGANISM: Homo sapiens

<400> SEQUENCE: 77

Leu Pro Pro Glu Ile Gln Ala Lys Phe Leu Cys Val Leu Glu Arg Thr
           1               5                  10                 15

Cys Pro Ser Lys Glu Lys Ser Asn Ser Cys Arg Ile Leu Val Pro Ser
                          20                  25                 30

Tyr Arg Gln Lys Lys Asp Asp Met Leu Thr Arg Lys Ile Gln Ser Trp
                      35                  40                  45

Lys
```

<210> SEQ ID NO 78
<211> LENGTH: 39
<212> TYPE: PRT
<213> ORGANISM: Homo sapiens

<400> SEQUENCE: 78

Leu Pro His His Val Val Leu Gln Ile Phe Gln Tyr Leu Pro Leu Leu
 1               5                  10                  15

Asp Arg Ala Cys Ala Ser Ser Val Cys Arg Arg Trp Asn Glu Val Phe
            20                  25                  30

His Ile Ser Asp Leu Trp Arg
        35

<210> SEQ ID NO 79
<211> LENGTH: 43
<212> TYPE: PRT
<213> ORGANISM: Homo sapiens

<400> SEQUENCE: 79

Leu Trp Ala Trp Gly Glu Lys Gly Val Leu Ser Asn Ile Ser Ala Leu
 1               5                  10                  15

Thr Asp Leu Gly Gly Leu Asp Pro Val Trp Leu Val Cys Gly Ser Trp
            20                  25                  30

Arg Arg His Val Gly Ala Gly Leu Cys Trp Ala
        35                  40

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 80
agtagtaaca aaggtcaaag acagttgact gtatcgtcga ggatgccttc aattaagtt         59

<210> SEQ ID NO 81
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 81
gcggttactt acttagagct cgacgtctta cttacttagc tcacttctct tcacacca          58

<210> SEQ ID NO 82
<211> LENGTH: 12
<212> TYPE: PRT
<213> ORGANISM: Homo sapiens

<400> SEQUENCE: 82

Cys Asp Gly Glu Lys Asp Thr Tyr Ser Tyr Leu Ala
 1               5                  10

<210> SEQ ID NO 83
<211> LENGTH: 25
<212> TYPE: PRT
<213> ORGANISM: Homo sapiens

<400> SEQUENCE: 83

Cys Glu Ser Ser Phe Ser Leu Asn Met Asn Phe Ser Ser Lys Arg Thr

```
                 1               5              10              15
Lys Phe Lys Ile Thr Thr Ser Met Gln
                20              25
```

<210> SEQ ID NO 84
<211> LENGTH: 12
<212> TYPE: PRT
<213> ORGANISM: Homo sapiens

<400> SEQUENCE: 84

```
Cys Glu Glu Ala Gln Val Arg Lys Glu Asn Gln Trp
 1               5                  10
```

<210> SEQ ID NO 85
<211> LENGTH: 19
<212> TYPE: PRT
<213> ORGANISM: Homo sapiens
<220> FEATURE:
<221> NAME/KEY: Phosphorylation
<222> LOCATION: 8
<223> OTHER INFORMATION: Phosothreonine

<400> SEQUENCE: 85

```
Asn Ala Gly Ser Val Glu Gln Thr Pro Lys Lys Pro Gly Leu Arg Arg
 1               5                  10                  15

Arg Gln Thr
```

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 86
cctgggggat gttctca                                                      17

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 87
ggcttccggg catttag                                                      17

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 88
catctggcac gattcca                                                      17

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence:

-continued

```
        Oligonucleotide

<400> SEQUENCE: 89
ccgctcatcg tatgaca                                            17

<210> SEQ ID NO 90
<211> LENGTH: 19
<212> TYPE: PRT
<213> ORGANISM: Homo sapiens
<220> FEATURE:
<221> NAME/KEY: Phosphorylation
<222> LOCATION: 8
<223> OTHER INFORMATION: Phosotyrosine

<400> SEQUENCE: 90

Ala Glu Ile Gly Val Gly Ala Tyr Gly Thr Val Tyr Lys Ala Arg Asp
  1               5                  10                  15

Pro His Ser
```